United States Patent
Herr et al.

(10) Patent No.: US 9,211,201 B2
(45) Date of Patent: *Dec. 15, 2015

(54) HYBRID TERRAIN-ADAPTIVE LOWER-EXTREMITY SYSTEMS

(71) Applicant: iWalk, Inc., Bedford, MA (US)

(72) Inventors: Hugh Miller Herr, Somerville, MA (US); Rick Casler, Lowell, MA (US); Zhixiu Han, Acton, MA (US)

(73) Assignee: iWalk, Inc., Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/832,491

(22) Filed: Mar. 15, 2013

(65) Prior Publication Data

US 2013/0312483 A1 Nov. 28, 2013

Related U.S. Application Data

(63) Continuation of application No. 12/552,036, filed on Sep. 1, 2009, now Pat. No. 8,419,804.

(60) Provisional application No. 61/094,125, filed on Sep. 4, 2008, provisional application No. 61/161,999, filed on Mar. 20, 2009, provisional application No. 61/231,754, filed on Aug. 6, 2009.

(51) Int. Cl.
*A61F 2/72* (2006.01)
*A61F 2/60* (2006.01)
(Continued)

(52) U.S. Cl.
CPC ... *A61F 2/72* (2013.01); *A61F 2/60* (2013.01); *A61F 2/6607* (2013.01); *A61F 2/68* (2013.01);
(Continued)

(58) Field of Classification Search
None
See application file for complete search history.

(56) References Cited

U.S. PATENT DOCUMENTS

| 45,169 A | 11/1864 | Neubert |
| 360,446 A | 4/1887 | Kreemer |

(Continued)

FOREIGN PATENT DOCUMENTS

| EP | 1 393 866 A1 | 3/2004 |
| EP | 1 408 892 | 4/2004 |

(Continued)

OTHER PUBLICATIONS

Abbas J. and Chizeck H., Neural Network Control of Functional Neuromuscular Stimulation Systems: Computer Simulation Studies, IEEE Transactions on Biomedical Engineering, vol. 42, No. 1, Nov. 1995, pp. 1117-1127.

(Continued)

*Primary Examiner* — David H Willse
(74) *Attorney, Agent, or Firm* — Kacvinsky Daisak Bluni PLLC—Boston

(57) ABSTRACT

Hybrid terrain-adaptive lower-extremity apparatus and methods that perform in a variety of different situations by detecting the terrain that is being traversed, and adapting to the detected terrain. In some embodiments, the ability to control the apparatus for each of these situations builds upon five basic capabilities: (1) determining the activity being performed; (2) dynamically controlling the characteristics of the apparatus based on the activity that is being performed; (3) dynamically driving the apparatus based on the activity that is being performed; (4) determining terrain texture irregularities (e.g., how sticky is the terrain, how slippery is the terrain, is the terrain coarse or smooth, does the terrain have any obstructions, such as rocks) and (5) a mechanical design of the apparatus that can respond to the dynamic control and dynamic drive.

20 Claims, 64 Drawing Sheets

(51) Int. Cl.
  *A61F 2/66* (2006.01)
  *A61F 2/68* (2006.01)
  *H02K 7/06* (2006.01)
  *G01P 21/00* (2006.01)
  *B25J 9/00* (2006.01)
  *A61F 2/76* (2006.01)
  *A61F 2/50* (2006.01)
  *A61F 2/70* (2006.01)
  *H02K 7/116* (2006.01)

(52) U.S. Cl.
  CPC *G01P 21/00* (2013.01); *H02K 7/06* (2013.01); *A61F 2002/503* (2013.01); *A61F 2002/5003* (2013.01); *A61F 2002/5007* (2013.01); *A61F 2002/5018* (2013.01); *A61F 2002/5087* (2013.01); *A61F 2002/701* (2013.01); *A61F 2002/704* (2013.01); *A61F 2002/763* (2013.01); *A61F 2002/764* (2013.01); *A61F 2002/7625* (2013.01); *A61F 2002/7635* (2013.01); *A61F 2002/7645* (2013.01); *A61F 2002/7665* (2013.01); *B25J 9/0006* (2013.01); *H02K 7/116* (2013.01)

(56) References Cited

U.S. PATENT DOCUMENTS

| | | | |
|---|---|---|---|
| 595,634 A | 12/1897 | King |
| 2,489,291 A | 11/1949 | Henschke et al. |
| 2,529,968 A | 11/1950 | Sartin |
| 3,098,645 A | 7/1963 | Owens |
| 3,207,497 A | 9/1965 | Schoonover |
| 3,546,712 A | 12/1970 | Tarte |
| 3,844,279 A | 10/1974 | Konvalin |
| 4,442,390 A | 4/1984 | Davis |
| 4,463,291 A | 7/1984 | Usry |
| 4,518,307 A | 5/1985 | Bloch |
| 4,532,462 A | 7/1985 | Washbourn et al. |
| 4,546,295 A | 10/1985 | Wickham et al. |
| 4,546,296 A | 10/1985 | Washbourn et al. |
| 4,546,297 A | 10/1985 | Washbourn et al. |
| 4,546,298 A | 10/1985 | Wickham et al. |
| 4,569,352 A | 2/1986 | Petrofsky et al. |
| 4,600,357 A | 7/1986 | Coules |
| 4,657,470 A | 4/1987 | Clarke et al. |
| 4,697,808 A | 10/1987 | Larson et al. |
| 4,843,921 A | 7/1989 | Kremer |
| 4,865,376 A | 9/1989 | Leaver et al. |
| 4,872,803 A | 10/1989 | Asakawa |
| 4,909,535 A | 3/1990 | Clark et al. |
| 4,921,293 A | 5/1990 | Ruoff et al. |
| 4,921,393 A | 5/1990 | Andeen et al. |
| 4,923,474 A | 5/1990 | Klasson et al. |
| 4,923,475 A | 5/1990 | Gosthnian et al. |
| 4,936,295 A | 6/1990 | Crane |
| 4,964,402 A | 10/1990 | Grim et al. |
| 4,989,161 A | 1/1991 | Oaki |
| 5,012,591 A | 5/1991 | Asakawa |
| 5,049,797 A | 9/1991 | Phillips |
| 5,062,673 A | 11/1991 | Mimura |
| 5,088,478 A | 2/1992 | Grim |
| 5,092,902 A | 3/1992 | Adams et al. |
| 5,112,296 A | 5/1992 | Beard et al. |
| 5,174,168 A | 12/1992 | Takagi et al. |
| 5,181,933 A | 1/1993 | Phillips |
| 5,252,102 A | 10/1993 | Singer et al. |
| 5,282,460 A | 2/1994 | Boldt |
| 5,294,873 A | 3/1994 | Seraji |
| 5,311,109 A | 5/1994 | Ozawa |
| RE34,661 E | 7/1994 | Grim |
| 5,327,790 A | 7/1994 | Levin et al. |
| 5,330,417 A | 7/1994 | Petersen et al. |
| 5,367,790 A | 11/1994 | Gamow et al. |
| 5,383,939 A | 1/1995 | James |
| 5,405,409 A | 4/1995 | Knoth |
| 5,442,270 A | 8/1995 | Tetsuaki |
| 5,443,521 A | 8/1995 | Knoth et al. |
| 5,456,341 A | 10/1995 | Garnjost et al. |
| 5,458,143 A | 10/1995 | Herr |
| 5,476,441 A | 12/1995 | Durfee et al. |
| 5,502,363 A | 3/1996 | Tasch et al. |
| 5,514,185 A | 5/1996 | Phillips |
| 5,556,422 A | 9/1996 | Powell, III et al. |
| 5,571,205 A | 11/1996 | James |
| 5,643,332 A | 7/1997 | Stein |
| 5,650,704 A | 7/1997 | Pratt et al. |
| 5,662,693 A | 9/1997 | Johnson et al. |
| 5,701,686 A | 12/1997 | Herr et al. |
| 5,718,925 A | 2/1998 | Kristinsson et al. |
| 5,748,845 A | 5/1998 | Labun et al. |
| 5,776,205 A | 7/1998 | Phillips |
| 5,885,809 A | 3/1999 | Effenberger et al. |
| 5,888,212 A | 3/1999 | Petrofsky et al. |
| 5,888,213 A | 3/1999 | Sears et al. |
| 5,898,948 A | 5/1999 | Kelly et al. |
| 5,910,720 A | 6/1999 | Williamson et al. |
| 5,932,230 A | 8/1999 | DeGrate |
| 5,944,760 A | 8/1999 | Christensen |
| 5,971,729 A | 10/1999 | Kristinsson et al. |
| 5,972,036 A | 10/1999 | Kristinsson et al. |
| 5,980,435 A | 11/1999 | Joutras et al. |
| 6,029,374 A | 2/2000 | Herr et al. |
| 6,056,712 A | 5/2000 | Grim |
| 6,067,892 A | 5/2000 | Erickson |
| 6,071,313 A | 6/2000 | Phillips |
| 6,095,991 A | 8/2000 | Krausman et al. |
| 6,136,039 A | 10/2000 | Kristinsson et al. |
| 6,144,385 A | 11/2000 | Girard |
| 6,202,806 B1 | 3/2001 | Sandrin et al. |
| 6,223,648 B1 | 5/2001 | Erickson |
| 6,240,797 B1 | 6/2001 | Morishima et al. |
| 6,267,742 B1 | 7/2001 | Krivosha et al. |
| 6,416,703 B1 | 7/2002 | Kristinsson et al. |
| 6,443,993 B1 | 9/2002 | Koniuk |
| 6,456,884 B1 | 9/2002 | Kenney |
| 6,478,826 B1 | 11/2002 | Phillips et al. |
| 6,485,776 B2 | 11/2002 | Janusson et al. |
| 6,500,138 B1 | 12/2002 | Irby et al. |
| 6,507,757 B1 | 1/2003 | Swain et al. |
| 6,511,512 B2 | 1/2003 | Phillips et al. |
| 6,517,503 B1 | 2/2003 | Naft et al. |
| 6,532,400 B1 | 3/2003 | Jacobs |
| 6,585,774 B2 | 7/2003 | Dean, Jr. et al. |
| 6,589,289 B2 | 7/2003 | Ingimarsson |
| 6,592,539 B1 | 7/2003 | Einarsson et al. |
| 6,610,101 B2 | 8/2003 | Herr et al. |
| 6,626,952 B2 | 9/2003 | Janusson et al. |
| 6,645,252 B2 | 11/2003 | Asai et al. |
| 6,660,042 B1 | 12/2003 | Curcie et al. |
| 6,666,796 B1 | 12/2003 | MacCready, Jr. |
| 6,706,364 B2 | 3/2004 | Janusson et al. |
| 6,752,774 B2 | 6/2004 | Townsend et al. |
| 6,764,520 B2 | 7/2004 | Deffenbaugh et al. |
| 6,811,571 B1 | 11/2004 | Phillips |
| 6,821,233 B1 | 11/2004 | Colombo et al. |
| D503,480 S | 3/2005 | Ingimundarson et al. |
| D503,802 S | 4/2005 | Bjarnason |
| 6,887,279 B2 | 5/2005 | Phillips et al. |
| 6,923,834 B2 | 8/2005 | Karason |
| 6,936,073 B2 | 8/2005 | Karason |
| 6,942,629 B2 | 9/2005 | Hepburn et al. |
| 6,945,947 B2 | 9/2005 | Ingimundarson et al. |
| 6,966,882 B2 | 11/2005 | Horst |
| 6,969,408 B2 | 11/2005 | Lecomte et al. |
| 6,992,455 B2 | 1/2006 | Kato et al. |
| 7,001,563 B2 | 2/2006 | Janusson et al. |
| 7,025,793 B2 | 4/2006 | Egilsson |
| 7,029,500 B2 | 4/2006 | Martin |
| 7,037,283 B2 | 5/2006 | Karason et al. |
| D523,149 S | 6/2006 | Bjarnason |
| 7,063,727 B2 | 6/2006 | Phillips et al. |
| 7,077,818 B2 | 7/2006 | Ingimundarson et al. |
| 7,094,058 B2 | 8/2006 | Einarsson |

(56) References Cited

U.S. PATENT DOCUMENTS

| | | | |
|---|---|---|---|
| 7,094,212 B2 | 8/2006 | Karason et al. |
| D527,825 S | 9/2006 | Ingimundarson et al. |
| D529,180 S | 9/2006 | Ingimundarson et al. |
| 7,101,487 B2 | 9/2006 | Hsu et al. |
| 7,105,122 B2 | 9/2006 | Karason |
| 7,107,180 B2 | 9/2006 | Karason |
| 7,118,601 B2 | 10/2006 | Yasui et al. |
| 7,118,602 B2 | 10/2006 | Bjarnason |
| 7,136,722 B2 | 11/2006 | Nakamura et al. |
| D533,280 S | 12/2006 | Wyatt et al. |
| 7,144,429 B2 | 12/2006 | Carstens |
| 7,145,305 B2 | 12/2006 | Takenaka et al. |
| 7,154,017 B2 | 12/2006 | Sigurjonsson et al. |
| 7,161,056 B2 | 1/2007 | Gudnason et al. |
| 7,169,188 B2 | 1/2007 | Carstens |
| 7,169,189 B2 | 1/2007 | Bjarnason et al. |
| 7,169,190 B2 | 1/2007 | Phillips et al. |
| 7,190,141 B1 | 3/2007 | Ashrafiuon et al. |
| 7,198,071 B2 | 4/2007 | Bisbee, III et al. |
| 7,198,610 B2 | 4/2007 | Ingimundarson et al. |
| 7,217,060 B2 | 5/2007 | Ingimarsson |
| 7,220,889 B2 | 5/2007 | Sigurjonsson et al. |
| 7,223,899 B2 | 5/2007 | Sigurjonsson |
| 7,227,050 B2 | 6/2007 | Sigurjonsson et al. |
| 7,230,154 B2 | 6/2007 | Sigurjonsson |
| 7,235,108 B2 | 6/2007 | Carstens |
| 7,240,876 B2 | 7/2007 | Doubleday et al. |
| 7,266,910 B2 | 9/2007 | Ingimundarson |
| 7,270,644 B2 | 9/2007 | Ingimundarson |
| 7,278,954 B2 | 10/2007 | Kawai et al. |
| 7,279,009 B2 | 10/2007 | Herr et al. |
| 7,288,076 B2 | 10/2007 | Grim et al. |
| 7,295,892 B2 | 11/2007 | Herr et al. |
| RE39,961 E | 12/2007 | Petrofsky et al. |
| 7,303,538 B2 | 12/2007 | Grim et al. |
| 7,304,202 B2 | 12/2007 | Sigurjonsson et al. |
| 7,311,686 B1 | 12/2007 | Iglesias et al. |
| 7,313,463 B2 | 12/2007 | Herr et al. |
| D558,884 S | 1/2008 | Ingimundarson et al. |
| 7,335,233 B2 | 2/2008 | Hsu et al. |
| 7,347,877 B2 | 3/2008 | Clausen et al. |
| D567,072 S | 4/2008 | Ingimundarson et al. |
| 7,371,262 B2 | 5/2008 | Lecomte et al. |
| 7,377,944 B2 | 5/2008 | Janusson et al. |
| RE40,363 E | 6/2008 | Grim et al. |
| 7,381,860 B2 | 6/2008 | Gudnason et al. |
| 7,390,309 B2 | 6/2008 | Dariush |
| 7,393,364 B2 | 7/2008 | Martin |
| 7,396,975 B2 | 7/2008 | Sigurjonsson et al. |
| 7,402,721 B2 | 7/2008 | Sigurjonsson et al. |
| 7,411,109 B2 | 8/2008 | Sigurjonsson et al. |
| D576,781 S | 9/2008 | Chang et al. |
| D577,828 S | 9/2008 | Ingimundarson et al. |
| 7,423,193 B2 | 9/2008 | Sigurjonsson et al. |
| 7,427,297 B2 | 9/2008 | Patterson et al. |
| 7,429,253 B2 | 9/2008 | Shimada et al. |
| 7,431,708 B2 | 10/2008 | Sreeramagiri |
| 7,431,737 B2 | 10/2008 | Ragnarsdottir et al. |
| 7,438,843 B2 | 10/2008 | Asgeirsson |
| 7,449,005 B2 | 11/2008 | Pickering et al. |
| 7,455,696 B2 | 11/2008 | Bisbee, III et al. |
| D583,956 S | 12/2008 | Chang et al. |
| 7,459,598 B2 | 12/2008 | Sigurjonsson et al. |
| 7,465,281 B2 | 12/2008 | Grim et al. |
| 7,465,283 B2 | 12/2008 | Grim et al. |
| 7,468,471 B2 | 12/2008 | Sigurjonsson et al. |
| 7,470,830 B2 | 12/2008 | Sigurjonsson et al. |
| 7,488,349 B2 | 2/2009 | Einarsson |
| 7,488,864 B2 | 2/2009 | Sigurjonsson et al. |
| D588,753 S | 3/2009 | Ingimundarson et al. |
| 7,503,937 B2 | 3/2009 | Asgeirsson et al. |
| 7,513,880 B2 | 4/2009 | Ingimundarson et al. |
| 7,513,881 B1 | 4/2009 | Grim et al. |
| D592,755 S | 5/2009 | Chang et al. |
| D592,756 S | 5/2009 | Chang et al. |
| 7,527,253 B2 | 5/2009 | Sugar et al. |
| 7,531,006 B2 | 5/2009 | Clausen et al. |
| 7,531,711 B2 | 5/2009 | Sigurjonsson et al. |
| 7,534,220 B2 | 5/2009 | Cormier et al. |
| 7,544,214 B2 | 6/2009 | Gramnas |
| 7,549,970 B2 | 6/2009 | Tweardy |
| D596,301 S | 7/2009 | Campos et al. |
| 7,578,799 B2 | 8/2009 | Thorsteinsson et al. |
| 7,581,454 B2 | 9/2009 | Clausen et al. |
| 7,597,672 B2 | 10/2009 | Kruijsen et al. |
| 7,597,674 B2 | 10/2009 | Hu et al. |
| 7,597,675 B2 | 10/2009 | Ingimundarson et al. |
| 7,618,463 B2 | 11/2009 | Oddsson et al. |
| 7,628,766 B1 | 12/2009 | Kazerooni et al. |
| 7,632,315 B2 | 12/2009 | Egilsson |
| 7,637,957 B2 | 12/2009 | Ragnarsdottir et al. |
| 7,637,959 B2 | 12/2009 | Clausen et al. |
| 7,641,700 B2 | 1/2010 | Yasui |
| 7,650,204 B2 | 1/2010 | Dariush |
| 7,662,191 B2 | 2/2010 | Asgeirsson |
| D611,322 S | 3/2010 | Robertson |
| 7,674,212 B2 | 3/2010 | Kruijsen et al. |
| 7,691,154 B2 | 4/2010 | Asgeirsson et al. |
| 7,696,400 B2 | 4/2010 | Sigurjonsson et al. |
| 7,704,218 B2 | 4/2010 | Einarsson et al. |
| D616,555 S | 5/2010 | Thorgilsdottir et al. |
| D616,556 S | 5/2010 | Hu |
| 7,713,225 B2 | 5/2010 | Ingimundarson et al. |
| D616,996 S | 6/2010 | Thorgilsdottir et al. |
| D616,997 S | 6/2010 | Thorgilsdottir et al. |
| D618,359 S | 6/2010 | Einarsson |
| 7,727,174 B2 | 6/2010 | Chang et al. |
| 7,736,394 B2 | 6/2010 | Bedard et al. |
| 7,745,682 B2 | 6/2010 | Sigurjonsson et al. |
| D620,124 S | 7/2010 | Einarsson |
| 7,749,183 B2 | 7/2010 | Ingimundarson et al. |
| 7,749,281 B2 | 7/2010 | Egilsson |
| 7,762,973 B2 | 7/2010 | Einarsson et al. |
| 7,770,842 B2 | 8/2010 | Benson |
| 7,771,488 B2 | 8/2010 | Asgeirsson et al. |
| 7,780,741 B2 | 8/2010 | Janusson et al. |
| 7,794,418 B2 | 9/2010 | Ingimundarson et al. |
| 7,794,505 B2 | 9/2010 | Clausen et al. |
| 7,811,333 B2 | 10/2010 | Jonsson et al. |
| 7,811,334 B2 | 10/2010 | Ragnarsdottir et al. |
| D627,079 S | 11/2010 | Robertson |
| 7,833,181 B2 | 11/2010 | Cormier et al. |
| 7,842,848 B2 | 11/2010 | Janusson et al. |
| D628,696 S | 12/2010 | Robertson |
| D629,115 S | 12/2010 | Robertson |
| 7,846,213 B2 | 12/2010 | Lecomte et al. |
| 7,862,620 B2 | 1/2011 | Clausen et al. |
| 7,863,797 B2 | 1/2011 | Calley |
| 7,867,182 B2 | 1/2011 | Iglesias et al. |
| 7,867,284 B2 | 1/2011 | Bedard |
| 7,867,285 B2 | 1/2011 | Clausen et al. |
| 7,867,286 B2 | 1/2011 | Einarsson |
| 7,868,511 B2 | 1/2011 | Calley |
| 7,874,223 B2 | 1/2011 | Sugar et al. |
| 7,879,110 B2 | 2/2011 | Phillips |
| 7,891,258 B2 | 2/2011 | Clausen et al. |
| 7,892,195 B2 | 2/2011 | Grim et al. |
| D634,438 S | 3/2011 | Hu |
| D634,852 S | 3/2011 | Hu |
| 7,896,826 B2 | 3/2011 | Hu et al. |
| 7,896,827 B2 | 3/2011 | Ingimundarson et al. |
| 7,896,927 B2 | 3/2011 | Clausen et al. |
| 7,909,884 B2 | 3/2011 | Egilsson et al. |
| 7,910,793 B2 | 3/2011 | Sigurjonsson et al. |
| 7,914,475 B2 | 3/2011 | Wyatt et al. |
| 7,918,765 B2 | 4/2011 | Kruijsen et al. |
| D637,942 S | 5/2011 | Lee et al. |
| 7,935,068 B2 | 5/2011 | Einarsson |
| D640,380 S | 6/2011 | Tweardy et al. |
| D640,381 S | 6/2011 | Tweardy et al. |
| 7,955,398 B2 | 6/2011 | Bedard et al. |
| 7,959,589 B2 | 6/2011 | Sreeramagiri et al. |
| D641,482 S | 7/2011 | Robertson et al. |
| D641,483 S | 7/2011 | Robertson et al. |

(56) References Cited

U.S. PATENT DOCUMENTS

| | | |
|---|---|---|
| 7,981,068 B2 | 7/2011 | Thorgilsdottir et al. |
| 7,985,193 B2 | 7/2011 | Thorsteinsson et al. |
| 7,985,265 B2 | 7/2011 | Moser et al. |
| D643,537 S | 8/2011 | Lee |
| 7,992,849 B2 | 8/2011 | Sugar et al. |
| 7,998,221 B2 | 8/2011 | Lecomte et al. |
| 8,002,724 B2 | 8/2011 | Hu et al. |
| 8,007,544 B2 | 8/2011 | Jonsson et al. |
| 8,016,781 B2 | 9/2011 | Ingimundarson et al. |
| 8,021,317 B2 | 9/2011 | Arnold et al. |
| 8,025,632 B2 | 9/2011 | Einarsson |
| 8,025,699 B2 | 9/2011 | Lecomte et al. |
| 8,026,406 B2 | 9/2011 | Janusson et al. |
| D646,394 S | 10/2011 | Tweardy et al. |
| D647,622 S | 10/2011 | Lee et al. |
| D647,623 S | 10/2011 | Thorgilsdottir et al. |
| D647,624 S | 10/2011 | Thorgilsdottir et al. |
| 8,034,120 B2 | 10/2011 | Egilsson et al. |
| 8,038,636 B2 | 10/2011 | Thorgilsdottir et al. |
| 8,043,244 B2 | 10/2011 | Einarsson et al. |
| 8,043,245 B2 | 10/2011 | Campos et al. |
| 8,048,007 B2 | 11/2011 | Roy |
| 8,048,013 B2 | 11/2011 | Ingimundarson et al. |
| 8,048,172 B2 | 11/2011 | Jonsson et al. |
| 8,052,760 B2 | 11/2011 | Egilsson et al. |
| 8,057,550 B2 | 11/2011 | Clausen et al. |
| 8,075,633 B2 | 12/2011 | Herr et al. |
| 8,142,370 B2 | 3/2012 | Weinberg et al. |
| 8,181,520 B2 | 5/2012 | Kadota et al. |
| 8,202,325 B2 | 6/2012 | Albrecht-Laatsch et al. |
| 8,287,477 B1 | 10/2012 | Herr et al. |
| 8,419,804 B2 | 4/2013 | Herr et al. |
| 8,551,184 B1 | 10/2013 | Herr |
| 2001/0029400 A1 | 10/2001 | Deffenbaugh et al. |
| 2002/0052663 A1 | 5/2002 | Herr et al. |
| 2002/0092724 A1 | 7/2002 | Koleda |
| 2002/0138153 A1 | 9/2002 | Koniuk |
| 2003/0093021 A1 | 5/2003 | Goffer |
| 2003/0125814 A1 | 7/2003 | Paasivaara et al. |
| 2003/0139783 A1 | 7/2003 | Kilgore et al. |
| 2003/0163206 A1 | 8/2003 | Yasui et al. |
| 2003/0195439 A1 | 10/2003 | Caselnova |
| 2004/0039454 A1 | 2/2004 | Herr et al. |
| 2004/0049290 A1 | 3/2004 | Bedard |
| 2004/0054423 A1 | 3/2004 | Martin |
| 2004/0064195 A1 | 4/2004 | Herr |
| 2004/0083528 A1 | 5/2004 | Stewart et al. |
| 2004/0088025 A1 | 5/2004 | Gesotti |
| 2004/0172097 A1 | 9/2004 | Brodard et al. |
| 2004/0181118 A1 | 9/2004 | Kochamba |
| 2004/0181289 A1 | 9/2004 | Bedard et al. |
| 2004/0255711 A1 | 12/2004 | Takenaka et al. |
| 2004/0261561 A1 | 12/2004 | Takenaka et al. |
| 2005/0007834 A1 | 1/2005 | Hidaka |
| 2005/0043614 A1 | 2/2005 | Huizenga et al. |
| 2005/0049652 A1 | 3/2005 | Tong |
| 2005/0059908 A1 | 3/2005 | Bogert |
| 2005/0070834 A1 | 3/2005 | Herr et al. |
| 2005/0085948 A1 | 4/2005 | Herr et al. |
| 2005/0155444 A1 | 7/2005 | Otaki et al. |
| 2005/0179417 A1 | 8/2005 | Takenaka et al. |
| 2005/0197717 A1 | 9/2005 | Ragnarsdottir et al. |
| 2005/0209707 A1 | 9/2005 | Phillips et al. |
| 2005/0228515 A1 | 10/2005 | Musallam et al. |
| 2005/0251079 A1 | 11/2005 | Carvey et al. |
| 2006/0004299 A1 | 1/2006 | Endo et al. |
| 2006/0004307 A1 | 1/2006 | Horst |
| 2006/0055358 A1 | 3/2006 | Ogawa et al. |
| 2006/0064047 A1 | 3/2006 | Shimada et al. |
| 2006/0069448 A1 | 3/2006 | Yasui |
| 2006/0094989 A1 | 5/2006 | Scott et al. |
| 2006/0135883 A1 | 6/2006 | Jonsson et al. |
| 2006/0173552 A1 | 8/2006 | Roy |
| 2006/0184280 A1 | 8/2006 | Oddsson et al. |
| 2006/0211956 A1 | 9/2006 | Sankai |
| 2006/0213305 A1 | 9/2006 | Sugar et al. |
| 2006/0214621 A1 | 9/2006 | Ogawa et al. |
| 2006/0224246 A1 | 10/2006 | Clausen et al. |
| 2006/0249315 A1 | 11/2006 | Herr et al. |
| 2006/0258967 A1 | 11/2006 | Fujil et al. |
| 2006/0264790 A1 | 11/2006 | Kruijsen et al. |
| 2006/0276728 A1 | 12/2006 | Ashihara et al. |
| 2007/0016329 A1 | 1/2007 | Herr et al. |
| 2007/0043449 A1 | 2/2007 | Herr et al. |
| 2007/0050044 A1 | 3/2007 | Haynes et al. |
| 2007/0123997 A1 | 5/2007 | Herr et al. |
| 2007/0129653 A1 | 6/2007 | Sugar et al. |
| 2007/0145930 A1 | 6/2007 | Zaier |
| 2007/0156252 A1 | 7/2007 | Jonsson et al. |
| 2007/0162152 A1 | 7/2007 | Herr et al. |
| 2007/0233279 A1 | 10/2007 | Kazerooni et al. |
| 2007/0267791 A1 | 11/2007 | Hollander et al. |
| 2008/0039756 A1 | 2/2008 | Thorsteinsson et al. |
| 2008/0114272 A1 | 5/2008 | Herr et al. |
| 2008/0155444 A1 | 6/2008 | Pannese et al. |
| 2008/0161937 A1 | 7/2008 | Sankai |
| 2008/0234608 A1 | 9/2008 | Sankai |
| 2009/0030530 A1 | 1/2009 | Martin |
| 2009/0171469 A1 | 7/2009 | Thorsteinsson et al. |
| 2009/0192619 A1 | 7/2009 | Martin et al. |
| 2009/0222105 A1 | 9/2009 | Clausen |
| 2010/0004860 A1 | 1/2010 | Chernoguz et al. |
| 2010/0025409 A1 | 2/2010 | Hunter |
| 2010/0094188 A1 | 4/2010 | Goffer et al. |
| 2010/0113980 A1 | 5/2010 | Herr et al. |
| 2010/0114329 A1 | 5/2010 | Casler et al. |
| 2010/0174384 A1 | 7/2010 | Herr et al. |
| 2010/0174385 A1 | 7/2010 | Casler et al. |
| 2010/0179668 A1 | 7/2010 | Herr et al. |
| 2010/0312363 A1 | 12/2010 | Herr et al. |
| 2011/0082566 A1 | 4/2011 | Herr et al. |
| 2011/0105966 A1 | 5/2011 | Kazerooni et al. |
| 2011/0224804 A1 | 9/2011 | Clausen et al. |
| 2011/0245931 A1 | 10/2011 | Clausen et al. |
| 2011/0257764 A1 | 10/2011 | Herr et al. |
| 2011/0260380 A1 | 10/2011 | Hollander et al. |
| 2011/0264230 A1 | 10/2011 | Herr et al. |
| 2011/0278857 A1 | 11/2011 | Sugar et al. |
| 2011/0295384 A1 | 12/2011 | Herr et al. |
| 2011/0295385 A1 | 12/2011 | Herr et al. |
| 2012/0209405 A1 | 8/2012 | Herr et al. |
| 2012/0259429 A1 | 10/2012 | Han et al. |
| 2012/0259430 A1 | 10/2012 | Han et al. |
| 2012/0259431 A1 | 10/2012 | Han et al. |
| 2012/0271433 A1 | 10/2012 | Galea et al. |
| 2012/0283845 A1 | 11/2012 | Herr et al. |

FOREIGN PATENT DOCUMENTS

| | | |
|---|---|---|
| EP | 1 534 117 | 6/2005 |
| JP | 2005-000500 | 1/2005 |
| WO | WO 94/09727 A2 | 5/1994 |
| WO | WO 03/003953 A1 | 1/2003 |
| WO | WO 03/068453 A1 | 8/2003 |
| WO | WO 2004/017872 A2 | 3/2004 |
| WO | WO 2004/019832 A1 | 3/2004 |
| WO | WO 2006/110895 | 10/2006 |
| WO | WO 2007/025116 A2 | 3/2007 |
| WO | WO 2009/082249 | 7/2009 |
| WO | WO 2010/025403 A1 | 3/2010 |
| WO | WO 2010/025409 | 3/2010 |
| WO | WO 2010/027968 A2 | 3/2010 |
| WO | WO 2011/005482 A2 | 1/2011 |

OTHER PUBLICATIONS

Abul-haj, C. and Hogan, N., Functional assessment of control systems for cybernetic elbow prostheses. Part I, Part II, IEEE Transactions on Biomedical Engineering, vol. 37, No. 11, Nov. 1990, Cambridge, MA, pp. 1037-1047.

Akazawa, K., et al, Biomimetic EMG prosthesis-hand, Proceedings of the 18th Annual International Conference of the IEEE Engineering in Medicine and Biology Society, vol. 2, Oct. 1996, Amsterdam, Netherlands, pp. 535-536.

(56) References Cited

OTHER PUBLICATIONS

Aminian, Estimation of Speed and Incline of Walking Using Neural Network, IEEE Transactions on Biomedical Engineering, vol. 44, No. 3, Jun. 1995, pp. 743-746.

Anderson, F. and Pandy M., Dynamic optimization of human walking, Journal of Biomechanical Engineering, vol. 123, Oct. 2001, pp. 381-390.

Andrews, et al., Hybrid FES Orthosis incorporating closed loop control and sensory feedback, J. Biomed Eng., vol. 10, Apr. 1988, pp. 189-195.

Arakawa, T. and Fukuda, T., Natural motion generation of biped locomotion robot using hierarchical trajectory generation method consisting of GA, EP layers, Proceedings of the 1997 IEEE International Conference on Robotics and Automation, Apr. 1997, Albuquerque, NM, pp. 211-216.

Au, S. and Herr H., Initial experimental study on dynamic interaction between an amputee and a powered ankle-foot prosthesis, Workshop on Dynamic Walking: Mechanics and Control of Human and Robot Locomotion, May 2006, Ann Arbor, MI, p. 1.

Au, S., An EMG-position controlled system for an active ankle-foot prosthesis: an initial experimental study, Proc. Of the 2006 IEEE International Conference on Rehabilitation Robotics, Jul. 2005, Chicago, IL, pp. 375-379.

Au, S., et al. An ankle-foot emulation system for the study of human walking biomechanics, Proc. of the 2006 IEEE Int. Conf. on Robotics and Automation, May 2006, Orlando, FL, pp. 2939-2945.

Au, S., et al., Biomechanical design of a powered ankle-foot prosthesis, Proc. of the 2007 IEEE Int. Conf. on Rehabilitation Robotics, Jun. 2007, Noordwijk, Netherlands, pp. 298-303.

Au, S., et al., Powered Ankle-foot Prosthesis Improves Walking Metabolic Economy, IEEE Trans. on Robotics, vol. 25, No. 1, Feb. 2009, pp. 51-66.

Au, S., et al., Powered ankle-foot prosthesis to assist level-ground and stair-descent gaits, Neural Networks, vol. 21, No. 4, Mar. 2008, pp. 654-666.

Au., et al., Powered Ankle-Foot Prosthesis for the Improvement of Amputee Ambulation, Proceedings of the 29th Annual International Conference of the IEEE, Aug. 2007, Lyon, France, pp. 3020-3026.

Barth, D.., et al., Gait analysis and energy cost of below-knee amputees wearing six different prosthetic feet, Journal of Prosthetics & Orthotics, vol. 4, No. 2, Winter, 1992, pp. 63-75.

Baten, et al., Inertial Sensing in Ambulatory back load Estimation, 18 Annual International Conferences of IEEE Engineering in Medicine and Biology Society, Amsterdam 1996, pp. 497-498.

Bateni, H. and Olney S., Kinematic and kinetic variations of below-knee amputee gait, Journal of Prosthetics & Orthotics, vol. 14, No. 1, Mar. 2002, pp. 2-13.

Blaya et al., Adaptive control of a variable-impedance ankle-foot orthosis to assist drop-foot gait, IEEE Transactions on Neural Systems and Rehabilitation Engineering, vol. 12, No. 1, Mar. 2004, pp. 24-31.

Blaya, et al., Active Ankle Foot Orthoses (AAFO). http://www.ai.mit.edu. Artificial Intelligence Laboratory, Massachusetts Institute of Technology, Cambridge, Massachusetts. 2001. 3 pages.

Blaya, J.A., Force-Controllable Ankle Foot Orthosis (AFO) to Assist Drop Foot Gait, submitted to the Department of Mechanical Engineering,Massachusetts Institute of Technology, Cambridge, Massachusetts (Feb. 2003). 88 pages.

Blickhan, R., The spring-mass model for running and hopping, J of Biomech. Feb. 22, 1989, Great Britain, pp. 1217-1227.

Bortz, A New Mathematical Formulation for Strapdown Inertial Navigation, IEEE Transactions of Aerospace and Electronic Systems, vol. AES-7, No. 1, Jan. 1971, p. 61-66.

Bouten et al., Assessment of energy expenditure for physical activity using a triaxial accelerometer. Med Sci Sports Exerc. Dec. 1994;26(12):1516-23.

Bouten, A Triaxial Accelerometer and Portable Data Processing Unit for the Assessment of Daily Physical Activity, IEEE Transactions on Biomedical Engineering, vol. 44, No. 3, Mar. 1997, pp. 136-147.

Brockway, J., Derivation of formulae used to calculate energy expenditure in man, Human Nutrition Clinical Nutrition, vol. 41, Nov. 1987, pp. 463-471.

Brown, R., On the nature of the fundamental activity of the nervous centres: together with an analysis of the conditioning of rhythmic activity in progression, and a theory of the evolution of function in the nervous system, J Physiol, vol. 48,No. 1, Mar. 1914, pp. 18-46.

Chang, et al., Ischemic Colitis and Complications of Constipation Associated with the use of Alosetron Under a Risk Management Plan: Clinical Characteristics, Outcomes, and Incidences the Americal Journal of Gastronenterology, vol. 105, No. 4, Apr. 2010, pp. 866-875.

Chu, A., Kazerooni, H. and Zoss, A., On the Biomimetic Design of the Berkeley Lower Extremity Exoskeleton (BLEEX), Proceedings of the 2005 IEEE International Conference on Robotics and Automation, Apr. 2005, Barcelona, Spain, pp. 4356-4363.

Colborne, G. R., S. Naumann, P. E. Longmuir, and D. Berbrayer, Analysis of mechanical and metabolic factors in the gait of congenital below knee amputees, Am. J. Phys. Med. Rehabil., vol. 92, pp. 272-278, Oct. 1992.

Colgate, The control of dynamically interacting systems. MIT. Aug. 1988. 1-19.

Collins, et al., Controlled Energy Storage and Return Prosthesis Reduces Metabolic cost of Walking, ASB 29.sup.th Annual Meeting, Cleveland, Ohio, Jul. 31-Aug. 5, 2005, 1 page.

Collins, et al., Supporting Online Material for Efficient bipedal robots based on passive-dynamic walkers, Mechanical Engineering, University of Michigan, Feb. 2005, Ann Arbor, MI, pp. 1-8.

Crago P., et al., New Control Strategies for neuroprosthetic systems, Journal of Rehabilitation Research and Development, vol. 33, No. 2, Apr. 1996, pp. 158-172.

Daley, M. A., Felix, G., Biewener, A. A., 2007. Running stability is enhanced by a proximo-distal gradient in joint neuromechanical control. J Exp Biol 210 (Pt 3), Nov. 2006, pp. 383-394.

Dapena, J. and McDonald, C., Three-dimensional analysis of angular momentum in the hammer throw, Med. Sci. in Sports Exerc., vol. 21, No. 2, Apr. 1989, pp. 206-220.

Davids et al., Disorders of Bone and Mineral Metabolism. Book reviews. J Ped Orthopaedics. 1992;12(6):815.

Dietz, V., Proprioception and locomotor disorders, Nat Rev Neurosci, vol. 3, Oct. 2002, pp. 781-790.

Dietz, V., Spinal Cord Pattern Generators for Locomotion, download Feb. 6, 2012, http://www.Clinph-journal.com/article/PIIS1388245703001202/fullt- ext, 12 pages.

Doerschuk, et al., Upper extremity limb function discrimination using EMG signal analysis, IEEE Transactions on Biomedical Engineering. vol. 30., No. 1., Jan. 1983, pp. 18-28.

Doke, J., et al., Mechanics and energetics of swinging the human leg, The Journal of Experimental Biology, vol. 208, Feb. 2005, pp. 439-445.

Dollar, et al., Lower Extremity Exoskeletions and Active Orthoses: Challenges and State-of-the-Art, IEEE Transcations on Robotics, vol. 24, No. 1, Feb. 2008, 15 pages.

Donelan, J., et al. Simultaneous positive and negative external mechanical work in human walking, Journal of Biomechanics, vol. 35, Jan. 2002, pp. 117-124.

Donelan, J., et al., Force regulation of ankle extensor muscle activity in freely walking cats, J Neurophysiol, vol. 101, No. 1, Nov. 2008, pp. 360-371.

Donelan, J., et al., Mechanical work for step-to-step transitions is a major determinant of the metabolic cost of human walking, J. Exp. Biol., vol. 205, Dec. 2002, pp. 3717-3727.

Drake, C., Ankle & Foot Splints or Orthoses (AFOs), HemiHelp, Last updated Jun. 2009, 8 pages.

Drake, C., Ankle & Foot Splints or Orthoses, HemiHelp, Information Sheet 13 Last updated Jun. 2009, 5 pages.

Drake, Foot & Ankle Splints or Orthoses. HemiHelp Information Sheet, London, United Kingdom. Jun. 2009;1-5.

Eilenberg, M., A Neuromuscular-Model Based Control Strategy for Powered Ankle-Foot Prostheses, Masters Thesis, Massachusetts Institute of Technology, Cambridge, Mass., 2009.

(56) References Cited

OTHER PUBLICATIONS

Ekeberg, O. and Grillner, S., Simulations of neuromuscular control in lamprey swimming, Philos Trans R Soc Lond B Biol Sci, vol. 354, May 1999, pp. 895-902.
Ekeberg, O. and Pearson, K., Computer simulation of stepping in the hind legs of the cat: an examination of mechanisms regulating the stance-to-swing transition, J Neurophysiol, vol. 94, No. 6, Jul. 2005, pp. 4256-4268.
Endo, K., et al., A quasi-passive model of human leg function in level-ground walking, Proc. of 2006 IEEE/RSJ International Conference on Intelligent Robots and Systems (IROS), Oct. 2006, Beijing, China, pp. 4935-4939.
Eppinger, S. Seering W., Three dynamic problems in robot force control, IEEE Transactions on Robotics and Automation, vol. 8, No. 6, Dec. 1992, pp. 751-758.
Esquenazi, A. and DiGiacomo, R., Rehabilitation After Amputation, Journ Am Podiatr Med Assoc, vol. 91, No. 1, Jan. 2001, pp. 13-22.
Farley, C. and McMahon, T., Energetics of walking and running: insights from simulated reduced-gravity experiments, The American Physiological Society, Dec. 1992, pp. 2709-2712.
Farry, K. A., et al., Myoelectric teleoperation of a complex robotic hand, IEEE Transactions on Robotics and Automation. vol. 12, No. 5, Oct. 1996, pp. 775-788.
Featherstone, R., 1987, Robot Dynamic Algorithms, Boston, Mass., Kluwer Academic Publishers, pp. 155-172.
Fisekovic et al., New controller for functional electrical stimulation systems, Medical Engineering & Physics vol. 23, 2001, pp. 391-399.
Fite, K., et al., Design and Control of an Electrically Powered Knee Prosthesis, Proc. of 2007 IEEE 10th International Conference on Rehabilitation Robotics (ICORR), Jun. 2007, pp. 902-905.
Flowers, W. A Man-Interactive Simulator System for Above-Knee Prosthetic Studies, Ph.D. thesis, Massachusetts of Institute Technology, Department of Mechanical Engineering. Jul. 10, 1973.
Fod, A., et al., Automated Derivation of Primitives for Movements Classification, Autonomous Robots, vol. 12, No. 1, Jan. 2002, pp. 39-54.
Foerster et al., Detection of posture and motion by accelerometry a validation study in ambulatory monitoring, Computer in Human Behavior, 1999, pp. 571-583.
Foxlin et al., Miniature 6-DOF inertial system for tracking HMDs, in SPIE vol. 3362, Helmet and Head-Mounted Displays III, AeroSense 98, Orlando, FL, Apr. 13-14, 1998, 15 pages.
Frigon, A. and Rossignol, S., Experiments and models of sensorimotor interactions during locomotion, Biol Cybern, vol. 95, No. 6, Nov. 2006, pp. 607-627.
Fujita K, et al., Joint angle control with command filter for human ankle movement using functional electrical stimulation, Proc. of IEEE Ninth Annual Conference for the Engineering in Medicine and Biology Society, Nov. 1987, Boston, MA, pp. 1719-1720.
Fukuda, O. et al., a human-assisting manipulator teleoperated by EMG signals and arm motions, IEEE Transactions on Robotics and Automation. vol. 19, No. 2, Apr. 2003, pp. 210-222.
Gates, D., Characterizing ankle function during stair ascent, descent, and level walking for ankle prosthesis and orthosis design, Masters thesis, Boston University, 2004, pp. 1-82.
Geiritsen, K., et al., Direct dynamics simulation of the impact phase in heel-toe running, J. Biomech., vol. 28, No. 6, Jun. 1995, Great Britain, pp. 661-668.
Geyer, H. and Herr H., A muscle-reflex model that encodes principles of legged mechanics predicts human walking dynamics and muscle activities, IEEE Transactions on Neural Systems and Rehabilitations Engineering, vol. 18, No. 3, Jun. 2010, pp. 263-273.
Geyer, H., et al., Compliant leg behaviour explains the basic dynamics of walking and running, Proc. R. Soc. Cond. B 273, Aug. 2006, pp. 2861-2867.
Geyer, H., et al., Positive force feedback in bouncing gaits?, Proceedings of Royal Society B-Biological Sciences, vol. 270, No. 1529, Aug. 2003, pp. 2173-2183, 2003.
Ghigliazza, R., et al., A simply stabilized running model, SIAM J. Applied. Dynamical Systems, vol. 2, No. 2, May 2004, pp. 187-218.

Giszter et al., Convergent force fields organized in the frog's spinal cord. J Neurosci. Feb. 1993;13(2):467-91.
Godha, el al., Integrated GPS/INS System for Pedestrian Navigation in a Signal Degraded Environment, ION GNSS, Sep. 2006, Fort Worth, TX, pp. 1-14.
Goswami, A. and Kallem, V., Rate of change of angular momentum and balance maintenance of biped robots, Proceedings of the 2004 IEEE International Conference on Robotics and Automation, Apr. 2004, New Orleans, La., pp. 3785-3790.
Goswami, A., Postural stability of biped robots and the foot-rotation indicator (FRI) point, International Journal of Robotics Research, vol. 18, No. 6, Jun. 1999, pp. 523-533.
Graupe, D., et al., A microprocessor system for multifunctional control of upper-limb prostheses via myoelectric signal identification, IEEE Transaction on Automatic Control. vol. AC-23, vol. 4, Aug. 1978, pp. 538-544.
Gregoire, L., and et al, Role of mono- and bi-articular muscles in explosive movements, International Journal of Sports Medicine 5, 614-630. Dec. 1984. 301-305.
Grillner, S. and Zangger, P., On the central generation of locomotion in the low spinal cat, Exp Brain Res, vol. 34, No. 2, Jan. 1979, pp. 241-261.
Grimes, D. L., An active multi-mode above-knee prosthesis controller, Ph.D. Thesis, Massachusetts Institute of Technology, Jul. 20, 1979.
Gu, W., The Regulation of Angular Momentum During Human Walking, Undergraduate Thesis, Massachusetts Institute of Technology, Physics Department, Jun. 2003, pp. 2-48.
Gunther, M. and Ruder, H., Synthesis of two-dimensional human walking: a test of the A-model, Biol. Cybern., vol. 89, May 2003, pp. 89-106.
Gunther, M., et al., Human leg design: optimal axial alignment under constraints, J. Math. Biol., vol. 48, Mar. 2004, pp. 623-646.
Hanafusa et al., A Robot Hand with Elastic Fingers and Its Application to Assembly Process, pp. 337-359, Robot Motion, Brady et al., MITPress, Cambridge, MA, 1982.
Hansen, A. H., Childress, D. S., Miff, S. C., Gard, S. A., Mesplay, K. P., The human ankle during walking: implication for the design of biomimetic ankle prosthesis, Journal of Biomechanics, vol. 37, No. 10, Oct. 2004, pp. 1467-1474.
Hashimoto et al., An instrumented compliant wrist using a parallel mechanism, Japan/USA Symposim on Flexible Automation, vol. 1, pp. 741-744, ASME, 1992.
Hayes et al., Leg Motion Analysis During Gait by Multiaxial Accelerometry: Theoretical Foundations and Preliminary Validations, Journal of Biomechanical Engineering, vol. 105, Aug. 1983, pp. 283-289.
Heglund, A Simple Design for a Force-Plat to Measure Ground Reaction Forces, J. exp. Biol., vol. 93, pp. 333-338, 1981.
Herr, H. and Wilkenfeld A., User-adaptive control of a magnetorheologicalprosthetic knee, Industrial Robot: An International Journal, vol. 30, No. 1, 2003, pp. 42-55.
Herr, H., et al, A model of scale effects in mammalian quadrupedal running, J Exp Biol 205 (Pt 7), Apr. 2002, pp. 959-967.
Herr, New Horizons for Orthotic and Prosthetic Technology: Artificial Muscle for Ambulation. MIT Media Laboratory. 2004:1-9.
Heyn et al., The Kinematice of the Swing Phase Obtained from Accelerometer and Gyroscope Measurements, 18.sup.th Annual International Conference of the IEEE Engineering in Medicine and Biology Society, Nov. 1996, Amsterdam, Netherlands, pp. 463-464.
Hill, V., The heat of shortening and the dynamic constants of muscle, Proceedings of the Royal Society London B, vol. 126, No. 843, Oct. 1938, pp. 136-195.
Hirai, K., et al., The development of Honda humanoid robot, Proceedings on IEEE/RSJ International Conference on Intelligent Robots and Systems, May 1998, Leuven, Belgium, pp. 1321-1326.
Hitt, J., R. Bellman, M. Holgate, T. Sugar, and K. Hollander, The sparky (spring ankle with regenerative kinetics) projects: Design and analysis of a robotic transtibial prosthesis with regenerative kinetics, in Proc. IEEE Int. Conf. Robot. Autom.Orlando, Fla., pp. 1587-1596, Sep. 2007.

(56) References Cited

OTHER PUBLICATIONS

Hof. A., et al., Calf muscle moment, work and efficiency in level walking; role of series elasticity, Journal of Biomechanics, vol. 16, No. 7, Sep. 1983, pp. 523-537.

Hofbaur, M. and Williams, B., Hybrid Diagnosis with Unknown Behavioral Modes, Proceedings of the 13.sup.th International Workshop on Principles of Diagnosis (DX02), May 2002, pp. 1-10, 9 pages.

Hofbaur, M. and Williams, B., Mode Estimation of Probabilistic Hybrid Systems, HSSC 2002, LNCS 2289, Mar. 25, 2002, pp. 253-266.

Hofmann, A., et al., A Sliding Controller for Bipedal Balancing Using Integrated Movement of Contact and Non-Contact Limbs, Proceedings of the IEEE/RSJ International Conference on Intelligent Robots and Systems, Sep. 2004, Sendai, Japan, pp. 1952-1959.

Hofmann, A., et al., Robust Execution of Bipedal Walking Tasks from Biomechanical Principles, Doctor of Philosophy at the Massachusetts Institute of Technology, Jan. 2006, 407 pages.

Hogan, N and Buerger S., Impedance and Interaction Control, Robotics and Automation Handbook, CRC Press, Jun. 2004, pp. 19.1-19.24.

Hogan, N. (1976) A review of the methods of processing EMG for use as a proportional control signal. Biomedical Engineering. pp. 81-86.

Hogan, N., Impedance Control: An Approach to Manipulation, Dept. of Mechanical Engineering and Labortory of Manufacturing and Productivity, Massachusetts Institute of Technology, Cambridge MA, pp. 304-313, (Jun. 1984).

Hogan, N., Impedance Control: An Approach to Manipulation: Part II—Implementation, Journal of Dynamic Systems, Measurement, and Control, 107:8-16, (1985).

Hogan, N., Impedance Control: An Approach to Manipulation: Part I—Theory, Journal of Dynamic Systems, Measurement, and Control, vol. 107, Mar. 1985, pp. 1-7, pp. 304-313.

Hogan, N., Impedance Control: An Approach to Manipulation: Part III—Application, Journal of Dynamics Systems, Measurement, and Control, 107:17-24, (1985).

Hollander, K. W., T. G. Sugar, and D. E. Herring, Adjustable robotic tendon using a 'Jack Springs'.TM., Proceedings on IEEE International Conference on Rehabilitation Robotics, Chicago, pp. 113-118, Jun. 28, 2005.

Howard, Joint and Actuator Design for Enhanced Stability in Robotic Force Control, Ph.D. thesis, Massachusetts Inst. of Technology, Dept. of Aeronautics and Astronautics, Sep. 19, 1990.

Huang, H. and Chen. C., Development of a myoelectric discrimination system for a multi-degree prosthetic hand, Proceeding of the 1999 IEEE International Conference on Robotics and Automation, May 1999, Detroit, MI, pp. 2392-2397.

Huang, Q., Planning walking patterns for a biped robot, IEEE Transactions on Robotics and Automation, vol. 17, No. 3, Jun. 2001, pp. 280-289.

Hultborn, H., Spinal reflexes, mechanisms and concepts: from Eccles to Lundberg and beyond, Prog Neurobiol, vol. 78, Feb. 2006, pp. 215-232.

Ijspeert, A. J., 2008, Central pattern generators for locomotion control in animals and robots: a review, Neural Netw, vol. 21, No. 4, May 2008, pp. 642-653.

Ijspeert, A., et al., From swimming to walking with a salamander robot driven by a spinal cord model, Science, vol. 315, No. 5817, Mar. 2007, pp. 1416-1420.

Isakower, Design Charts for Torsional Properties of Non-circular Shafts, Technical Report ARMIDTR-78001, ARRADCOM, MISD, DRDAR-MSA, Dover,NJ, Nov. 1978.

Ivashko, D., et al, Modeling the spinal cord neural circuitry controlling cat hindlimb movement during locomotion, Neurocomputing, vol. 52-54, Mar. 2003, pp. 621-629.

Johansson, J., et al., A clinical comparison of variable damping and mechanically passive prosthetic knee devices, American Journal of Physical Medicine & Rehabilitation, vol. 84, No. 8, Aug. 2005, pp. 563-575.

Johnson, C. and Lorenz R., Experimental identification of friction and its compensation in precise, position controlled mechanisms, IEEE Trans. on Industry Applications, vol. 28, No. 6, Dec. 1992, pp. 1392-1398.

Jonic S, et al., Three machine learning techniques for automatic determination of rules to control locomotion, IEEE Trans Biomed Eng, vol. 46, No. 3, Mar. 1999, pp. 300-310.

Kadaba, M., et al., Measurement of lower extremity kinematics during level walking, J. Orthop. Res., vol. 8, May 1990, pp. 383-392.

Kadaba, M., et al., Repeatability of kinematic, kinetic, and electromyographic data in normal adult gait, J. Orthop. Res., vol. 7, Nov. 1989, pp. 849-860.

Kajita, K., et al., Biped walking on a low friction floor, Proceedings of the 2004 IEEE/RSJ International Conference on Intelligent Robots and Systems, Oct. 2004, Sendai, Japan., pp. 3546-3551.

Kajita, S., et al., A Hop towards Running Humanoid Biped, Proceedings of the 2004 IEEE International Conference on Robotics and Automation, Apr. 2004, New Orleans, La., pp. 629-635.

Kajita, S., et al., Resolved Momentum Control: Humanoid Motion Planning based on the Linear and Angular Momentum, Proceedings of the 2003 IEEE/RSJ International Conference on Intelligent Robots and Systems, Oct. 2003, Las Vegas, Nev., pp. 1644-1650.

Kaneko, K., et al., Humanoid robot HRP-2, Proc. IEEE Int. Conf. on Robotics and Automation, Apr. 2004, New Orleans, La., pp. 1083-1090.

Kapti, A. and Yucenur M., Design and control of an active artificial knee joint, Mechanism and Machine Theory, vol. 41, Apr. 2006, pp. 1477-1485.

Katic, D. and Vukobratovic, M., Survey of intelligent control techniques for humanoid robots, Journal of Intelligent and Robotics Systems, vol. 37, Jun. 2003, pp. 117-141.

Kerrigan, D, et al., A refined view of the determinants of gait: significance of heel rise, Arch. Phys. Med. Rehab., vol. 81, Aug. 2000, pp. 1077-1080.

Kerrigan, D, et al., Quantification of pelvic rotation as a determinant of gait, Arch. Phys. Med. Rehab., vol. 82, Feb. 2001, pp. 217-220.

Khatib, O., et al., Coordination and decentralized cooperation of multiple mobile manipulators, Journal of Robotic Systems, vol. 13, No. 11, Nov. 1996, pp. 755-764.

Khatib, O., et al., Whole body dynamic behavior and control of human-like robots, International Journal of Humanoid Robotics, vol. 1, No. 1, Mar. 2004, pp. 29-43.

Kidder, et al., A System for the Analysis of Foot and Ankle Kinematics During Gait, IEEE Transactions on Rehabilitation Engineering, vol. 4, No. 1, Mar. 1996, pp. 25-32.

Kim, et al., Realization of Dynamic Walking for the Humaniod Robot Platform KHR-1, Advanced Robotics, vol. 18, No. 7, pp. 749-768, (2004).

Kirkwood C, et al., Automatic detection of gait events: a case study using inductive learning techniques., J Biomed Eng, vol. 11, Nov. 1989, pp. 511-516.

Kitayama, I., Nakagawa N, Amemori K, A microcomputer controlled intelligent A/K prosthesis, Proceedings of the 7th' World Congress of the International Society for Prosthetics and Orthotics, Chicago. Jun. 28, 1992, 4 pages.

Klute et al., Powering Lower Limb Prosthestics with Muscle-Like Actuators, Abstract in: Proceeding of the 1st Annual Meeting of the VA Rehabilitation Research and Development Service, Enabling Veterans: Meeting the Challenge of Rehabilitation inthe Next Millennium, Washington, D.C., Oct. 1-3, 1998, p. 52.

Klute et al.,Variable Stiffness Prosthesis for Transtibial Amputees. Dept of Veteran Affairs, Seattle, WA USA, 2005. 2 pages.

Klute, et al., Artificial Muscles: Actuators for Biorobotic Systems, The International Journal of Robotics Research, vol. 21, No. 4, Apr. 2002, pp. 295-309.

Klute, et al., Artificial Tendons: Biomechanical Design Properties for Prosthetic Lower Limbs, Chicago 2000 World Congress on Medical Physics and Biomedical Engineering, Chicago on Jul. 24-28, 2000, 4 pages.

Klute, et al., Lower Limb Prostheses Powered by Muscle-Like Pneumatic Actuator, Submitted to Oleodinamica e Pneumatica, Publishe Tecniche Nuove, Milamo, Italy, Mar. 15, 2000, 6 pages.

(56) References Cited

OTHER PUBLICATIONS

Klute, et al., McKibben Artificial Muscles: Pneumatic Actuators with Biomechanical Intelligence, IEEE/ASME 1999 Inernational Conference on Advanced Intelligent Mechatronics, Atlanta, GA, Sep. 19-22, 1999, pp. 221-226.
Klute, et al., Muscle-Like Pneumatic Actuators for Below-Knee Prostheses, Actuator2000:7th International Conference on New Actuators, Bremen, Germany on Jun. 9-21, 2000, pp. 289-292.
Klute, et al., Artificial Muscles: Actuators for Lower Limb Prostheses, Abstract in: Proceedings of the 2nd Annual Meeting of the VA rehabilitation Research and Development Service, Feb. 20-22, 2000, p. 107.
Klute, et al., Intelligent Transtibial Prostheses with Muscle-Like Actuators,: 2002 American Physiological Society Intersociety Meeting: The Power of Comparative Physiology: Evolution, Integration, and Applied, 1 page.
Klute, G., et al., Mechanical properties of prosthetic limbs adapting to the patient, Journal of Rehabilitation Research and Development, vol. 38, No. 3, May 2001, pp. 299-307.
Koganezawa, K. and Kato, I., Control aspects of artificial leg, IFAC Control Aspects of Biomedical Engineering, 1987, pp. 71-85.
Kondak, K. and Hommel, G., Control and online computation of stable movement for biped robots, Proc. of the 2003 IEEE/RSJ International Conference on Intelligent Robots and Systems (IROS), Oct. 2003, Las Vegas, Nev., pp. 874-879.
Kostov A., et al., Machine learning in control of functional electrical stimulation (FES) systems for locomotion, IEEE Trans on Biomed Eng, vol. 42, No. 6, Jun. 1995, pp. 541-551.
Kuo, A., A simple model of bipedal walking predicts the preferred speed-step length relationship, Journal of Biomechanical Engineering, vol. 123, Jun. 2001, pp. 264-269.
Kuo, A., Energetics of actively powered locomotion using the simplest walking model, Journal of Biomechanical Engineering, vol. 124, Feb. 2002, pp. 113-120.
LaFortune, Three-Dimensional Acceleration of the Tibia During Walking and Running, J. Biomechanics, vol. 24, No. 10, 1991, pp. 877-886.
LeBlanc, M. and Dapena, J., Generation and transfer of angular momentum in the javelin throw, Presented at the 20th annual meeting of the American Society of Biomechanics, Oct. 1996, Atlanta, Ga., pp. 17-19.
Lee et al., activity and Location recognition Using Wearable Sensors, Pervasive Computing, Jul.-Sep. 2002, pp. 24-32.
Li et al., (Jun. 25, 2006) Research and development of the intelligently-controlled prosthetic ankle joint. Proc. of IEEE Int. Conf. on Mechatronics and Automation. Luoyang, China, pp. 1114-1119.
Light, et al., Skeletal Transients on Heel Strike in Normal Walking With Different Footwear. J. Biomechanics vol. 13, pp. 477-480, (1980).
Liu, X., Low, K. H., Yu, H. Y., (2004) 'Development of a Lower Extremity Exoskeleton for Human performance Enhancement', IEEE Conf. on Intelligent Robots and Systems, Sendai, Japan, 3889-3894.
Lloyd R. and Cooke C., Kinetic changes associated with load carriage using two rucksack designs, Ergonomics, vol. 43, No. 9, Sep. 2000, pp. 1331-1341.
Luinge, Inertial Sensing of Human Movement, Twente University Press, ISBN 9036518237, 2002, pp. 1-80, 80 pages.
Lundberg, A., Oct. 19, 1968. Reflex control of stepping. In: The Nansen memorial lecture V, Oslo: Universitetsforlaget, 5-42.
Maganaris, C., Force-length characteristics of in vivo human skeletal muscle, Acta Physiol. Scand., vol. 172, Aug. 2001, pp. 279-285.
Maganaris, C., Force-length characteristics of the in vivo human gastrocnemius muscle, Clin. Anat., vol. 16, May 2003, pp. 215-223.
Martens, W.L.J., Exploring the Information Content and Some Applications of Body Mounted Piezo-Resistive Accelerometers, in: P.H. Veltink and R.C. van Lummel (eds.), Dynamic Analysis using Body Fixed Sensors, ISBN 90-9007328-0, 1994, pp. 9-12.
Maufroy, C., Towards a general neural controller for quadrupedal locomotion, Neural Netw, vol. 21, No. 4, Apr. 2008, pp. 667-681.

Mayagoitia R., et al., Accelerometer and rate gyroscope measurement of kinematics: an inexpensive alternative to optical motion analysis systems, Journal of Biomechanics, vol. 35, Apr. 2002, pp. 537-542.
McFadyen et al., An integrated biomechanical analysis of normal stair ascent and descent. J Biomech. 1988;21(9):733-44.
McGeer T., Passive Dynamic Walking, International Journal of Robotics, vol. 9, No. 2, May 1988, pp. 62-82.
McGeer, T., Principles of walking and running, Advances in Comparative and Environmental Physiology, vol. 11, Ch. 4, Apr. 1992, pp. 113-139.
McIntosh, A., et al., Gait dynamics on an inclined walkway, Journal of Biomechanics, vol. 39, Sep. 2005, pp. 2491-2502.
McMahon, T., The mechanics of running: how does stiffness couple with speed?, J. of Biomecb., vol. 23, 1990, pp. 65-78.
McMahon, T., et al., Groucho Running, Journal of Applied Physiology, vol. 62, No. 6, Jun. 1987, pp. 2326-2337.
Minassian, K., et al., Human lumbar cord circuitries can be activated by extrinsic tonic input to generate locomotor-like activity, Hum. Mov. Sci., vol. 26, Mar. 2007, pp. 275-295.
Mochon, S., et al., Ballistic walking, Journal of Biomechanics, vol. 13, Dec. 1980, pp. 49-57.
Moe-Nilssen, A new method for evaluating motor control in gait under real-life environmental conditions, Part 2: Gait analysis, Clinical biomechanics, vol. 13, 1998, pp. 328-335.
Molen, N., Energy/speed relation of below-knee amputees walking on motor-driven treadmill, Int. Z. Angew. Physio, vol. 31, Mar. 1973, pp. 173.
Morris, Accelerometry—A Technique for the Measurement of Human Body Movements, J. Biomechanics, vol. 6, Nov. 1973, pp. 729-736.
Muraoka, T., et al, Muscle fiber and tendon length changes in the human vastus lateralis during slow pedaling, J. Appl. Physiol., vol. 91, Nov. 2001, pp. 2035-2040.
Nakagawa A., Intelligent Knee Mechanism and the Possibility to Apply the Principle to the Other Joints, Proceedings of the 20.sup.th Annual International Conference of the IEEE Engineering in Medicine and Biology Society, Vo. 20, No. 5, Oct. 1998,pp. 2282-2287.
Neal R. and Hinton G., A view of the EM algorithm that justifies incremental, sparse, and other variants, in Michael I. Jordan (editor), Learning in Graphical Models, 1999, Cambridge, MA, pp. 1-14.
Ng, et al., Fuzzy Model Identification for Classification of Gait Events in Paraplegics, IEEE Transactions on Fuzzy Systems, vol. 5, No. 4, Nov. 1997, pp. 536-544.
Nielsen, D., et al., Comparison of energy cost and gait efficiency during ambulation in below-knee amputees using different prosthetic feet—a preliminary report, Journal of Prosthetics & Orthotics, vol. 1, No. 1, 1989, pp. 24-29.
Oda et al., In Vivo Length-Force Relationships on Muscle Fiber and Muscle Tendon Complex in the Tibialis Anterior Muscle. Int. J. Sport and Health Sci. 2005;3:245-252.
Ogihara, N. and Yama7aki, N., Generation of human bipedal locomotion by a bio-mimetic neuro-musculo-skeletal model, Biol Cybern, vol. 84, No. 1, Jan. 2001, pp. 1-11.
Palmer, M., Sagittal plane characterization of normal human ankle function across a range of walking gait speeds, Master's Thesis, MIT, Feb. 2002, Cambridge, MA, pp. 1-71.
Paluska, D. and Herr, H., Series Elasticity and Actuator Power Output, Proceedings of the 2006 IEEE International Conference on Robotics and Automation, May 2006, Orlando, FL, pp. 1830-1833.
Paluska, D., and Herr, H., The effect of series elasticity on actuator power and work output: implications for robotic and prosthetic joint design, Robotics and Autonomous Systems, vol. 54, Jun. 2006, pp. 667-673.
Pang, M., et al., The initiation of the swing phase in human infant stepping: importance of hip position and leg loading, J Physiol, vol. 528, No. 2, Oct. 2000, pp. 389-404.
Pasch, K. A., and W. P. Seering, On the drive systems for high performance machines, AMSE J. Mechanisms, Transmissions, and Automation in Design vol. 106, pp. 102-108, Mar. 1984.
Paul, C., et al., Development of a human neuro-musculo-skeletal model for investigation of spinal cord injury, Biol Cybern, vol. 93, No. 3, Aug. 2005, pp. 153-170.

(56) References Cited

OTHER PUBLICATIONS

Pearson, K., Generating the walking gait: role of sensory feedback, Prog Brain Res, vol. 143, 2004, pp. 123-129.
Perry, Gait Analysis: Normal and Pathological Function, New Jersey: SLACK Inc.; 1992, Book Review, 1 page.
Perry, J. and S. Shanfield, Efficiency of dynamic elastic response prosthetic feet, Journal of Rehabilitation Research and Development, vol. 30, No. 1, 1993 pp. 137-143.
Petrofsky et al., Feedback Control System for Walking in Man, Comput. Biol. Med., vol. 14, No. 2, Mar. 1984, pp. 135-149.
Pfeffer et al., Experiments with a Dual-Armed, Cooperative, Flexible-Drivetrain Robot System, Proc. 1993 IEEE Int. Conf. on Robotics & Automation, vol. 3, pp. 601-608, May 5, 1993.
Popovic D., et al., Control Aspects of Active Above-Knee Prosthesis, Int. Journal Man-Machine Studies, (1991) 35, pp. 751-767.
Popovic, D., Control of Movement for the Physically Disabled, Springer-Verlag London Limited, May 2000, pp. 270-302.
Popovic, et al., Gait Identification and Recognition Sensor, Proceedings of 6th Vienna International Workshop on Functional Electrostimulation, Sep. 1998, pp. 1-4.
Popovic, M. and Herr, H., Global Motion Control and Support Base Planning, Proceedings of the IEEE/RSJ International Conference on Intelligent Robots and Systems, Aug. 2005, Alberta, Canada, pp. 1-8.
Popovic, M., Angular Momentum Primitives for Human Walking: Biomechanics and Control, Proc. of the 2004 IEEE/RSJ International Conference on Intelligent Robots and Systems, Sep. 2004, Sendai, Japan., pp. 1685-1691.
Popovic, M., et al., Angular Momentum Regulation during human walking: Biomechanics and Control, Proceedings of the 2004 IEEE International Conference on Robotics and Automation, Apr. 2004, New Orleans, LA, pp. 2405-2411.
Popovic, M., et al., Ground Reference Points in Legged Locomotion: Definitions, Biological Trajectories and Control Implications, International Journal of Robotics Research, Dec. 2006, pp. 79-104.
Popovic, M., et al., Zero spin angular momentum control: definition and applicability, Proceedings of the IEEE-RAS/RSJ International Conference on Humanoid Robots, Nov. 2004, Los Angeles, CA, pp. 1-16.
Popovic, M.B., W. Gu and H. Herr, Conservation of Angular Momentum in Human Movement, MIT AI Laboratory-Research Abstracts, Sep. 2002. pp. 231-232, 2002.
Pratt, G. and Williamson M., Series elastic actuators, Proceedings on IEEE/RSJ International Conference on Intelligent Robots and Systems, Jan. 1995, Pittsburgh, PA, pp. 399-406.
Pratt, G., Legged Robots: What's New Since Raibert, IEEE Robotics and Automation Magazine, Research Perspectives, Sep. 2000, pp. 15-19.
Pratt, G., Low Impedance Walking Robots, Integ. and Comp. Biol., vol. 42, Feb. 2002, pp. 174-181.
Pratt, J., et al., The RoboKnee: An Exoskeleton for Enhancing Strength and Endurance During Walking, IEEE Conf. on Robotics and Automation, Apr. 2004, New Orleans, LA, pp. 2430-2435.
Prochazka, A. and Yakovenko, S., The neuromechanical tuning hypothesis, Prog Brain Res, vol. 165, Oct. 2007, pp. 257-268.
Prochazka, A., et al., Positive force feedback control of muscles, J. of Neuro-phys., vol. 77, Jun. 1997, pp. 3226-3236.
Prochazka, A., et al., Sensory control of locomotion: reflexes versus higher-level control, Adv Exp Med Biol, vol. 508, 2002, pp. 357-367.
Raibert, M., Legged Robots that Balance, The MIT Press, Nov. 1986, Cambridge, MA, p. 89.
Rassier, D., et al., Length dependence of active force production in skeletal muscle, Journal of Applied Physiology, vol. 86, Issue 5, May 1999, pp. 1455-1457.
Reitman, et al., Gait analysis in prosthetics: opinions, ideas and conclusions, Prosthetics and Orthotics International, 2002, 26, 50-57.
Riener, R., et al., Stair ascent and descent at different inclinations, Gait Posture, vol. 15, Feb. 2002, pp. 32-44.

Robinson, D., Design and an analysis of series elasticity in closed-loop actuator force control, Ph.D. Thesis, MIT, Jun. 2000, Cambridge, MA, pp. 1-123.
Robinson, D., Series elastic actuator development for a biomimetic walking robot, Proceedings of IEEE/ASME International Conference on Advanced Intelligent Mechatronics, Sep. 1999, pp. 561-568.
Rosen, J., et al., A myosignal-based powered exoskeleton system, IEEE Transactions on Systems, Man, and Cybernetics—Part A: Systems and Humans, vol. 31, No. 3, May 2001, pp. 210-222.
Ruina, A., et al., A collisional model of the energetic cost of support work qualitatively explains leg sequencing in walking and galloping, pseudo-elastic leg behavior in running and the walk-to-run transition, Journal of Theoretical Biology, vol. 237, Issue 2, Jun. 2005, pp. 170-192.
Rybak et al., Modelling spinal circuitry involved in locomotor pattern generation: insights from the effects of afferent stimulation. J Physiol. Dec. 1, 2006;577(Pt 2):641-58. Epub Sep. 28, 2006.
Rybak, I., et al., Modelling spinal circuitry involved in locomotor pattern generation: insights from deletions during fictive locomotion, J Physiol, vol. 577 (Pt 2), Dec. 2001, 617-639.
Sanderson, D., et al., Lower extremity kinematic and kinetic adaptations in unilateral below-knee amputees during walking, Gait and Posture, vol. 6, No. 2, Oct. 1997, pp. 126-136.
Sanger, T., Human arm movements described by a low-dimensional superposition of principal component, Journal of NeuroScience, vol. 20, No. 3, Feb. 2000, pp. 1066-1072.
Saranli, U., RHex: A simple and highly mobile hexapod robot, Int. Jour. Rob. Res., vol. 20, No. 7, Jul. 2001, pp. 616-631.
Sarrigeorgidis K. and Kyriakopoulos K., Motion control of the N.T. U.A. robotic snamek on a planar surface, Proc. of the 1998 IEEE International Conference on Robotics and Automation, May 1998, pp. 2977-2982.
Schaal, S. and Atkeson, C., Constructive incremental learning from only local information, Neural Computation, vol. 10, No. 8, Nov. 1998, pp. 2047-2084.
Schaal, S., Is imitation learning the route to humanoid robots? Trends in Cognitive Sciences, vol. 3, Jun. 1999, pp. 233-242.
Scott, S. and Winter, D., Biomechanical model of the human foot: kinematics and kinetics during the stance phase of walking, J. Biomech., vol. 26, No. 9, Sep. 1993, 1091-1104.
Sekine et al., Classification of waist-acceleration signals in a continuous walking record, Medical Engineering & Physics, vol. 22, 2000, pp. 285-291.
Sentis, L. and O. Khatib, Task-Oriented Control of Humanoid Robots Through Prioritization, IEEE-RAS/RSJ International Conference on Humanoid Robots, Nov. 2004, Santa Monica, CA, pp. 1-16.
Seyfarth, A., Swing-leg retraction: a simple control model for stable running, J. Exp. Biol., vol. 206, Aug. 2003, pp. 2547-2555.
Seyfarth, A., et al., A movement criterion for running, J. of Biomech., vol. 35, May 2002, pp. 649-655.
Seyfarth, A., et al., Stable operation of an elastic three-segmented leg, Biol.Cybern., vol. 84, 2001, pp. 365-382.
Sin et al., Significance of non-level walking on transtibial prosthesis fitting with particular reference to the effects of anterior-posterior alignment, Journal of Rehabilitation Research and Development, vol. 38, No. 1, Jan./Feb. 2001, p. 1-6.
Sinkjaer, T., et al., Major role for sensory feedback in soleus EMG activity in the stance phase of walking in man, J Physiol, vol. 523, No. 3, Mar. 2000, 817-827.
Skinner, H. and Effeney D., Gait analysis in amputees, Am J Phys Med, vol. 64, Apr. 1985, pp. 82-89.
Smidt et al., An Automated Accelerometry System for Gait Analysis, J. Biomechanics, vol. 10, 1977, pp. 367-375.
Srinivasan, M., Energetics of legged locomotion: Why is total metabolic cost proportional to the cost of stance work, Proc. on ISB XXth Congress and the American Society of Biomechanics Annual Meeting, Jul. 2003, Cleveland, OH, pp. 829.
Stepien, J., et al., Activity Levels Among Lower-Limb Amputees: Self-Report Versus Step Activity Monitor, Arch. Phys. Med. Rehabil., vol. 88, No. 7, Jul. 2007, pp. 896-900.
Sugano et al., Force Control of the Robot Finger Joint equipped with Mechanical Compliance Adjuster, Proc. of the 1992 IEEE/RSJ Int. Conf. on Intell. Robots & Sys., Jul. 1992, pp. 2005-2013.

(56) References Cited

OTHER PUBLICATIONS

Sugihara, T., et al., Realtime Humanoid Motion Generation through ZMP Manipulation based on Inverted Pendulum Control, Proceedings of the 2002 IEEE International Conference on Robotics and Automation, May 2002, Washington, DC, pp. 1404-1409.

Sup, F., Design and Control of a Powered Transfemoral Prosthesis, The International Journal of Robotics Research, vol. 27, No. 2, Feb. 2008, pp. 263-273.

Taga, G., A model of the neuro-musculo-skeletal system for human locomotion, Biol. Cybern., vol. 73, No. 2, Jul. 1995, pp. 97-111.

Takayuki Biped Locomotion using Multiple Link Virtual Inverted Pendulum Model, Publication of Electronics Information and Systems Society, vol. 120, No. 2, Feb. 2000, 8 pages.

Thoroughman, K. and R. Shadmehr, Learning of action through adaptive combination of motor primitives, Nature, vol. 407, Oct. 2000, pp. 742-747.

Tomovic R. et al., A Finite State Approach to the Synthesis of Bioengineering Control Systems, IEEE Transations on Human Factors in Electronics, vol. 7, No. 2, Jun. 1966, pp. 65-69.

Tong et al., Virtual artificial sensor technique for functional electricial stimulation, Medical Engineering & Physics, vol. 20, 1998, pp. 458-468.

Tong, et al., A Practical Gait Analysis System Using Gyroscopes, Medical Engineering & Physics, vol. 21, Mar. 1999, pp. 87-94.

Turker, K., Electromyography: some methodological problems and issues, Physical Therapy, vol. 73, No. 10, Oct. 1993, pp. 698-710.

van den Bogert, A., Exotendons for assistance of human locomotion, Biomedical Engineering Online, Oct. 2003, pp. 1-8.

van den Bogert, et al. A Method for Inverse Dynamic Analysis Using Accelerometry, Journal Biomechanics, vol. 29, No. 7, 1996, pp. 949-954.

van der Kooij et al., A multisensory integration model of human stance control, Biological Cybernetics, 1999, pp. 299-308.

Veltink P., et al., The Feasibility of Posture and Movement Detection by Accelerometry, D-7803-1377-I/93, IEEE, Oct. 1993, pp. 1230-1231.

Veltink, Dection of Static and Dynamic Activities Using Uniaxial Accelerometers, IEEE. Transactions on Biomedical Engineering, vol. 4. No. 4, Dec. 1996, pp. 375-385.

Vukobratovic M. and Juricic, D., Contributions to the synthesis of biped gait, IEEE Transactions on Biomedical Engineering, vol. BME-16, No. 1, Jan. 1969, pp. 1-6.

Vukobratovic M. and Stepanenko J., Mathematical models of general anthropomorphic systems, Mathematical Biosciences, vol. 17, Aug. 1973, pp. 191-242.

Walsh, C., Biomimetic Design of an Under-Actuated Leg Exoskeleton for Load-Carrying Augmentation, Master's Thesis, MIT, Feb. 2006, pp. 1-94.

Waters, RL., Energy cost of walking amputees: the influence of level of amputation, J Bone Joint Surg., vol. 58, No. 1, Jan. 1976, pp. 42-46.

Wilkenfeld, A. J., Biologically inspired auto adaptive control of a knee prosthesis, Ph.D. Thesis, Massachusetts Institute of Technology, Oct. 23, 2000, pp. 1-107.

Wilkenfeld, A., An Auto-Adaptive External Knee Prosthesis, Artificial Intelligence Laboratory, MIT, Sep. 2000, Cambridge, MA, pp. 1-3.

Willemsen A., et al., Automatic Stance-Swing Phase Detection from Accelerometer Data for Peroneal Nerve Stimulation, IEEE Transactions on Human Factors in Electronics, vol. 37, No. 12, Dec. 1990, pp. 1201-1208.

Willemsen A., et al., Real-Time Gait Assessment Utilizing a New Way of Accelerometry, Journal of Biomechanics, vol. 23, No. 8, 1990, pp. 859-863.

Williams, B., Mode Estimation of Model-based Programs: Monitoring Systems with Complex Behavior, Proceedings of the International Joint Conference on Artificial Intelligence, Aug. 2001, Seattle, WA, pp. 1-7.

Williamson, M., Series Elastic Actuators, Artificial Intelligence Laboratory, MIT, Jan. 1995, Cambridge, MA, pp. 1-74, 74 pages.

Winter, D, and Robertson D., Joint torque and energy patterns in normal gait, Biol. Cybem., vol. 29, May 1978, pp. 137-142.

Winter, D. A, Energy generation and absorption at the ankle and knee during fast, natural, and slow cadences, Clinical Orthopedics and Related Research, vol. 175, May 1983, pp. 147-154.

Winter, D. and Sienko S., Biomechanics of below-knee amputee gait, Journal of Biomechanics, vol. 21, No. 5, Aug. 1988, pp. 361-367.

Wisse, M., Essentails of Dynamic Walking, Analysis and Design of two-legged robots, Phd Thesis, Technical University of Delft, 2004, pp. 1-195, 195 pages.

Woodward et al., Skeletal Accelerations measured during different Exercises, Proceedings of the Institution of Mechanical Engineers, Part H: Journal of Engineering in Medicine, vol. 207, Jun. 1993, pp. 79-85.

Wu, The Study of Kinematic Transients in Locomotion Using the Integrated Kinematic Sensor, IEEE Transactions on Rehabilitation Engineering, vol. 4, No. 3, Sep. 1996, p. 193-200.

Yakovenko, S., et al., Contribution of stretch reflexes to locomotor control: a modeling study, Biol Cybern, vol. 90, No. 2, Jan. 2004, pp. 146-155.

Yun X., Dynamic state feedback control of constrained robot manipulators, Proc. of the 27th conference on Decision and Control, Dec. 1988, pp. 622-626.

Zlatnik, D , et al., Finite-state control of a trans-femoral prosthesis, IEEE Trans. on Control System Technology, vol. 10, No. 3, May 2002, pp. 408-420.

| | WALKING STATE | | | | |
|---|---|---|---|---|---|
| PHASE | 1. CONTROLLED PLANTAR FLEXION 102 | 2. CONTROLLED DORSIFLEXION 106 | 3. POWERED PLANTAR FLEXION 110 | 4. EARLY SWING 114 | 5. LATE SWING 118 |
| % OF CYCLE | STANCE 60% | | | SWING 40% | |
| INITIATING EVENT | FOOT-STRIKE | FOOT-FLAT | MAXIMUM DORSIFLEXION | TOE-OFF | VERTICAL ANKLE VELOCITY IS APPROXIMATELY ZERO |
| FUNCTION | IMPEDANCE (SPRING-DOMINATED) | TORQUE SOURCE + NONLINEAR IMPEDANCE | TORQUE SOURCE + IMPEDANCE | POSITION CONTROL | LINEAR SPRING |

FIG. 1A

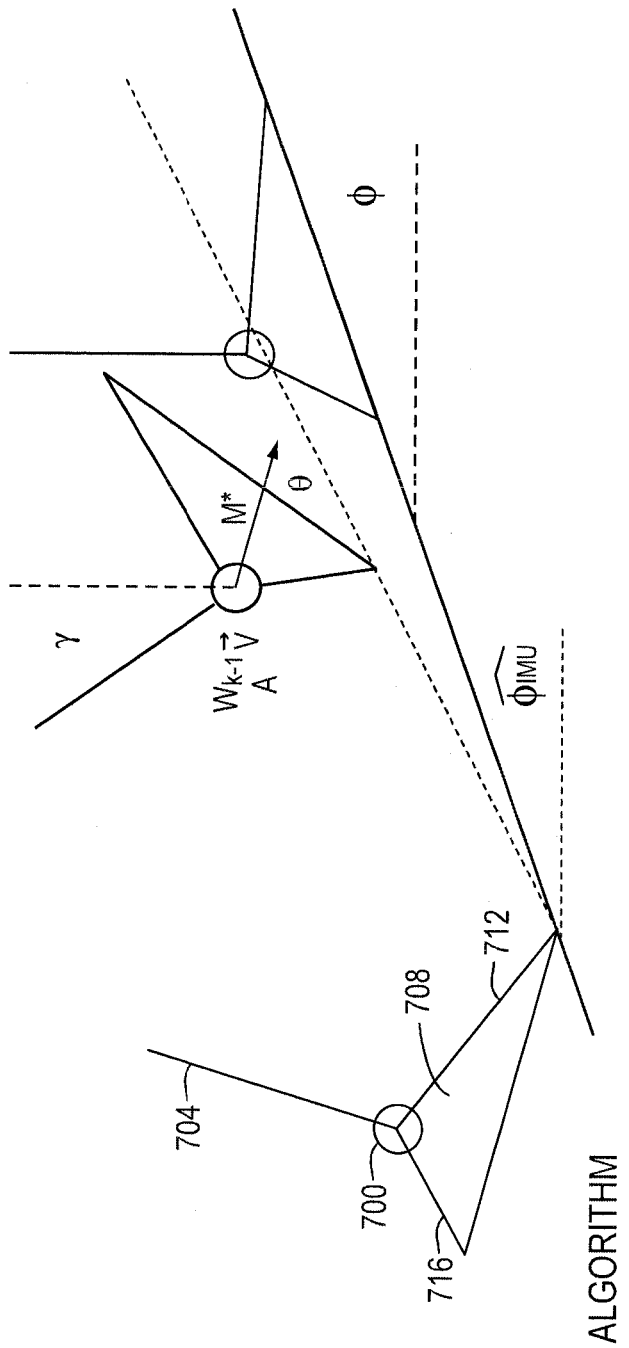

ALGORITHM

1. WAIT UNTIL $^{W_{k-1}}\vec{V}_A < 0$.
2. ESTIMATE f FROM THE 6 DOF IMU STATE VECTOR RELATIVE TO 'TOE OFF'.
3. KEEP THE ANKLE ANGLE AT θ* UNTIL HEEL OR TOE STRIKE (IDENTIFIED BY SERIES SPRING TORQUE DISTURBANCE OR OTHER) WHERE θ* OPTIMIZES A COST CRITERION BASED UPON THE FORCE OF IMPACT ($f_{\parallel} = M^*V_{\parallel}\omega_N$) AND THE FORCE OF TOUCHDOWN ($f_{\perp} = M^*V_{\perp}^2/r/(\gamma+\theta-\phi)$) WHERE r IS THE DISTANCE BETWEEN THE ANKLE PIVOT AND EITHER THE HEEL OR TOE.
4. CALCULATE THE OPTIMAL COMPLEX IMPEDANCE, $\underline{K}^*(s)$, NECESSARY TO ACHIEVE THE HEEL/TOE DOWN TIMING CONSTRAINTS.
5. APPLY STANCE PHASE IMPEDANCE CONTROL AFTER HEEL/TOE STRIKE.

FIG. 7A

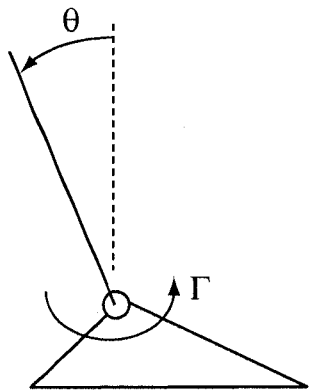

MECHANICAL IMPEDANCE RELATION $\Gamma = -(k(\theta - \theta_0) + b\dot{\theta} + j\ddot{\theta})$

FIG. 10D

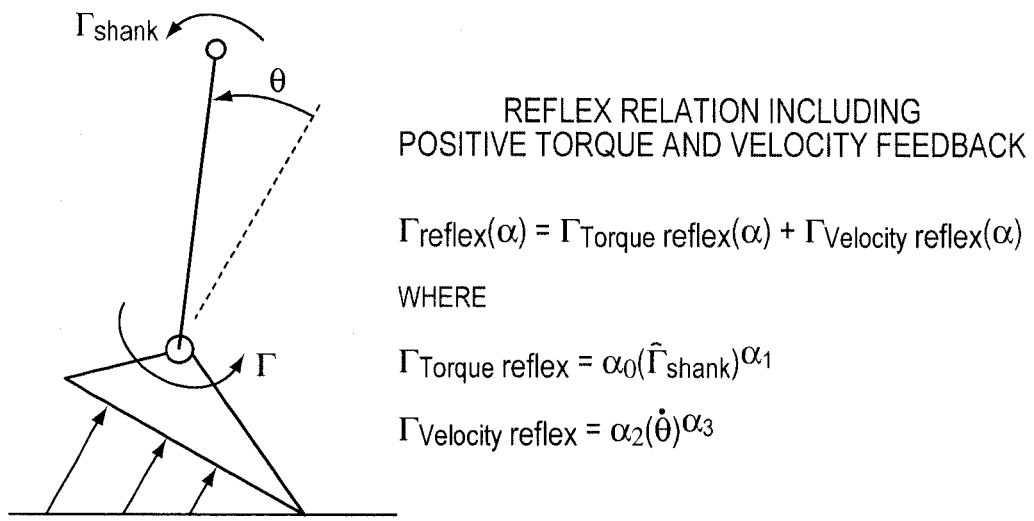

REFLEX RELATION INCLUDING
POSITIVE TORQUE AND VELOCITY FEEDBACK $\Gamma_{reflex}(\alpha) = \Gamma_{Torque\ reflex}(\alpha) + \Gamma_{Velocity\ reflex}(\alpha)$

WHERE $\Gamma_{Torque\ reflex} = \alpha_0(\tilde{\Gamma}_{shank})^{\alpha_1}$ $\Gamma_{Velocity\ reflex} = \alpha_2(\dot{\theta})^{\alpha_3}$

FIG. 10E

A TERRAIN-ADAPTIVE ROBOTIC ANKLE PROSTHESIS
SENSOR PROCESSING AND CONTROL SEQUENCE OPTIMIZES ANKLE POSITION,
IMPEDANCE AND REFLEX FOR ANY AMBULATION TASK CONTEXT "ON-THE-FLY"

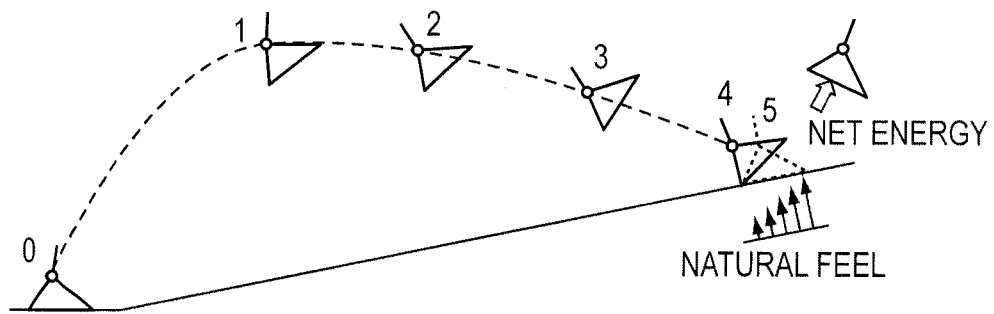

KEY

0: ANKLE POSITION DURING THE LAST STANCE PHASE
0-1: CALCULATE ANKLE TRAJECTORY VIA NUMERICAL INTEGRATION
 OF THE IMU RATE AND ACCELERATION
1-2: DETERMINE THE AMBULATION TASK TYPE (LEVEL-GROUND,
 RAMP, STAIR, ETC.) VIA INTELLIGENT MODELING
3-4: APPLY OPTIMAL "PRE-STRIKE" ANKLE POSITION AND IMPEDANCE
 VIA BIOMIMETIC MODELING
4-5: APPLY OPTIMAL IMPEDANCE TO ELIMINATE FOOT SLAP
5-6: APPLY OPTIMAL IMPEDANCE AND REFLEX TO ACHIEVE BIOMIMETIC
 OPTIMIZATION OF NET WORK AND NATURAL FEEL

FIG. 14A

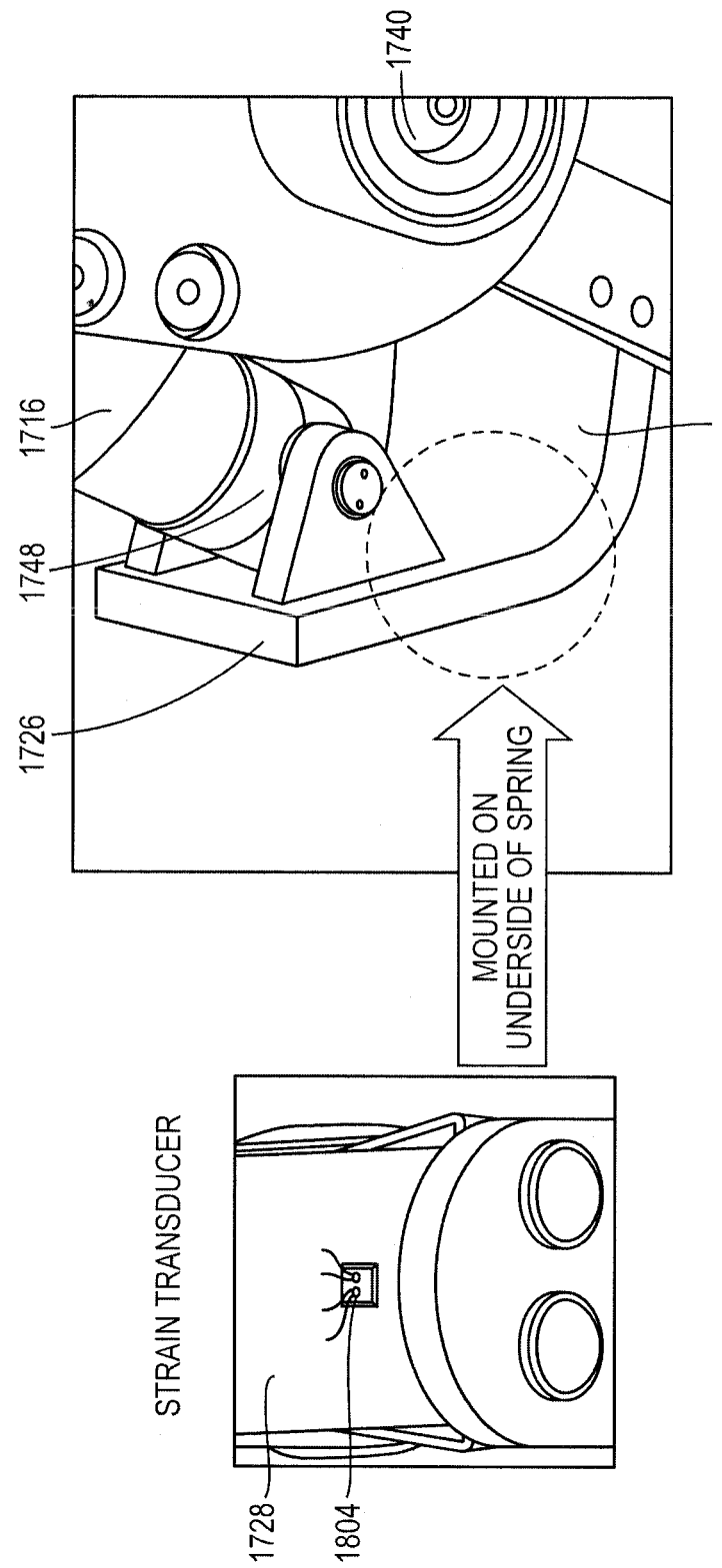

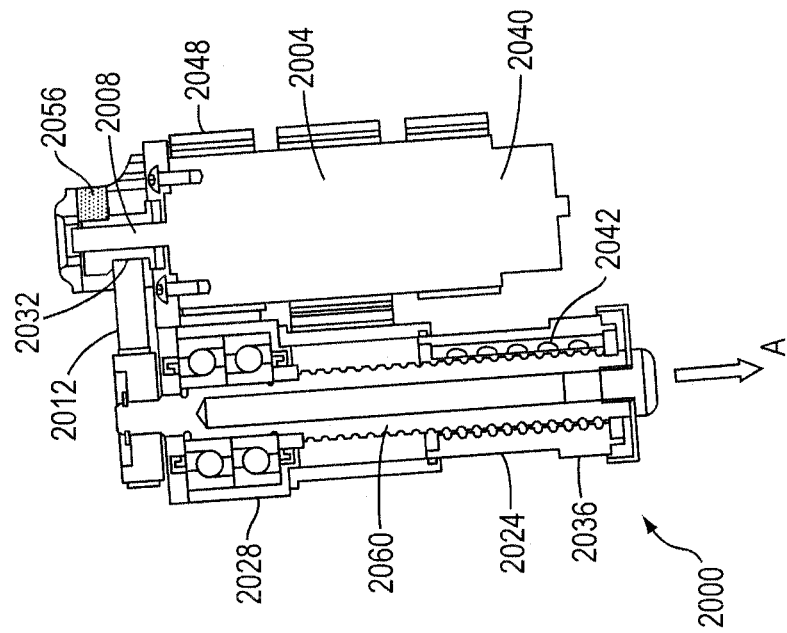
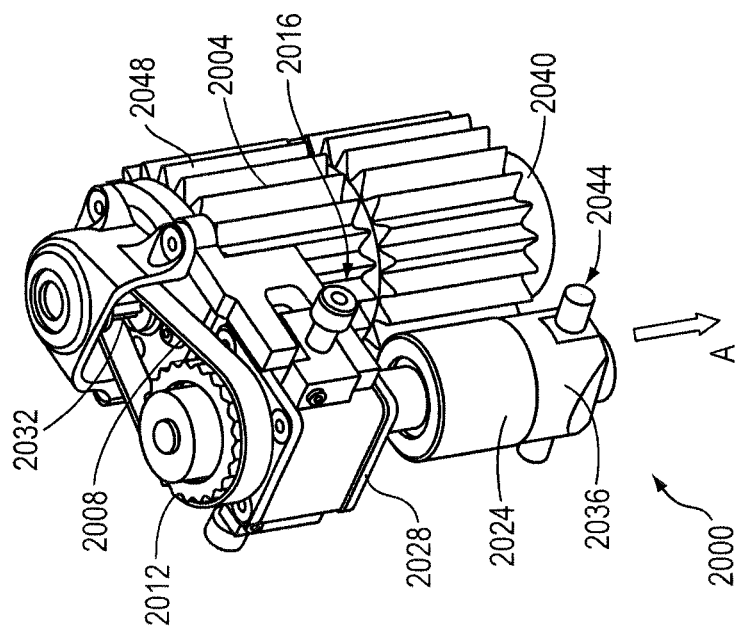
FIG. 20A
FIG. 20B

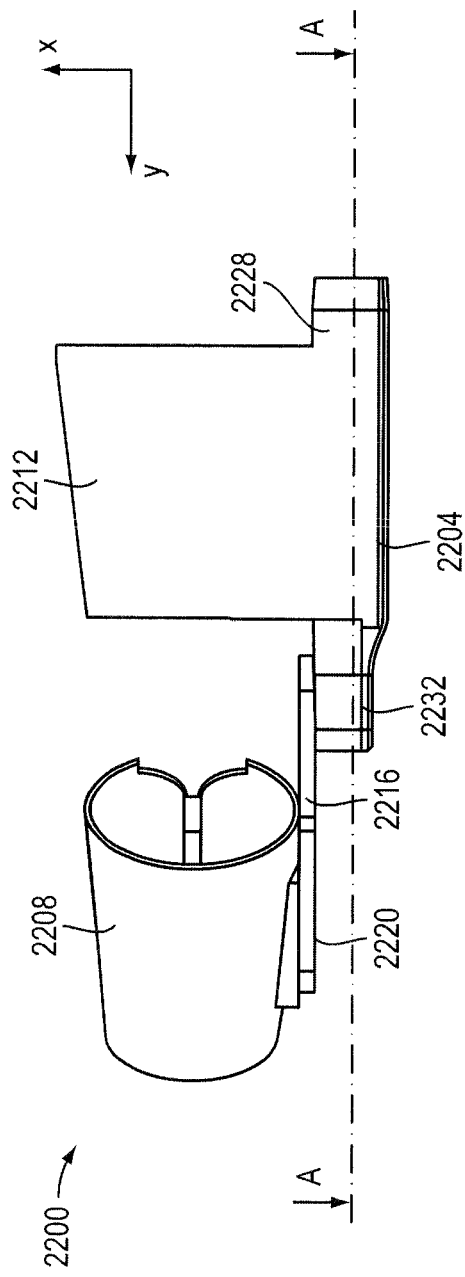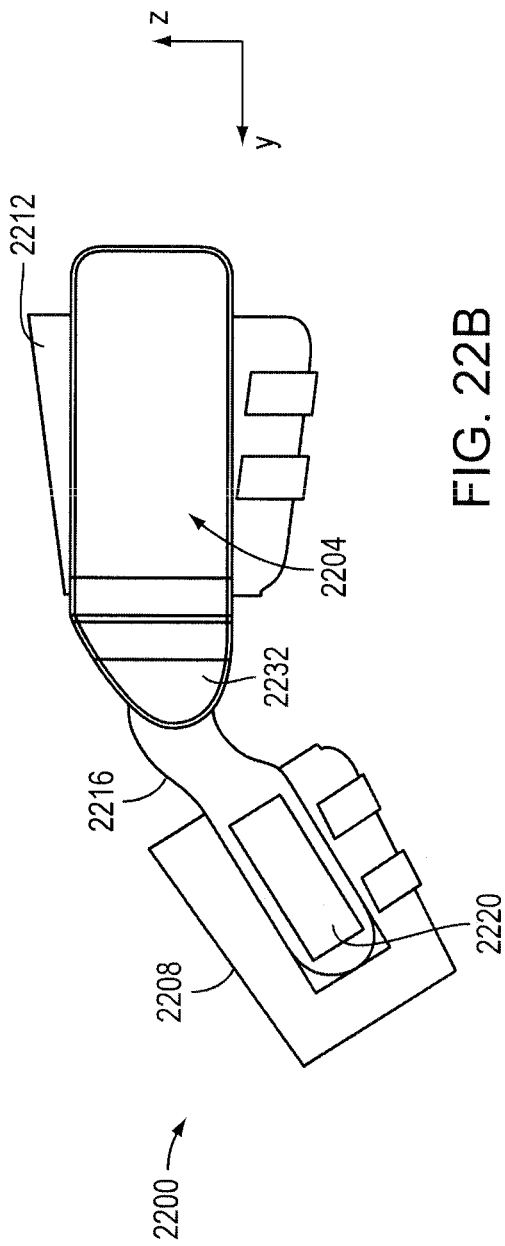

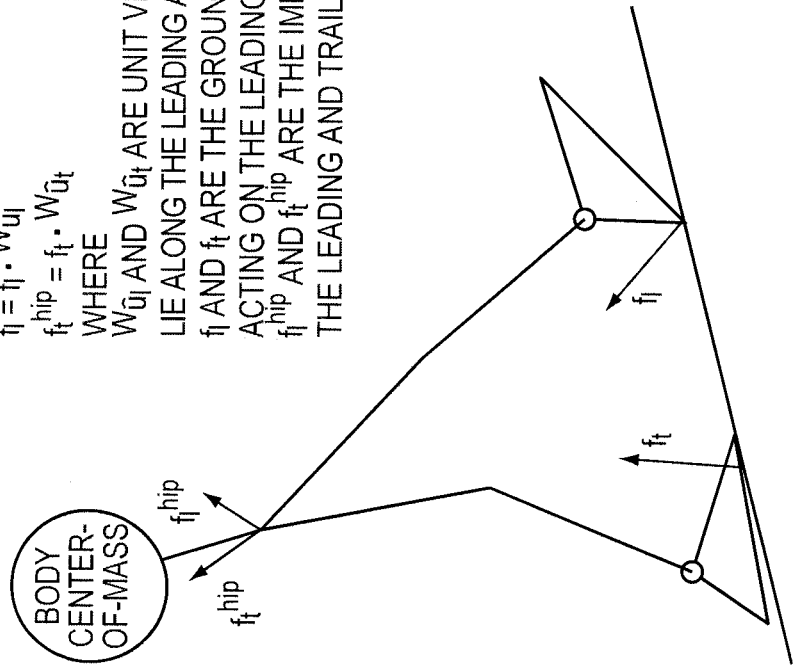

FIG. 25B $f_l = f_l \cdot {}^W\hat{u}_l$
$f_t^{hip} = f_t \cdot {}^W\hat{u}_t$
WHERE
${}^W\hat{u}_l$ AND ${}^W\hat{u}_t$ ARE UNIT VECTORS IN WORLD COORDINATES THAT LIE ALONG THE LEADING AND TRAILING THIGH BONES RESPECTIVELY.
$f_l$ AND $f_t$ ARE THE GROUND REACTION FORCES ACTING ON THE LEADING AND TRAILING FEET RESPECTIVELY.
$f_l^{hip}$ AND $f_t^{hip}$ ARE THE IMPACT FORCES ON THE LEADING AND TRAILING HIP JOINTS RESPECTIVELY.

ically a continuation of U.S. patent application Ser. No. 12/552,036 filed on Sep. 1, 2009, which claims# HYBRID TERRAIN-ADAPTIVE LOWER-EXTREMITY SYSTEMS

RELATED APPLICATIONS

This application is a continuation of U.S. patent application Ser. No. 12/552,036 filed on Sep. 1, 2009, which claims priority to U.S. Provisional Patent Application Ser. No. 61/094,125, filed on Sep. 4, 2008, Ser. No. 61/161,999, filed on Mar. 20, 2009 and Ser. No. 61/231,754, filed on Aug. 6, 2009, the entire contents of each application are hereby incorporated by reference in their entirety.

TECHNICAL FIELD

This invention relates generally to lower-extremity prosthetic, orthotic and exoskeleton apparatus, components thereof, and methods for controlling the same.

BACKGROUND

Over 100,000 people in the United States lose their feet through amputation every year. Many hundreds of thousands suffer this debilitating loss world-wide. Additionally, there are 700,000 individuals that survive a stroke each year in the United States often causing a variety of lower limb pathologies that constrain ambulation. Until recently, lower-extremity prosthetic and orthotic systems have employed predominantly passive or low-power mechanisms incapable of delivering the non-conservative positive work on each stride that the body needs to achieve an economical walking motion even on flat terrain—let alone on uneven surfaces such as stairs and steps.

It is helpful to understand the normal biomechanics associated with a gait cycle of a subject to appreciate the requirements of lower-extremity prosthetic, orthotic and exoskeleton apparatus. Specifically, the function of human ankle under sagittal plane rotation is described below for different locomotor conditions.

The mechanical characteristics of conventional passive ankle/foot prostheses ("AFPs") like the Ossur Flex-Foot® remain essentially constant throughout the life of the device. U.S. Patent Published Application No. US 2006/0249315 ("the '315 application") represented a significant advance over those conventional AFPs. The '315 application, the entire contents of which are hereby incorporated by reference in its entirety, recognized that performance can be improved by dividing the walking cycle into five phases, and by optimizing the mechanical characteristics of the device independently for each of those five phases.

FIG. 1A. is a schematic illustration of the different phases of a subject's gait cycle over level ground. The gait cycle is typically defined as beginning with the heel strike of one foot and ending at the next heel strike of the same foot. The gait cycle is broken down into two phases: the stance phase (about 60% of the gait cycle) and the subsequent swing phase (about 40% of the gait cycle). The swing phase represents the portion of the gait cycle when the foot is off the ground. The stance phase begins at heel-strike when the heel touches the floor and ends at toe-off when the same foot rises from the ground surface. The stance phase is separated into three sub-phases: Controlled Plantarflexion (CP), Controlled Dorsiflexion (CD), and Powered Plantarflexion (PP).

CP begins at heel-strike illustrated at 102 and ends at foot-flat at 106. CP describes the process by which the heel and forefoot initially make contact with the ground. Researchers have shown that that CP ankle joint behavior is consistent with a linear spring response where joint torque is proportional to the displacement of the joint in relation to an equilibrium position of the joint position. The spring behavior is, however, variable; joint stiffness is continuously modulated by the body from step to step within the three sub-phases of stance and late swing state.

After the CP period, the CD phase continues until the ankle reaches a state of maximum dorsiflexion and begins powered plantarflexion PP as illustrated at 110. Ankle torque versus position during the CD period is described as a nonlinear spring where stiffness increases with increasing ankle position. The ankle stores the elastic energy during CD which is necessary to propel the body upwards and forwards during the PP phase.

The PP phase begins after CD and ends at the instant of toe-off illustrated at 114. During PP, the ankle applies torque in accordance with a reflex response that catapults the body upward and forward. The catapult energy is then released along with the spring energy stored during the CD phase to achieve the high plantarflexion power during late stance. This catapult behavior is necessary because the work generated during PP is more than the negative work absorbed during the CP and CD phases for moderate to fast walking speeds. The foot is lifted off the ground during the swing phase, from toe-off at 114 until the next heel strike at 118.

Because the kinematic and kinetic patterns at the ankle during stair ascent/descent are different from that of level-ground walking, a separate description of the ankle-foot biomechanics is presented in FIGS. 1B and 1C. FIG. 1B shows the human ankle biomechanics during stair ascent. The first phase of stair ascent is called Controlled Dorsiflexion 1 (CD 1), which begins with foot strike in a dorsiflexed position seen at 130 and continues to dorsiflex until the heel contacts the step surface at 132. In this phase, the ankle can be modeled as a linear spring. The second phase is Powered Plantar flexion 1 (PP 1), which begins at the instant of foot flat (when the ankle reaches its maximum dorsiflexion at 132) and ends when dorsiflexion begins once again at 134. The human ankle behaves as a torque actuator to provide extra energy to support the body weight.

The third phase is Controlled Dorsiflexion 2 (CD 2), in which the ankle dorsiflexes until heel-off at 136. For the CD 2 phase, the ankle can be modeled as a linear spring. The fourth and final phase is Powered Plantar flexion 2 (PP 2) which begins at heel-off 136 and continues as the foot pushes off the step, acting as a torque actuator in parallel with the CD 2 spring to propel the body upwards and forwards, and ends when the toe leaves the surface at 138 to begin the swing phase that ends at 140.

FIG. 1C shows the human ankle-foot biomechanics for stair descent. The stance phase of stair descent is divided into three sub-phases: Controlled Dorsiflexion 1 (CD 1), Controlled Dorsiflexion 2 (CD2), and Powered Plantar flexion (PP). CD1 begins at foot strike illustrated at 150 and ends at foot-flat 152. In this phase, the human ankle can be modeled as a variable damper. In CD2, the ankle continues to dorsiflex forward until it reaches a maximum dorsiflexion posture seen at 154. Here the ankle acts as a linear spring, storing energy throughout CD2. During PP, which begins at 154, the ankle plantar flexes until the foot lifts from the step at 156. In this final PP phase, the ankle releases stored CD2 energy, propelling the body upwards and forwards. After toe-off at 156, the foot is positioned controlled through the swing phase until the next foot strike at 158.

For stair ascent depicted in FIG. 1B, the human ankle-foot can be effectively modeled using a combination of an actuator and a variable stiffness mechanism. However, for stair descent, depicted in FIG. 1C, a variable damper needs also to be included for modeling the ankle-foot complex; the power absorbed by the human ankle is much greater during stair descent than the power released during stair ascent. Hence, it is reasonable to model the ankle as a combination of a variable-damper and spring for stair descent.

Conventional passive prosthetic, orthotic and exoskeleton apparatus do not adequately reproduce the biomechanics of a gait cycle. They are not biomimetic because they do not actively modulate impedance and do not apply the reflexive torque response; neither on level ground, ascending or descending stairs or ramps, or changing terrain conditions. A need therefore exists for improved lower-extremity prosthetic, orthotic and exoskeleton apparatus, components thereof, and methods for controlling the same.

SUMMARY

The inventors have recognized that during the course of an ordinary day, a person's lower limbs are used to perform and adapt to many different activities in addition to ordinary walking, such as ascending and descending stairs, and walking on inclined ramps. The ankle-foot components require the most power and must exhibit the most terrain-adaptive behavior because these are in the most direct contact with the underlying terrain. The inventors have further recognized that the performance of AFPs can be dramatically improved by dynamically optimizing the mechanical characteristics of the device in different ways and dynamically controlling the device in different ways for each of those activities.

For example, when a person is walking on flat ground, it is better to control the angle of the foot so that the heel is lower than the toe when the foot touches down on the ground. However, when a person is ascending stairs, it is better to control the angle of the foot so that the toe is lower than the heel when the foot touches down on the next step.

This application describes various embodiments of AFPs that perform appropriately in each of these different situations by detecting the terrain that is being traversed, and automatically adapting to the detected terrain. In some embodiments, the ability to control the AFP for each of these situations builds upon five basic capabilities: (1) determining the activity being performed; (2) dynamically controlling the characteristics of the AFP based on the activity that is being performed; (3) dynamically driving the AFP based on the activity that is being performed; (4) determining terrain texture irregularities (e.g., how sticky is the terrain, how slippery is the terrain, is the terrain coarse or smooth, does the terrain have any obstructions, such as rocks) and responding to these with appropriate fraction control and (5) a mechanical design of the AFP that can respond to the dynamic control and dynamic drive.

The inventors have determined that an exemplary way to figure out what activity is being performed is to track the trajectory of a spot (typically at the virtual center of rotation of the ankle joint) on the lower leg (or shank) between the ankle joint and knee joint. FIG. 6A shows the shank trajectories that correspond to five different activities, with additional ramp trajectories to distinguish between steep and shallow ramps. The system can use this information to figure out what activity is being performed by mapping the tracked trajectory onto a set of activities.

By looking at the trajectory of the lower leg (shank) it is possible to distinguish between flat terrain, ascending or descending stairs, or ascending or descending ramps. For example, when the system recognizes a trajectory it would switch into an appropriate mode, and dynamically control (drive) the AFP as previously established for the mode. Where a trajectory does not fall neatly within a classification, the AFP controller would optimize the response to minimize an objective function in a stochastic control sense or would apply fuzzy logic or adhoc controls based upon the likelihood the terrain falls into a classification.

One suitable way to track the trajectory of the shank is by mounting an inertial measurement unit (IMU) at the forward face at the top of the lower leg member (shank), and processing the signals that are output by the IMU. A suitable way to distinguish the various trajectories is to monitor the velocity of the ankle joint angle of attack. These topics are described in greater detail below.

In addition to dynamically optimizing the mechanical characteristics and dynamically controlling the device in different ways for each of the different activities, the inventors have recognized that the performance of the device can be further improved by fine-tuning the characteristics and control of the AFP based on various parameters.

For example, when a person is walking slowly (e.g., at a rate of less than 0.9 meters per second), performance can be improved by increasing the impedance of the ankle joint with respect to the impedance used for normal walking. Or when a person is walking quickly (e.g., at a rate of 1.7 meters per second), performance can be improved by decreasing the impedance of the ankle joint with to the impedance used for normal walking.

In addition, when the controller determines that the ankle joint is not responding as we would expect it to when traversing normal terrain, the controller can take into account (and modify the output of the controller) that there may be features, texture or irregularities in the terrain (e.g., how sticky is the terrain, how slippery is the terrain, is the terrain coarse or smooth, does the terrain have any obstructions, such as rocks).

Each of the five capabilities identified above (i.e., figuring out what activity is being performed; figuring out whether there are features, texture or irregularities of the terrain; dynamically controlling the characteristics of the AFP; dynamically driving the AFP; and the mechanical design of the AFP) is described in greater detail below.

The inventions described herein relate generally to lower-extremity prosthetic, orthotic and exoskeleton apparatus. Typical use cases for various embodiments of the invention include, for example, metabolic augmentation, permanent assistance for subjects with a permanent limb pathology, or rehabilitation for wearers with temporary limb pathology.

An example of a use case for an exemplary lower-extremity prosthetic apparatus (e.g., apparatus 1700 of FIGS. 17A-17G) involves the prosthetic replacing the ambulation function of a lower limb of the wearer. An example of a use case for an exemplary lower-extremity orthotic apparatus (e.g., apparatus 2200 of FIGS. 22A-22C—orthosis) features a method for determining a level of assistance desired for apparatus to apply to a wearer wearing the apparatus. In some embodiments, the level of assistance performed by the orthosis is reduced based on impedance and torque contribution of the wearer to the apparatus. In some embodiments, the impedance and torque contribution of the wearer is determined based on a dynamic, biomechanical model of the wearer and apparatus and measurements of the wearer during operation of the apparatus. In some embodiments, the measurements of the wearer include at least one of rotation and acceleration of at least one joint of the apparatus. In some embodiments, the axial force and moment applied to the lower leg member of the apparatus is determined based on sensor measurements made using a structural member (pyramid) coupled to the lower leg member of the apparatus. The pyramid is an instrumented structure that is a component of a prosthesis and which couples to the limb socket of the wearer. In one embodiment, the pyramid (structural element) measurements are used by a controller to determine axial force and moment applied to the lower leg member. In some embodiments, the apparatus includes at least one of an ankle joint that connects a foot member of the apparatus to a lower leg member of the apparatus, or a knee joint for connecting a thigh member of the apparatus to the lower leg member of the apparatus, or a hip joint for connecting a torso member of the apparatus to the thigh member of the apparatus.

The invention, in one aspect, features a low noise linear actuator that includes a rotary motor comprising a motor shaft output. The actuator also includes a screw transmission assembly that includes a threaded shaft coupled to the motor shaft output, the threaded shaft comprising a hollowed out portion containing an acoustic damping material and a nut assembly. The screw transmission assembly translates rotational motion of the motor shaft output to a linear motion of the nut assembly.

In some embodiments, the screw transmission assembly is a ball-screw transmission assembly and the nut assembly is a ball-nut assembly, wherein the ball-nut assembly also includes a plurality of ball bearings and a plurality of ball tracks for holding the ball bearings and for recirculating the ball bearings in the ball bearing assembly. In some embodiments, the actuator includes a pulley coupling the motor shaft output to the threaded shaft via a plurality of belts connected in parallel between the pulley and the threaded shaft of the ball-screw transmission assembly. In some embodiments, the linear actuator includes a sensor that validates belt integrity during operation. The pulley can be welded to the motor shaft output.

In some embodiments, the actuator includes a radial and thrust bearing coupling the plurality of belts to the threaded shaft to support loads applied by tension in the belts and the threaded shaft. In some embodiments, the ball-screw transmission assembly includes at least one seal for protecting the ball-screw transmission assembly from contaminants. In some embodiments, the linear actuator is a component of a lower extremity prosthesis orthosis, or exoskeleton. In some embodiments, the linear actuator includes a transmission that employs traction wheels that couple the motor shaft output to the threaded shaft of the ball-screw transmission assembly. The screw transmission assembly can be a lead screw transmission assembly.

The invention, in another aspect, features a linear actuator that includes a rotary motor comprising a motor shaft output and a motor drive transmission assembly coupled to the motor shaft output to translate rotational motion of the motor shaft output to a linear motion at an output of the motor drive transmission. The linear actuator also includes at least one elastic element with bi-directional stiffness connected in series with the motor drive transmission assembly to store energy in tension and compression.

In some embodiments, the linear actuator includes a strain sensor coupled to the at least one elastic element for measuring strains in the at least one elastic element. The at least one elastic element can be a series or parallel elastic element coupled to the output of the motor drive transmission assembly. In some embodiments, the linear actuator includes a controller for receiving measured strain signals for performing closed loop control of the linear actuator thrust force. The at least one elastic element can be a substantially flat spring divided along a longitudinal axis of the spring minimizing out-of-plane moment applied by the spring to the output of the motor drive transmission assembly. The at least one elastic element can be a series elastic strain element coupled to the output of the motor drive transmission assembly, and the linear actuator can also include a sensor that measures motor position or position of the output of the motor drive transmission assembly, and at least one sensor that measures the output of the series elastic element, and signal processing electronics that estimates thrust force of the linear actuator for closed loop control of the linear actuator thrust force.

The invention, in another aspect, features a lower-extremity prosthesis, orthosis or exoskeleton apparatus that includes a foot member, a lower leg member and an ankle joint for connecting the foot member to the lower leg member. The apparatus also includes a first actuator for applying torque to the ankle joint to rotate the foot member with respect to the lower leg member. The apparatus also includes at least one passive elastic members that is a non-compliant stop connected in parallel with the actuator between the lower leg member and the foot member, wherein the non-compliant stop stores little or no energy during dorsiflexion and limits further rotation of the ankle beyond a predefined angle during powered plantar flexion.

In some embodiments, the apparatus includes an angle adjustment mechanism for setting a pre-specified angle of the foot member relative to the lower leg member at which the non-compliant stop limits further rotation. The angle adjustment mechanism can include a screw adjustable component for setting the pre-specified angle. The angle adjustment mechanism can include an actuator for setting the pre-specified angle. In some embodiments, the actuator adjusts the pre-specified angle based on a property of the underlying terrain. In some embodiments, the property of the underlying terrain is selected from the group consisting of ascending ramp, descending ramp, ascending stair, descending stair, level surface. In some embodiments, a controller associated with the apparatus determines the property of the underlying terrain on an intra-cycle basis.

The invention, in another aspect, features a lower-extremity prosthesis that includes a foot member, a lower leg member, and an ankle joint for connecting the foot member to the lower leg member. The prosthesis includes a first actuator for applying torque to the ankle joint to rotate the foot member with respect to the lower leg member. The prosthesis also includes a structural element coupled to the lower leg member and comprising an interface for coupling to a limb socket member of a wearer, wherein the structural element comprises a plurality of strain gages for determining the torque applied to the lower leg member by the actuator and the axial force applied to the lower leg member.

In some embodiments, the prosthesis includes an inertial measurement unit for determining an inertial pose of the lower leg member. The inertial measurement unit can be coupled to the lower leg member. The inertial measurement unit can be coupled to the foot member. In some embodiments, the prosthesis includes a controller for calculating ground reaction force and zero moment pivot coordinates imparted by an underlying surface onto the foot member based on an inertial pose of the lower leg member, the torque applied to the lower leg member by the actuator, axial force applied to the lower leg member, and an angle between the foot member and lower leg member. In some embodiments, the controller is coupled to the actuator and is configured to control the actuator for modulating at least one of an impedance, position or torque of the prosthesis throughout a walking cycle of the prosthesis based on the inertial pose trajectory of the lower leg member, the angle between the foot member and lower leg member, and the ground reaction force and the zero moment pivot coordinates. In some embodiments, the controller is coupled to the actuator and is configured to control the actuator for modulating an impedance of the prosthesis as the wearer stands up from a seated position or sits down from a standing position based on the inertial pose of the lower leg member, the angle between the foot member and lower leg member, and the ground reaction force and the zero moment pivot coordinates.

The invention, in another aspect, features a lower-extremity prosthesis that includes a foot member, a lower leg member and an ankle joint for connecting the foot member to the lower leg member. The prosthesis includes a first actuator for applying torque to the ankle joint to rotate the foot member with respect to the lower leg member. The prosthesis also includes a structural element coupled to the lower leg member and includes an interface for coupling to a limb socket member of a wearer. The prosthesis also includes a displacement sensing apparatus for measuring deflection of the structural element for determining the torque applied to the lower leg member by the actuator and the axial force applied to the lower leg member.

In some embodiments, the displacement sensing apparatus includes a plurality of sensors and the displacement sensing apparatus measures the distance between each sensor and a surface of the structural element. The sensors can be selected from the group consisting of contact displacement sensors, non-contact displacement sensors, inductive coils, optical sensors, force-sensitive resistors, piezoelectric sensors, or strain sensors. In some embodiments, the plurality of sensors include a plurality of inductive coils on a circuit board. In some embodiments, changes in inductance of the inductive coils relative to a surface of the structural element are used to determine the displacement of the structural element.

In some embodiments, the prosthesis includes an inertial measurement unit for determining an inertial pose of the lower leg member. In some embodiments, the inertial measurement unit is coupled to the lower leg member. In some embodiments, the inertial measurement unit is coupled to the foot member.

In some embodiments, the prosthesis includes a controller for calculating ground reaction force and zero moment pivot coordinates imparted by an underlying surface onto the foot member based on an inertial pose trajectory of the lower leg member, the torque applied to the lower leg member by the actuator, axial force applied to the lower leg member, and an angle between the foot member and lower leg member. In some embodiments, the controller is coupled to the actuator and is configured to control the actuator for modulating an impedance of the prosthesis throughout a walking cycle of the prosthesis based on the inertial pose trajectory of the lower leg member, the angle between the foot member and lower leg member, and the ground reaction force and the zero moment pivot coordinates. In some embodiments, the controller is coupled to the actuator and is configured to control the actuator for modulating an impedance of the prosthesis as the wearer stands up from a seated position or sits down from a standing position based on the inertial pose trajectory of the lower leg member, the angle between the foot member and lower leg member, and the ground reaction force.

The invention, in another aspect, features an active knee orthosis that includes a thigh member attachable to a thigh of a wearer, a lower leg member attachable to a lower leg of the wearer and a knee joint for connecting the thigh member to the lower leg member. The orthosis also includes a rotary motor comprising a motor shaft output. The orthosis also includes a motor drive transmission assembly coupled to the motor shaft output to translate rotational motion of the motor shaft output to a linear motion at an output of the motor drive transmission assembly. The orthosis also includes a drive transmission assembly coupled to the output of the motor drive transmission, an output of the drive transmission assembly is coupled to the lower leg member for applying torque to the knee joint to rotate the lower leg member with respect to the thigh member. The orthosis also includes a motor angle sensor for determining motor position. The orthosis also includes a controller for controlling the rotary motor for modulating impedance, position or torque of the of the orthosis throughout a walking cycle of the orthosis based on the motor position.

In some embodiments, the orthosis includes an angle sensor for determining position of a drum of the drive transmission assembly relative to the output of the motor drive transmission assembly and wherein the controller controls the rotary motor for modulating impedance, position or torque based on the position. In some embodiments, the orthosis includes a displacement sensor for measuring displacement of a series spring in the motor drive transmission assembly for determining force on the series spring and wherein the controller controls the rotary motor for modulating impedance, position or torque based on the force on the spring.

In some embodiments, the orthosis includes an inertial measurement unit coupled to the thigh member or lower leg member for determining an inertial pose trajectory of the lower leg member and wherein the controller controls the rotary motor for modulating impedance, position or torque based on the inertial pose. In some embodiments, the orthosis includes a sensor for determining the force applied to at least one of the lower leg member and thigh member by the drive transmission assembly and wherein the controller controls the rotary motor for modulating impedance, position or torque based on the torque applied to the lower leg member.

In some embodiments, the orthosis includes an angle sensor for determining an angle between the thigh member and lower leg member and wherein the controller controls the rotary motor for modulating impedance, position or torque based on the angle between the thigh member and lower leg member. In some embodiments, the orthosis includes the drive transmission is selected from the group consisting of a belt drive transmission, band drive transmission and cable drive transmission. In some embodiments, the orthosis includes a cuff coupled to the thigh member for attaching the orthosis to the thigh of the wearer. In some embodiments, the orthosis includes a cuff coupled to the lower leg member for attaching the orthosis to the lower leg of the wearer. In some embodiments, the orthosis augments lower extremity functions of the wearer. In some embodiments, the orthosis treats a lower extremity pathology of the wearer. In some embodiments, the controller is configured to vary assistance provided by the orthosis to the wearer during rehabilitation of a lower extremity pathology of the wearer.

The invention, in another aspect, features an active knee orthosis that includes a thigh member attachable to a thigh of a wearer, a lower leg member attachable to a lower leg of the wearer, and a knee joint for connecting the thigh member to the lower leg member. The orthosis also includes a rotary motor comprising a motor shaft output. The orthosis also includes a screw transmission assembly coupled to the motor shaft output for converting the rotary motion of the motor shaft output to a linear motion output by the screw transmission assembly. The orthosis also includes a belt, band or cable drive transmission assembly coupled to the output of the screw transmission assembly to convert a linear motion output by the screw transmission assembly to a rotary motion for applying torque to the knee joint to rotate the lower leg member with respect to the thigh member. The orthosis also includes a motor angle sensor for determining motor position. The orthosis also includes a controller for controlling the rotary motor for modulating impedance, position or torque of the of the orthosis throughout a walking cycle of the orthosis based on the motor position.

In some embodiments, the orthosis includes a displacement sensor for measuring displacement of a series spring in the belt, band or cable drive transmission for determining force on the series spring and wherein the controller controls the rotary motor for modulating impedance, position or torque based on the force on the spring. In some embodiments, the orthosis includes an inertial measurement unit coupled to the thigh member or lower leg member for determining, within a gait cycle, an inertial pose trajectory of the lower leg member and wherein the controller controls the rotary motor for modulating impedance, position or torque based on the inertial pose trajectory during the gait cycle.

In some embodiments, the orthosis includes a torque sensor for determining torque applied to the lower leg member by the belt, band or cable drive transmission and wherein the controller controls the rotary motor for modulating impedance, position or torque within the gait cycle based on the force applied to the lower leg member. In some embodiments, the orthosis includes an angle sensor for determining an angle between the thigh member and lower leg member and wherein the controller controls the rotary motor for modulating impedance, position or torque based on the angle between the thigh member and lower leg member within the gait cycle. In some embodiments, the belt, band or cable drive transmission comprises at least two drive transmissions, wherein a first of the at least two drive transmissions is configured to convert a first direction of a linear motion output by the screw transmission assembly to a first rotary motion for applying torque to the knee joint to rotate the lower leg member with respect to the thigh member and wherein a second of the at least two transmissions is configured to convert an opposite direction of a linear motion output by the screw transmission assembly to an opposite rotary motion for applying torque to the knee joint to rotate the lower leg member with respect to the thigh member.

The invention, in another aspect, features a method for determining ground reaction forces and zero moment pivot imparted by an underlying surface onto a foot member of a lower extremity prosthetic apparatus worn by a wearer. The apparatus includes a foot member, a lower leg member, and an ankle joint for connecting the foot member to the lower leg member and a first actuator for applying torque to the ankle joint to rotate the foot member with respect to the lower leg member. The method involves calculating the ground reaction force based on an inertial pose of the lower leg member, the torque applied to the lower leg member by the actuator, axial force applied to the lower leg member, and an angle between the foot member and lower leg member.

In some embodiments, the method includes controlling the actuator for modulating an impedance of the apparatus throughout a walking cycle of the apparatus based on the inertial pose of the lower leg member, the angle between the foot member and lower leg member, the ground reaction force and the zero moment pivot. In some embodiments, the method includes controlling the actuator for modulating an impedance of the apparatus as the wearer stands up from a seated position or sits down from a standing position based on the inertial pose of the lower leg member, the angle between the foot member and lower leg member, the ground reaction force and the zero moment pivot. In some embodiments, the inertial pose of the lower leg member is determined based on an output of an inertial measurement unit coupled to the lower leg member.

The invention, in another aspect, features a method for minimizing the effect of accelerometer and rate gyro errors on a lower extremity prosthesis or orthosis that includes a foot member, a lower leg member, and an ankle joint for connecting the foot member to the lower leg member. The method includes determining at least one velocity error contribution for an accelerometer signal output by an accelerometer coupled to the lower leg member when the ankle joint is substantially stationary during a walking cycle of the prosthesis or orthosis. The method also includes determining at least one velocity error contribution for an inertial pose misalignment signal output by an inertial measurement unit coupled to the lower leg member when the ankle joint is substantially stationary during a walking cycle of the prosthesis or orthosis.

In some embodiments, the inertial pose misalignment signal output by the inertial measurement unit is a rate gyro signal output by a rate gyro. In some embodiments, the method includes computing the pose of the lower leg member using signals output by the accelerometer and rate gyro. In some embodiments, the method includes correcting the computed pose of the lower leg member using the velocity error contributions. In some embodiments, the method includes the velocity error contributions are determined during a portion of a controlled dorsiflexion state of the walking cycle.

In some embodiments, the method includes determining velocity error contributions for an accelerometer signal and rate gyro signal output by an accelerometer and rate gyro coupled to a thigh member of the prosthesis or orthosis when the ankle joint is substantially stationary during a walking cycle of the prosthesis or orthosis. In some embodiments, the method includes determining velocity error contributions for an accelerometer signal and rate gyro signal output by an accelerometer and rate gyro coupled to a thigh member of the prosthesis or orthosis when a computed position on a foot member is substantially stationary.

In some embodiments, the method includes measuring the angle of the lower leg member relative to the thigh member. In some embodiments, the method includes determining velocity error contributions for an accelerometer signal and rate gyro signal output by an accelerometer and rate gyro coupled to a wearer's torso when the ankle joint is substantially stationary during a walking cycle of the prosthesis or orthosis. In some embodiments, the method includes measuring the angle of the thigh member relative to the wearer's torso.

The invention, in another aspect, features a method for controlling balance of a wearer wearing a lower extremity prosthetic, orthotic or exoskeleton apparatus that includes a foot member, a lower leg member, and an ankle joint for connecting the foot member to the lower leg member. The method includes adjusting at least one of the ankle joint impedance, position or torque of the apparatus based on inertial pose of the lower leg member, angle between the lower leg member and the foot member and ground reaction force and the zero moment pivot imparted by an underlying surface onto the foot member.

In some embodiments, the actuator coupled to the lower leg member and foot member, adjusts the at least one of the ankle joint impedance, position or torque to control the balance of the wearer. In some embodiments, a controller calculates the ground reaction force and the zero moment pivot based on an inertial pose of the lower leg member, the torque applied to the lower leg member by the actuator, axial force applied to the lower leg member, and an angle between the foot member and lower leg member, the controller is coupled to the actuator to control the actuator to adjust the at least one of the ankle joint impedance, position or torque to control the balance of the wearer. In some embodiments, the controller calculates the inertial pose of the lower leg based on a signal output from an inertial measurement unit coupled to the lower leg. In some embodiments, a controller coupled to the actuator controls the actuator to adjust the at least one of the ankle joint impedance, position or torque to control the balance of the wearer. In some embodiments, the controller receives signals from one or more sensors to calculate the inertial pose of the lower leg member, angle between the lower leg member and the foot member and the ground reaction force imparted by the underlying surface onto the foot member.

In some embodiments, the method includes controlling balance of the wearer as the wearer transitions from a sitting position to a standing position based on an increase in the ground reaction force. In some embodiments, the method includes driving the lower leg member forward with an actuator coupled to the lower leg based on the increase in the ground reaction force.

The invention, in another aspect, features a method for determining a change in traction between a foot member of an orthotic, prosthetic or exoskeleton apparatus and an underlying surface, the apparatus includes g a foot member, a lower leg member, an ankle joint for connecting the foot member to the lower leg member and a first actuator for applying torque to the ankle joint to rotate the foot member with respect to the lower leg member. The method includes calculating ground reaction force and the zero moment pivot imparted by an underlying surface onto the foot member based on an inertial pose of the lower leg member, the torque applied to the lower leg member by the actuator, axial force applied to the lower leg member, and an angle between the foot member and lower leg member. The method also includes calculating velocity of the foot member zero moment pivot based on the inertial pose of the lower leg member, the torque applied to the lower leg member by the actuator, the axial force applied to the lower leg member, and the angle between the foot member and lower leg member.

In some embodiments, wherein it is determined that the foot member is slipping or sinking if the velocity of the foot member zero moment pivot decreases during a portion of a gait cycle of the wearer between a foot-flat and toe-off condition. In some embodiments, the method includes reducing torque applied to the lower leg member in response to determining that the foot member is slipping or sinking. In some embodiments, the method includes reducing the torque applied to the lower leg member by an attenuation factor. The attenuation factor can be a predetermined attenuation factor. The attenuation factor can be determined based on the zero moment pivot velocity. In some embodiments, the method includes reducing the torque applied to the lower leg member in response to the zero moment pivot velocity being below a predetermined threshold.

The invention, in another aspect, features a linear actuator having intrinsic safety features. The actuator includes a rotary motor that includes a motor shaft output, wherein a pulley is coupled to the motor shaft output. The actuator also includes a ball-screw transmission assembly that includes a threaded shaft coupled to the motor shaft output by a plurality of belts connected in parallel between the pulley and the threaded shaft of the ball-screw transmission assembly. The ball-screw transmission assembly translates rotational motion of the motor shaft output to a linear motion of a portion of the ball-screw transmission assembly.

In some embodiments, the linear actuator includes an angular encoder for determining angular alignment between the rotary motor's rotor and stator. In some embodiments, the linear actuator includes a controller configured to short three leads of the rotary motor to ground in response to a belt breakage sensor detecting a failure of one or more of the plurality of belts. In some embodiments, shorting the three leads results in the rotary motor functioning as a stiff, viscous brake. In some embodiments, the temperature of the motor is determined by applying a fixed current to a winding of the motor winding and measuring a corresponding voltage in the winding to determine the winding resistance. In some embodiments, the temperature of the motor is determined by applying a fixed voltage to a winding of the motor winding and measuring a corresponding current in the winding to determine the winding resistance. In some embodiments, the linear actuator includes a motor temperature sensor for measuring the temperature of the motor. In some embodiments, the linear actuator includes a controller coupled to the motor for controlling torque output by the actuator based on temperature of the motor.

The invention, in another aspect, features a method for controlling throughout a gait cycle at least one of joint position, impedance or torque of a lower-extremity prosthetic, orthotic, or exoskeleton apparatus worn by a wearer based on an inertially-referenced, intra-cycle trajectory of a portion of the apparatus over underlying terrain.

In some embodiments, the apparatus includes a foot member, a lower leg member, and an ankle joint for connecting the foot member to the lower leg member. In some embodiments, the apparatus includes a lower leg member, a thigh member, and a knee joint for connecting the lower leg member to the thigh member. In some embodiments, the apparatus includes a thigh member, a torso member, and a hip joint for connecting the thigh member to the torso member. In some embodiments, the apparatus includes a thigh member and a knee joint for connecting the lower leg member to the thigh member. In some embodiments, the apparatus includes a torso member, and a hip joint for connecting the thigh member to the torso member. In some embodiments, the apparatus includes a torso member, and a hip joint for connecting the thigh member to the torso member.

In some embodiments, the trajectory is determined for the lower leg member. In some embodiments, the trajectory is determined based on an inertial pose of the lower leg member and an angle between the foot member and lower leg member. In some embodiments, the spring equilibrium position of the foot member is adjusted to a foot-flat position relative to the underlying terrain to coincide with the lower leg member being in a vertical position relative to a world coordinate system. In some embodiments, the impedance of the apparatus is adjusted to minimize a cost function based on projected force imparted on the lower leg member during a period of time between when a foot member strikes the underlying terrain and when the foot member is positioned in a flat-foot position relative to the underlying terrain. In some embodiments, the impedance of the apparatus is adjusted to minimize a cost function based on projected force imparted on the lower leg member during a period of time between when a foot member strikes the underlying terrain to when the foot member is positioned in a flat-foot position relative to the underlying terrain.

In some embodiments, the impedance of the apparatus is adjusted to minimize foot slap of the foot member. In some embodiments, the position of the foot member is adjusted to a toe down position relative to the underlying terrain based on the trajectory of the lower leg member. In some embodiments, the trajectory of the lower leg member is representative of trajectory when the underlying surface comprises one or more stairs. In some embodiments, the at least one of joint position, impedance or torque is updated continuously during the gait cycle by a processor in communication with at least one sensor and one actuator of the apparatus. In some embodiments, the impedance and torque on the joint of the apparatus is controlled during a late stance phase of the gait cycle based on at least one of ambulation speed, terrain context or terrain texture. In some embodiments, the impedance and torque are controlled to achieve a desired amount of work.

In some embodiments, the impedance of the apparatus is adjusted during a controlled plantar flexion phase of the gait cycle to minimize forefoot collisions with the underlying terrain. In some embodiments, the at least one of joint position, impedance or torque of the apparatus is controlled based on speed of a portion the apparatus.

In some embodiments, the apparatus is a lower-leg apparatus and the portion is a location between a knee joint and ankle joint of the lower-leg apparatus. In some embodiments, throughout the gait cycle, at least two of the joint position, the impedance or the torque are controlled. In some embodiments, the apparatus includes, throughout the gait cycle, the joint position, the impedance and the torque are controlled.

The invention, in another aspect, features a method for reducing, throughout a gait cycle, hip impact force and hip impact force rate of a lower-extremity prosthetic, orthotic, or exoskeleton apparatus worn by a wearer. The method includes generating a cost function based on hip impact force and force rate generated by transmission of foot contact with underlying terrain. The method also includes controlling at least one of position, impedance or torque of at least one joint of the lower-extremity prosthetic, orthotic, or exoskeleton apparatus based on minimizing the cost function wearer to reducing hip impact forces generated during a gait cycle over the underlying terrain.

In some embodiments, the apparatus includes a first foot member, first lower leg member and a first ankle joint for connecting the first foot member to the first lower leg member, and the method also includes adjusting impedance of the first ankle joint and an angle between the first foot member and first lower leg member during a time interval between a foot-strike condition and foot-flat condition of the first foot member of the apparatus. In some embodiments, the impedance of the first ankle joint and the angle between the first foot member and the first lower leg member is adjusted to minimize a cost function based on an estimation of force to be imparted on the first ankle joint between the foot-strike condition and the foot-flat condition of the first foot member of the apparatus. In some embodiments, the foot-strike condition includes the foot member heel first striking the underlying terrain. In some embodiments, the foot-strike condition comprises the foot member toe first striking the underlying terrain.

In some embodiments, the underlying terrain includes at least one ascending or descending stair, and the method also includes constraining the first foot member to achieve a toe first striking of the underlying terrain while minimizing the cost function based on the estimation of force to be imparted on the first ankle joint between the foot-strike condition and the foot-flat condition of the first foot member of the apparatus.

In some embodiments, the apparatus includes a second leg member, a second foot member and a second ankle joint for connecting the second leg member to the second foot member, and the method also includes applying a torque to the second ankle joint at or before time of impact of the first foot member with the underlying terrain. In some embodiments, the method includes controlling at least two of the joint position, the impedance or the torque. In some embodiments, the method includes controlling the joint position, the impedance and the torque.

The invention, in another aspect, features a method for minimizing, throughout a gait cycle, work performed by a lower-extremity prosthetic, orthotic, or exoskeleton apparatus worn by a wearer. The method includes generating a cost function for estimating intra-step transition work performed by a combination of the apparatus and subject on center of mass of the combination during double support. The method also includes controlling at least one of position, impedance or torque of at least one joint of the lower-extremity prosthetic, orthotic, or exoskeleton apparatus based on minimizing the cost function wearer to reducing the work performed by the wearer and apparatus generated during a gait cycle.

In some embodiments, the apparatus includes a first foot member, first lower leg member and a first ankle joint for connecting the first foot member to the first lower leg member, and the method also includes adjusting impedance of the first ankle joint and an angle between the first foot member and first lower leg member during a time interval between a foot-strike condition and foot-flat condition of the first foot member of the apparatus. In some embodiments, the impedance of the first ankle joint and the angle between the first foot member and the first lower leg member is adjusted to minimize a cost function based on an estimation of force to be imparted on the first ankle joint between the foot-strike condition and the foot-flat condition of the first foot member of the apparatus. The foot-strike condition can include the foot member heel first striking underlying terrain. The foot-strike condition can include the foot member toe first striking underlying terrain.

In some embodiments, the terrain underlying the wearer includes at least one ascending or descending stair, and the method also includes constraining the first foot member to achieve a toe first striking of the underlying terrain while minimize the cost function based on the estimation of force to be imparted on the first ankle joint between the foot-strike condition and the foot-flat condition of the first foot member of the apparatus.

In some embodiments, the apparatus includes a second leg member, a second foot member and a second ankle joint for connecting the second leg member to the second foot member, and the method also includes applying a torque to the second ankle joint at or before time of impact of the first foot member with underlying terrain. In some embodiments, the method includes controlling throughout the gait cycle at least two of the joint position, the impedance or the torque. In some embodiments, the method includes controlling throughout the gait cycle the joint position, the impedance and the torque.

The invention, in another aspect, features a method for controlling at least one of joint impedance, position or torque of a lower-extremity prosthetic, orthotic or exoskeleton apparatus worn by a wearer during intra-cycle ambulation. The method also includes determining trajectory of a location between an ankle joint and knee joint of the apparatus in a coordinate system throughout a walking cycle. The method also includes adjusting the articulation of a foot member of the apparatus based on the trajectory.

In some embodiments, the ankle joint connects the foot member to a first end of the lower leg member of the apparatus and the knee joint is connected to an opposite end of the lower leg member. In some embodiments, the apparatus includes the location is the ankle joint.

In some embodiments, the method includes adjusting the articulation of the foot member to a heel down position when the predetermined condition is representative of the presence of level ground, an ascending ramp, or a descending ramp in underlying terrain. In some embodiments, the method includes adjusting the articulation of the foot member to a toe down position when the predetermined condition is indicative of the presence of an ascending stair or a descending stair in underlying terrain. In some embodiments, the foot member is adjusted to a dorsiflexed position relative to a lower leg member of the apparatus when the predetermined condition is representative of the presence of an ascending stair. In some embodiments, the foot member is adjusted to a plantar flexed position relative to a lower leg member of the apparatus when the predetermined condition is representative of the presence of a descending stair.

In some embodiments, the method includes adjusting the articulation of the foot member to a heel down position when the predetermined condition is representative of the presence of level ground, an ascending ramp, or a descending ramp in underlying terrain, and adjusting the articulation of the foot member to a toe down position when the predetermined condition is representative of the presence of an ascending stair or a descending stair in underlying terrain. In some embodiments, the trajectory is determined based on an inertial pose of a lower leg member of the apparatus and an angle between the foot member and lower leg member. In some embodiments, the method includes adjusting the articulation of the foot member of the apparatus to a predetermined orientation when the trajectory satisfies a predetermined condition.

The invention, in another aspect, features an active lower extremity prosthetic, orthotic or exoskeleton apparatus. The apparatus includes a foot member, a lower leg member, and an ankle joint for connecting the foot member to the lower leg member. The apparatus also includes a first actuator for applying torque to the ankle joint to rotate the foot member with respect to the lower leg member and an inertial measurement unit for determining an inertial pose of the lower leg member. The apparatus also includes a torque sensor for determining torque applied to the lower leg member by the actuator. The apparatus also includes a force sensor for determining axial force applied to the lower leg member. The apparatus also includes an angle sensor for determining an angle between the foot member and lower leg member. The apparatus also includes a controller for controlling the actuator for modulating at least one of joint impedance, position or torque of the apparatus throughout a walking cycle of the apparatus based on the inertial pose, torque, axial force and angle.

In some embodiments, the apparatus includes one or more passive elastic members connected between the lower leg member and the foot member for storing energy when the foot member rotates about the ankle joint toward the lower leg member and for releasing energy to apply additional torque to rotate the foot member away from the lower leg member. In some embodiments, the one or more passive elastic members is attached to the apparatus in parallel with the actuator. In some embodiments, the one or more passive elastic members is a unidirectional spring and is not engaged during plantar flexion of the foot member relative to the lower leg member.

In some embodiments, the actuator includes a series elastic actuator. In some embodiments, the series elastic actuator comprises a brushless motor that drives a ball-screw, a carbon-fiber spring in series with an output of the ball-screw, and a strain sensor coupled to the spring. In some embodiments, the inertial measurement unit comprises a three-axis rate gyro and a three-axis accelerometer.

In some embodiments, the apparatus includes a structural element coupled to the lower leg member and which also includes an interface for coupling to a limb socket member of a wearer, wherein the structural element comprises a plurality of strain gages for determining the torque applied to the lower leg member by the actuator and the axial force applied to the lower leg member. In some embodiments, the actuator adjusts stiffness of the apparatus during controlled plantar flexion phase of the walking cycle to minimize forefoot collisions with an underlying surface. In some embodiments, the actuator controls impedance and torque on the ankle joint of the apparatus during a late stance phase of the walking cycle based on at least one of ambulation speed, terrain context or terrain texture. In some embodiments, the actuator modulates impedance of the apparatus based on a ground reaction force and zero moment pivot coordinates imparted by an underlying surface onto the foot member, the inertial pose of the lower leg member, the torque applied to the lower leg member by the actuator, the axial force applied to the lower leg member, and the angle between the foot member and lower leg member.

In some embodiments, the actuator modulates the impedance of the apparatus as the wearer stands up from a seated position or sits down from a standing position based on the inertial pose of the lower leg member, the angle between the foot member and lower leg member, and the ground reaction force and zero moment pivot coordinates.

In some embodiments, the apparatus is used to treat drop foot gait. In some embodiments, the apparatus is used to treat a wearer having anterior muscle weakness, posterior muscle weakness, or a combination thereof.

In some embodiments, the apparatus includes a thigh member, a knee joint for connecting the thigh member to the lower leg member and a second actuator for applying torque to the knee joint to rotate the lower leg member with respect to the thigh member. The apparatus also includes a second inertial measurement unit for determining an inertial pose of the thigh member and a second torque sensor for determining torque applied to the thigh member by the second actuator. The apparatus also includes a second force sensor for determining axial force applied to the thigh member. The apparatus also includes a second angle sensor for determining an angle between the thigh member and lower leg member. The apparatus also includes a controller that controls the first and second actuator for modulating an impedance of the apparatus throughout a walking cycle of the apparatus based on the inertial pose, torque, axial force and angle determined using the first and second devices.

In some embodiments, the apparatus includes a torso member and a hip joint for connecting the torso member to the thigh member. The apparatus also includes a third actuator for applying torque to the hip joint to rotate the thigh member with respect to the torso member. The apparatus also includes a third inertial measurement unit for determining an inertial pose of the torso member and a third torque sensor for determining torque applied to the torso member by the third actuator. The apparatus also includes a third force sensor for determining axial force applied to the torso member and a third angle sensor for determining an angle between the torso member and the thigh member, wherein the controller controls the first, second and third actuator for modulating an impedance of the apparatus throughout a walking cycle of the apparatus based on the inertial pose, torque, axial force and angle determined using the first, second, and third devices.

In some embodiments, the lower leg member is attachable to a leg of the wearer. In some embodiments, the foot member is attachable to a foot of the wearer. In some embodiments, the thigh member is attachable to a thigh of the wearer.

In some embodiments, the controller controls the actuator to modulate at least two of joint impedance, position or torque of the apparatus throughout a walking cycle of the apparatus. In some embodiments, the controller controls the actuator to modulate joint impedance, position and torque of the apparatus throughout a walking cycle of the apparatus.

The invention, in another aspect, features a method for determining a level of assistance desired for a lower-extremity orthotic or exoskeleton apparatus to apply to a wearer wearing the apparatus. The method includes specifying a physical therapy protocol defining a level of assistance performed by the apparatus on the wearer over a period of time and reducing the level of assistance performed by the apparatus on the wearer to assist in rehabilitation of the limb pathology.

In some embodiments, the level of assistance by the apparatus is reduced based on impedance and torque contribution of the wearer to the apparatus. In some embodiments, the apparatus includes the impedance and torque contribution of the wearer is determined based on a biomechanical model of the wearer and apparatus and measurements of the wearer during operation of the apparatus. In some embodiments, the measurements of the wearer include at least one of rotation and acceleration of at least one joint of the apparatus. In some embodiments, the at least one joint of the apparatus includes at least one of a) an ankle joint that connects a foot member of the apparatus to a lower leg member of the apparatus; b) a knee joint for connecting a thigh member of the apparatus to the lower leg member of the apparatus; or c) a hip joint for connecting a torso member of the apparatus to the thigh member of the apparatus.

The invention, in another aspect, features a method for rehabilitation of a wearer with a limb pathology using a lower-extremity orthotic or exoskeleton apparatus worn by a wearer. The method includes estimating impedance and torque contribution of the wearer to at least one joint of the apparatus based on a biomechanical model of the wearer and apparatus and measurements of the wearer during operation of the apparatus and providing a signal to an actuator of the apparatus that commands the actuator to provide additional torque to at least one joint of the apparatus such that a predetermined level of torque is achieved in the apparatus during operation.

In some embodiments, the measurements of the wearer include at least one of rotation and acceleration of at least one joint of the apparatus. In some embodiments, the at least one joint of the apparatus includes at least one of a) an ankle joint that connects a foot member of the apparatus to a lower leg member of the apparatus; b) a knee joint for connecting a thigh member of the apparatus to the lower leg member of the apparatus; or c) a hip joint for connecting a torso member of the apparatus to the thigh member of the apparatus.

The invention, in another aspect, features a method for estimating a condition of underlying terrain while a wearer is traversing the underlying terrain. The method includes determining an inertially-referenced trajectory of points on a lower limb of a wearer and orientation of the lower limb of the wearer traversing underlying terrain and analyzing the inertially-referenced trajectory relative to at least one predetermined trajectory model to estimate an underlying terrain condition.

In some embodiments, the underlying terrain condition is at least one of stair ascent, ramp ascent, level ground, ramp descent, or stair descent. In some embodiments, the method includes determining the inertially-referenced trajectory of the wearer traversing underlying terrain, wherein the underlying terrain includes stair ascent, ramp ascent, level ground, ramp descent, and stair descent. In some embodiments, the determining an inertially-referenced trajectory of a wearer traversing underlying terrain is performed during late swing phase of a gait cycle of the wearer.

In some embodiments, analyzing the inertially-referenced trajectory relative to at least one predetermined trajectory model includes using at least one pattern recognition technique. In some embodiments, the at least one pattern recognition technique is performed using a processor coupled to at least one sensor and one actuator coupled to a lower-extremity prosthetic, orthotic, or exoskeleton apparatus worn by a wearer. In some embodiments, the at least one pattern recognition technique is selected from the group techniques consisting of Bayesian pattern classification, neural nets, fuzzy logic or hierarchical temporal memory.

In some embodiments, the method includes controlling at least one of joint impedance, position or torque of a lower-extremity prosthetic, orthotic, or exoskeleton apparatus worn by a wearer based on the underlying terrain condition estimate.

In some embodiments, the method includes determining a change in traction between a foot member of the apparatus and the underlying surface in which the apparatus includes a foot member, a lower leg member, an ankle joint for connecting the foot member to the lower leg member and a first actuator for applying torque to the ankle joint to rotate the foot member with respect to the lower leg member. The method can include calculating ground reaction force imparted by the underlying surface onto the foot member based on an inertial pose of the lower leg member, the torque applied to the lower leg member by the actuator, axial force applied to the lower leg member, and an angle between the foot member and lower leg member; and calculating velocity of the foot member zero moment pivot based on the inertial pose of the lower leg member, the torque applied to the lower leg member by the actuator, the axial force applied to the lower leg member, and the angle between the foot member and lower leg member.

In some embodiments, it is determined that the foot member is slipping or sinking if at least one component of the velocity of the foot member zero moment pivot decreases during a portion of a gait cycle of the wearer between a foot-flat and toe-off condition. In some embodiments, the method includes reducing torque applied to the lower leg member in response to determining that the foot member is slipping or sinking. In some embodiments, the method includes reducing the torque applied to the lower leg member by an attenuation factor. In some embodiments, the attenuation factor is a predetermined attenuation factor. In some embodiments, the attenuation factor is determined based on the zero moment pivot velocity. In some embodiments, the method includes reducing the torque applied to the lower leg member in response to the zero moment pivot velocity being below a predetermined threshold.

The invention, in another aspect, features a method for discriminating between properties of terrain underlying a lower extremity prosthetic, orthotic, or exoskeleton apparatus worn by a wearer, in which the apparatus includes a foot member, a lower leg member, and an ankle joint for connecting the foot member to the lower leg member. The method includes estimating an inertial velocity vector attack angle of the ankle joint of the apparatus throughout a gait cycle and discriminating between terrain properties based on whether the inertial velocity vector attack angle lies within a predetermined range.

In some embodiments, the method includes adjusting the impedance of the apparatus to minimize a cost function based on projected force imparted on the lower leg member during a period of time between when a heel of the foot member strikes the underlying terrain to when the foot member is positioned in a flat-foot position relative to the underlying terrain. In some embodiments, the method includes controlling at least one of ankle joint impedance, position or torque of the apparatus based on whether the inertial velocity vector attack angle lies within a predetermined range. In some embodiments, the foot member is attachable to a foot of the wearer and the lower leg member is attachable to a leg of the wearer. In some embodiments, the foot member and lower leg member replace the foot and lower leg of the wearer.

The invention, in another aspect, features a method for controlling at least one of joint impedance, position or torque of a lower extremity prosthetic, orthotic, or exoskeleton apparatus worn by a wearer, wherein the apparatus includes a foot member, a lower leg member, and an ankle joint for connecting the foot member to the lower leg member. In some embodiments, the method includes estimating an inertial velocity vector attack angle of the ankle joint of the apparatus throughout a gait cycle and adjusting the position of a foot member of the apparatus to a toe down position when the velocity vector attack angle lies within a predefined range.

In some embodiments, the method includes adjusting the position of the foot member to a heel down position when the inertial velocity vector attack angle is outside of the predetermined range. In some embodiments, the method includes adjusting the impedance of the apparatus to minimize a cost function based on projected force imparted on the lower leg member during a period of time between when a heel of the foot member strikes the underlying terrain to when the foot member is positioned in a flat-foot position relative to the underlying terrain. In some embodiments, the foot member is attachable to a foot of the wearer and the lower leg member is attachable to a leg of the wearer. In some embodiments, the foot member and lower leg member replace the foot and lower leg of the wearer.

The invention, in another aspect, features a method of operating a lower-extremity prosthesis or orthosis apparatus, in which the apparatus includes a foot member and an ankle joint. The method includes tracking a trajectory of a portion of the apparatus and determining whether the tracked trajectory corresponds to stairs. The method also includes optimizing operation of the apparatus for locomotion on stairs, in situations where the tracked trajectory corresponds to stairs. The method also includes determining whether the tracked trajectory corresponds to non-stair terrain. The method also includes optimizing operation of the apparatus for locomotion on non-stair terrain, in situations where the tracked trajectory corresponds to non-stair terrain.

In some embodiments, determining whether the tracked trajectory corresponds to stairs comprises determining that a velocity vector attack angle $\Psi$ of the ankle joint in a late swing phase is below a threshold value, and the step of determining whether the tracked trajectory corresponds to non-stair terrain comprises determining that a velocity vector attack angle $\Psi$ of the ankle joint is above the threshold value. In some embodiments, optimizing operation of the apparatus for walking on stairs comprises adjusting a position of the foot member to a toe down position prior to foot strike, and wherein the step of optimizing operation of the apparatus for locomotion on non-stair terrain comprises adjusting a position of the foot member to a heel down position prior to foot strike.

In some embodiments, optimizing operation of the apparatus for walking on non-stair terrain includes dynamically controlling an impedance of the ankle joint during different phases of a single step, dynamically controlling a position of the ankle joint during different phases of a single step, and dynamically controlling torque of the ankle joint during different phases of a single step.

In some embodiments, optimizing operation of the apparatus for walking on stairs includes dynamically controlling an impedance of the ankle joint during different phases of a single step, dynamically controlling a position of the ankle joint during different phases of a single step, and dynamically controlling torque of the ankle joint during different phases of a single step.

In some embodiments, the method includes determining whether the tracked trajectory corresponds to an ascending ramp; optimizing operation of the apparatus for ascending a ramp in situations where the tracked trajectory corresponds to an ascending ramp; determining whether the tracked trajectory corresponds to a descending ramp; and optimizing operation of the apparatus for descending a ramp in situations where the tracked trajectory corresponds to a descending ramp.

In some embodiments, optimizing operation of the apparatus for ascending a ramp includes dynamically controlling an impedance of the ankle joint during different phases of a single step, dynamically controlling a position of the ankle joint during different phases of a single step, and dynamically controlling torque of the ankle joint during different phases of a single step, and the step of optimizing operation of the apparatus for descending a ramp includes dynamically controlling an impedance of the ankle joint during different phases of a single step, dynamically controlling a position of the ankle joint during different phases of a single step, and dynamically controlling torque of the ankle joint during different phases of a single step.

In some embodiments, determining whether the tracked trajectory corresponds to stairs includes determining that a velocity vector attack angle $\Psi$ of the ankle joint in a late swing phase is below a threshold value, and the step of determining whether the tracked trajectory corresponds to non-stair terrain comprises determining that a velocity vector attack angle $\Psi$ of the ankle joint is above the threshold value; wherein the step of optimizing operation of the apparatus for walking on stairs comprises adjusting a position of the foot member to a toe down position prior to foot strike, and wherein the step of optimizing operation of the apparatus for locomotion on non-stair terrain includes adjusting a position of the foot member to a heel down position prior to foot strike, and wherein the step of optimizing operation of the apparatus for walking on non-stair terrain includes the steps of dynamically controlling an impedance of the ankle joint during different phases of a single step, dynamically controlling a position of the ankle joint during different phases of a single step, and dynamically controlling torque of the ankle joint during different phases of a single step.

The invention, in another aspect, features a lower-extremity prosthesis or orthosis apparatus that includes a foot member, a lower leg member and an ankle joint operatively connected between the foot member and the lower member to permit articulation of the foot member with respect to the lower leg member. The apparatus includes a motor configured to drive the ankle joint and an inertial measurement unit configured to track a trajectory of the lower leg member and generate an output that represents the trajectory. The apparatus also includes a controller that is configured to (a) determine whether the tracked trajectory corresponds to stairs based on the output, (b) optimize operation of the ankle joint for walking on stairs when the tracked trajectory corresponds to stairs, (c) determine whether the tracked trajectory corresponds to non-stair terrain, and (d) optimize operation of the ankle joint for walking on non-stair terrain when the tracked trajectory corresponds to non-stair terrain.

In some embodiments, the controller determines whether the tracked trajectory corresponds to stairs by determining that a velocity vector attack angle $\Psi$ of the ankle joint in a late swing phase is below a threshold value, and wherein the controller determines whether the tracked trajectory corresponds to non-stair terrain by determining that a velocity vector attack angle $\Psi$ of the ankle joint is above the threshold value. In some embodiments, the controller optimizes operation of the ankle joint for walking on stairs by adjusting a position of the foot member to a toe down position prior to foot strike, and wherein the controller optimizes operation of the ankle joint for locomotion on non-stair terrain by adjusting a position of the foot member to a heel down position prior to foot strike.

In some embodiments, the controller optimizes operation of the ankle joint for walking on non-stair terrain by dynamically controlling an impedance of the ankle joint during different phases of a single step, dynamically controlling a position of the ankle joint during different phases of a single step, and dynamically controlling torque of the ankle joint during different phases of a single step. In some embodiments, the controller optimizes operation of the ankle joint for walking on stairs by dynamically controlling an impedance of the ankle joint during different phases of a single step, dynamically controlling a position of the ankle joint during different phases of a single step, and dynamically controlling torque of the ankle joint during different phases of a single step.

In some embodiments, the controller is further configured to (e) determine, based in the output, whether the tracked trajectory corresponds to an ascending ramp, (f) optimize operation of the ankle joint for walking on an ascending ramp when the tracked trajectory corresponds to an ascending ramp, (g) determine whether the tracked trajectory corresponds to a descending ramp, and (h) optimize operation of the ankle joint for walking on a descending ramp when the tracked trajectory corresponds to a descending ramp.

In some embodiments, the controller optimizes operation of the ankle joint for ascending a ramp by dynamically controlling an impedance of the ankle joint during different phases of a single step, dynamically controlling a position of the ankle joint during different phases of a single step, and dynamically controlling torque of the ankle joint during different phases of a single step, and wherein the controller optimizes operation of the ankle joint for descending a ramp by dynamically controlling an impedance of the ankle joint during different phases of a single step, dynamically controlling a position of the ankle joint during different phases of a single step, and dynamically controlling torque of the ankle joint during different phases of a single step.

BRIEF DESCRIPTION OF THE DRAWINGS

The foregoing and other objects, feature and advantages of the invention, as well as the invention itself, will be more fully understood from the following illustrative description, when read together with the accompanying drawings which are not necessarily to scale.

FIG. 1A is a schematic illustration of the different phases of a wearer's gait cycle over level ground.

FIG. 7A illustrates a method for positioning an ankle joint prior to foot strike, according to an illustrative embodiment of the invention.

FIG. 10D is a schematic illustration of the mechanical impedance relation that governs the impedance control performed in FIG. 10A.

FIG. 10E is a schematic illustration of the impedance and reflex relation that governs the impedance and reflex control performed in FIG. 10B.

FIG. 14A illustrates a method for employing step-by-step terrain adaptation, according to an illustrative embodiment of the invention.

FIGS. 18A-18D are illustrations of a passive series-elastic member, according to an illustrative embodiment of the invention.

FIG. 20A is an illustration of a perspective view of a linear actuator capable of being used in various lower-extremity prosthetic, orthotic, and exoskeleton apparatus, according to an illustrative embodiment of the invention.

FIG. 20B is an illustration of a cross-sectional view of the linear actuator of FIG. 20A.

FIG. 22A is a schematic illustration of a top view of a lower-extremity orthotic or exoskeleton apparatus (wearable robotic knee brace), according to an illustrative embodiment of the invention.

FIG. 22B is a side view of the apparatus of FIG. 22A.

FIG. 25B illustrates a definition of hip impact forces.

DETAILED DESCRIPTION

Determining Activity Being Performed

Inertial Pose and Trajectory Estimation

Figure 1B:
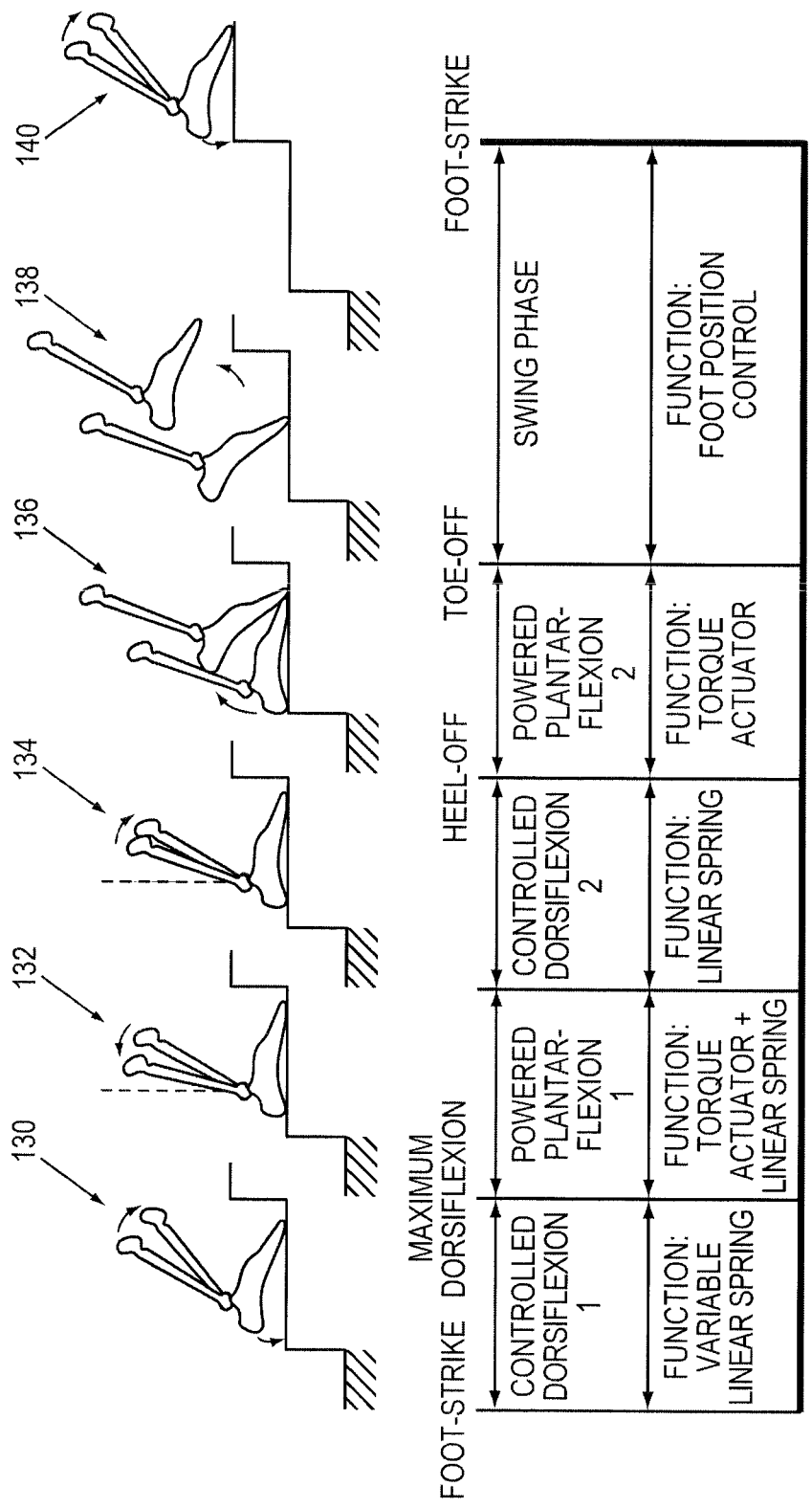
FIG. 1B is a schematic illustration of the different phases of a wearer's gait cycle ascending stairs.
Figure 1C:
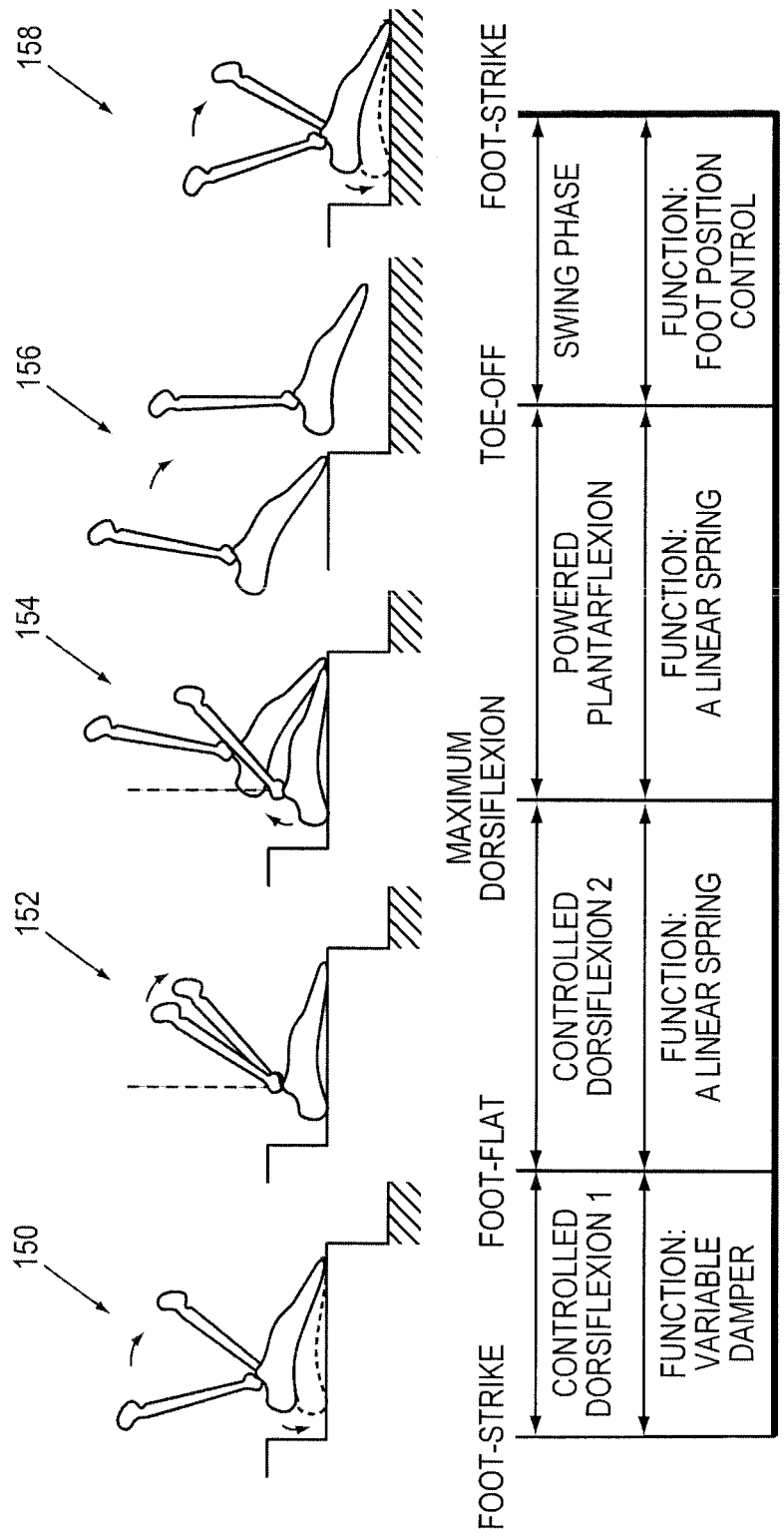
FIG. 1C is a schematic illustration of the different phases of a wearer's gait cycle descending stairs.
Figure 2A:
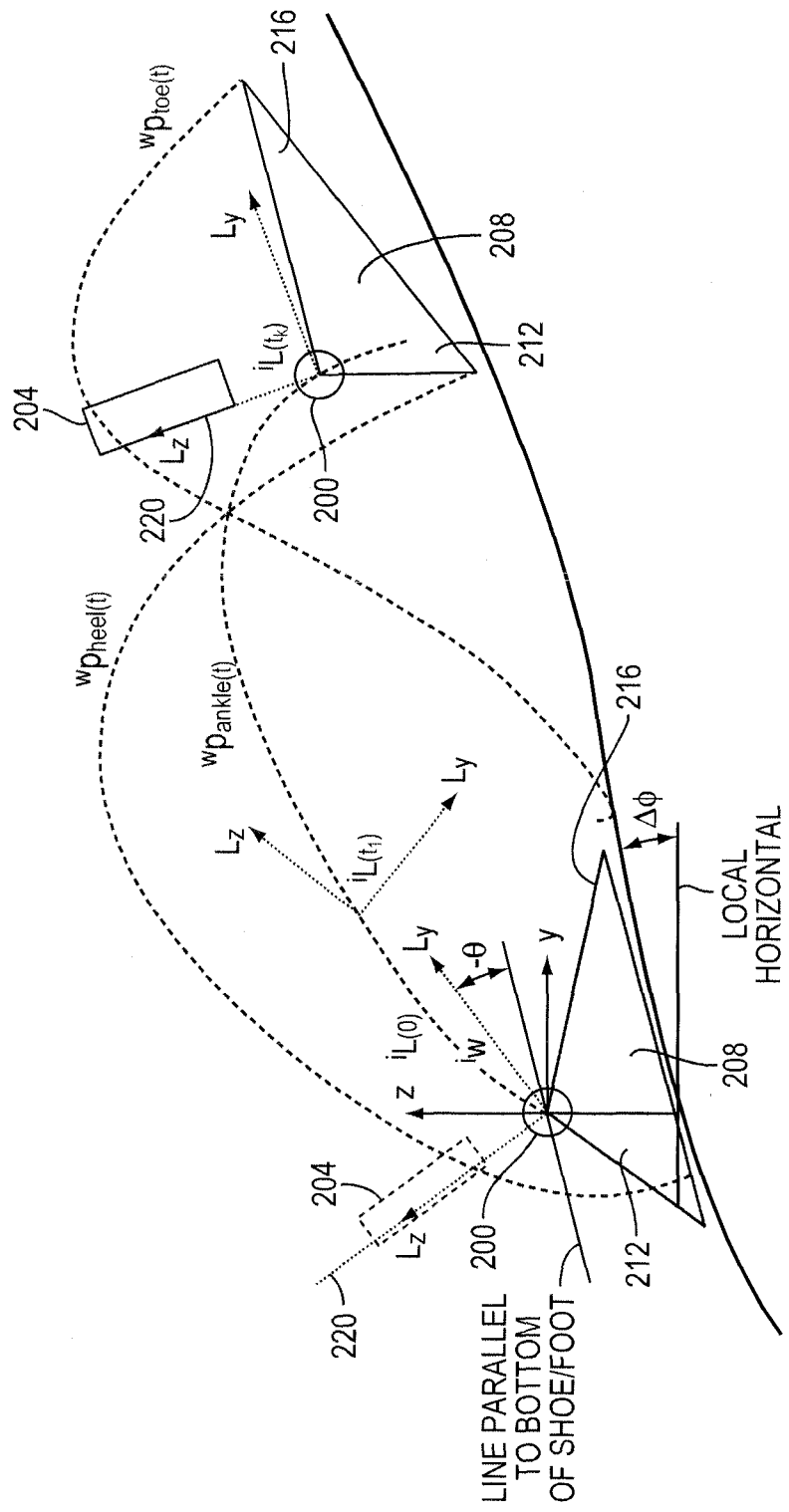
FIG. 2A is a schematic illustration of a method for determining ankle joint, heel and toe trajectories of a prosthetic, orthotic, or exoskeleton apparatus, according to an illustrative embodiment of the invention.

FIG. 2 is a schematic illustration of a method for determining ankle joint 200, heel 212 and toe 216 trajectories of a prosthetic, orthotic, or exoskeleton apparatus (for example, apparatus 1700 of FIG. 17A) based on the inertial pose of a lower leg member 220 coupled to the ankle joint 200, and the angle between the lower leg member 220 and foot member 208. Pose is the position and orientation of a coordinate system. The apparatus 1700 includes an inertial measurement unit 204 coupled to the lower leg member 220. The inertial measurement unit 204 includes a three-axis rate gyro for measuring angular rate and a three-axis accelerometer for measuring acceleration. Placing the inertial measurement unit on the lower leg member 220 collocates the measurement of angular rate and acceleration for all three axes of the lower leg member 220. The inertial measurement unit 204 provides a six-degree-of-freedom estimate of the lower leg member 220 pose, inertial (world frame referenced) orientation and ankle-joint 200 (center of rotation of the ankle-foot) location.

In some embodiments, the lower leg member 220 pose is used to compute the instantaneous location of the knee joint. By using knowledge of the ankle joint 200 angle ($\theta$) the instantaneous pose of the bottom of the foot 208 can be computed, including location of the heel 212 and toe 216. This information in turn can be used when the foot member 208 is flat to measure the terrain angle in the plane defined by the rotational axis of the ankle joint/foot member. Mounting the inertial measurement unit 204 on the lower leg member 220 has advantages over other potential locations. Unlike if it were mounted on the foot member 208, the lower leg member 220 mounting protects against physical abuse and keeps it away from water exposure. Further, it eliminates the cable tether that would otherwise be needed if it were on the foot member 208—thereby ensuring mechanical and electrical integrity. Finally, the lower leg member 220 is centrally located within the kinematic chain of the hybrid system (referring to FIG. 15), facilitating the computation of the thigh and torso pose with a minimum of additional sensors.

The inertial measurement unit 204 is used to calculate the orientation, $_{ankle}{}^{w}O$, position, $_{ankle}{}^{w}p$, and velocity, $_{ankle}{}^{w}v$, of the lower-extremity prosthetic apparatus in a ground-referenced world frame. $_{ankle}{}^{w}O$ may be represented by a quaternion or by a 3×3 matrix of unit vectors that define the orientation of the x, y and z axes of the ankle joint in relation to the world frame. The ankle joint 200 coordinate frame is defined to be positioned at the center of the ankle joint axis of rotation with its orientation tied to the lower leg member 220. From this central point, the position, velocity and acceleration can be computed. For points of interest in, for example, the foot (e.g., the heel 212 or toe 216), a foot member-to-ankle joint orientation transformation, $_{foot}{}^{ankle}O(\theta)$ is used to derive the position using the following relation $$_{point-of-interest}^{w}P = {}_{ankle}^{w}P + {}_{ankle}^{w}O(\gamma){}_{foot}^{ankle}O(\theta)({}^{foot}r_{point-of-interest}) \quad \text{EQN. 1}$$

where $$_{foot}^{ankle}O(\gamma) = \begin{bmatrix} 1 & 0 & 0 \\ 0 & \cos(\gamma) & -\sin(\gamma) \\ 0 & \sin(\gamma) & \cos(\gamma) \end{bmatrix} \quad \text{EQN. 2}$$

where $\gamma$ is the inertial lower leg member angle, and $$_{foot}^{ankle}O(\theta) = \begin{bmatrix} 1 & 0 & 0 \\ 0 & \cos(\theta) & -\sin(\theta) \\ 0 & \sin(\theta) & \cos(\theta) \end{bmatrix} \quad \text{EQN. 3}$$

where $\theta$ is the ankle joint angle.

Figure 17A:
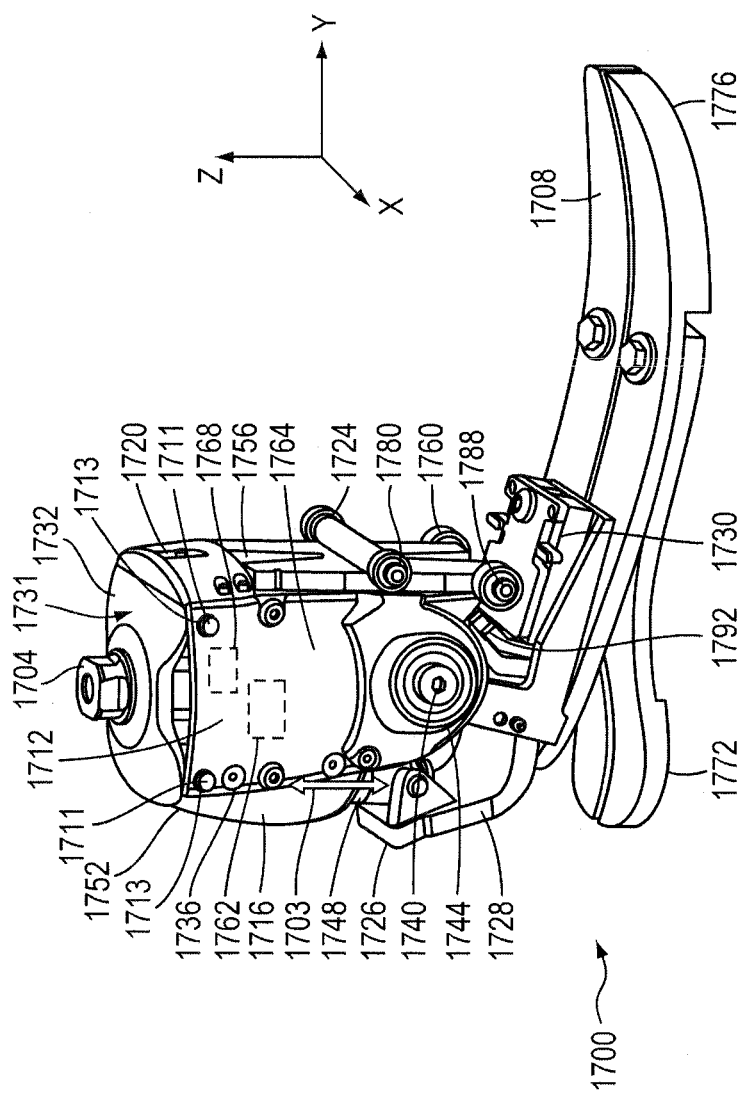
FIG. 17A is an illustration of a lower-extremity prosthetic apparatus, according to an illustrative embodiment of the invention.

In this embodiment, the inertial measurement unit 204, including the three-axis accelerometer and three-axis rate gyro, is located on the forward face at the top of the lower leg member 220 (as shown in, for example, FIG. 17A). It is necessary to remove the effect of scale, drift and cross-coupling on the world-frame orientation, velocity and position estimates introduced by numerical integrations of the accelerometer and rate gyro signals

Zero-Velocity Update

Inertial navigation systems typically employ a zero-velocity update (ZVUP) periodically by averaging over an extended period of time, usually seconds to minutes. This placement of the inertial measurement unit is almost never stationary in the lower-extremity prosthetic apparatus. However, the bottom of the foot is the only stationary location, and then only during the controlled dorsiflexion state of the gait cycle. An exemplary zero-velocity update method, which is not impacted by this limitation, for use with various embodiments of the invention is described further below.

To solve this problem, orientation, velocity and position integration of ankle joint is performed. After digitizing the inertial measurement unit acceleration, $^{IMU}a$, the ankle joint acceleration ($^{IMU}a_{ankle}$) is derived with the following rigid body dynamic equation:

$$^{IMU}a_{ankle} = {}^{IMU}a + {}^{IMU}\vec{\omega} X {}^{IMU}\vec{\omega} X_{ankle}{}^{IMU}\vec{r} + \vec{\omega} X_{ankle}{}^{IMU}\vec{r} \quad \text{EQN. 4}$$

where $^{IMU}\vec{\omega}$ and $^{IMU}\vec{\dot\omega}$ are the vectors of angular rate and angular acceleration, respectively, in the inertial measurement unit frame and X denotes the cross-product.

The relationship is solved $_{ankle}{}^{w}O = {}_{IMU}{}^{w}O$ similarly as in EQNS. 1-3 using standard strapdown inertial measurement unit integration methods, in accordance with the following relationships known to one skilled in the art:

$$_{ankle}{}^{w}\dot{\hat\Phi} = {}^{w}\hat\Omega({}^{w}\hat\omega)_{ankle}{}^{w}\hat\Phi \quad \text{EQN. 5}$$

$$^{w}\hat{\dot v}_{ankle} = {}^{w}\hat a_{ankle} - [0,0,g]^{T} \quad \text{EQN. 6}$$

$$^{w}\hat{\dot p}_{ankle} = {}^{w}\hat v_{ankle} \quad \text{EQN. 7}$$

$$_{foot}{}^{w}\hat\Phi = {}_{ankle}{}^{w}\hat\Phi {}_{foot}{}^{ankle}\hat\Phi = {}_{ankle}{}^{w}\hat\Phi \text{Rotation}_{x}(\hat\Theta) \quad \text{EQN. 8}$$

$$^{w}\hat{\dot v}_{heel} = {}^{w}\hat{\dot v}_{ankle} + {}^{w}\hat\Omega(_{ankle}{}^{w}\hat\Phi[\hat{\dot\Theta}\,0\,0]^{T}){}^{w}r_{heel\text{-}ankle} \quad \text{EQN. 9}$$

$$^{w}\hat{\dot v}_{toe} = {}^{w}\hat{\dot v}_{ankle} + {}^{w}\hat\Omega(_{ankle}{}^{w}\hat\Phi[\hat{\dot\Theta}\,0\,0]^{T}){}^{w}r_{toe\text{-}ankle} \quad \text{EQN. 10}$$

$$^{w}\hat{\dot p}_{heel} = {}^{w}\hat{\dot p}_{ankle} + {}^{w}r_{heel\text{-}ankle} \quad \text{EQN. 11}$$

$$^{w}\hat{\dot p}_{toe} = {}^{w}\hat{\dot p}_{ankle} + {}^{w}r_{toe\text{-}ankle} \quad \text{EQN. 12}$$

$$^{w}r_{heel\text{-}ankle} = {}_{foot}{}^{w}\hat\Phi^{foot}(r_{heel} - r_{ankle}) \quad \text{EQN. 13}$$

$$^{w}r_{toe\text{-}ankle} = {}_{foot}{}^{w}\hat\Phi^{foot}(r_{toe} - r_{ankle}) \quad \text{EQN. 14}$$

In equations 5-14 above, the matrix, $\hat\Phi$, will be used interchangeably with the orientation matrix, $_{IMU}{}^{w}O$.

The world frame-referenced ankle joint velocity and position are then derived at a point in time after the time of the previous zero-velocity update ($i^{th}$ zero-velocity update) based on the following:

$$^{w}v_{ankle}(t) = \int_{ZVUP(i)}^{t}({}_{IMU}{}^{w}O){}^{IMU}a_{ankle}dt \quad \text{EQN. 15}$$

$$^{w}p_{ankle}(t) = \int_{ZVUP(i)}^{t}{}^{w}v_{ankle}dt \quad \text{EQN. 16}$$

where $^{w}p_{ankle}(t=ZVUP(i))$ is reset to zero for all i.

Figure 2B:
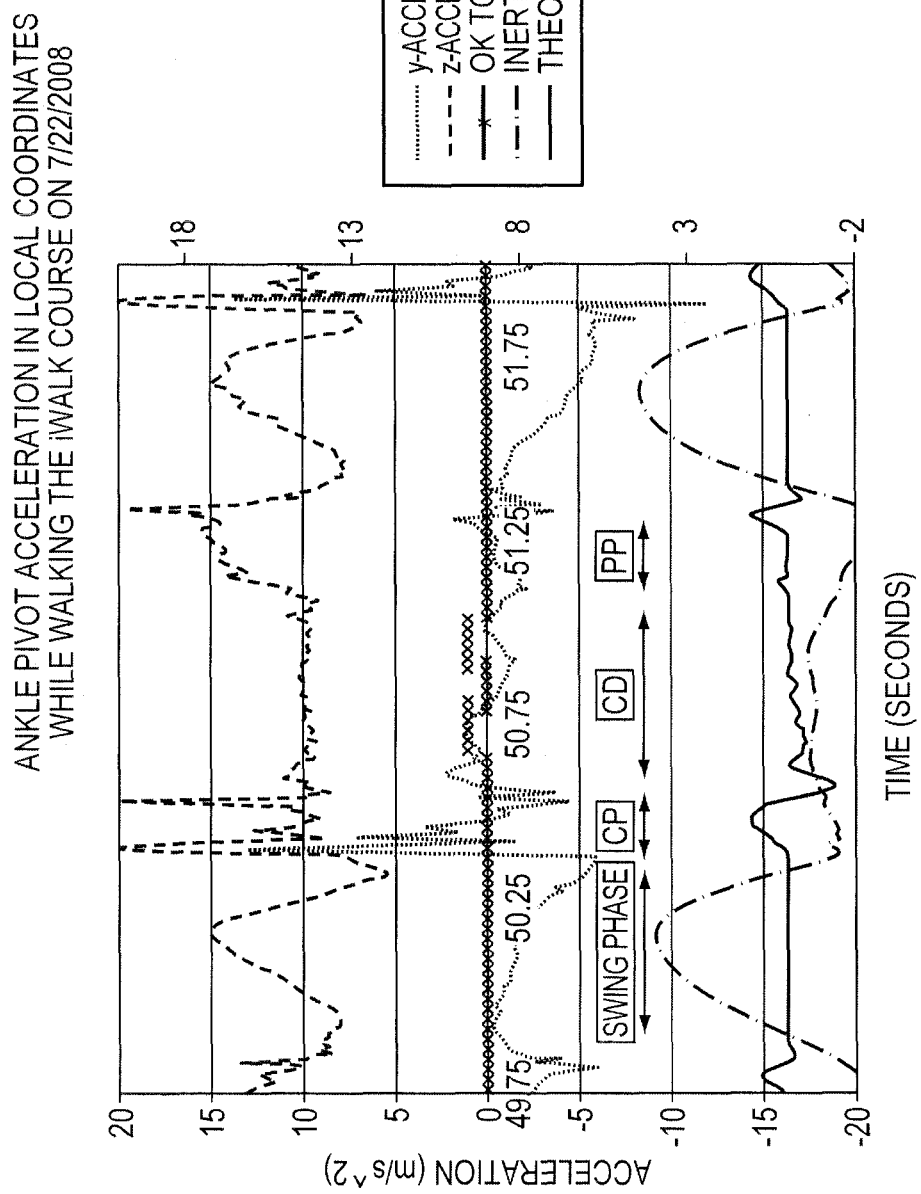
FIG. 2B is a plot of experimental data showing ankle joint acceleration during walking.

Through experimentation, using logs of inertial measurement unit data acquired from an exemplary lower-extremity prosthetic apparatus (e.g., lower-extremity prosthetic apparatus 1700 of FIG. 17A), we determined that the inertial measurement unit-referenced accelerations were sufficiently quiet early (see FIG. 2B at approximately 50.75 seconds and 50.9 seconds when the z-acceleration is equal to about 1 g (approximately 9.8 m/s²) in the controlled dorsiflexion state and the variance of the z-acceleration is less than a predetermined value (<0.005 g²)—indicating a period in time where the lower leg member 220 is rotating about a stationary ankle joint 200. In another embodiment of this technique, a suitable quiet period can be detected on some part of the foot. Knowledge of the acceleration, angular rate and angular acceleration of the ankle joint can be combined with the knowledge of the sensed ankle angle (angle between the foot member and the lower leg member), angle rate and angle acceleration to calculate the acceleration of any point on the foot. Some point on the bottom of the foot can often be used to perform a zero velocity update on successive gait cycles. Once this velocity is known, the velocity of the ankle joint can be computed a posteriori. This velocity (rather than zero) can be used as a reference from which the zero velocity update can be performed.

In the lower-extremity prosthetic apparatus, a quiet period nearly always exists in the Controlled Dorsiflexion state, so a zero-velocity update may be performed for every step that the wearer takes. During each zero-velocity update, the velocity error contribution from each of three terms are preferably evaluated—the tip, $\delta\theta_x$ of the world frame z-axis about the x-axis (the vector aligned with the ankle joint axis of rotation during the zero-velocity update on the previous step); the tilt, $\delta\theta_y$ of the world frame z-axis about the y-axis (a vector defined as the cross-product of the world-frame vertical (opposing the gravity vector) and the world frame x-axis); and the inertial measurement unit scaling along the vertical axis, $\delta g$. The values of these terms are used to correct the computed pose, inertial orientation and previous computed poses and inertial orientations of the different components of the apparatus (e.g., the lower leg member 1712 of FIG. 17A).

While performing the orientation, velocity and position integration, a sensitivity matrix, M(t) is calculated that relates the velocity error that would be introduced by the vector of errors, $\alpha = [\delta\theta_x\ \delta\theta_y\ \delta g]^T$. M(t) based on the following relationship:

$$M(t) = \frac{\partial}{\partial \alpha}(_{IMU}^{w}O^{IMU}a_{ankle}) \quad \text{EQN. 17}$$

in which, M(t) is integrated numerically to generate the overall terminal velocity sensitivity, M*, $$M^* = \int_{ZVUP_{i-1}}^{ZVUP_i} M(t)dt \quad \text{EQN. 18}$$

In some embodiments, the vector of errors is expanded to include accelerometer bias offsets if these errors are significant, thereby increasing the number of columns in M(t) and in M*. In this case, $M^{*-1}$ takes the form of the Penrose pseudo-inverse or, by an optimal innovations gain, K*. K* can be computed using standard optimal linear filtering methods. To one skilled in the art, other terms can be included or used without loss of generality.

At the zero-velocity update for step i, the value of α that would have generated the estimated non-zero ankle joint velocity, $^{w}v_{ankle}(ZVUP_i)$, is determined based on:

$$\alpha = M^{*-1}{}^{w}v_{ankle}(ZVUP_i) \quad \text{EQN. 19}$$

where α is the innovations correction vector. Since the non-zero velocity results in part from noise in the accelerometers and angular rate measurements, not all of the innovations correction (α) is applied. Instead, the correction is scaled by a filtering constant (fraction), k, depending on the magnitude of the noise. At this point, the new orientation matrix ($_{ankle}^{w}O$) and gravity magnitude (g) are determined based on:

$$_{ankle}^{w}O(ZVUP_i^+) = O_x(-k\alpha(1))O_y(-k\alpha(2))_{ankle}^{w}O(ZVUP_i^-) \quad \text{EQN. 20}$$

$$g(ZVUP^+) = g(ZVUP^-) - k\alpha(3) \quad \text{EQN. 21}$$

where $O_x$(tip) and $O_y$(tilt) denote incremental rotations of tip and tilt about the x and y axes respectively, and $ZVUP_i^+$ and $ZVUP_i^-$ denote the times after and before the ZVUP, respectively.

It is possible to extend the zero velocity update to estimate accelerometer and rate gyro bias offsets using linear estimators. Consistent angular alignment errors (e.g., about a given axis) could be used to estimate the rate gyro bias about that axis. In one embodiment, this is performed by creating linear stochastic models of accelerometer and rate gyro bias and using the zero-velocity update prediction residuals as inputs to the linear filter applied to those models.

The above method is a method for continually updating the orientation and apparent gravity magnitude. An initialization procedure is used in this embodiment when the lower-extremity prosthetic apparatus is first powered on. In this method, the wearer will, when requested by the apparatus (e.g., by a vibration code transmitted by the apparatus or an alternative user interface), take one step forward and stop, then take one step back to the original position. In this process, the steps will be taken on the affected leg (for bilateral amputees, this calibration will be executed in a serial fashion as selected by the amputee). The calibration will invoke two ZVUP's—one to initialize the orientation and gravity magnitude, the second to check the result. This will ensure integrity of the inertial measurement unit signals, processing and controller communication.

The above process accomplishes an initialization of the inertial orientation. It is, however, of general interest to accomplish a full calibration of the IMU, to account for the vector (ε) of error sources—a vector that includes bias offset, scale and cross-sensitivity embodied within the accelerometer and gyro signals. In manufacturing, a robot or other six degree-of-freedom machine can carry the IMU and apply reference trajectories in succession as a means of measuring the effect of these error sources. The sensitivity matrix (M(ε)) of the sensed reference trajectories to each of the error sources can be easily computed by those skilled in the art. By measuring the sensed deviations from a rich set of reference trajectories—typically the deviation of the end-point of each trajectory segment—the vector (ε) can be estimated using regression or other linear estimation methods—provided that the set of reference trajectories is rich enough to excite the influence of each error source. The inventors have found that reference trajectories that include closed paths like polygons and circles in three orthogonal planes are sufficient to calibrate the full vector of error sources. Such reference trajectories can also be conducted by the wearer to recalibrate key elements of the vector (accelerometer bias, scale and cross-sensitivity) by, for example, walking in a sequence of closed patterns on a horizontal plane and by rotating in sequence about a vertical axis.

Figure 16:
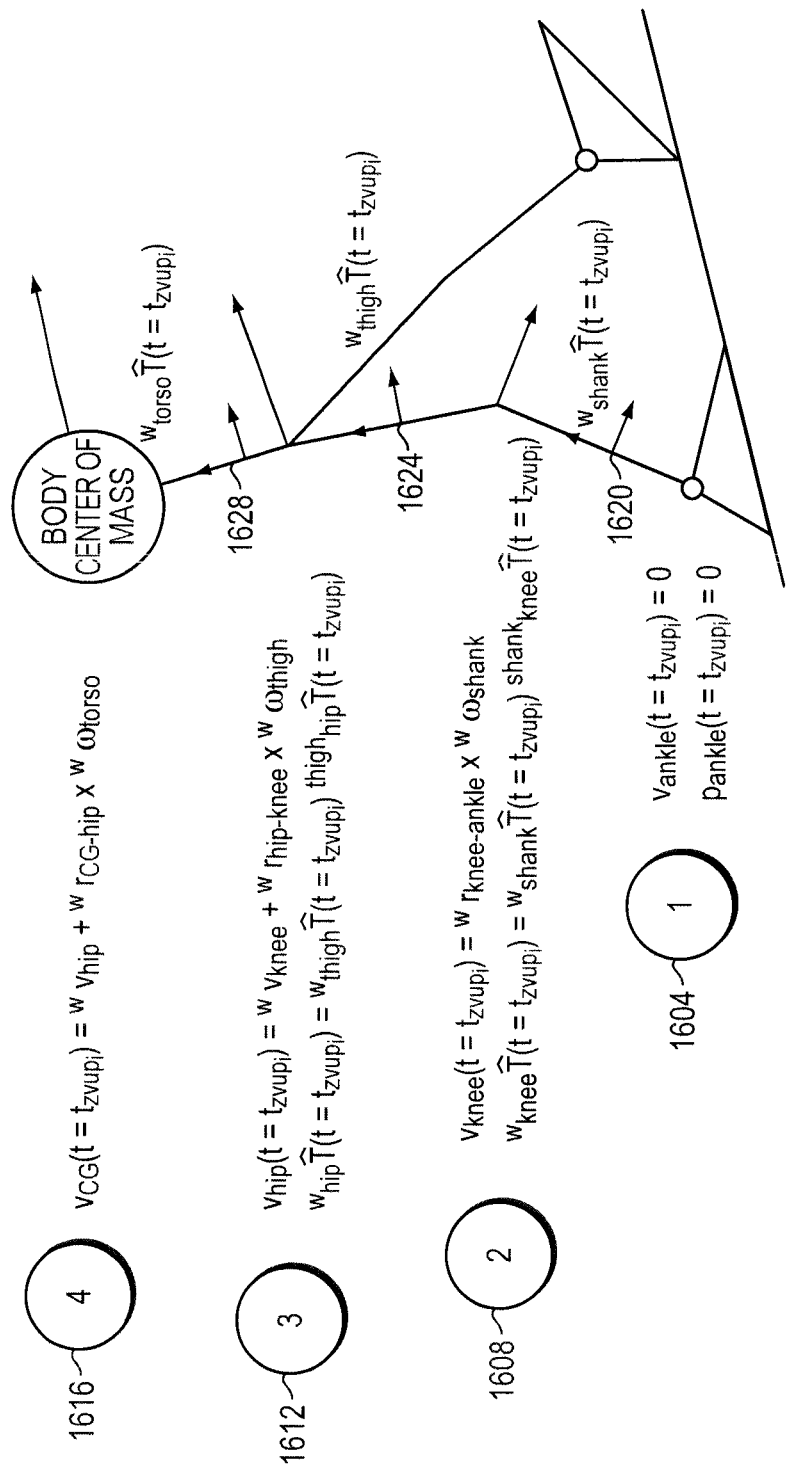
FIG. 16 illustrates a method of pose reconstruction for torso pose, thigh pose and torso/body center-of-mass pose, according to an illustrative embodiment of the invention.

In some embodiments of the invention, these principles of the method are similarly applied to correcting or minimizing the effect of accelerometer and rate gyro drift error associated with accelerometers and rate gyros located on, for example, the thigh member and/or torso of a wearer in which the prosthetic, orthotic, or exoskeleton apparatus treats or augments performance of these portions of a wearer's body. In one embodiment, the method includes determining offset values for an accelerometer signal and rate gyro signal output by an accelerometer and rate gyro coupled to a thigh member of the prosthesis or orthosis when the ankle joint is substantially stationary during a walking cycle of the prosthesis or orthosis. The method also can include measuring the angle of the lower leg member relative to the thigh member. In another embodiment, the method also includes determining offset values for an accelerometer signal and rate gyro signal output by an accelerometer and rate gyro coupled to a wearer's torso when the ankle joint is substantially stationary during a walking cycle of the prosthesis or orthosis. The method also can include measuring the angle of the thigh member relative to the wearer's torso. The methods can therefore be extended to the thigh member and/or torso of a wearer by performing these measurements and relying on the linkage constraint relationships and related methods, as shown in FIG. 16. At the time of the zero velocity update, the linkage constraints enable propagation of the joint velocity references backwards from the ground-referenced zero velocity of the lowest link in the kinematic chain (e.g., the linkage that defines the hybrid human-robot system). These velocity references can be used as the input to the pose realignment and gravity compensation as defined above.

Exemplary Ankle Joint Trajectories and Terrain Context Discrimination

Figure 3:
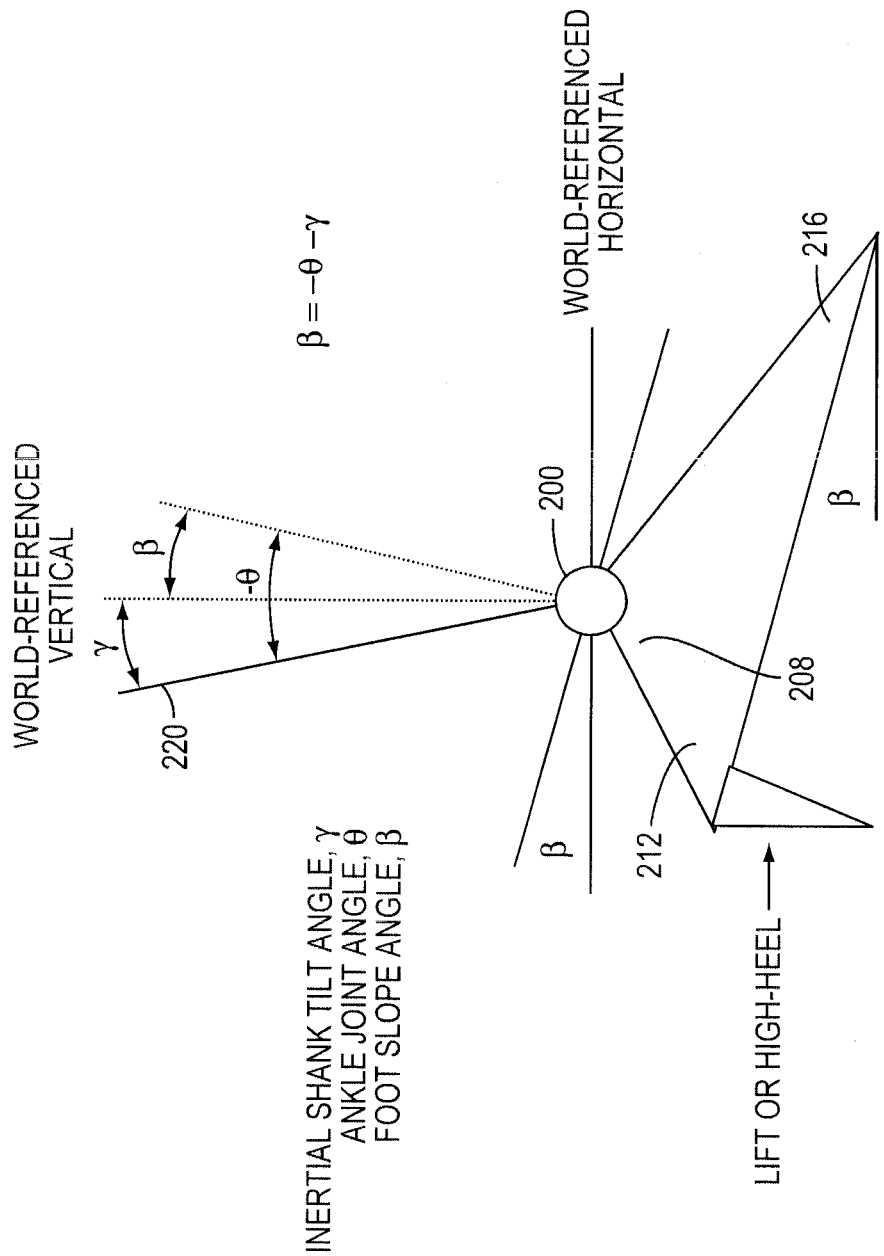
FIG. 3 is a schematic illustration of a method for determining foot slope (heel height), according to an illustrative embodiment of the invention.

Once the inertial measurement unit offsets have been calculated and corrected (zeroed), the foot-slope ($\beta$) (alternatively referred to as heel height) is determined as illustrated in, for example, FIG. 3. From the illustration it is easy to see that when the wearer is standing with her foot flat on the ground that $\beta=-(\theta+\gamma)$. By averaging over a period of about a tenth of a second an accurate estimate of $\beta$ can be determined. Thereafter, the orientation component of the transformation that defines the foot to ankle coordinate system, $_{foot}^{ankle}O$, is computed based on the following:

$$_{foot}^{ankle}O(\beta,\gamma) = \begin{bmatrix} 1 & 0 & 0 \\ 0 & \cos(\beta+\gamma) & -\sin(\beta+\gamma) \\ 0 & \sin(\beta+\gamma) & \cos(\beta+\gamma) \end{bmatrix} \quad \text{EQN. 22}$$

As before, the translational component of this transform will remain zero.

Once the foot-slope is defined, it is then necessary to determine the heel 212 and toe 216 coordinates in the foot coordinate system. In one exemplary method for determining this, $^{foot}\vec{p}_{heel}$ and $^{foot}\vec{p}_{toe}$ are defined as the vector coordinates of the heel and toe in the new foot coordinate system. Because the rotational contribution of $\beta$ has already been incorporated, the z-component of these vectors is the same. It can be assumed that the x-component of these vectors are both zero. So these vectors take the form:

$$^{foot}\vec{p}_{heel} = \begin{bmatrix} 0 \\ y_{heel} \\ z_0 \end{bmatrix} \quad \text{EQN. 23}$$

$$^{foot}\vec{p}_{toe} = \begin{bmatrix} 0 \\ y_{toe} \\ z_0 \end{bmatrix} \quad \text{EQN. 24}$$

where $z_0$ defines the z-coordinate of the bottom of the foot (shoe).

Figure 4:
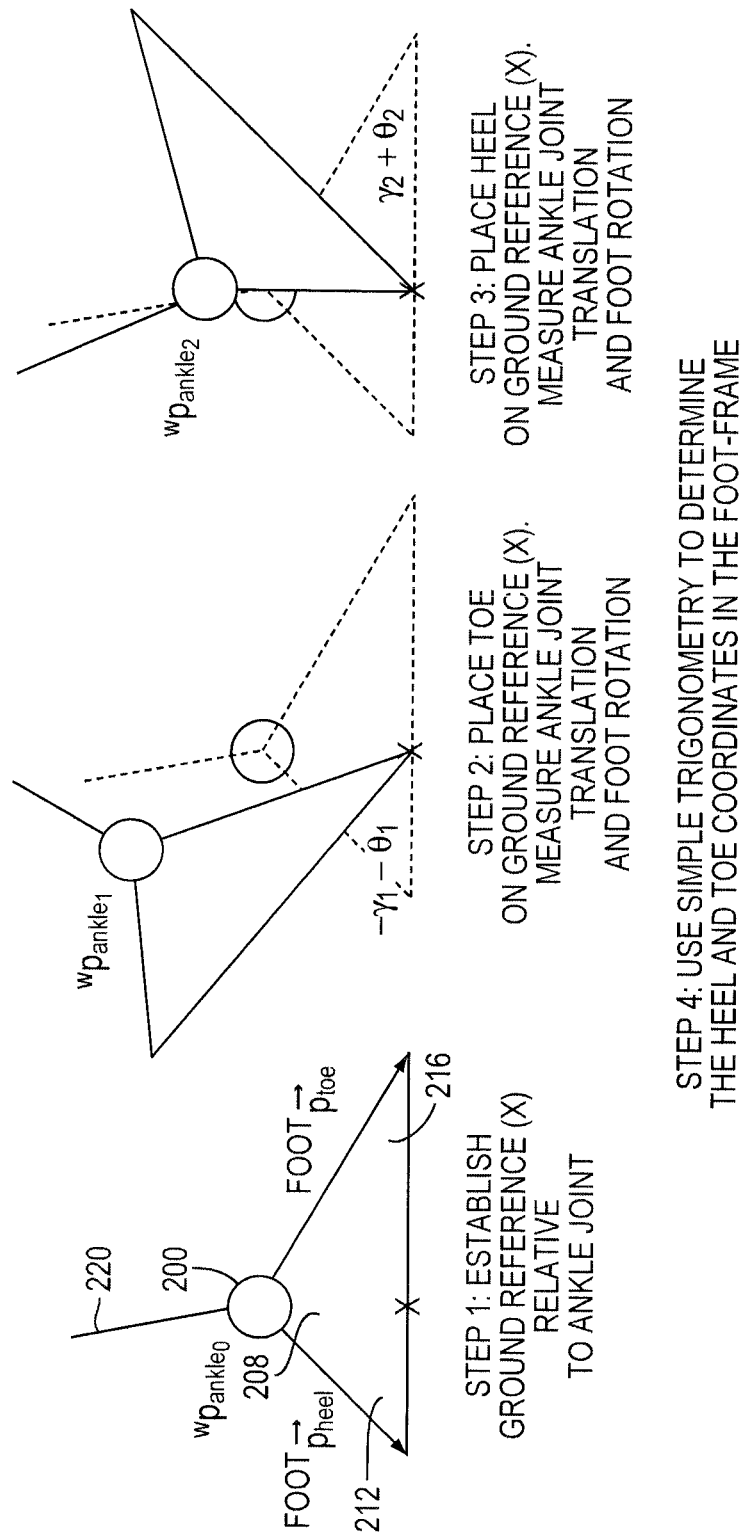
FIG. 4 is a schematic illustration of a method for determining the coordinates of the heel and toe in relation to the ankle joint in the foot frame of reference, according to an illustrative embodiment of the invention.

FIG. 4 is a schematic illustration of a method for determining the coordinates of the heel 212 and toe 216 in relation to the ankle joint 200 in the foot frame of reference, according to an illustrative embodiment of the invention. In the first step of the foot calibration method defined in FIG. 4, the y-coordinate of the ankle joint 200 is aligned to a ground reference (e.g., seam in the pavement, a prominent feature on a rug or on a linoleum surface). We arbitrarily define this ground reference to be the origin of the world coordinate system. In mathematical notation, this alignment takes the form:

$$^{world}p_{ankle_0} = \begin{bmatrix} 0 \\ 0 \\ -z_0 \end{bmatrix} \quad \text{EQN. 25}$$

where $^{world}p_{ankle_0}$ is the starting position for the moves that take place in steps 2 and 3. In the second step, the toe 216 is placed onto the ground reference. In mathematical notation, this alignment takes the form:

$$\begin{bmatrix} 0 \\ 0 \\ 0 \end{bmatrix} = {^{world}p_{ankle_1}} + O(\gamma)O(\theta+\beta) \begin{bmatrix} 0 \\ y_{toe} \\ z_0 \end{bmatrix} \quad \text{EQN. 26}$$

or $$^{foot}\vec{p}_{toe} = \begin{bmatrix} 0 \\ y_{toe} \\ z_0 \end{bmatrix} = -O^{-1}(\gamma)O^{-1}(\theta+\beta)^{world}p_{ankle_1} \quad \text{EQN. 27}$$

A similar relationship is determined during the alignment in step 3. When the equations above are solved independently, two different estimates of $z_0$ are obtained. By combining the two constraint equations into one, a least-squares estimate of $y_{heel}$, $y_{toe}$ and $z_0$ can be obtained.

The heel 212 and toe 216 calibration method described above involves a series of steps that would be used the first time a new pair of feet/shoes are worn. Such a calibration could be performed at, for example, the prosthetist office.

Figure 5:
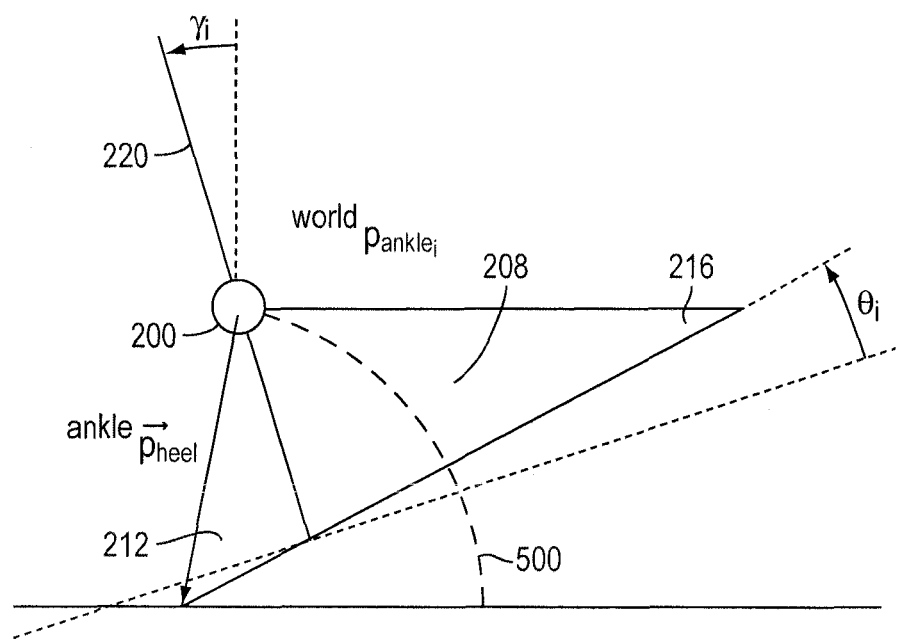
FIG. 5 is a schematic illustration of a method for estimating a heel vector, according to an illustrative embodiment of the invention.

In another exemplary method, the heel and toe vectors are calculated on-the-fly. As shown in FIG. 5, the ankle joint 200 traces an arc 500 in the early stance phase between foot-strike and foot-flat. The radius and orientation (midpoint angle) of the arc 500 fully determine the heel and toe vectors. Mathematically, this is described as a series of ankle positions ($^{world}p_{ankle_i}$) that are recorded during early stance. Two ankle position measurements are needed, corresponding to two statistically distinct lower leg member 220 ($\gamma_i$,) and ankle joint 200 angle ($\theta_i$,) positions, yielding:

$$^{world}p_{heel_1} = {^{world}p_{ankle_1}} + O(\gamma_1)O(\theta_1)^{foot}\vec{p}_{heel} \quad \text{EQN. 28}$$

$$^{world}p_{heel_2} = {^{world}p_{ankle_2}} + O(\gamma_2)O(\theta_2)^{foot}\vec{p}_{heel} \quad \text{EQN. 29}$$

Then, by differencing the equations, the vector solution becomes:

$$^{foot}\vec{p}_{heel} = (O(\gamma_2)O(\theta_2) - O(\gamma_1)O(\theta_1))^{-1} \\ (^{world}p_{ankle_2} - {^{world}p_{ankle_1}}) \quad \text{EQN. 30}$$

The solution requires that $(O(\gamma_2)O(\theta_2)-O(\gamma_1)O(\theta_1))$ is invertible. And from an optimal linear filtering standpoint, this "gain matrix" must be large enough so as to yield a statistically significant result.

Considering the fact that the lower-extremity prosthetic apparatus undergoes significant vibration during the early stance phase, the equations above can be extended to N sets of ankle joint position/angle measurements. The resulting N−1 equations can be solved using least-squares techniques to get an optimal estimate of the vector. The equations above are similarly adapted to solve for the toe vector when toe-strike initiates the early stance phase.

Figure 6A:
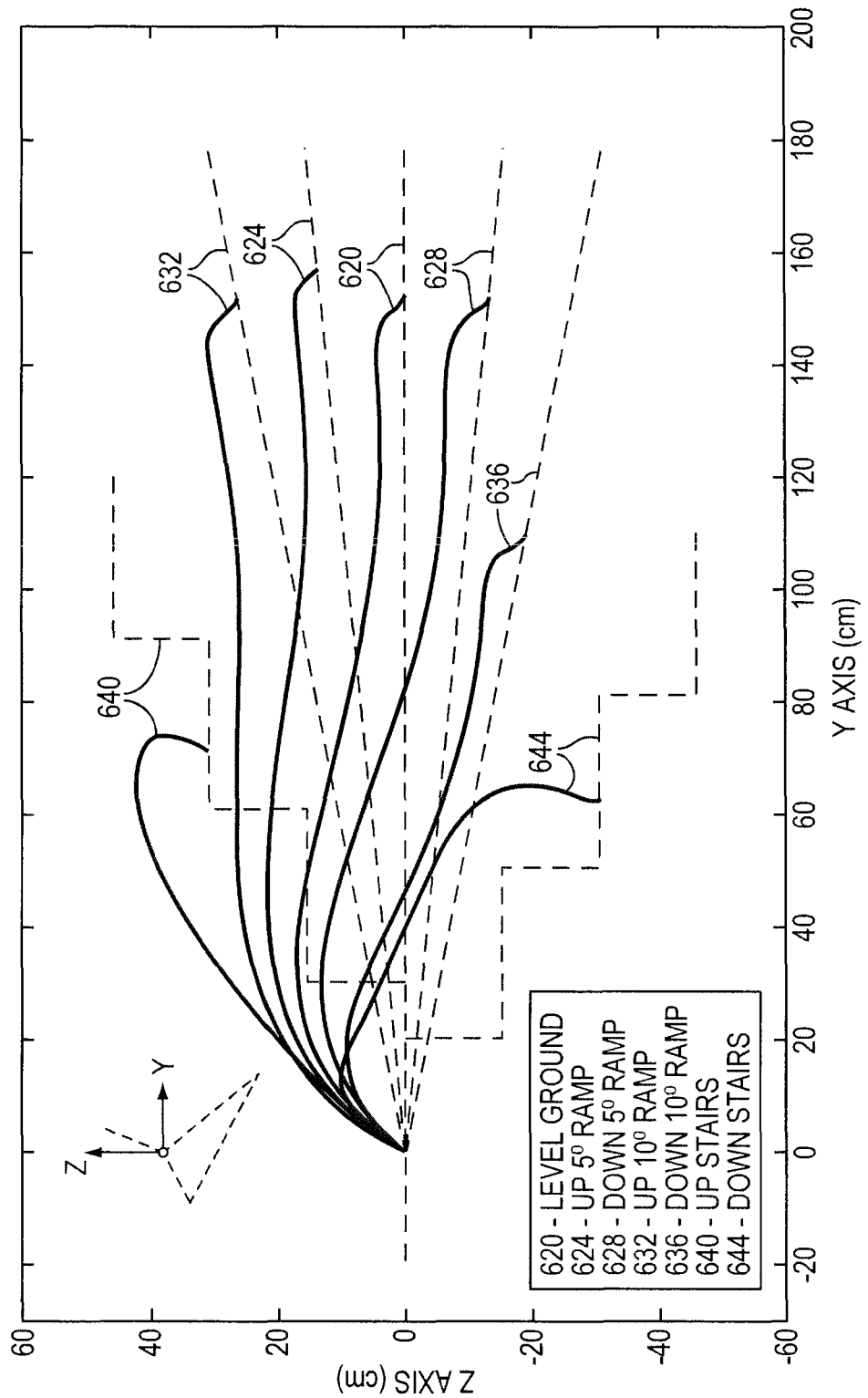
FIG. 6A illustrates the inertial measurement unit-computed ankle joint pivot trajectories in different ambulation contexts.

FIG. 6A illustrates the inertial measurement unit-computed ankle joint pivot trajectories in different ambulation contexts for a wearer walking on various terrain: level ground (620), up a 5° ramp (624), down a 5° ramp (628), up a 10° ramp (632), down a 10° ramp (636), up stairs (640), and down stairs (644). Context is the shape of the terrain and how the wearer interacts with the terrain.

Figure 6B:
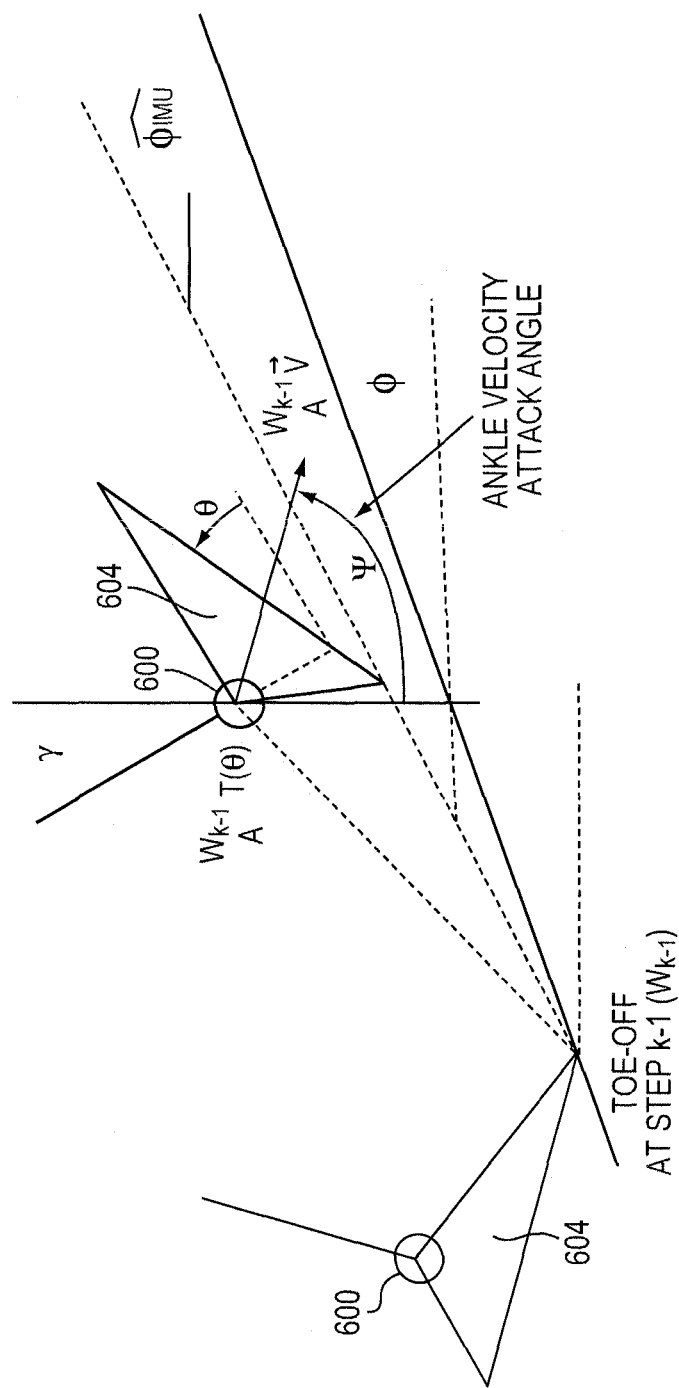
FIG. 6B illustrates the 2-D geometry that describes the in-flight trajectory of the ankle joint of the prosthetic apparatus.

FIG. 6B illustrates the 2-D geometry that describes the in-flight trajectory of the ankle joint of the prosthetic apparatus. If we treat level-ground walking as a subset of the ramp ascent/descent ambulation context (in which level ground is a zero degree ramp), then context discrimination devolves into discrimination of stair ascent/descent from ramp ascent/descent. This discrimination is important because typically in the stair context, plantarflexion (rather than dorsiflexion) of the ankle joint 600 is required to optimize foot-strike kinetics whereas in ramp ambulation typically the ankle joint 600 is dorsiflexed (or held neutral) to optimize foot-strike kinetics. In the latter context, it is only in extremely steep descent that a plantar flexed ankle would be the appropriate orientation.

Figure 6C:
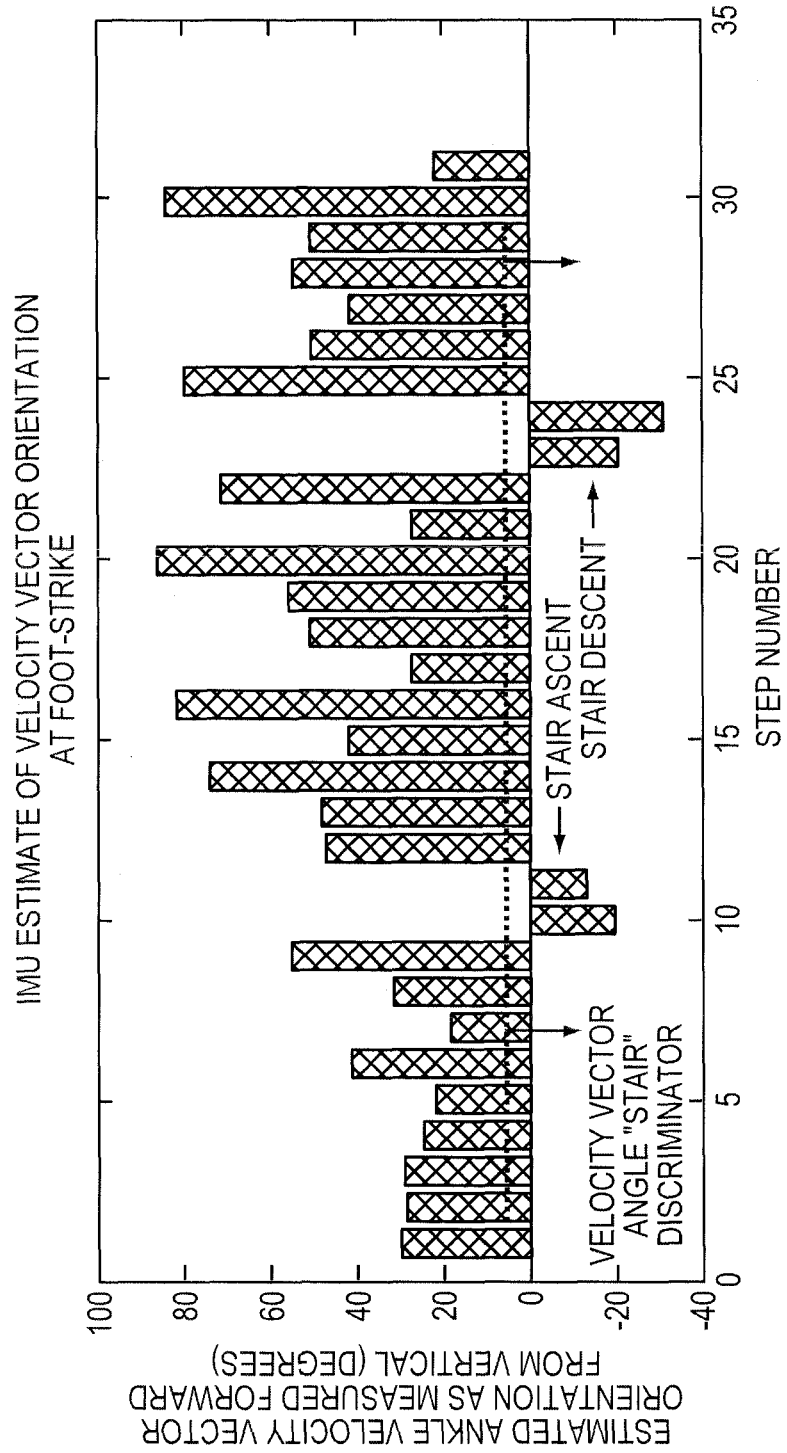
FIG. 6C illustrates how a stair-ramp discriminator can be built using the ankle angle attack angle as the trajectory feature that discriminates between the stair and ramp ambulation context, according to an illustrative embodiment of the invention.

FIG. 6C illustrates how a stair-ramp discriminator can be built using the ankle angle attack angle ($\Psi$) as the trajectory feature that discriminates between the stair and ramp ambulation context in a set of recorded data. FIG. 6C is a plot of the estimated velocity vector attack angle of the ankle joint 600 of the apparatus throughout a gait cycle versus each step taken by the wearer. In this data, an amputee fitted with the prosthetic apparatus 1700 of FIG. 17A on his right foot took thirty-one (31) steps (meaning walking cycles referenced to the right foot) in the following manner:

1. Steps 1-6: Six (6) steps up the 5° ramp
2. Step 7: One (1) step on the landing
3. Steps 8-9: Three (3) steps down the 10° ramp
4. Recording gap
5. Steps 10-11: Two (2) steps up the stairs
6. Step 12: One (1) step on the landing
7. Step 14-17: Four (4) steps down the 5° ramp
8. Steps (18-19): Two (2) steps on level-ground
9. Steps (20-21): Two (2) steps up the 10° ramp
10. Step (22): One (1) step from the 10° ramp to the landing
11. Steps (23-24): Two (2) steps down the stairs
12. Steps (25-31): Seven (7) steps on level-ground.

The steps taken during this recording included both ramp and stair ascent and descent. FIG. 6C shows that stairs can be differentiated from ramps while the ankle is in-flight prior to foot-strike by monitoring the ankle velocity attack angle ($\Psi$). When $\Psi$ drops below a small positive value in this recording (and other similar recordings) the foot 604 always lands on a stair. In all other cases, the foot lands on a ramp, irrespective of ramp angle (0°, −5°, +5°, −10°, +10°). $\Psi$ is therefore a suitable ambulation task context discriminator that can be used by the processor to determine what activity is being performed.

Alternative methods for stair-ramp discrimination can be employed in other embodiments of the invention. The attitude (orientation in inertial space) lower leg member 608 (shank) and the ankle velocity attack angle ($\Psi$) can be used in one embodiment of the invention to distinguish between stairs or a ramp/level ground. The trajectory of the ankle joint 600 in the y-z plane (referring to FIG. 6A) could be used in an alternative embodiment of the invention for stair-ramp discrimination.

Swing Phase Ankle Positioning

The stair ramp discriminator provides a real-time prediction of the terrain slope angle, $\hat{\phi}(t)$. If the discriminator detects a step, including level-ground, then $\hat{\phi}(t)=0$. Otherwise, the slope angle is assumed to be:

$$\hat{\phi}(t) = \min\left(\tan^{-1}\left(\frac{({}^w p_{heel}(t) - {}^w p_{toe}(0))_z}{({}^w p_{heel}(t) - {}^w p_{toe}(0))_y}\right), \tan^{-1}\left(\frac{({}^w p_{toe}(t) - {}^w p_{toe}(0))_z}{({}^w p_{toe}(t) - {}^w p_{toe}(0))_y}\right)\right)$$ EQN. 31

This slope angle corresponds to the minimum value possible given that the foot has not struck the ground. $\hat{\phi}(t)$ is this the minimum value of two possible slope angles—the angle that the heel currently makes relative to the toe position from the last step and the angle that the toe makes relative to the toe position from the last step.

Once $\hat{\phi}(t)$ is known, it is possible to apply various different methods to position the ankle in a way that adapts to this predicted terrain slope. Two examples of such methods are described below. In one embodiment of the invention, the discriminator methodology described above is used to control at least one of joint impedance, position or torque of a lower extremity prosthetic, orthotic, or exoskeleton apparatus worn by a wearer (e.g., the apparatus 1700 of FIG. 17A). The method involves estimating a velocity vector attack angle of the ankle joint of the apparatus throughout a late swing (e.g., the y-axis values of the data in FIG. 6C). In one embodiment, the method also involves adjusting the position of the foot member of the apparatus to a toe down position when the velocity vector attack angle has a predetermined sign (e.g., a negative value in the case of the data in FIG. 6C). In an another embodiment of the invention, the method involves adjusting the position of the foot member of the apparatus to a heel down position when the velocity vector attack angle has an opposite sign as the predetermined sign (a positive sign).

In some embodiments, the method includes adjusting the impedance of the apparatus (e.g., the ankle joint impedance) to minimize a cost function based on projected force imparted on the lower leg member during a period of time between when a heel of the foot member strikes the underlying terrain to when the foot member is positioned in a flat-foot position relative to the underlying terrain.

FIG. 7A illustrates a method for positioning the ankle joint 700 prior to foot strike. In this method, the ankle joint angle is optimized so as to minimize a cost functional based upon the projected force (f(t)) imparted on the ankle joint 700 from foot member 708 strike to foot-flat. Both heel-first 716 and toe-first 712 strategies are evaluated, and a strategy, including optimal ankle joint 700 angle, which minimizes the cost functional is selected. FIG. 7A describes the method used.

Figure 7B:
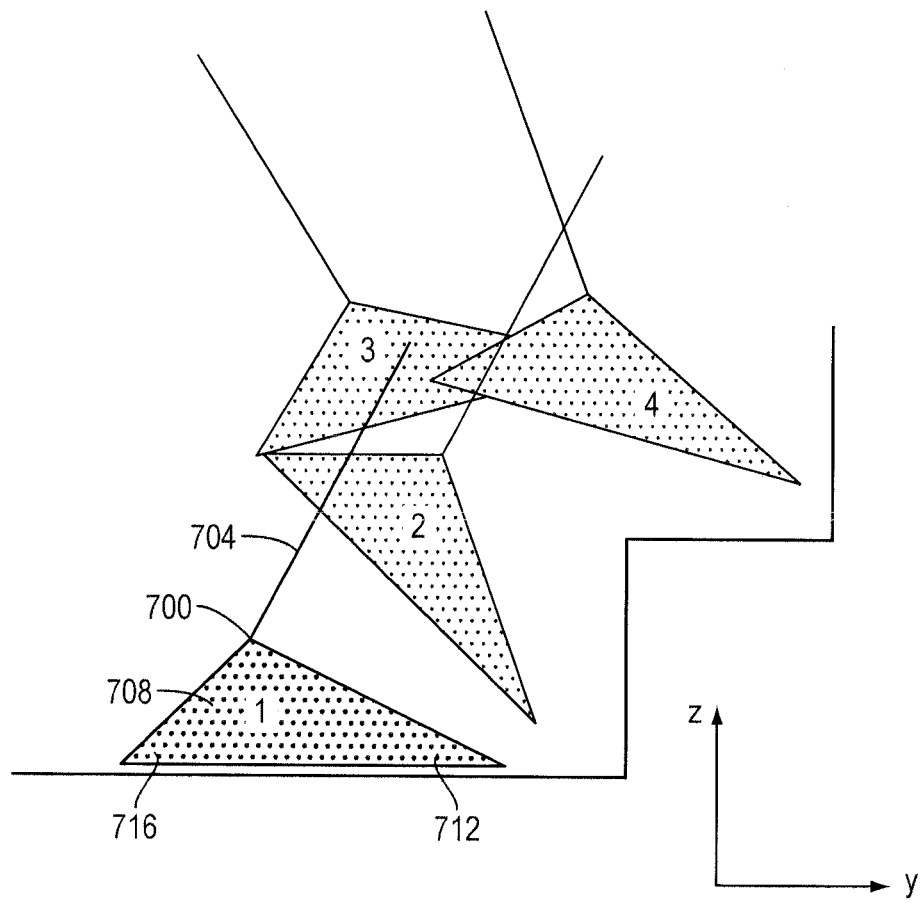
FIG. 7B illustrates how the method of FIG. 7A can be used to sense the presence of stairs and overhang of the foot on the landing of the stair, according to an illustrative embodiment of the invention.

In another embodiment, the method of FIG. 7A is augmented as shown in FIG. 7B to sense the presence of stairs, and to constrain the angle-of-attack optimization to toe-strike only in the event of stairs with short landing areas. For ascending or descending a steep, narrow set of stairs, the prosthetic apparatus is programmed to keep track of the volume swept by the foot during ascent—a volume for which there has been no contact between the foot and the stairs. If in late swing, there is determined to be no landing area for, for example, the heel, the optimization is constrained to be the toe-down solution. In this embodiment, a z-rotation is a rotation about the longitudinal axis of the lower leg member 704

(e.g., the z-axis of FIG. 17A) of the apparatus. If one descends stairs and rotates the foot member 708 in this way, it is likely that the landing area is limited and the foot member 708 must be rotated to land squarely on the stair. In this case, the toe 712 down landing yields the only available minimum force solution for the method of FIG. 7A. Such z-rotation would signal the system that the landing area is limited, making a toe-down landing the safest alternative when compared to heel-down.

The complex impedance computation employed in the method above can be applied to any adaptive ankle positioning method as a means of minimizing foot slap or use of excessive braking force as the ankle joint 700 rotates to the foot down state. FIG. 7D illustrates how the method of FIG. 7A is adapted to use the optimized impedance. Once the optimum angle-of-attack ($\psi^*$) is found, an optimal control ($\Gamma_c^*(t)$) is found that will bring the linear and angular momentum of the ankle joint to zero without foot-slap. The corresponding ankle angle response ($\theta^*(t)$) is then used as the equilibrium trajectory. A corresponding optimal impedance, in relation to this optimal trajectory, can be derived to accommodate the uncertainty in the momentum and the local terrain angle.

Figure 7C:
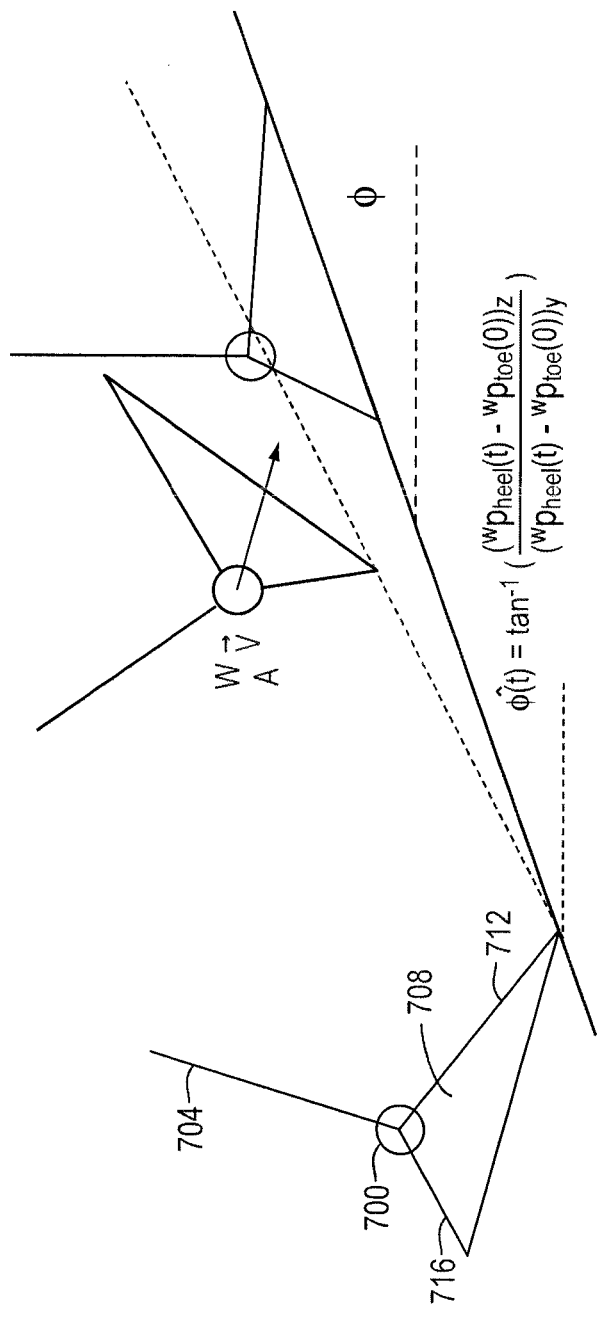
FIG. 7C illustrates a method for positioning an ankle joint in a ramp ambulation context, according to an illustrative embodiment of the invention.
Figure 7D:
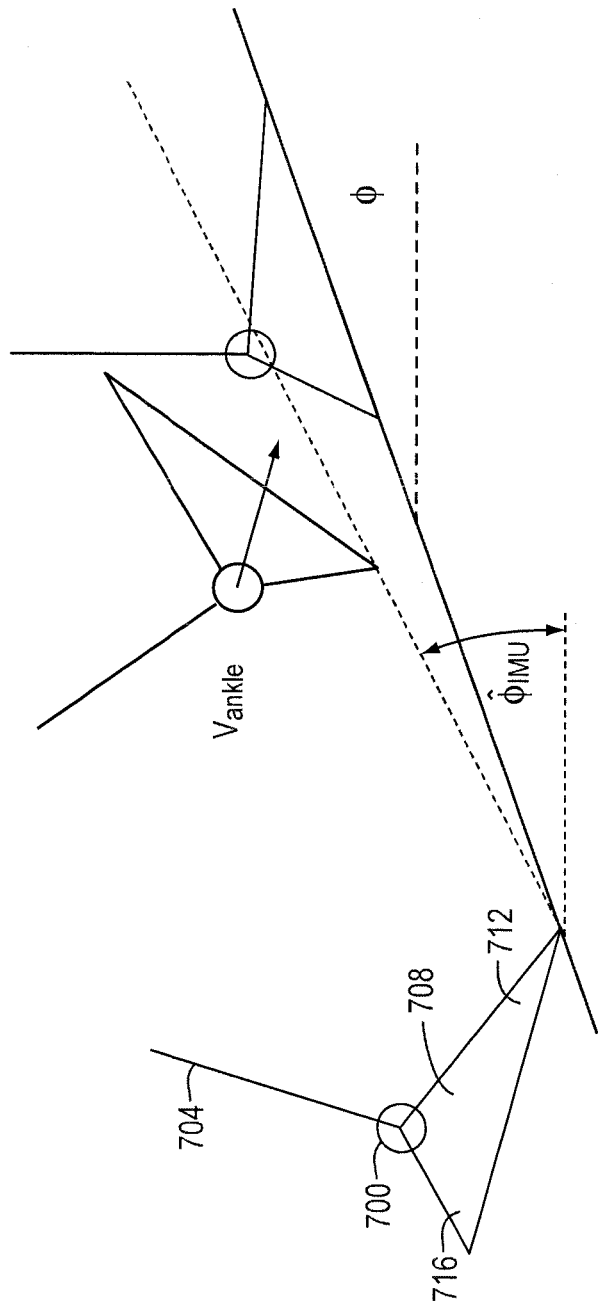
FIG. 7D illustrates how the method of FIG. 7B is adapted to use the optimized impedance, according to an illustrative embodiment of the invention.

A simpler method can also be used as shown in FIG. 7C. FIG. 7C illustrates a method for positioning the ankle joint in a ramp ambulation context. In this method, the ankle joint 700 angle is articulated so as to be in the foot-flat position on a sloped-terrain (with slope angle $\hat{\phi}(t)$) when the lower leg member 704 is vertical. It is also useful to generalize this method to adjust the ankle angle to be linearly related to the predicted slope angle by the relation:

$$\theta(t) = k\hat{\phi}(t) + \theta_0 \quad \text{EQN. 32}$$

Using this relationship the ankle angle can be adjusted to suit the wearer preferences.

In either of the two methods described above, the ankle joint angle 700 prior to foot-strike will be controlled (steered) continuously to coincide with the desired ankle joint 700 angle until the foot strikes the ground.

Stance Phase Impedance and Torque Control

Figure 8:
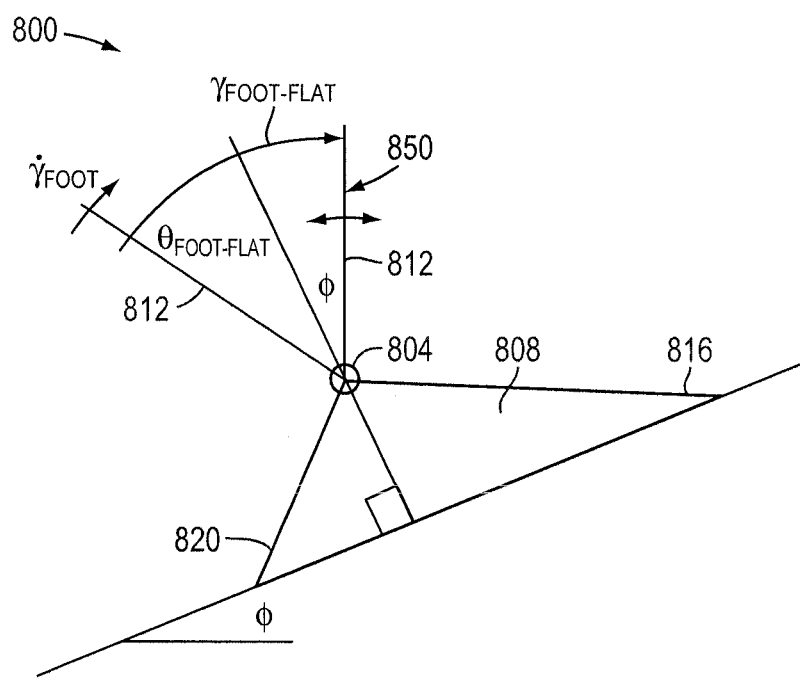
FIG. 8 illustrates a method for determining the inertially-referenced spring equilibrium based on the terrain angle at foot-flat.

The next step involves restoring the orientation of the lower leg (shank) to align with the local vertical during stance phase. FIG. 8 illustrates a method for determining the inertially-referenced spring equilibrium based on the terrain angle at foot-flat of a lower-limb prosthesis 800, for example, the prosthesis apparatus 1700 of FIG. 17A. The prosthesis 800 has a foot member 808 with a toe 816 and heel 820. The prosthesis also has an ankle joint 804 and lower leg member (shank) 812. The terrain angle ($\phi$) is an input to the control system. The control system shifts the curve ($\Gamma$–$\Theta$) (thereby altering the impedance of the ankle joint $K_{controlled\ plantarflexion}$) in FIG. 10A based on the change in terrain angle ($\phi$) to maintain or improve the overall balance (as described an illustrated in FIG. 10F) of the wearer during controlled plantarflexion. The control system sets the impedance of the ankle joint 804 of the prosthesis such that the ankle equilibrium angle is equal to the terrain angle ($\phi$); and the control system restores the orientation of the lower leg member 812 (shank) to align with the local vertical 850.

Figure 9:
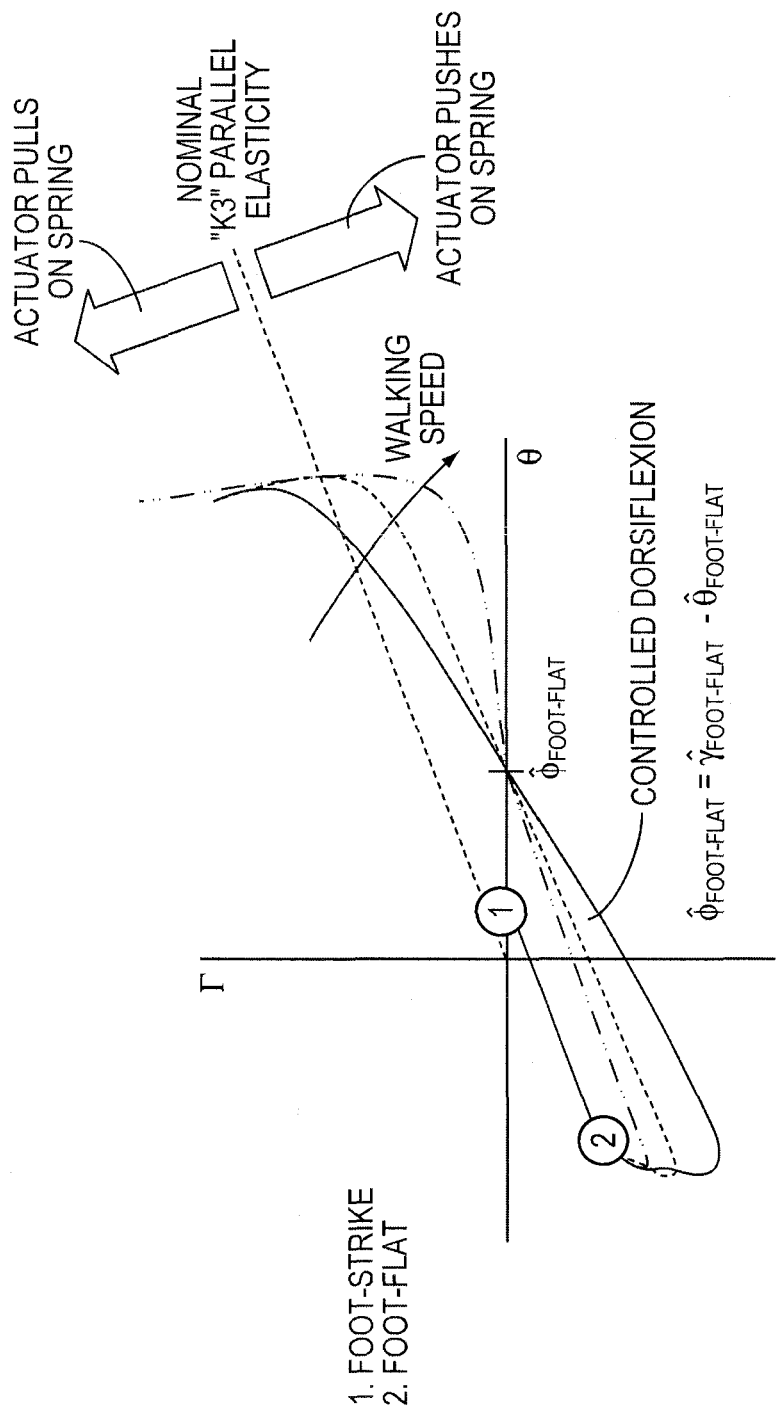
FIG. 9 illustrates the effect of walking speed on ankle torque versus ankle angle and shows how a push-pull actuator control applies to an appropriately selected parallel elastic element.

FIG. 9 illustrates the effect of walking speed on ankle torque versus ankle angle during controlled dorsiflexion. The control system shifts the curve ($\Gamma$–$\Theta$) (thereby altering the impedance of the ankle joint 804 $K_{controlled\ dorsiflexion}$) in FIG. 10A based on the change in terrain angle ($\phi$) to maintain or improve the overall balance of the wearer during controlled plantarflexion by commanding the ankle joint 804 to move the lower leg member (shank) 812 towards the equilibrium point.

Figure 10A:
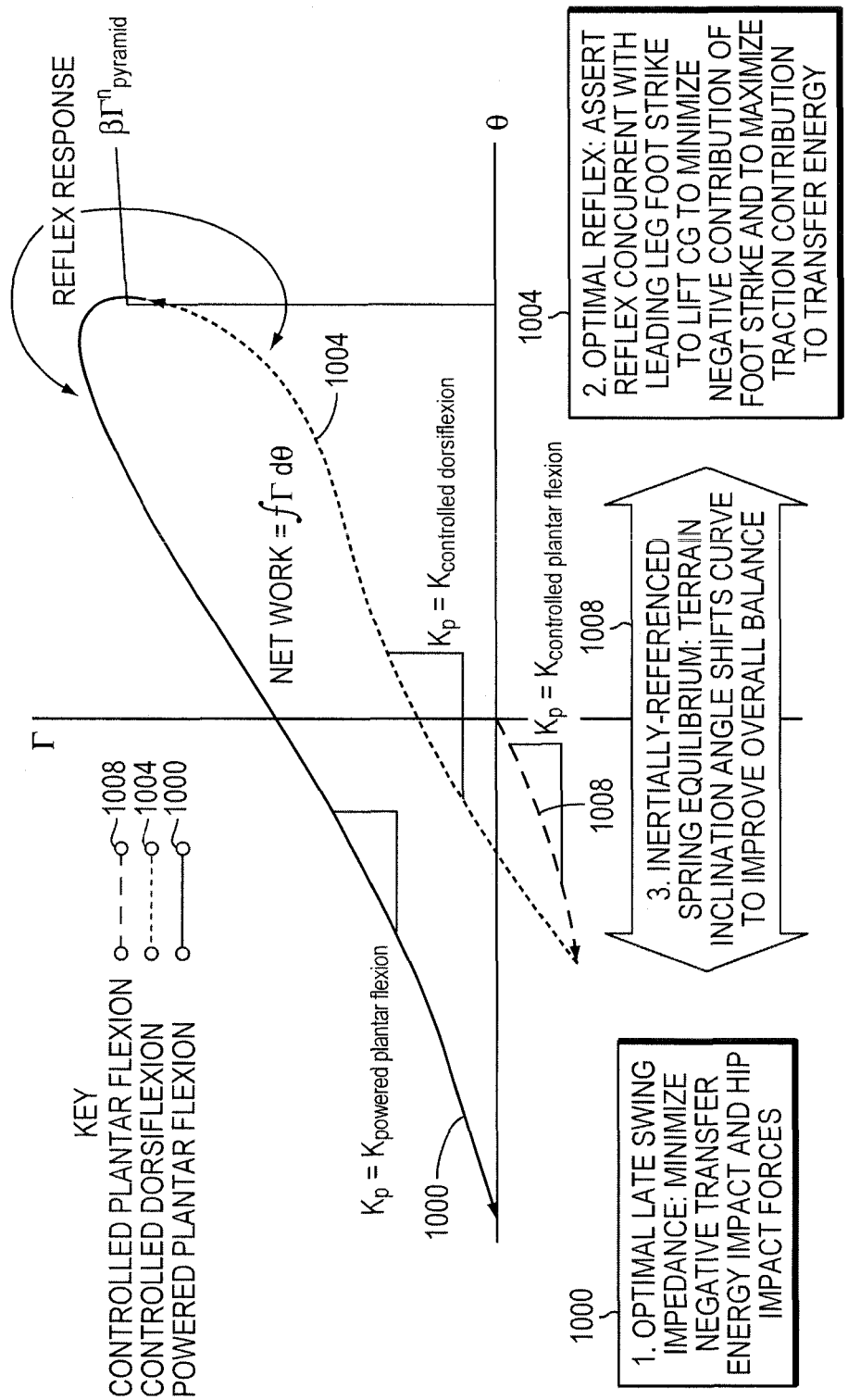
FIG. 10A illustrates a method for controlling a lower-extremity apparatus, according to an illustrative embodiment of the invention.

FIG. 10A illustrates a method for controlling a lower-extremity apparatus, according to an illustrative embodiment of the invention. As shown in FIG. 10A, this is achieved in the control system by 1) adjusting the late swing impedance (step 1000) (the dynamic stiffness and ankle-angle equilibrium angle) so as to soften the impact between the time interval between foot-strike and foot-flat, as described herein with respect to FIG. 7A (the controller shifts the curve ($\Gamma$–$\Theta$) (thereby altering the impedance of the ankle joint $K_{powered\ plantarflexion}$) based on a minimization of the negative transfer energy impact and hip impact forces during powered plantarflexion.
2) introducing a lifting force in the trailing leg—accomplished by asserting a reflex response in the ankle (and knee) at or before the time of impact of the leading leg (step 1004); and
3) maintaining an inertially-referenced equilibrium angle in the controlled dorsiflexion phase to maintain balance (equilibrium) (as described an illustrated in FIG. 10F) on sloping terrain (step 1008).

Figures 10B, 10C:
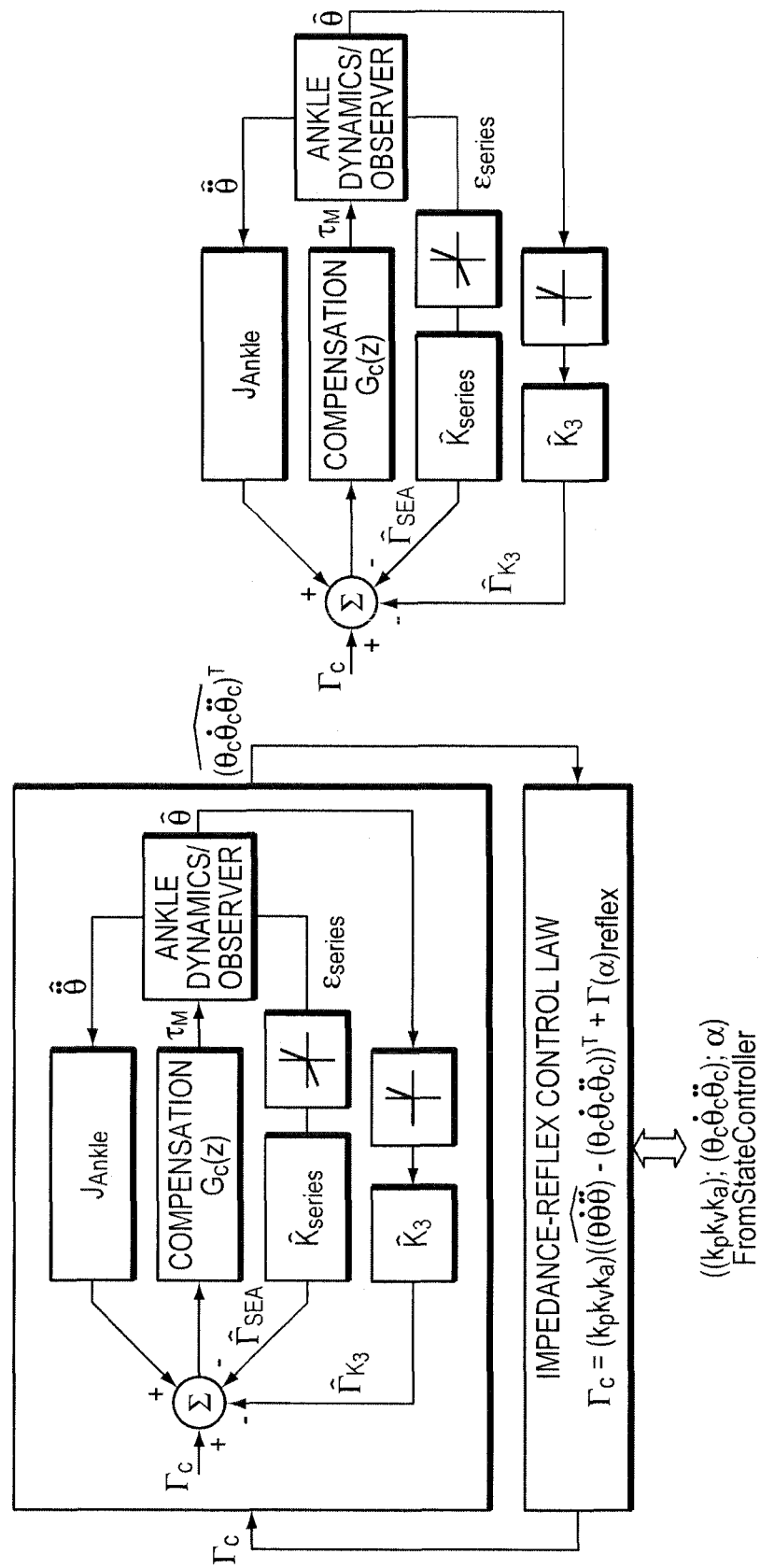
FIG. 10B is a schematic illustration of a model-based controller for implementing impedance and torque control in a lower-extremity prosthetic apparatus, according to an illustrative embodiment of the invention.
FIG. 10C is a schematic illustration of a model-based controller for implementing torque control in a lower-extremity prosthetic apparatus, according to an illustrative embodiment of the invention.

FIG. 10B is a schematic illustration of controller for implementing impedance and torque control in a lower-extremity prosthetic apparatus (e.g., the apparatus 1700 of FIGS. 17A-17E), according to an illustrative embodiment of the invention. FIG. 10E is a schematic illustration of the impedance and reflex relation that governs the impedance and reflex control performed in FIG. 10B.

As shown, the spring, damping and inertial components of the impedance are defined in relation to a trajectory, $\theta_0(t)$. Both the impedance gain matrix and trajectory illustrated in FIG. 10B are loaded adaptively and in real-time from the state controller processor in accordance with the phase in the gait cycle, the terrain context, terrain texture and walking speed as described above.

Studies have shown that intact limbs exhibit reflex responses that arise from non-linear positive torque (force) and non-linear positive joint velocity feedback. The reflex relations as illustrated in FIG. 10E employ both types of feedback. Other non-linear implementations of these positive feedback relations can be used, including piece-wise linear and piece-wise non-linear as would be obvious to those skilled in the art. In the preferred embodiment, positive torque feedback is achieved by measuring the torque in the shank of the ankle prosthesis and employing this as the non-linear feedback signal, $\hat{\Gamma}$. In other implementations, this reflex torque input can be estimated using a model-based computation of ankle dynamics.

The inventors have observed that the biomimetic impedance and reflex in stance are coupled when the effects of walking speed and terrain slope are taken into account as shown in FIG. 9. For this reason, in one preferred embodiment, the parallel elasticity (e.g., parallel, or K3 spring) for the prosthesis is picked so as to represent the stiffness for the slow walking speed as shown. In biomimetic systems, the stiffness component of the prosthesis is attenuated at higher walking speeds and the reflex response is steeper as shown in FIG. 9. Through this optimal biomimetic control and mechanical implementation, the response then requires the actuator to push on the parallel spring in controlled dorsiflexion and to pull on it in powered plantar flexion. We call this bipolar, or push-pull, operation. In non-optimal control and mechanical implementations, the reflex is implemented by a unipolar, pulling-force-only of twice the magnitude. The preferred embodiment thereby reduces the peak actuator force and motor current by a factor of two, thereby extending the actuator design-life by 8× and reducing ball-nut speed by nearly a factor of two when an appropriate bilateral series spring response is chosen. This has tremendous advantages in increasing the actuator durability, reducing actuator weight—the number of ball-bearings and ball-nut diameter needed to achieve a design life target are reduced—and reducing acoustic noise.

FIG. 10C is a schematic illustration of a controller for implementing impedance control in a lower-extremity prosthetic apparatus (e.g., the apparatus 1700 of FIGS. 17A-17E), according to an illustrative embodiment of the invention. FIG. 10D is a schematic illustration of the mechanical impedance relation that governs the impedance control performed in FIG. 10C. $\tau_M$ is the torque applied by the linear actuator to the ankle joint of a lower extremity prosthetic apparatus. Through suitable "high-gain" compensation, $G_c(z)$, where z denotes a discrete-time signal transform, it is obvious that the motor torque will work to make the sum of the torques applied by 1) the series-elastic actuator, 2) the "K3" parallel elasticity and 3) the acceleration torque on the ankle equal to the torque command, $\Gamma_c$, which is the desired result. The $\hat{K}_3$ and $\hat{K}_s$ are are used to denote model estimates for these mechanical parameters, hence the reference to model-based control.

Figure 10F:
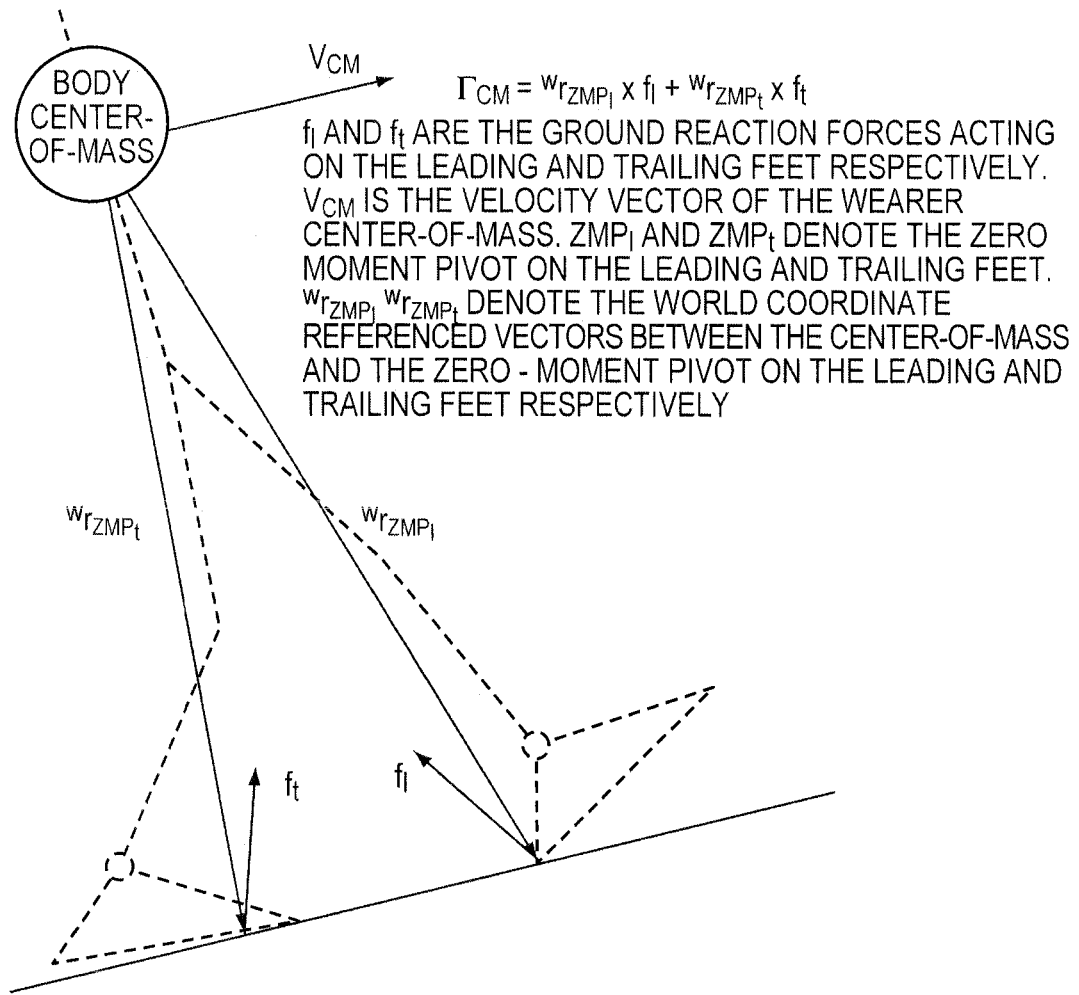
FIG. 10F is a schematic illustration of how zero moment pivot referenced ground reaction forces are used to determine the restoring torque necessary to stabilize inverted pendulum dynamics of a person wearing a prosthetic apparatus.

FIG. 10F is a schematic illustration of how zero moment pivot referenced ground reaction forces are used to determine the restoring torque necessary to stabilize inverted pendulum dynamics of a person wearing a prosthetic apparatus. The torque ($\Gamma_{CM}$) is applied at the center-of-mass of the system (combination of, for example, the person wearing the prosthetic and the prosthetic) to maintain the balance of the wearer based on the following:

$$\Gamma_{CM} = {}^w r_{ZMP_l} \times f_l + {}^w r_{ZMP_t} \times f_t \qquad \text{EQN. 33}$$

where $f_l$ and $f_t$ are the ground reaction forces acting on the leading and trailing feet, respectively. $v_{CM}$ is the velocity vector of the wearer center-of-mass. $ZMP_l$ and $ZMP_t$ denote the zero moment pivot on the leading and trailing feet. ${}^w r_{ZMP_l}$ and ${}^w r_{ZMP_t}$ denote the world coordinate referenced vectors between the center-of-mass and the zero moment pivots on the leading and trailing feet respectively. The term zero moment pivot refers to the inertially-referenced point on the foot about which the moment of the ground reaction force distribution is zero. We will also refer to this point as the center-of-pressure (CoP) interchangeably throughout the remainder of this document.

Ground Reaction Forces and Zero Moment Pivot

Ground reaction forces (GRF) are the forces imparted by and underlying surface onto the foot (or foot member of a lower-extremity apparatus). Ground reaction forces are important biomechanical inputs during stance. By knowing the aggregate ground reaction force acting at the zero moment pivot (referred to as ZMP and CoP herein), the control system (e.g., controller 1712 of FIG. 17A) of a lower-extremity prosthetic apparatus has a direct way of improving balance (of the wearer) and of optimizing power delivery during the stance phase. U.S. Pat. No. 7,313,463, issued to Herr et al. further describes estimating ground reaction forces and the zero moment pivot position as well as biomimetic motion and balance controllers for use in prosthetics, orthotics and robotics and methods (the entire contents of which are hereby incorporated by reference in its entirety).

Figure 11A:
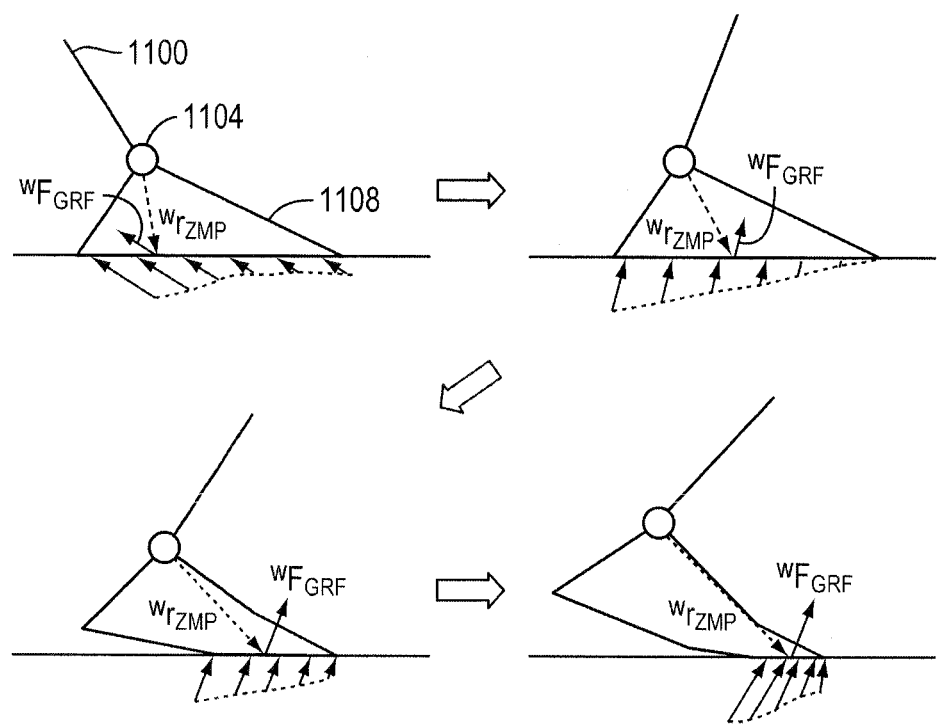
FIG. 11A is a schematic illustration of a lower leg foot member, ankle joint, and foot member of an ankle prosthesis showing ground reaction forces and the zero moment pivot.

FIG. 11A is a schematic illustration of a lower leg foot member 1100, ankle joint 1104, and foot member 1108 of a prosthesis (e.g., apparatus 1700 of FIG. 17A) that shows how the GRF components (specifically the vector from the ankle joint 1104 to the ZMP, ${}^w r_{ZMP}$, and the GRF vector, ${}^w F_{GRF}$) change during the stance phase in a typical walking cycle. The GRF estimation in research settings is often accomplished by applying sensors on the sole of the shoe. But, such extrinsic sensing may not be practical in prosthetic and orthotic devices because reliable packaging means should preferably survive the contact stresses over millions of walking cycles; which the sensors typically used in a research setting are unable to do so. Further, such means often require customization of the shoe which is often not acceptable to the wearer.

Figure 17B:
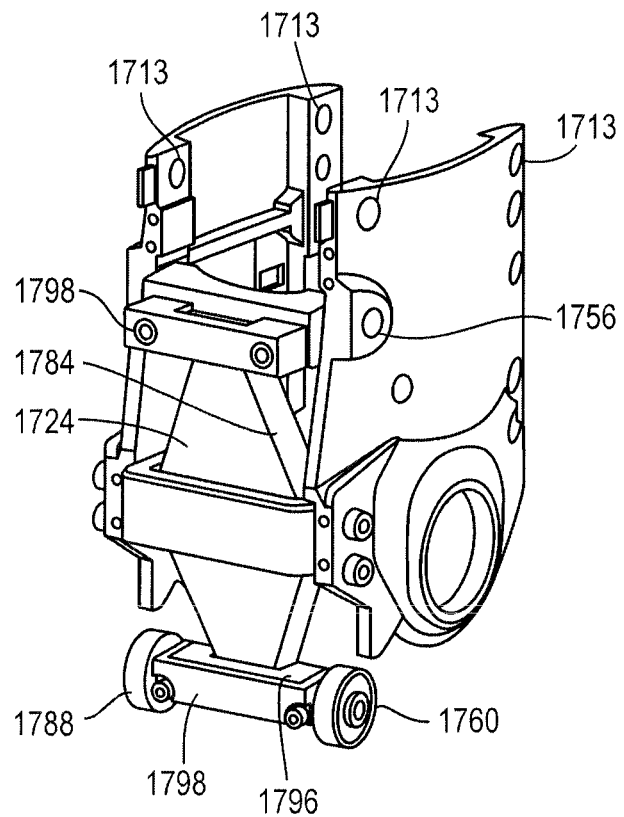
FIG. 17B is an illustration of a portion of the lower extremity apparatus of FIG. 17A that depicts a passive parallel elastic element.
Figure 17C:
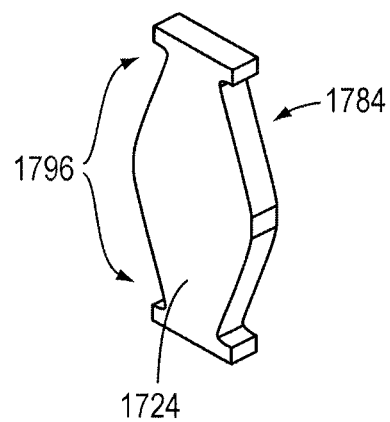
FIG. 17C is an illustration of the passive parallel elastic element of the apparatus of FIG. 17B.
Figure 17D:
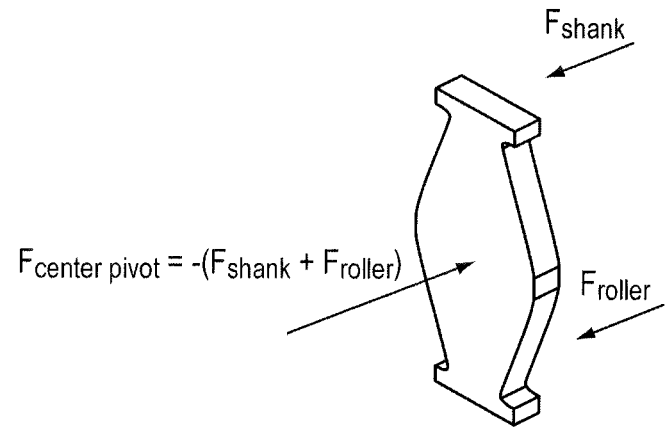
FIG. 17D is an illustration of the free-body diagram for the passive parallel elastic element of FIG. 17C, according to an illustrative embodiment of the invention.
Figure 17D:
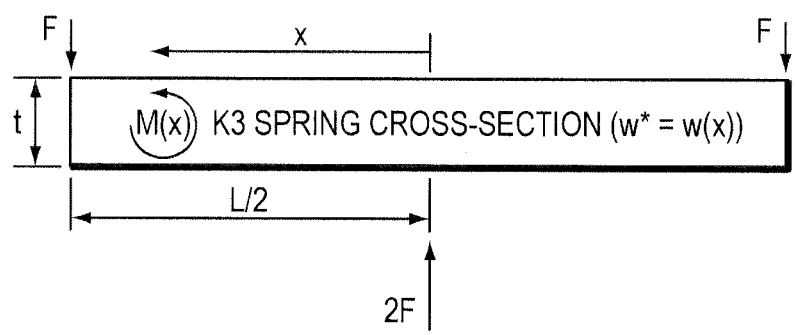
Figure 17E:
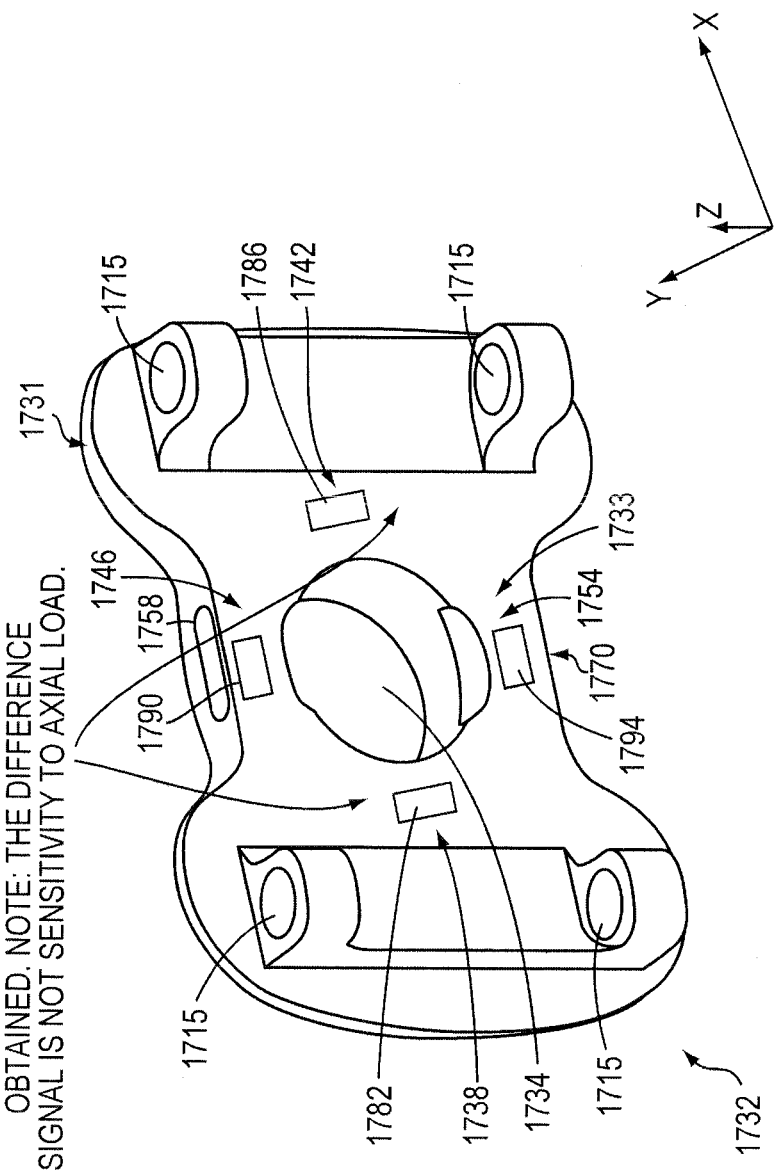
FIG. 17E is an illustration of a perspective view of the structural element (pyramid) of the apparatus of FIG. 17A, according to an illustrative embodiment of the invention.

In another embodiment of the invention, intrinsic sensing of the GRF is accomplished in a novel way by combining inertial state and lower leg member force/torque inputs 1112 (using, for example, the structural element 1732 of FIGS. 17A and 17E).

Figure 11B:
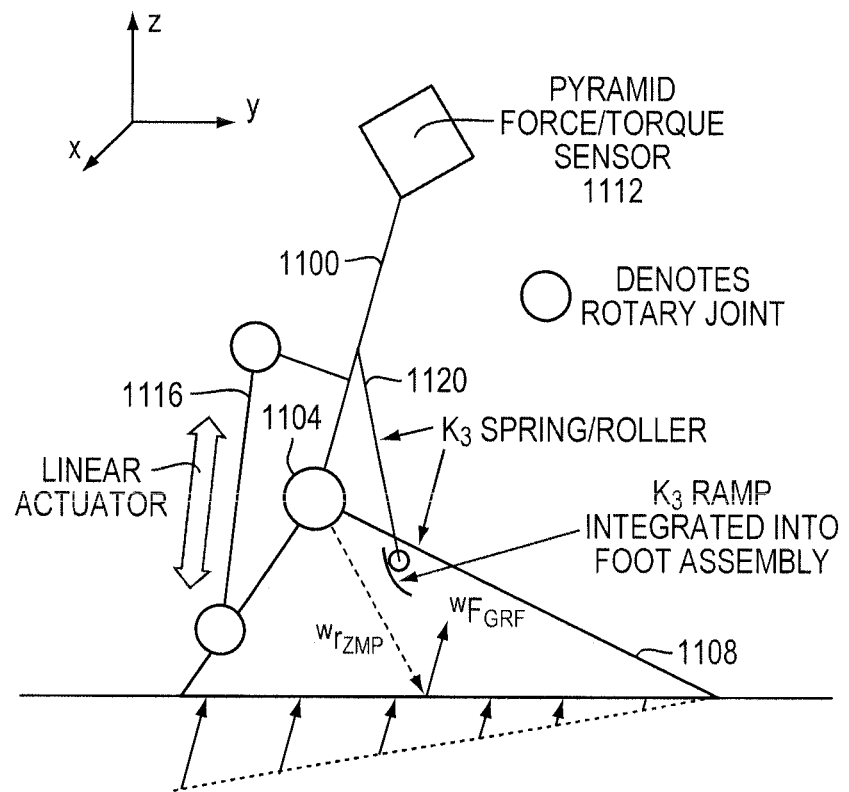
FIGS. 11B-11D are schematic illustrations of the components of an ankle prosthesis showing the force and moment relationships among the components necessary to determine the ground reaction forces and the zero moment pivot.
Figure 11C:
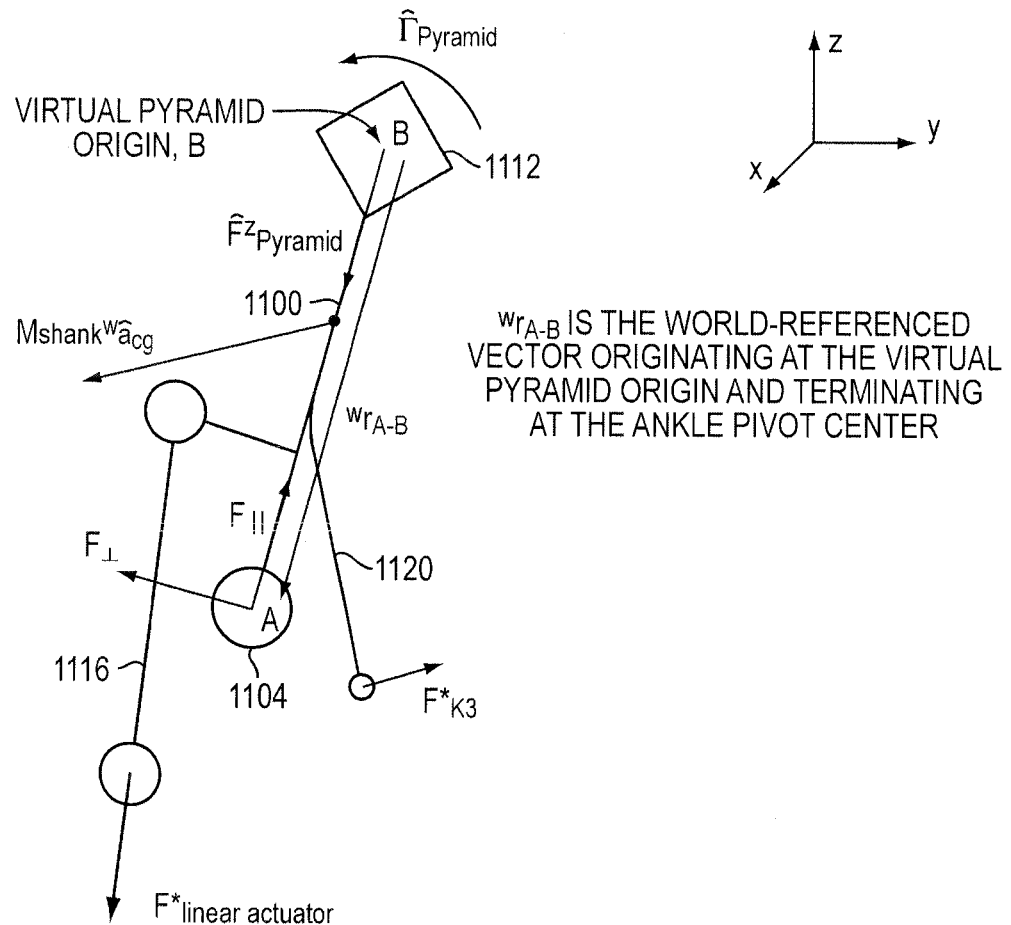
Figure 11D:
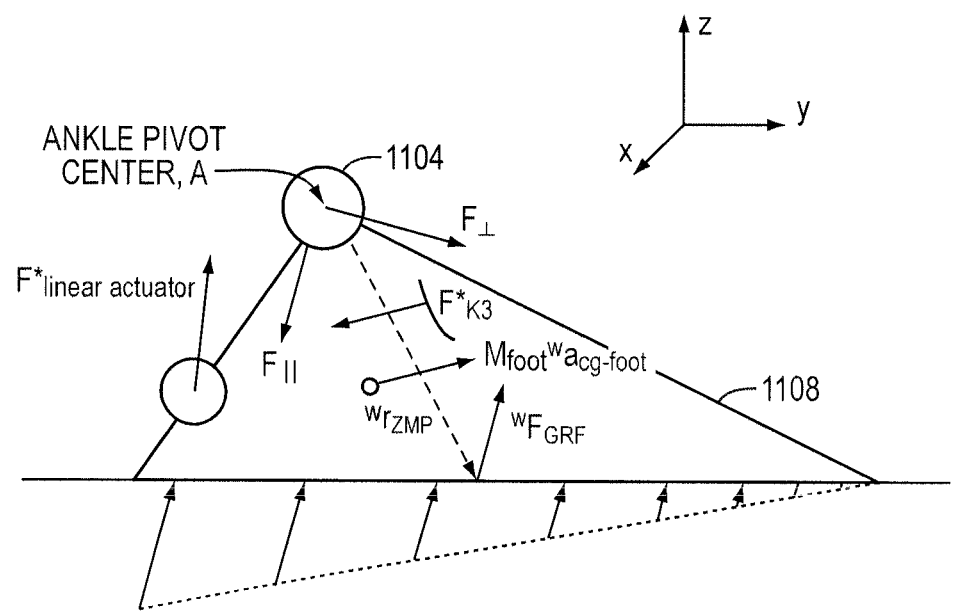

FIGS. 11B, 11C, and 11D are schematic illustration of the components of the apparatus 1700 of FIG. 17A. The figures also show the force and moment relationships among the components (linear series elastic actuator 1116 (e.g., combination of linear actuator 1716 plus series elastic member 1724 of FIG. 17A) and parallel spring 1120 (e.g., passive elastic member 1724 of FIG. 17A) necessary to determine the ground reaction forces and the zero moment pivot. ${}^w r_{ZMP}$ and ${}^w F_{GRF}$ are computed based on the following steps:

1. Update inertial state of the lower leg member 1100 and foot member 1108 using inertial measurement unit and ankle joint 1104 angle inputs. Using rigid-body assumptions, further calculate the world-referenced acceleration measured at the center-of-mass (CM) of the lower leg member 1100 and foot member 1108 and the angular velocity and acceleration of the lower leg member 1100 and foot member 1108.
2. Solve for F∥ as a function of the forces acting upon the lower leg member 1100 as these are resolved along the lower leg member 1100 axis.
3. Solve for F⊥ as a function of the moments applied by each of the force and moment components acting upon the lower leg member 1100.
4. Solve for ${}^w F_{GRF}$ using the values for F∥ and F⊥ computed in steps 2 and 3 above and then balancing the forces applied on the foot member 1100.
5. Balance the moments about the ankle joint 1104 assuming that ${}^w F_{GRF}$ is applied at the foot-ground boundary (i.e., ${}^w r_{ZMP}{}^z = 0$).
6. Solve for ${}^w r_{ZMP}{}^y$.

Ankle Joint Behavior Due to Terrain Texture

Figure 12A:
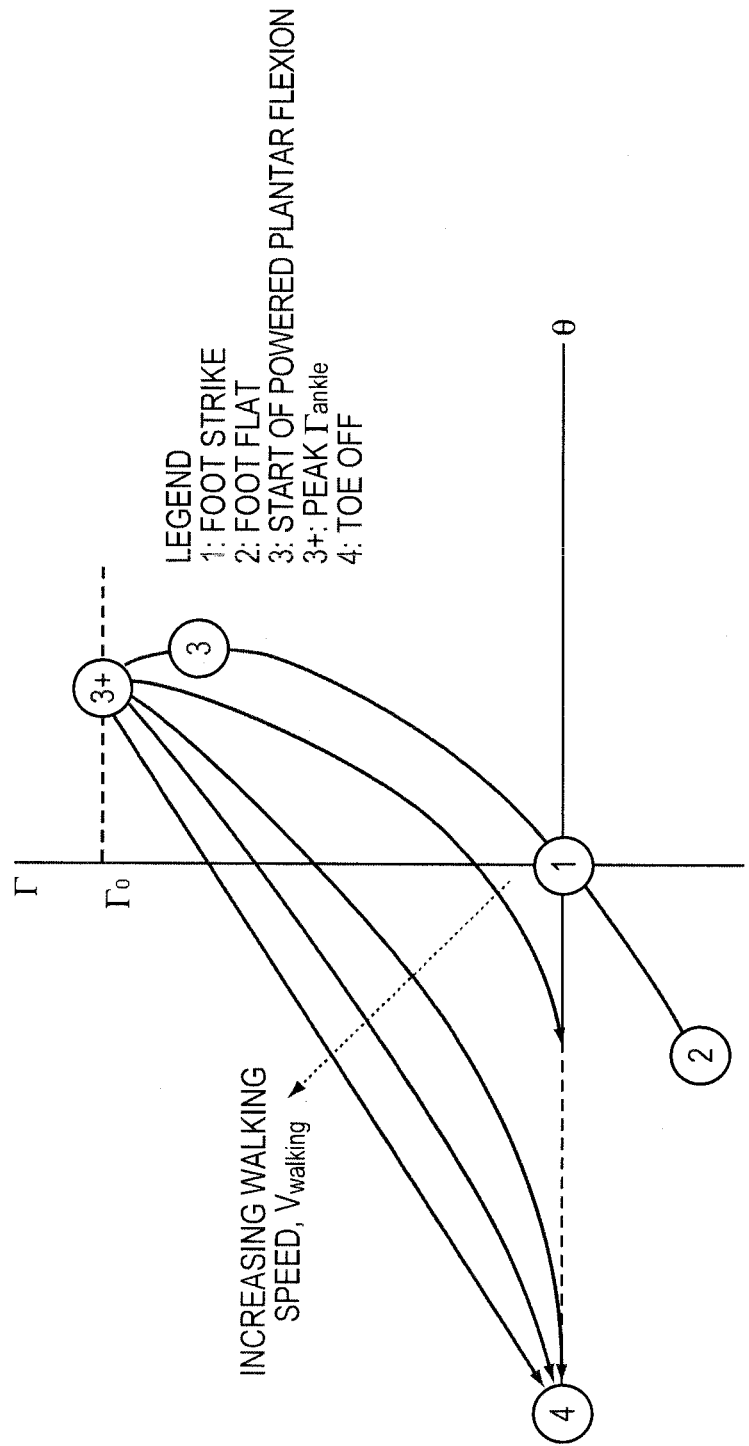
FIGS. 12A-12B illustrate the biomimetic (Γ-θ) behavior of an ankle prosthesis on level ground as a function of walking speed during powered plantarflexion.
Figure 12B:
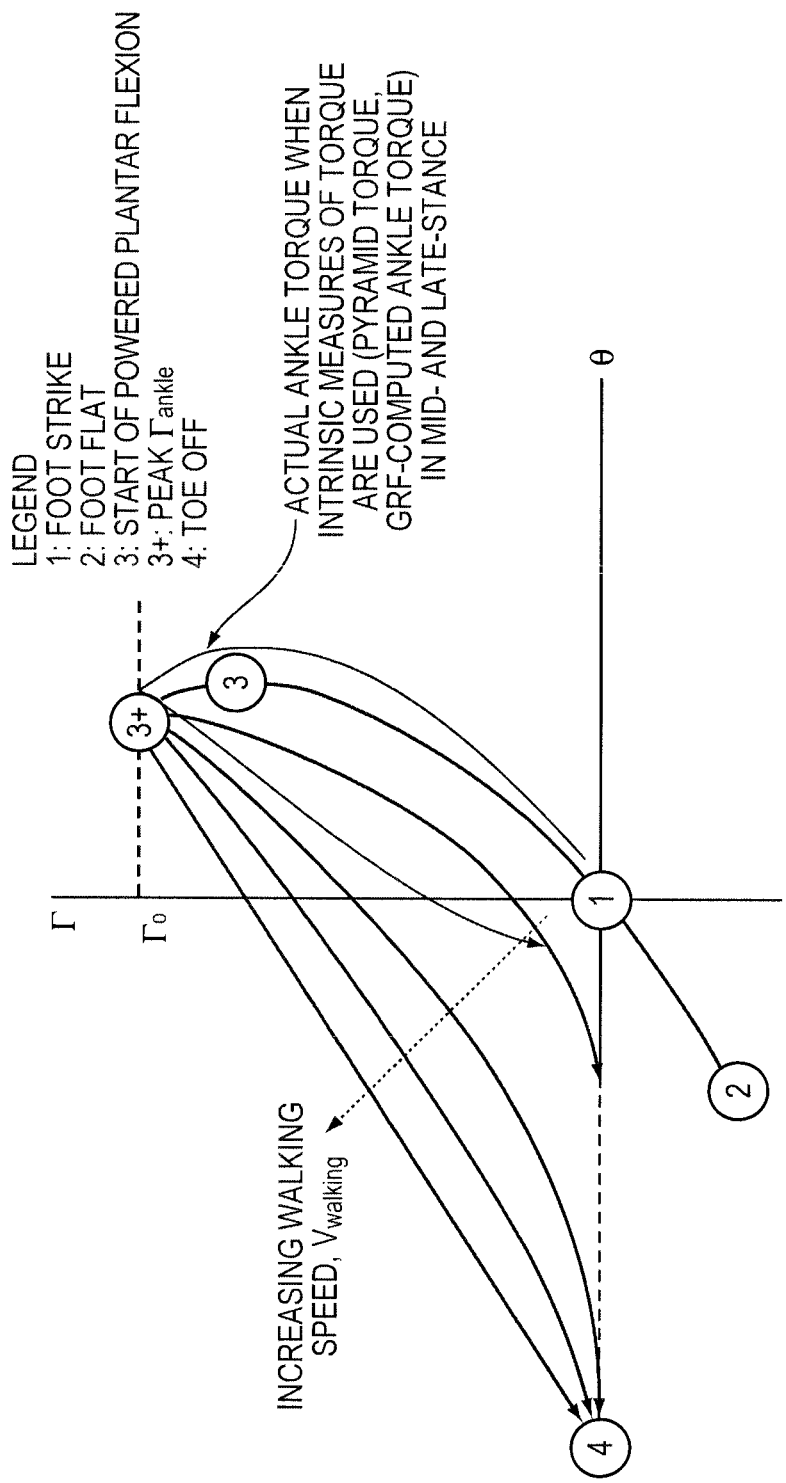

FIG. 12A illustrates the biomimetic Γ–θ behavior of a prosthetic apparatus (e.g., apparatus 1700 of FIG. 17A) on level ground as a function of walking speed. FIG. 12B shows that the applied ankle joint torque diminishes rapidly with angle during powered plantarflexion, thereby departing from the ideal biomimetic response and thereby significantly reducing the net work performed (area under the Γ–θ curve), particularly when walking at high speed.

In conventional robotic systems, trajectories or other playback means are employed to deliver repeatable and programmable responses. Such means are not preferable in prosthetic and orthotic devices because wearer intent may change in the middle of a playback segment. For instance, the wearer might be walking fast, then suddenly stop in front of a patch of ice for instance. If pre-programmed trajectories or other are played back, there is no easy way of aborting them without rapid changes of force and torque—and without introducing hazards. Indeed, that is why the intrinsic means are used.

Figure 12C:
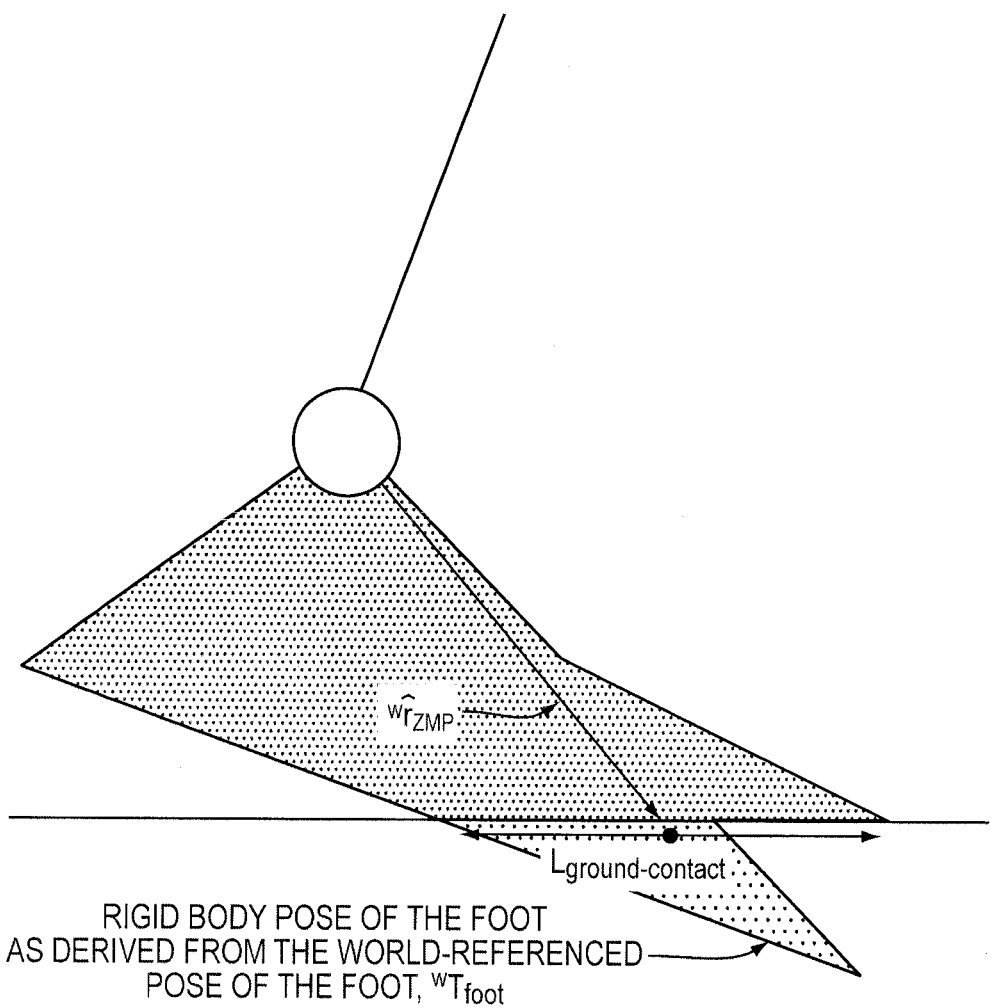
FIG. 12C-12D illustrate the effect of foot transitions on ground contact length.
Figure 12D:
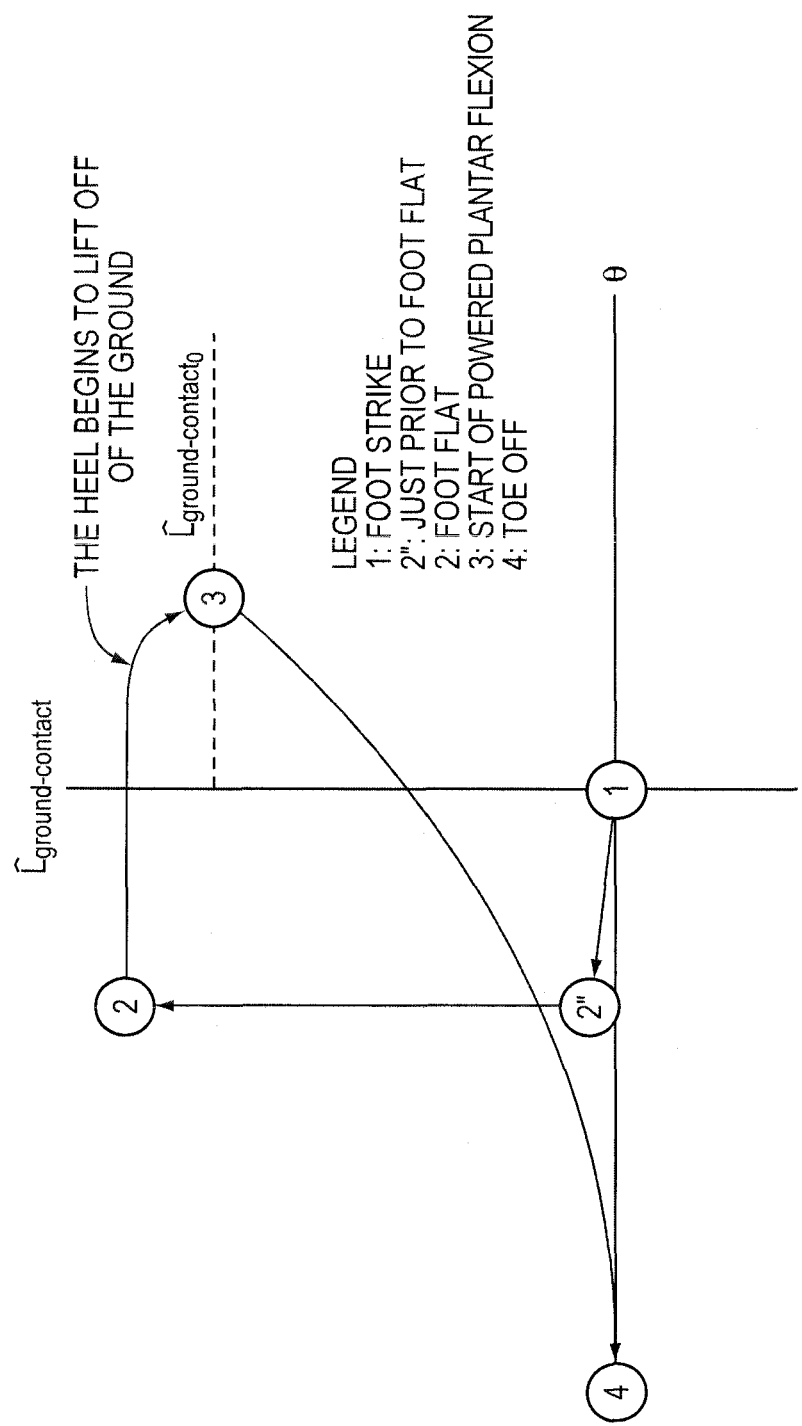

To extend the application of ankle joint torque during powered plantarflexion, walking speed-dependent normalized ground contact length are used as the means of attenuating the peak plantarflexion torque, $\Gamma_0$. Ground contact length is estimated by using an idealized model of the foot derived per the description related to FIGS. 2A-5 and by measuring the inertial pose of the foot member during controlled dorsiflexion and powered plantarflexion. As shown in FIG. 12C, as the foot transitions from foot flat to toe-off, sections of the idealized foot will fall below the terrain, enabling an estimate of ground contact length. FIG. 12D shows how $L_{ground-contact}$ changes from foot flat to toe off.

Figure 12E:
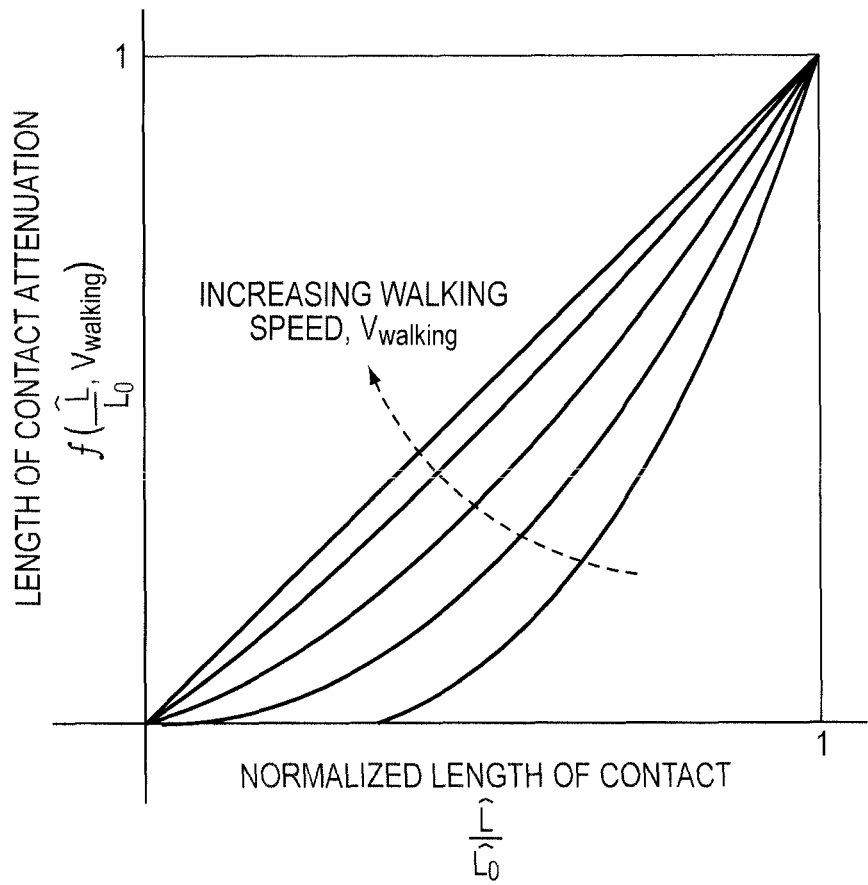
FIG. 12E illustrates how velocity-dependent tables of length of contact attenuation can use normalized ground contact length as a means to achieve biomimetic behavior during powered plantarflexion.

FIG. 12E illustrates how velocity-dependent tables of Length of Contact Attenuation can use normalized ground contact length as a means to achieve biomimetic behavior during powered plantarflexion. The tables can be computed by dynamically measuring the ground reaction force and foot member pose of non-amputees in controlled environments as a function of walking speed. The functional relationships between the attenuation function and ground contact length can be computed for each walking speed. These tables can be stored in the controller of the prosthetic apparatus as reference relationships. The functions can be shaped to suit specific wearer needs when the prosthetic apparatus is fitted to the wearer.

As described earlier, one of the motivations to use intrinsic feedback as opposed to explicit trajectory or playback means is to accommodate changes in wearer intent (e.g., decision to stop quickly). Intrinsic sensing using ground contact length as a means of attenuating ankle joint torque is not sufficiently general to accommodate changes in wearer intent involving stopping and changing direction. Referring to FIG. 12G, in one embodiment of the invention implemented on a prosthetic apparatus, a time-dependent attenuation factor ($e^{-t/\tau}$) is used in series with the ground contact length attenuation. The time constant for this attenuation, $\tau$, can be picked so as to extinguish the powered plantarflexion drive torque so as to prevent hazards associated with changes in wearer intent. $\tau$ will typically range from 50-100 msec.

Preferably, the prosthetic apparatus enables the wearer to walk faster with less effort on all terrain. It is not sufficient to accommodate just changes in terrain context (stairs, sloping ascent/descent). Changes in terrain texture as this might introduce slipping (e.g., Ice/snow) or sinking (mud, snow, sand, fine gravel) hazards should preferably be accommodated. Intrinsic sensing of the zero moment pivot trajectory can be used to optimize walking performance and/or to eliminate hazards while walking on varying terrain texture.

Figure 12F:
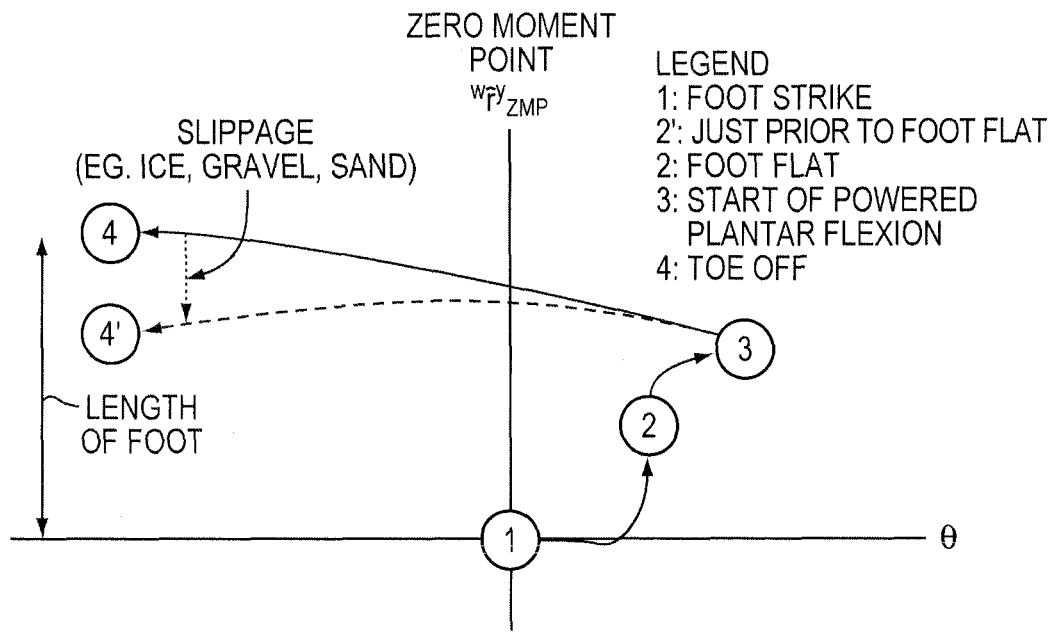
FIG. 12F illustrates how the estimated, y-component of the zero moment pivot vector changes during a typical walking motion.
Figure 12G:
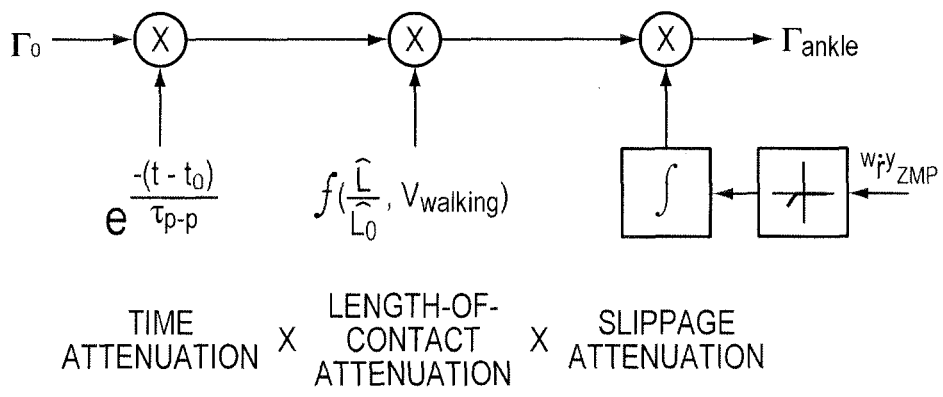
FIG. 12G illustrates a method for incorporating an attenuation factor into performance of an apparatus, according to an illustrative embodiment of the invention.

FIG. 12F illustrates how the estimated, y-component of the zero moment pivot vector, ${}^w\hat{r}_{CoP}{}^y$, changes during a typical walking motion. As shown, in a no-slip condition ${}^w\hat{r}_{CoP}{}^y$ must increase monotonically between the conditions of foot-flat (3) and toe-off (4). This is because it is the heel that is lifting off of the terrain surface during this period (increasingly as the walking cycle progresses). If the velocity of the zero moment pivot ever moves along the negative y-axis, the foot is slipping. In a fashion similar to how anti-lock brakes are implemented in vehicles, the prosthetic apparatus can reduce torque by an attenuation factor derived from the integral of the negative zero moment pivot velocity. In one embodiment, so as to reduce noise sensitivity, only negative velocities below a noise threshold are integrated.

Figure 13A:
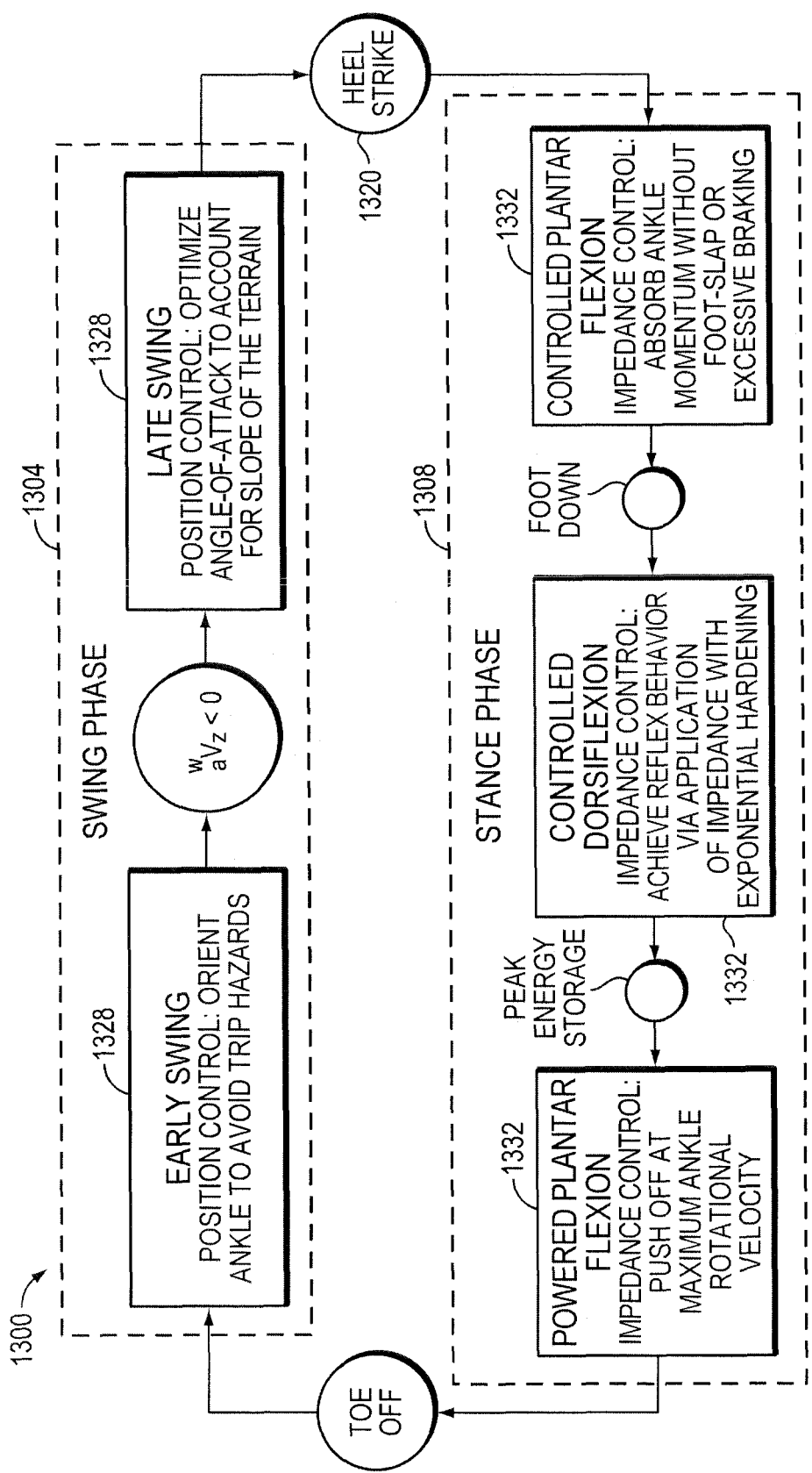
FIG. 13A is a schematic representation of a control system scheme for a heel strike case, according to an illustrative embodiment of the invention.
Figure 13B:
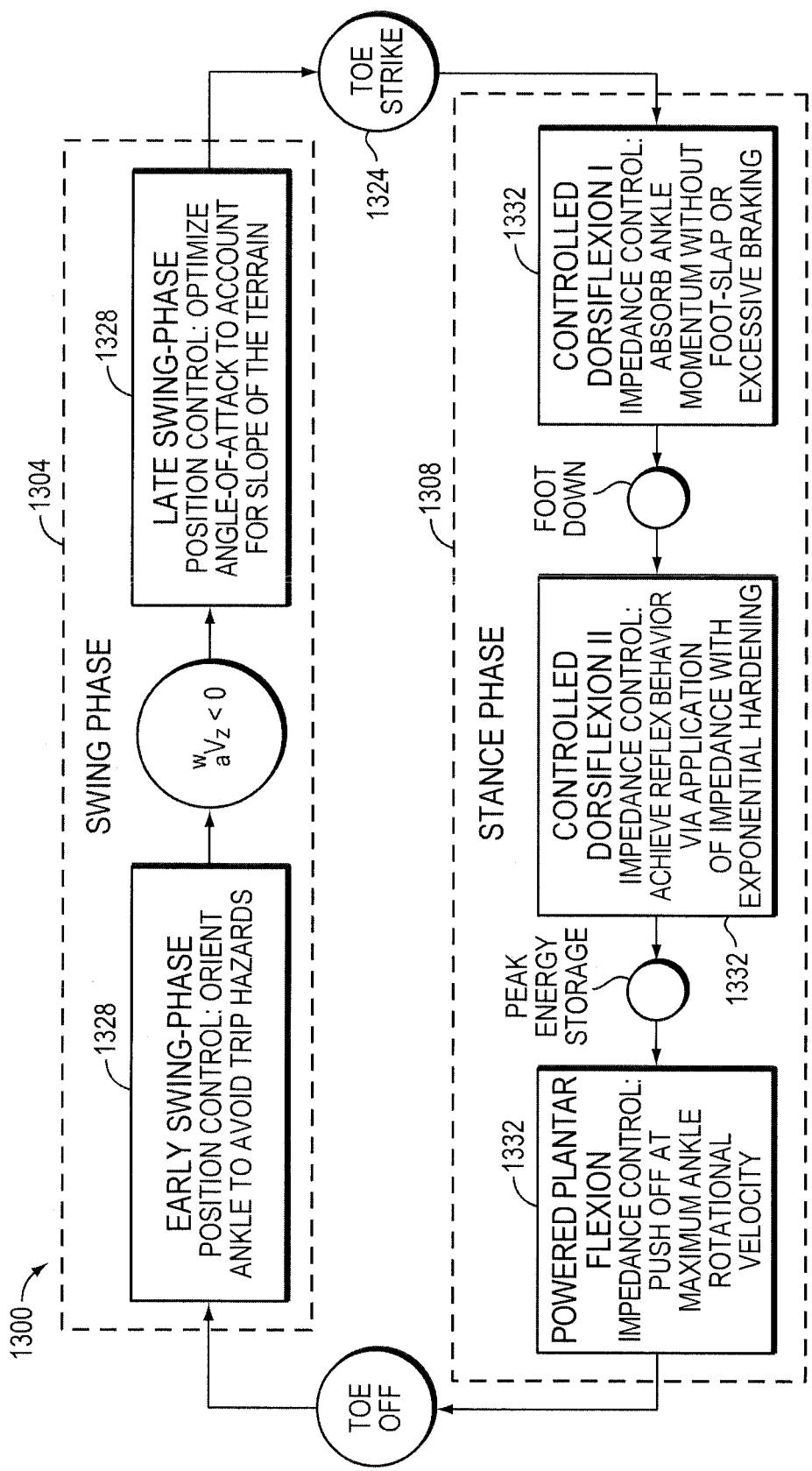
FIG. 13B is a schematic representation of a control system scheme for a toe strike case, according to an illustrative embodiment of the invention.

FIGS. 13A and 13B provide the state control context for an illustrative embodiment of the invention applied to, for example, apparatus 1700 of FIGS. 17A-17E. Normal walking involves the cycling between two phases: the swing phase and the stance phase. FIG. 13A depicts a control system scheme involving a walking motion in which the stance phase is initiated by the heel striking 1320 the ground. ${}_a{}^wV_z$ denotes the z-component of the ankle joint velocity in the ground-referenced, world frame. FIG. 13B shows a walking motion in which the stance phase is initiated by the toe striking 1324 the ground.

Exemplary Control System Behavior for Driving Prosthesis or Orthosis Through Gait Cycle FIGS. 13A and 13B illustrate that the control system 1300 changes ankle behavior as the ankle transitions between states in the swing 1304 and stance phases 1308. The control system 1300 applies position control 1328 in the swing phase—positioning the ankle so as to avoid trip hazards in the early swing phase state and so as to optimize heel-toe strike attack angle (adaptive ankle positioning) for specific terrain conditions (slope, stairs, steps) in the late swing phase state. The control system 1300 applies impedance and torque control 1332 in the stance phase—optimizing the inertial, spring and damping characteristics of the ankle—as the ankle transitions through the heel/toe strike, foot down, peak energy storage (dorsiflexion with exponential hardening), powered plantarflexion and toe-off events.

Figure 13C:
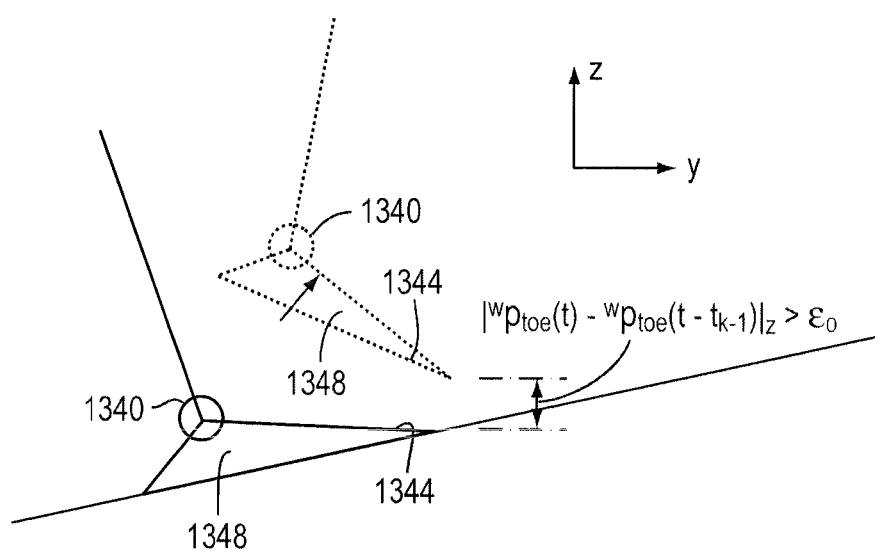
FIG. 13C illustrates a method for position control applied to an ankle prosthesis (e.g., apparatus 1700 of FIG. 17A), according to an illustrative embodiment of the invention.

FIG. 13C illustrates a method for position control applied to a lower limb apparatus (e.g., apparatus 1700 of FIG. 17A), according to an illustrative embodiment of the invention. It is desirable to not move the foot member 1348 forward until the wearer and/or the controller of the apparatus are sure the toe 1340 is going to clear the terrain in front of the wearer. One exemplary way to accomplish this is to wait until the toe 1340 of the foot member 1348 is a sufficient distance above the last known position of the toe 1340 with respect to the underlying terrain. In this embodiment, the control system 1300 applies position control 1328 by beginning to rotate the ankle joint 1340 only after the clearance distance measured along a normal vector to the terrain surface between the toe 1340 of the foot member 1348 at time t and at time $t_{k-1}$ is determined to be greater than ($\epsilon_0$). This minimizes the risk that the toe 1340 will encounter a trip hazard. In one embodiment, the position of the toe 1344 at the two different times (t and $t_{k-1}$) are determined using the inertial measurement unit measurements, as described previously herein. One skilled in the art would understand how to apply other schemes to determine when it is appropriate to move the foot member 1348 forward. In some embodiments, the controller may determine it is appropriate to move forward based on, for example, whether the swept volume of the foot, when dorsiflexed, achieves the desired clearance relative to the terrain surface.

In summary, this embodiment of the invention, the prosthetic apparatus employs step-by-step terrain adaptation with the intent to achieve true biomimetic behavior in all ambulation task contexts; including level-ground walking, stair ascent/descent and ramp ascent/descent. FIG. 14A outlines the process by which the step-by-step adaptation is accomplished. In the swing phase, the inertial measurement unit supplies the intrinsic sensing input (as opposed to say extrinsic neuronal/myoelectric inputs) that enables the apparatus to discern terrain context from cues supplied by swing-phase trajectory features. Adaptive swing-phase ankle positioning refers to the articulation of the ankle angle, θ, so as to achieve a natural heel or toe touchdown that is optimized for the most likely terrain context as determined by the terrain context discrimination on the swing phase trajectory cues.

Figure 14B:
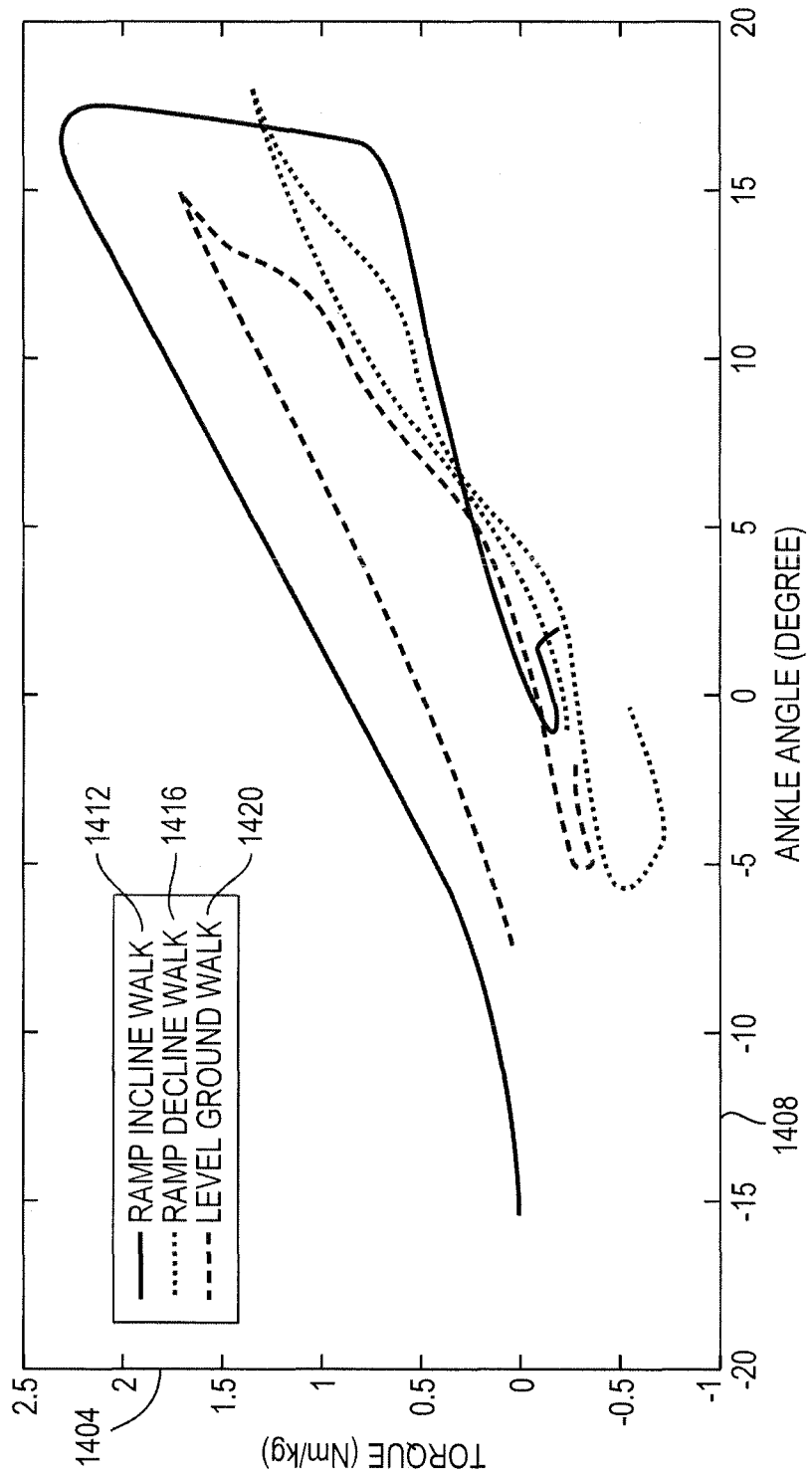
FIG. 14B illustrates exemplary impedance that an ankle joint prosthesis would apply for three different ambulation contexts.

FIG. 14B illustrates exemplary impedance that an ankle joint prosthesis would apply for three different ambulation contexts. FIG. 14B is a graph of required ankle torque 1404 (units of Nm/kg) versus ankle joint angle 1408 (units of degrees). The graph includes three curves 1412, 1416 and 1420. Curve 1412 illustrates the ankle joint torque 1404 versus ankle joint angle 1408 for walking on a ramp incline of 5 degrees. Curve 1416 illustrates the ankle joint torque 1404 versus ankle joint angle 1408 for walking on a ramp decline of 5 degrees. Curve 1420 illustrates the ankle joint torque 1404 versus ankle joint angle 1408 for walking on a ramp incline of 0 degrees (level ground). The slope of the curves is equal to the stiffness (or impedance in general). The area enclosed by the closed $\Gamma$-$\theta$ curve corresponds to the amount of non-conservative work required for the specific terrain context (e.g., slope, stairs) and walking speed. As can be seen in the graphs, an ankle joint prosthesis would be required to provide more work to accomplish the ambulation task of walking up an inclined ramp versus walking on level ground because the area within the curve 1412 is greater than the area within the curve 1416.

Generalization of the Hybrid Lower-Extremity Augmentation System

Figure 15:
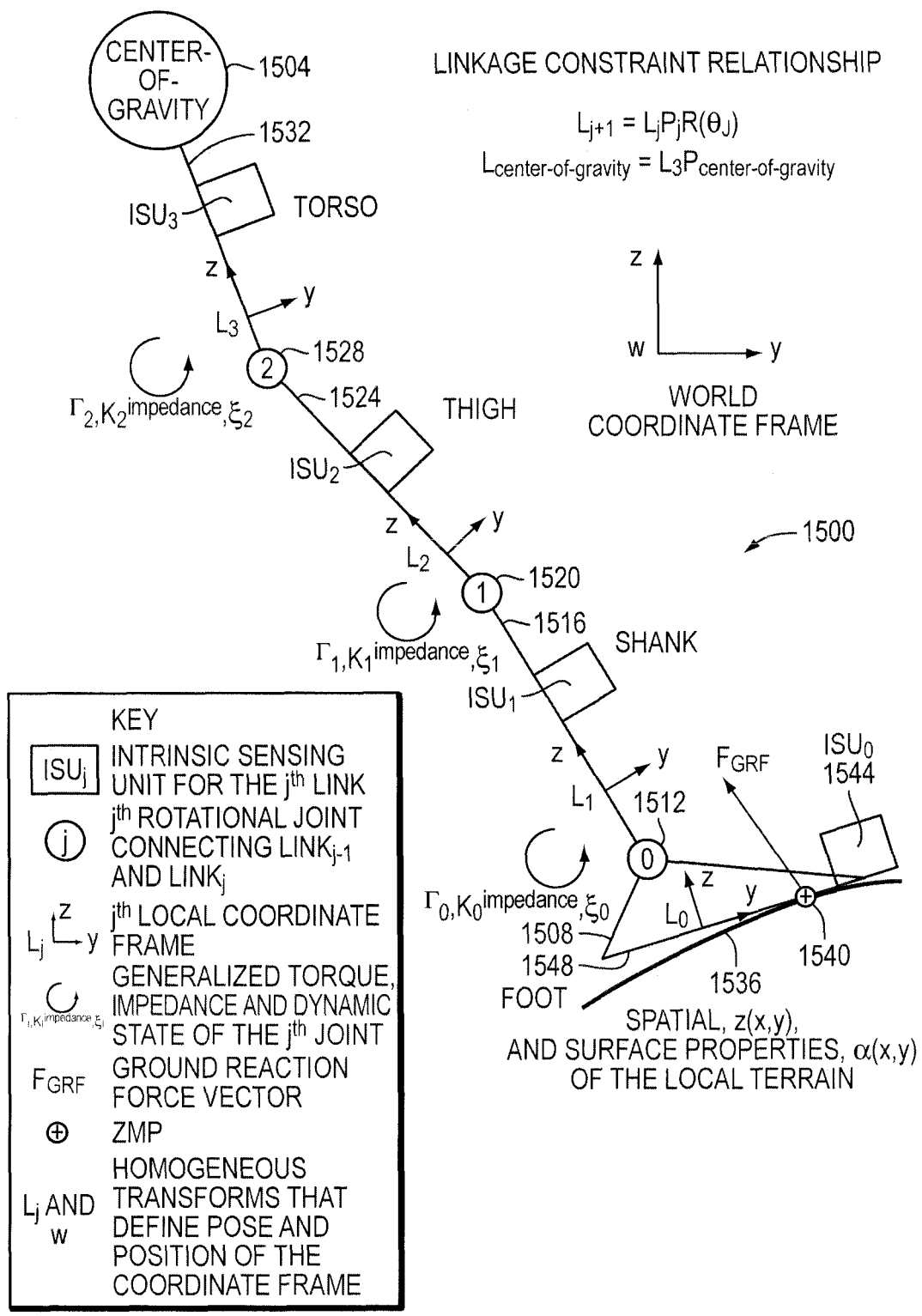
FIG. 15 is a schematic representation of a lower-extremity biomechanical system, according to an illustrative embodiment of the invention.

FIG. 15 is a schematic representation of a lower-extremity biomechanical apparatus 1500, according to an illustrative embodiment of the invention. In one embodiment, the apparatus 1500 is an orthotic apparatus that augments the ambulation abilities of the wearer. In another embodiment, the apparatus 1500 is an orthosis apparatus that attaches to a wearer's body to support and/or correct musculoskeletal deformities and/or abnormalities of a wearer's hip, thigh, lower leg and foot. In another embodiment, the apparatus 1500 is an exoskeleton apparatus that attaches to a wearer's body to assist or augment the wearer's lower-extremity biomechanical output (e.g., augment the lower-extremity strength or mobility of the wearer).

The apparatus 1500 is a linkage represented by a plurality of links (or members) and joints that connect the links. The apparatus 1500 includes a foot member 1508 ($L_0$) coupled to a lower leg member 1516 ($L_1$) by an ankle joint 1512. The apparatus 1500 also includes a thigh member 1524 ($L_2$) coupled to the lower leg member 1516 by a knee joint 1520. The apparatus also includes a hip joint 1528 that couples the thigh member 1524 to the torso 1532 ($L_3$) of the wearer. Center-of-mass 1504 is the center-of-mass of the combination of the apparatus 1500 and the wearer.

The foot member 1508 contacts the terrain 1536 underlying the foot member 1508 at the zero moment pivot 1540. The foot member 1508 includes a toe portion 1544 and a heel portion 1548. Each joint of the apparatus 1500 also includes an actuator with a generalized vector of torque (force) $\Gamma_j$, displacement $\xi_j$, and impedance $K_j$, where i=0 corresponds to the ankle joint 1512, i=1 corresponds to the knee joint, and i=2 corresponds to the hip joint. Each joint actuator may include a machine element (e.g., ball-screw actuator or rotary harmonic drive), human muscle, or both. Joint displacements typically take the form of angular displacement (rotation) but may also include a combination of linear and angular displacements as found in, for example, a typical knee joint. The pose of a link, i, is represented by a 4×4 matrix that defines the location of the link origin and the unit vectors of its coordinate frame in terms of the unit vectors in the world coordinate frame, W.

The pose of each link, j, can thereby be determined via linkage constraint relationships—specifically by multiplying the pose of link, i-1, by a transformation defined by the generalized displacement, $\xi_j$, and specific link parameters (link length, skew and convergence angles). For example, if the pose of the shank is known, the pose of the foot, thigh and torso can be computed provided that the generalized displacements for those linkages are known, either by directly sensing these or through the use of inertial sensors. The vector of sensor information intrinsic to each link is encapsulated in what we will call an intrinsic sensing unit (ISU). Examples of intrinsic sensors include direct or indirect measurement of generalized displacements; measurement of the angular rate and acceleration of the link (e.g., using, for example, an inertial measurement unit); measurement or estimation of the components of force or torque on the link; multi-modal computer imagery (e.g., a range map) or measurement of the outputs of specific neural pathways on or adjacent to the link.

The terrain is modeled as a contour function, z(x,y), with surface properties, $\alpha(x,y)$. In this context, the surface properties would include the elasticity/plasticity, damping characteristics and coefficient of friction of the surface sufficient to capture the ability of the foot to gain traction on the surface and to capture the surface energy as this would relate to the work required to touch down on the surface and to push off of it with the foot member.

FIG. 16 is a schematic illustration of a method for determining the pose of the thigh member, hip member and torso of a wearer, according to an illustrative embodiment of the invention. In lower-limb systems employing robotic knee prostheses or orthosis, the location of the human hip can also be computed, either by incorporating an inertial measurement unit on the thigh or by measuring the relative knee angle as referenced to the lower leg member. If an inertial measurement unit is further employed on the torso, the pose of the torso can also be instantaneously computed. Alternatively, the pose can be computed by measuring the two degree-of-freedom hip joint displacements. Compensation for the torso pose prediction errors arising from the rate gyro and accelerometer drift on the torso inertial measurement unit can be corrected during the lower leg member zero-velocity update through a chaining of velocity constraints through the hybrid system linkages.

FIG. 16 illustrates a method of pose reconstruction in which j, j-1 velocity constraints are used to correct the prediction of torso pose ($_{torso}{}^w\hat{T}(t=t_{zvup_i})$), thigh pose ($_{thigh}{}^w\hat{T}(t=t_{zvup_i})$) and torso/body center-of-mass pose ($^w v_{cg}(t=t_{zvup_i})$). Step 1 (1604) captures the output of the zero velocity update on the lower leg member 1620 (link 1) to determine the lower leg member pose, as described above with respect to FIGS. 2A-5. The solutions (steps 2 and 3) for the thigh member 1624 (link 2) and torso member 1628 (link 3), respectively, follow the example of step 1 (1604), but in these cases the velocity constraints are non-zero and are predicted by the translational and rotational velocity from the prior link.

Exemplary Mechanical Designs

FIG. 17A is an illustration of a lower-extremity prosthetic apparatus 1700, according to an illustrative embodiment of the invention. The apparatus 1700 has a mounting interface 1704 making it capable of attaching to a complementary lower-extremity limb socket member of a wearer. The apparatus 1700 also includes a structural element 1732 (also referred to herein as the pyramid) coupled to the mounting interface 1704 and a first end 1752 of a lower leg member 1712 (also referred to herein as a shank). In some embodiments, the axial force and moment applied to the lower leg member of the apparatus is determined based on sensor measurements made using the structural member (pyramid) coupled to the lower leg member of the apparatus. The pyramid is an instrumented structure that is a component of the prosthesis and which couples to the limb socket of the wearer. In one embodiment, the pyramid (structural element) measurements are used by a controller to determine axial force and moment applied to the lower leg member. In this embodiment, the structural element 1732 is coupled to the first end 1752 of the lower leg member 1712 with a set of pins 1711. The pins 1711 pass through a set of holes 1713 in the lower leg member 1712 and a set of holes 1715 (shown in FIG. 17E) in the structural element 1732.

The structural element 1732 has a top surface 1731 located towards the mounting interface 1704 and a bottom surface 1733 located towards the lower leg member 1712. The lower leg member 1712 is also coupled to a foot member 1708 at an ankle joint 1740 at a second end 1744 of the lower leg member 1712. The ankle joint 1740 (e.g., a rotary bearing) permits the foot member 1708 to rotate about the x-axis relative to the lower leg member 1712. The foot member includes a heel 1772 and a toe 1776.

The apparatus 1700 also includes a linear actuator 1716 with a first end 1736 and a second end 1748. The linear actuator 1716 generates a linear motion 1703. The first end 1736 of the linear actuator 1716 is coupled (with, for example, a rotary bearing) to the first end 1752 of the lower leg member 1712. The apparatus 1700 also includes a first passive elastic member 1728 in series with the linear actuator 1716. The passive elastic member 1728 is coupled to the foot member 1708 and the second end 1748 of the linear actuator 1716. The passive elastic member 1728 is coupled to the foot member 1708 (with, for example, a rotary bearing) at the proximal end 1730 of the passive elastic member 1728. A distal end 1726 of the passive elastic member 1728 is coupled between the second end 1748 of the linear actuator 1716 (with, for example a rotary bearing). The linear actuator 1716 applies torque about the ankle joint 1740.

The apparatus 1700 also includes an optional second passive elastic member 1724 with a first end 1756 and a second end 1760. The second passive elastic member 1724 provides a unidirectional spring force in parallel (provides parallel elasticity) with the lower leg member 1712. The first end 1756 of the second passive elastic member 1724 is coupled to the first end 1752 of the lower leg member 1712. The second end 1760 of the second passive elastic member 1724 is coupled to the foot member 1708. However, during plantarflexion the spring is not engaged, and therefore only provides a unidirectional spring force to the apparatus.

In some embodiments, the second passive elastic member 1724 is a non-compliant stop that stores little or no energy and limits further rotation of the ankle beyond a predefined angle during powered plantar flexion.

FIGS. 17B and 17C are illustrations of a portion of the lower extremity apparatus of FIG. 17A depicting the second passive elastic element 1724. The second passive elastic element 1724 stores energy during dorsiflexion but, not in plantarflexion. The elastic element 1724 has a double-cantilever engagement (clamped at a location 1780 between the first end 1756 and the second end 1760). The elastic member 1724 has a tapered shape 1784 that causes the elastic member 1724 to provide efficient energy storage by maximizing bending strain along the entire length (along the y-axis) of the elastic element 1724. In some embodiments, the normalized spring constant ranges from 0-12 Nm/rad/kg. At the high end of the range, the energy storage is approximately 0.25 J/kg.

A cam/ramp arrangement of the elastic member 1724 facilitates tailoring of the spring constant to the weight of the wearer. The cam element 1788 is located at the second end 1760 of the elastic member 1724. The ramp element 1792 is located on the foot member 1708. The cam element 1788 engages the ramp element 1792 during dorsiflexion; however, the cam element 1788 does not engage the ramp element 1792 or another portion of the apparatus 1700 during plantarflexion. Because the cam element 1788 does not engage the ramp element 1792 or another portion of the apparatus 1700 during plantarflexion, the elastic member 1724 stores energy only during dorsiflexion. In one embodiment, the position of the ramp element 1792 is screw-adjustable to allow the wearer or a second party to tailor the ramp engagement of the cam element 1788 so as to align the energy storage characteristics to the wearer's walking habits. An operator may adjust the position of the ramp element 1792 relative to the position of the cam element 1788 in order to modify the energy storage characteristics of the passive elastic member 1724.

In alternative embodiments, an actuator is integrated into the ramp to adjust the ankle joint angle at which the second passive elastic member 1724 (elastic member engagement angle) engages. This would enable the ankle joint 1740 to be dorsiflexed during the swing phase without engaging the elastic member 1724 when, for example, the wearer is ascending ramps and stairs, and while running.

The passive elastic element 1724 also functions to increase the frequency response of the apparatus 1700 when the elastic element 1724 is engaged in dorsiflexion. The apparatus 1700 dynamics in dorsiflexion benefit from a fast response (bandwidth) series elastic actuator (i.e., combination of the linear actuator 1716 and first passive elastic element 1728). The spring constant associated with the second passive elastic element 1724 increases the bandwidth of the apparatus 1700 by a factor, β, where:

$$\beta = (K_3(1+K_S/K_3)^{1/2}/K_S)^{1/2} \qquad \text{EQN. 34}$$

where $K_3$ is the spring constant of the second passive elastic member 1724 and $K_s$ is the spring constant of the combination of the linear actuator 1716 and first passive elastic element 1728. In one embodiment of the invention, the second passive elastic element provides a β from 1 to 3; thereby increasing the bandwidth of the apparatus 1700 from about 5 Hz to about 15 Hz.

The second passive elastic member 1724 employs a dovetail feature 1796 at both ends to enable clamping at both ends without use of mounting holes. In one embodiment, the second passive elastic member 1724 is fabricated from composite fiber materials. Mounting holes would form a stress intensity and cause fiber dislocations in the passive elastic member 1724 that would compromise the strength of the spring. The end clamps 1798 have complementary shapes that hold the passive elastic element 1724 in place. In one embodiment of the invention, epoxy is employed in the clamps to permanently secure the second passive elastic member 1724 in the end clamps. The epoxy joint would be more prone to failure in the absence of the dovetail features 1796.

The passive elastic element 1724 employs a tapered design to maximize energy storage in the element 1724 to ensure that energy storage density is constant over its length for a given deflection. Referring to FIG. 17D, we illustrate the free-body diagram for the passive elastic element 1724, showing how the roller force, $F_{roller}$, and the lower leg member force, $F_{shank}$, combine to create an equal and opposite force by the central pivot. In this embodiment, the roller force and the lower leg member force are applied equidistant from the center pivot. The forces at the end, F, combine to create a central pivot force of 17 F. Using standard thin beam relationships, the moment acting at a distance of x from the central pivot varies linearly—starting at a value of FL in the center and falling to zero at x=L, where L is the length of the passive elastic element 1724 between the locations at which the forces are applied. Energy storage density along x is proportional to the product of moment (M(x)) and the strain at the surface ($\epsilon_0(x)$), where:

$$M(x) = F\left(\frac{L}{2} - x\right) \quad \text{EQN. 35}$$

$$\epsilon_0(x) = \frac{M(x)}{EI\omega^*} = \frac{F\left(\frac{L}{2} - x\right)}{EI\omega^*} \quad \text{EQN. 36}$$

For a given layup of composite material, the surface strain is kept below a critical value, $\epsilon^*$. For a given moment, the energy density in the beam will be maximized when the surface strain is set to this critical value. To keep the energy density constant and at its maximum value, the optimal width of the beam, $w^*(X)$, is defined by the relation:

$$w^* = w^*(x) = \frac{F}{EI\epsilon_0^*}\left(\frac{L}{2} - x\right) \quad \text{EQN. 37}$$

In one embodiment, the taper 1784 varies linearly from the center of the beam. By using this design method, we have amplified the energy storage of the spring by over a factor of 2 when compared to a beam without a taper 1784. Because the composite spring material is not homogeneous and since the thin beam equations are not applicable, computational tools are used to estimate the energy storage density in the passive elastic member 1724. The shape that is able to store the most energy is highly dependent upon the fiber laminate, lamination design, thickness and the exact manner in which the passive elastic member 1724 is attached to the apparatus 1700. We have determined, however, that a linear taper delivers energy storage within about 10% of the optimal. In a preferred embodiment, the linear taper is used because of the relative ease by which a linear taper pattern may be cut from a sheet of laminated ply composite material using a water jet process. In alternative, less preferred embodiments, a non-tapered spring may be used.

FIG. 17E is an illustration of a perspective view of an embodiment of the structural element 1732 (also referred to herein as the pyramid). The structural element 1732 is coupled between the mounting interface 1704 and the first end 1752 of the lower leg member 1712. The structural element 1732 is coupled to the first end 1752 of the lower leg member 1712 with a set of pins 1711 (shown in FIG. 17A). The pins 1711 pass through the set of holes 1713 in the lower leg member 1712 and a set of holes 1715 in the structural element 1732. The pins 1711 allow a rotary degree of freedom for the strain in structural element 1732 from being falsely recorded as axial force and moment in the structural element 1732. In this embodiment, the structural element 1732 is capable of measuring the moment and axial load on the ankle joint 1740, enabling, for example, positive detection of "foot-down" for use by the controller 1762 state machine that controls the apparatus 1700 functions; measurement of applied moment for use by the positive-feedback reflex controls employed during powered plantarflexion; and positive detection of tripping for use by a safety system integrated into the controller 1762.

In this embodiment, the structural element 1732 is designed as a flexural element that amplifies the strain fields induced by the medial-lateral moment and axial force applied to the apparatus 1700 during operation. The structural element 1732 creates high magnitude strain fields of opposite sign (differential strain fields) in the regions 1738 and 1742 about the center adaptor mounting hole 1734 when a medial-lateral moment (moment about the x-axis) is applied. These differential strain fields are not present when only an axial force is applied. The structural element 1732 includes one strain gage (1782 and 1786) bonded to each of the two moment-sensitive regions (1738 and 1742, respectively) on the bottom surface 1733 of the structural element 1732. The gages are applied on opposing sides of a Wheatstone bridge. The controller 1762 is coupled to the Wheatstone bridge to measure the strains. The strain measurements are used to measure moment on the structural element 1732. In one embodiment, the sensitivity of the measurement is approximately in the 0.15 N-m range, where, in this context, sensitivity defines the minimum resolvable change (signal to noise$\cong$1) when digitally sampled at 500 Hz.

In contrast to the moment induced strains, high strains are introduced by axial forces along the medial-lateral axis in the regions 1746 and 1754 around the center adaptor mounting hole 1734. These strains appear in a 0.76 mm thickness region (regions 1746 and 1754) under the slots (1758 and 1770, respectively) machined along the medial-lateral axis. The section above the slot must be thick enough to transfer moment load with minimum strain in the thin lower section. The strain magnitude is significantly diminished in the thin section when a moment-only load is applied. The structural element 1732 includes one strain gage (1790 and 1794) bonded to each of the two axial load-sensitive regions (1746 and 1754, respectively) on the bottom surface 1733 of the structural element 1732. The gages are applied on opposing sides of a Wheatstone bridge. The controller 1762 is coupled to the Wheatstone bridge to measure the strains. The strain measurements are used to measure axial force on the structural element 1732, and consequently, axial force on the lower leg member 1712. The machined slots 1758 and 1770 amplify the axially-induced strains without compromising the structural integrity of the structural element 1732.

Since the structural element 1732 is in the critical chain of structural support between the residual limb socket of the wearer (not shown) and the apparatus 1700, in one embodiment it is preferably designed to withstand more than 60 N/kg of axial load. In this embodiment, the sensitivity of the axial measurement is in the range of approximately 50 N, which is well below the approximately 100 N threshold normally used in the apparatus 1700 to sense that the apparatus has been placed firmly on the ground. During calibration of the apparatus 1700 a 2×2 sensitivity matrix is determined, enabling true moment and axial force to be derived from the pairs of strain measurements.

Figure 17F:
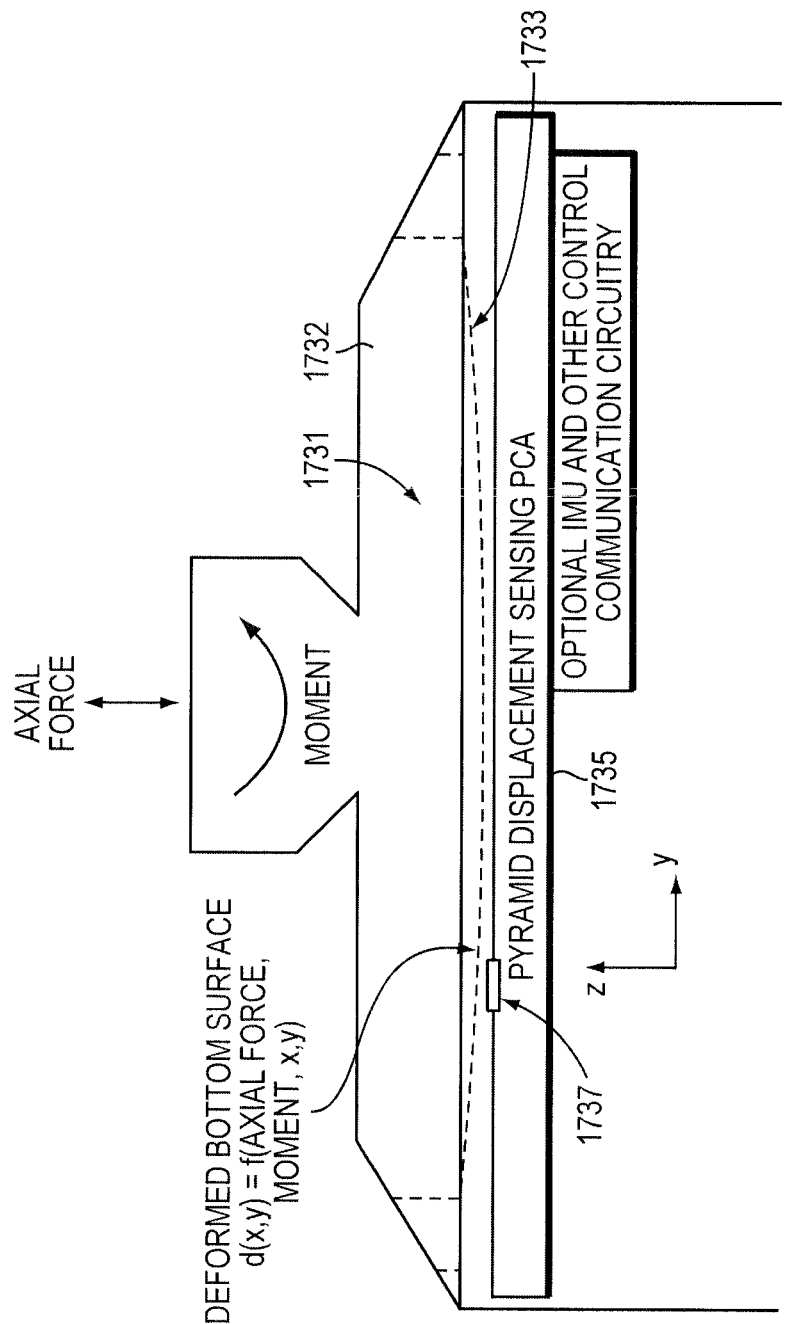
FIG. 17F is an illustration of a cross-sectional view of an alternative method for measuring axial force and moment applied to the lower leg member of FIG. 17A, according to an illustrative embodiment of the invention.

FIG. 17F is an illustration of a cross-sectional view of an alternative method for measuring axial force and moment applied to a lower leg member, according to an illustrative embodiment of the invention. In this embodiment, the structural element 1732 employs a flexural design that amplifies displacement of its bottom surface 1733 in such a way that the axial force and in-plane moment (two-degrees of freedom) can be derived in a redundant fashion. In this embodiment, the apparatus 1700 includes a displacement sensing apparatus 1735 for measuring deflection of the structural element 1732 to determine the moment (torque) and axial force applied to the lower leg member 1712.

In this embodiment, the displacement sensing apparatus 1735 includes a printed circuit assembly (PCA) employing one or more displacement sensors 1737 (e.g., contact or non-contact displacement sensors). The sensors measure, at each sense coordinate, the distance between the sensor 1737 and the bottom surface 1733 of the structural element 1732.

In one embodiment, changes in mutual inductance of coils printed on the PCA with respect to the bottom surface 1733 of the structural element 1732 are used to measure the local surface deformation (displacement). In this embodiment, counter-circulating "eddy" currents in the structural element 1732 serve to reduce the coil inductance inversely with the distance between the coil and the bottom surface 1733 of the structural element 1732. Other displacement sensing technologies could be employed, including non-contact capacitance and optical sensors or contact-based sensors that employ force-sensitive resistors, piezo or strain-gages integral to the PCA. By sampling the array of displacement sensors, the axial force and moments can be estimated using a sensitivity matrix that is computed during an off-line calibration process.

Figure 17G:
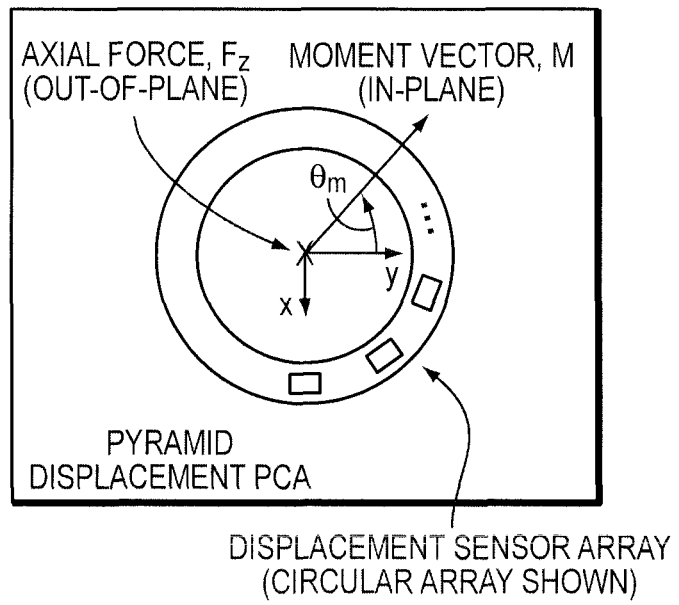
FIG. 17G is an illustration of a method for computing the in-plane moment vector and axial force using a circular array of displacement sensors on a printed circuit assembly, according to an illustrative embodiment of the invention.
Figure 17G:
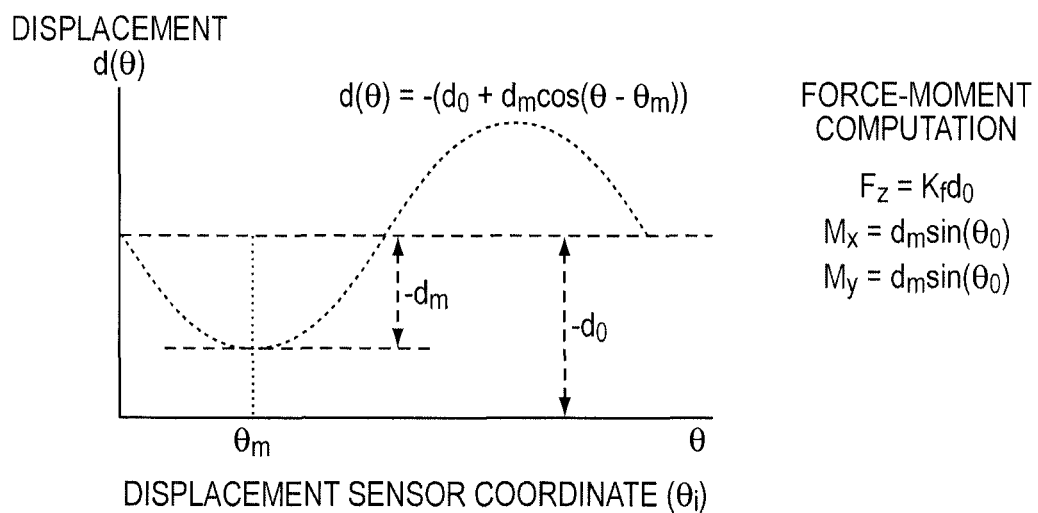

In this embodiment, the structural element 1732 is fastened to the lower leg member 1712 with screws, eliminating the need for the pins 1711 employed in the embodiment illustrated in FIG. 17E. The screw fastening method reduces weight and manufacturing complexity. Furthermore, this fastening method amplifies displacements measured in the center of the structural element 1732 where the displacement sensing apparatus 1735 is located. FIG. 17G illustrates how the in-plane moment vector and axial force may be computed using a circular array of displacement sensors on the printed circuit assembly. As shown, demodulation of the bias and sinusoidal-like displacement function is used to estimate the moment and force. Other displacement sensor array configurations could be used as a means of intrinsic sensing of moment and force.

Moment and force sensing is useful as a means of signaling walking state changes. In addition, measurement of lower leg member 1712 moment serves as a feedback means by which reflexive behavior is achieved in powered plantarflexion. When combined with inertial and actuator feedback, the intrinsic moment and force measurements are used to calculate ground reaction force and zero moment pivot, which are useful for traction control and balance. For these reasons, it is beneficial to package the intrinsic moment and force sensing with the inertial measurement unit and state control processing functions. FIG. 17F shows how these functions could be implemented on a PCA. Such a PCA could be implemented as a sandwich of FR-4 material with a stable core material (Invar for instance) serving as a stiff interposing substrate between the top-side displacement sensing FR4-based layer and a bottom FR-4-based layer that incorporates the signal processing layer. Integrating the materials and functions in a single assembly eliminates the need for cabling and other potentially unreliable means for interconnecting these functions. Such integration also allows for a stand-alone tool that can be used by prosthetists to setup a passive prosthetic and study, gait parameters, including energy return and walking statistics Referring to FIG. 17A, the apparatus 1700 also includes a controller 1762 coupled to the linear actuator 1716 for controlling the linear actuator 1716. In this embodiment, the controller is located within a housing 1764 of the apparatus 1700 to protect it from the environment. A battery 1768 in the housing 1764 provides power to the apparatus (e.g., the controller 1762 and various sensors associated with the apparatus 1700).

The apparatus 1700 includes an inertial measurement unit 1720 to predict the inertial pose trajectory of the ankle joint 1740, heel 1772 and toe 1776 relative to the previous toe-off position. The inertial measurement unit 1720 is electrically coupled to the controller 1762 and provides inertial measurement signals to the controller 1762 for controlling the linear actuator 1716 of the apparatus 1700. In one embodiment, the inertial measurement unit 1720 employs a three-axis accelerometer and a three-axis rate gyro. The three-axis accelerometer measures local acceleration along three orthogonal axes. The three-axis rate gyro measures angular rotation about three orthogonal axes. Through use of well-established methods of numerical integration, the position, velocity and pose of any point on the foot structure can be computed.

In some embodiments, the inertial measurement unit 1720 is used to detect the terrain slope and the presence of steps and stairs—thereby enabling optimization of the foot's "angle-of-attack" relative to the underlying terrain prior to touchdown and the ankle joint's spring equilibrium position in the stance phase. In some embodiments, the inertial measurement unit 1720 is used to determine ambulation speed of the wearer and conditions of the terrain (features, texture or irregularities of the terrain (e.g., how sticky is the terrain, how slippery is the terrain, is the terrain coarse or smooth, does the terrain have any obstructions, such as rocks)). This enables the wearer to walk confidently on all terrain types. The inertial pose comprises the three degree-of-freedom orientation of the lower leg member 1712 in a fixed ground-referenced (world) coordinate frame—often captured as the orientation component of a homogeneous transformation (three unit vectors defining the x, y and z axes in the world reference frame) or as a quaternion; the translation of the ankle joint 1740 in the world frame; and the velocity of the ankle joint 1740 in the world frame. In this embodiment, the inertial measurement unit 1720 is physically coupled to the lower leg member 1712. In some embodiments, the inertial measurement unit 1720 is coupled to the foot member 1708 of the apparatus 1700.

Figure 17H:
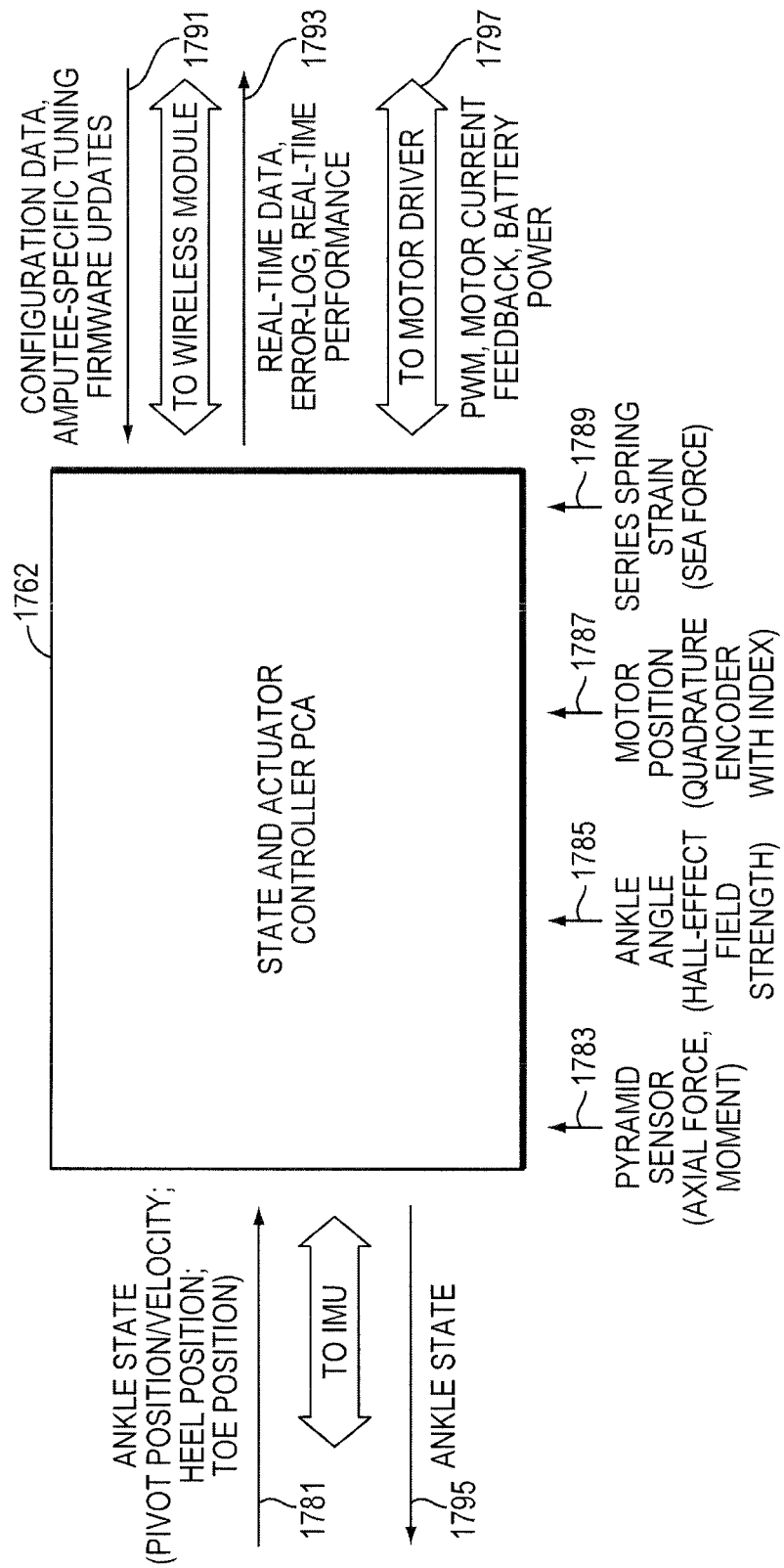
FIG. 17H is a schematic illustration of a state and actuator controller for use with the apparatus of FIGS. 17A-17G, according to an illustrative embodiment of the invention.

FIG. 17H is a schematic illustration of a state estimation and actuator controller (state and actuator control PCA-SAC) for use with the apparatus of FIGS. 17A-17G, according to an illustrative embodiment of the invention. In this embodiment, the controller 1762 employs dual 40 MHz dsPIC (manufactured by Microchip™) processors to control and coordinate linear actuator 1716 (e.g., rotary motor 504 of FIGS. 5A and 5B) and the inertial measurement unit 1720. In this embodiment, space-vector modulation is employed to implement the brushless motor control to create an optimum pulse width modulated drive that maximizes motor RPM. Space vector modulation is a PWM control algorithm for multi-phase AC generation, in which a reference signal is sampled regularly. PWM of a signal or power source involves the modulation of the three-phase motor winding voltage duty cycles (e.g., the rotary motor 504). After each sampling of the reference signal, non-zero active switching vectors adjacent to the reference vector and one or more of the zero switching vectors are selected for the appropriate fraction of the sampling period in order to synthesize the reference signal.

The controller 1762 receives a variety of input signals, including, inertial pose signals 1781 from the inertial measurement unit 1720, torque and axial force signals 1783 from the structural element 1732 strain measurements, ankle joint angle signals 1785 from a hall-effect transducer located in the ankle joint 1740, motor position signals 1787 (quadrature encoder with index and absolute motor position) from the encoder (e.g., encoder 2040 of FIG. 20A), strain signals 1789 from the strain sensor 1704 (referring to FIG. 18A) of the series elastic member 1728, and controller parameters 1791 (e.g., apparatus configuration data, wearer-specific tuning, firmware updates)). In addition, the controller 1762 outputs a variety of signals, including, apparatus performance data 1793 (e.g., real-time data, error log data, real-time performance data), ankle state updates 1795. In addition, the controller 1762 outputs commands to the linear actuator 1716 and receives actuator feedback signals from the linear actuator 1716 (generally signals 1797), for example, three-phase pulse width modulation signals provided to the power electronics for the linear actuator 1716, battery power to the linear actuator 1716, and current feedback measurements and temperature measurements from the linear actuator 1716.

This embodiment uses the sensor feedback to identify state changes as the apparatus 1700 transitions through the stance-phase and swing-phase states. By using the redundant and diverse sensor measurements, it also identifies fault conditions and drives the apparatus 1700 into an appropriate safe state. Using an on-board real-time clock, it time-tags the faults and stores these into an on-board e²PROM (error log). The contents of the error log are retrieved wirelessly by the prosthetist and/or manufacturer service personnel. In this embodiment, the Motor Driver PCA (MD) takes pulse-width modulation (PWM) commands from the SAC PCA to switch current into the motor windings. The MD passes sensed current and power information back to the SAC PCA so that it can apply closed-loop control.

In this embodiment, the IMU PCA is mounted nominally in the Sagittal plane (a local plane parallel to the front of the tibia) and employs a three-axis accelerometer, a dual-axis rate gyro ($\omega_z$ and $\omega_x$) and a single-axis rate gyro ($\omega_y$). In this embodiment, a coordinate frame definition is used that defines the y-axis as forward, z-axis as up and x-axis defined as the cross-product of the y and z axes (y×z). The IMU receives state information from the SAC at the system sampling rate of 500 Hz. It transmits the ankle state vector—specifically the position and velocity of the ankle pivot, the position of the heel and the position of the toe—all with respect to the foot-flat position from the previous step.

Figure 17I:
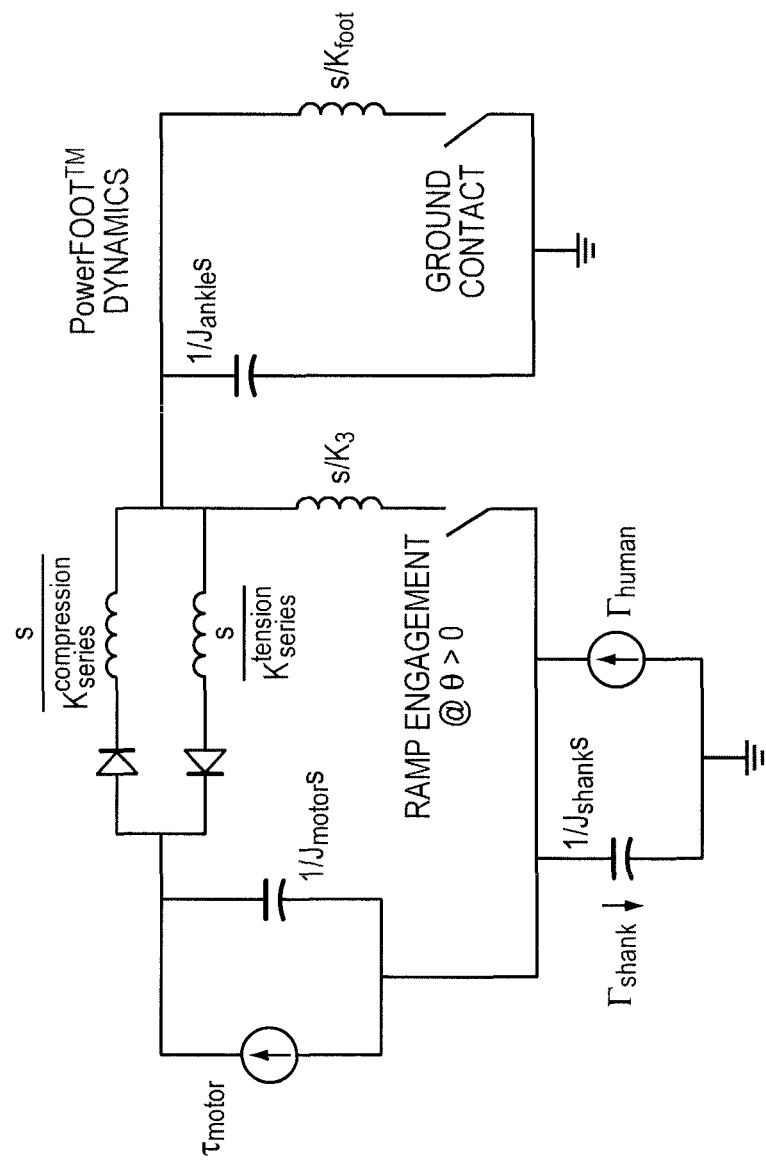
FIG. 17I is a schematic illustration of an electrical circuit equivalent of a lower extremity prosthetic apparatus, according to an illustrative embodiment of the invention.
Figure 17J:
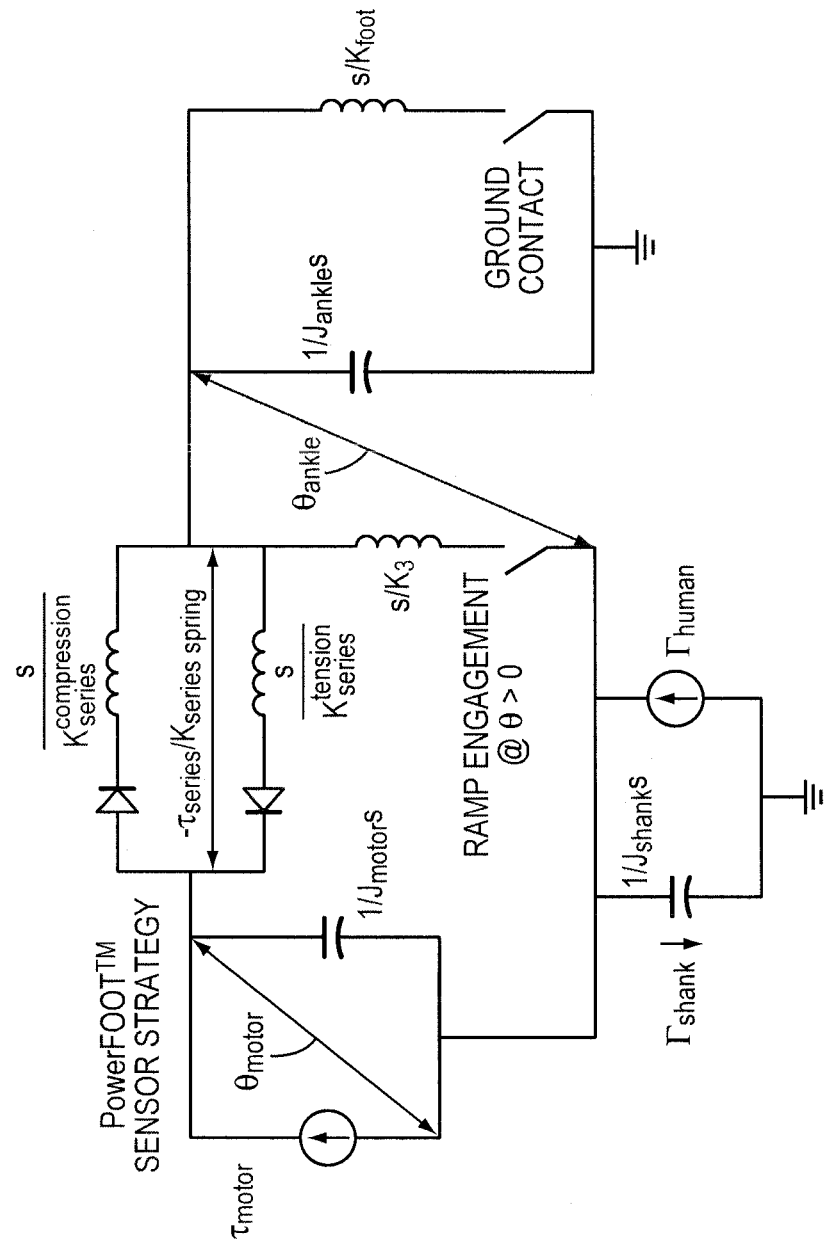
FIG. 17J is a schematic illustration of the electrical circuit of FIG. 17I including sensor measurements used in controlling the apparatus.

FIGS. 17I and 17J are schematic illustrations of an exemplary electrical equivalent of apparatus 1700 of FIG. 17A. Electrical circuit symbols are used to describe the mechanical elements—a resistor denoting a mechanical component with damping torque that is linear with velocity; a capacitor denoting a mechanical component with rotary inertia properties; and an inductor denoting a mechanical component with linear spring qualities. With this circuit notation, current corresponds with torque and voltage corresponds with angular velocity.

The circuit components are defined as follows: $J_{shank}$ is the unknown equivalent inertia of the lower leg member (shank) and residual limb below the knee (e.g., inertia of lower leg member 1712 of FIG. 17A); $J_{Motor}$ is the equivalent motor and ball-screw transmission assembly inertia (e.g., inertia of linear actuator 1716 of FIG. 17A); $K_{series}^{compression}$ is the torsional spring constant for the series spring (e.g., passive elastic element 1728 of FIG. 17A) when in compression; $K_{series}^{tension}$ is the torsional spring constant for the series spring when in tension; $K_3$ is the torsional spring constant for the unidirectional parallel spring (e.g., passive elastic member 1724 of FIG. 17A); and $J_{Ankle}$ is the rotary inertia of the foot structure below the ankle (e.g., foot member 1708 of FIG. 17A). The current (torque) sources within the model are defined as follows: $\Gamma_{Human}$ is the unknown torque applied by the wearer's body onto the lower leg member (e.g., lower leg member 1712); $\tau_{motor}$ is the torque applied by the actuator (e.g., linear actuator 1716); and $\Gamma_{shank}$ is the torque measured using the structural element (e.g., structural element 1732 of FIGS. 17A and 17E).

FIG. 17I illustrates the importance of the series and parallel springs as energy storage elements. Use of the stored energy reduces the power consumption that would otherwise be required by the linear actuator. In addition, an additional purpose of the $K_3$ spring is its function as a shunt across the ankle inertia that increases the ankle-spring resonance.

FIG. 17J illustrates how sensors have been employed in this embodiment to provide high-fidelity position and force control, and to achieve the sensor redundancy and diversity desirable for delivering an inherently safe design. As shown, the ankle joint position, $\hat{\theta}$, is derived from the following:

$$\hat{\theta} = \theta_{motor} - \frac{F_{series}}{K_{series}} \qquad \text{EQN. 38}$$

where $$K_{series} = \begin{cases} K_{series}^{compression}, & \text{if } \Gamma_{series} \geq 0 \\ K_{series}^{tension}, & \text{if } \Gamma_{series} < 0 \end{cases} \qquad \text{EQN. 39}$$

A redundant measure of $\theta$ is achieved through use of a Hall-effect angle transducer, thereby providing a verification that the ankle is being manipulated properly by the control system. In one embodiment, the Hall-effect transducer includes a Hall-effect device located on the SAC PCA in the housing 1764 of the apparatus 1700. The transducer also includes a magnet coupled to the foot member 1708. The field effect magnitude (signal output by the transducer) changes in a known way in response to angle joint rotation (i.e., motion of the magnet relative to the Hall-effect device). The Hall-effect transducer is calibrated during manufacturing of the apparatus 1700 by, for example, measuring the output of the transducer to known displacements of the Hall-effect device relative to the magnet. In other ankle angle measurement embodiments, the mutual inductance measured on a coil on the lower leg member has a known relationship as a function of ankle angle, and the inductance can be calibrated to compute angular displacement in a way that is not sensitive to the magnetic fields generated by the motor in the linear actuator or by other stray fields. Also, as shown in FIG. 17J, the ankle moment as applied by the wearer is also measured. This enables the linear actuator to adapt (e.g., to increase stiffness) to achieve reflex behavior.

FIGS. 18A, 18B, 18C and 18D are illustrations of the passive elastic member 1728 of FIG. 17A, according to an illustrative embodiment of the invention. The passive elastic member 1728 provides bidirectional stiffness and is connected in series with the linear actuator 1716 and the foot member 1708. The passive elastic member 1728 is coupled at one end to the second end 1748 of the linear actuator 1716, and at the other end to the foot member (not shown). The passive elastic member 1728 includes a strain sensor 1704 coupled to the passive elastic member 1728 for measuring strains in the passive elastic member 1728. In this embodiment, the strain sensor 1704 is a strain gage whose response is calibrated to measure the force applied by the linear actuator 1716—and in turn, the moment about the ankle joint 1740 that is applied by the linear actuator 1716. The strain gage signal is measured using the controller 1762 of FIG. 17A.

In this embodiment, the passive elastic member 1724 is a formed carbon-fiber layup that delivers a desired bidirectional (functions in bending in both directions) normalized drive stiffness. In one embodiment, the passive elastic member 1724 has a preferred compression of 14-25 N-m/rad/kg and tension: 4-8 N-m/rad/kg. Biomechanical forces and torques strongly scale with body mass of a wearer. When scaling prosthetic and orthotic devices, design parameter specifications are typically normalized. For example, series and parallel elasticity such devices can be scaled with body mass, or designed to provide discrete values that are intended to cover several ranges of body mass. The ranges of compression and tension reflect the variation in torque that results from the difference in the linear actuator moment arm to the ankle joint across the entire range of rotation-from maximum plantarflexion to maximum dorsiflexion. The series spring constant is optimized to be relatively non-compliant during swing-phase dorsiflexion position control (while the spring is in compression) such as when the ankle is being repositioned immediately following toe-off in walking. However, some compliance is maintained to isolate the linear actuator from shock loads.

Figure 18C:
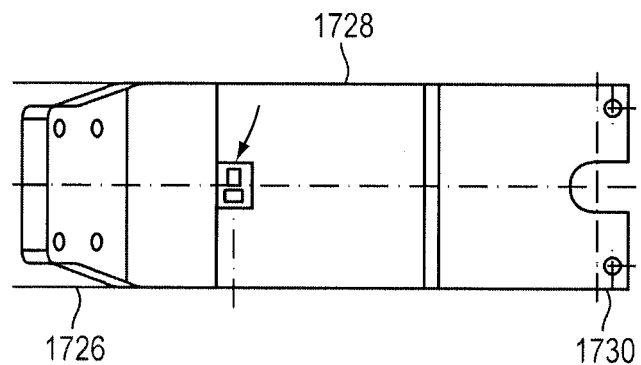
Figure 18D:
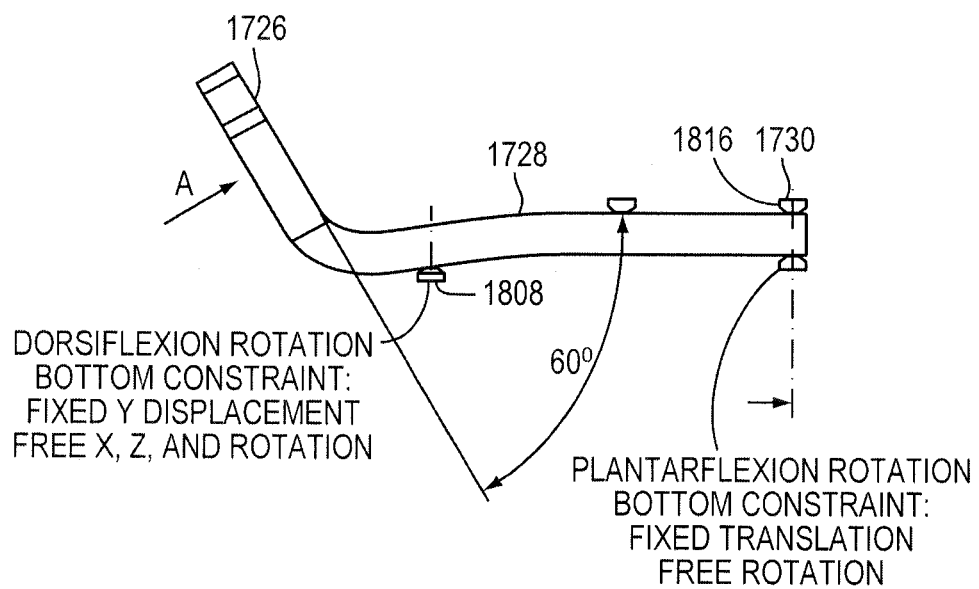

Referring to FIGS. 18C and 18D, high stiffness is achieved in the passive elastic member 1728 in compression by inserting a dorsiflexion rotation bottom constraint 1708 towards the distal end 1726 of the passive elastic member (spring) 1728. This restraint reduces the effective moment arm of the linear actuator 1716 on the bending of the series spring 1728 during compression (towards dorsiflexion). In tension, the moment arm is effectively increased by placing the plantarflexion top constraint 1716 more towards the proximal end 1730 of the spring restraint. With the longer moment arm, the spring beam will bend more freely, thereby reducing the spring constant in tension. In addition to the bilateral stiffness characteristics, in some embodiments, the spring constant of the passive elastic member 1728 is optimized to minimize ball-screw rotational speed By design, this embodiment of the elastic member 1728 has asymmetrical characteristics—delivering higher compliance in tension than in compression. The higher compliance in tension increases the energy storage in the series spring 1728 for use in powered plantarflexion. The energy is released in about the first 100 ms involved in powered plantarflexion, thereby reducing the energy contribution required of the linear actuator 1716. In embodiments of the invention that use a ball-screw transmission assembly in conjunction with a rotary motor for the linear actuator (e.g., ball-screw transmission assembly 2024 of FIGS. 20A-20B), this has the added benefit of reducing the required operating speed of the ball-nut assembly portion of the ball-screw transmission assembly and also the motor drive requirements for the rotary motor. The spring catapults the foot member without requiring high-speed ball-nut positioning in this case. Optimized values for the series elasticity are in the range of 3-4 Nm/rad/kg.

Figure 19A:
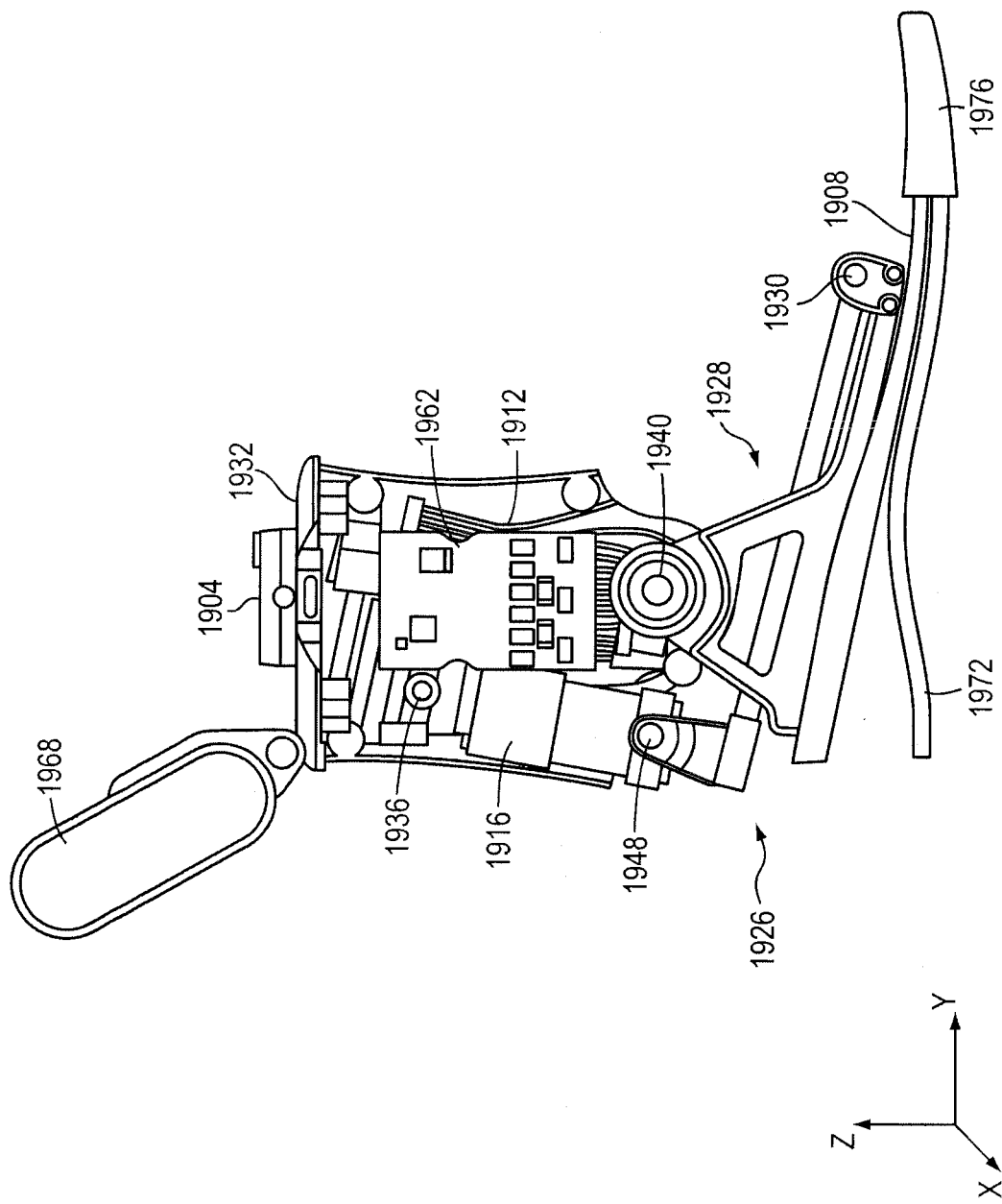
FIG. 19A is an illustration of a lower-extremity prosthetic apparatus incorporating a flat series spring, according to an illustrative embodiment of the invention.

FIG. 19A is an illustration of a lower-extremity prosthetic apparatus 1900 incorporating a flat series spring 1928, according to an illustrative embodiment of the invention. The apparatus 1900 has a mounting interface 1904 making it capable of attaching to a complementary lower-extremity limb socket member of a wearer. The apparatus 1900 includes a lower leg member 1912 coupled to the mounting interface 1904. The lower leg member 1912 is also coupled to a foot member 1908 at an ankle joint 1940 of the apparatus 1900. The ankle joint 1940 permits the foot member 1908 to rotate about the x-axis relative to the lower leg member 1912. The foot member includes a heel 1972 and a toe 1976.

The apparatus 1900 also includes a linear actuator 1916 with a first end 1936 and a second end 1948. The first end 1936 of the linear actuator 1916 is coupled to the lower leg member 1912. The apparatus 1900 also includes passive elastic member 1928 in series with the linear actuator 1916. The passive elastic member 1928 is coupled between the foot member 1908 and the second end 1948 of the linear actuator 1916. The passive elastic member 1928 is coupled to the foot member 1908 at the proximal end 1930 of the passive elastic member 1928. The distal end 1926 of the passive elastic member 1928 is coupled to the second end 1948 of the linear actuator 1916. The linear actuator 1916 applies torque about the ankle joint 1940.

The apparatus 1900 also includes a controller 1960 coupled to the linear actuator 1916 for controlling the linear actuator 1916. In this embodiment, the controller 1960 is located within a housing 1964 of the apparatus 1900 to protect it from the environment; however, a portion of the housing is removed in this figure to expose the contents within the housing). A battery 1968 coupled to the apparatus 1900 provides power to the apparatus 1900 (e.g., the controller 1960 and various sensors associated with the apparatus 1900).

The passive elastic member 1928 of FIG. 19A is a flat spring (e.g., fabricated with water-cut equipment). A flat spring reduces the cost of the passive elastic member 1900 and makes it easier to configure the spring constant to align with the body mass of the wearer. In one embodiment, the spring is split longitudinally (along the y-axis) to reduce the out-of-plane moment on the components of a ball-nut (see, e.g., FIGS. 20A and 20B) of the linear actuator 1916 due to lack of parallelism between the rotation axis of the ball-nut and the series passive elastic member 1928. In this embodiment, no strain sensing is employed in the actuator torque feedback loop. Rather, the torque transmitted through the spring is estimated by multiplying the known spring constant of the flat spring by the measured spring deflection (difference between measured ankle joint 1940 angle, θ and the angle, β, kinematically defined as the ankle joint 1940 angle that would result from a specific ball-nut position along the screw when the spring deflection is zero.

Figure 19B:
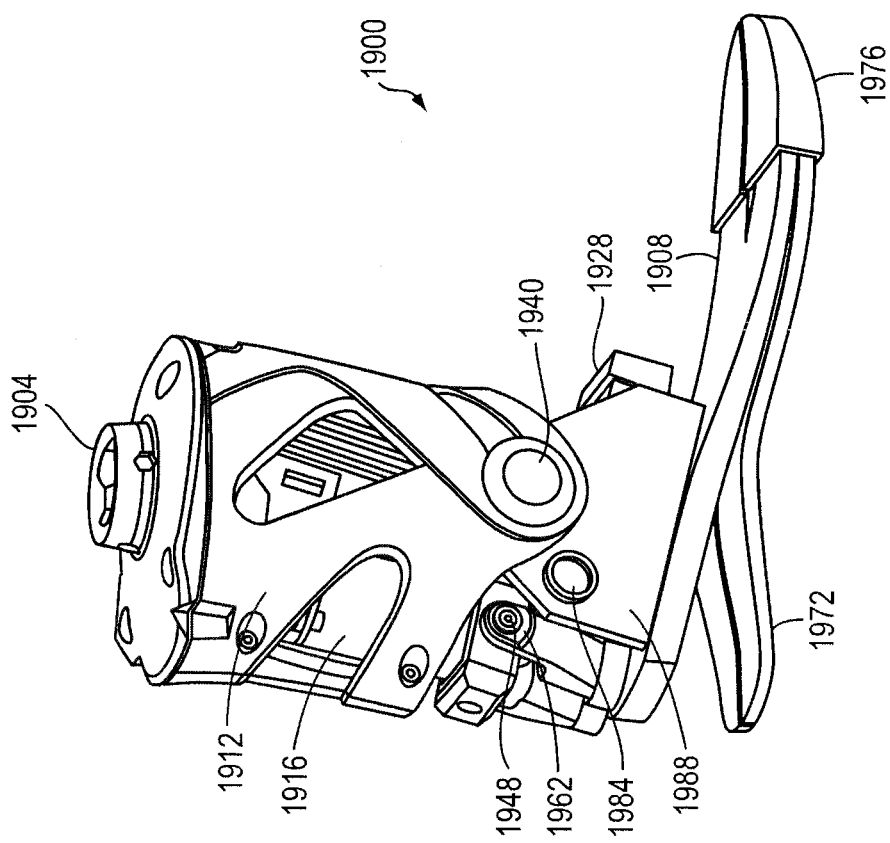
FIGS. 19B-19C are illustrations of a prosthetic apparatus using an alternative series spring, according to an illustrative embodiment of the invention.
Figure 19C:
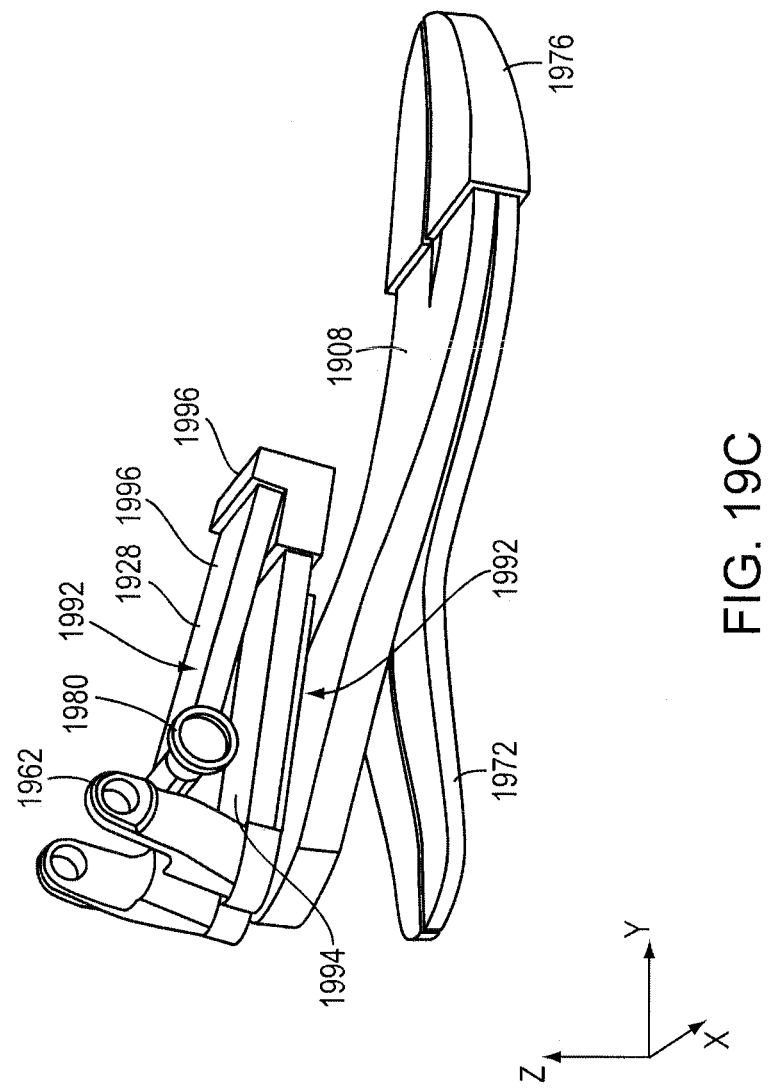

FIGS. 19B and 19C are illustrations of an alternative two-piece series-elastic spring of a prosthesis apparatus 1900, according to an illustrative embodiment of the invention. The apparatus 1900 has a mounting interface 1904 making it capable of attaching to a complementary lower-extremity limb socket member of a wearer. The apparatus 1900 includes a lower leg member 1912 coupled to the mounting interface 1904. The lower leg member 1912 is also coupled to a foot member 1908 at an ankle joint 1940 of the apparatus 1900. The ankle joint 1940 permits the foot member 1908 to rotate about the x-axis relative to the lower leg member 1912. The foot member includes a heel 1972 and a toe 1976. The apparatus 1900 also includes a linear actuator 1916 with a first end 1936 and a second end 1948. The first end of the linear actuator 1916 is coupled to the lower leg member 1912. The apparatus 1900 also includes a coupling member 1988 (e.g., bracket) that couples the foot member 1908 to the lower leg member 1912 at the ankle joint 1940 with a bearing that allows the foot member 1908 to rotate about the x-axis of the ankle joint 1940.

The apparatus 1900 also includes passive elastic member 1928 in series with the linear actuator 1916. Referring to FIG. 19C, the passive elastic member 1928 has two member sections (e.g., beam-like sections) 1994 and 1996. The elastic member 1928 also has a first end 1962 on the first member 1994 and a second end 1980 on the second member 1996. The elastic member 1928 also has an intermediate location 1996 at which the two members 1994 and 1996 meet and at which the two members 1994 and 1996 pivot with respect to each other around the x-axis. As the second member 1996 pivots towards the first member 1994, the elastic member stores energy in compression during dorsiflexion (shown by the arrow 1992).

The first end 1962 of the elastic element 1928 is coupled to the second end 1948 of the linear actuator 1916 with a bearing that allows for rotation about the x-axis. The second end 1980 of the elastic element 1928 couples to a location on the coupling member 1988 with a bearing that allows for rotation about the x-axis.

Exemplary Linear Actuator

FIGS. 20A and 20B are illustrations of a linear actuator 2000 for use in various lower-extremity prosthetic, orthotic, and exoskeleton apparatus, according to an illustrative embodiment of the invention. FIG. 20A is a perspective view of the linear actuator 2000. FIG. 20B is a cross-sectional view of the linear actuator 2000. The linear actuator 2000 can be used as, for example, the linear actuator 1716 of apparatus 1700 of FIG. 17A or apparatus 400 of FIG. 4. The actuator 2000 includes a motor 2004 and screw transmission assembly 2024 (in this embodiment, it is a ball-screw transmission assembly, also referred to as a ball-screw assembly) for delivering linear power along the A axis. The screw transmission assembly 2024 functions as a motor drive transmission to translate rotational motion of the motor 2004 to linear motion. In one embodiment, the ball-screw transmission assembly 2024 is a custom ball-screw transmission assembly manufactured by Nook Industries (offices in Cleveland, Ohio). The custom ball-screw transmission assembly has the following specifications: 14 mm×3 mm pitch screw, 4000 N of thrust at 150 mm/s, and an L1 rated life in the instant application of 5 million cycles. In some embodiments, the screw transmission assembly is a lead-screw transmission assembly (also referred to as a lead-screw assembly).

The actuator 2000 includes a rotary motor 2004 that has a motor shaft output 2008. The motor shaft output 2008 has a pulley 2032 coupled (e.g., welded) to the motor shaft output 2008. In one embodiment, the rotary motor 2004 is a high-speed brushless motor (model EC30 motor manufactured by Maxon Motor AG, Maxon Precision Motors, Inc. with offices in Fall River, Mass.). The motor 2004 includes an inductive incremental-absolute angular encoder 2040 that is integrated into the motor 2004 to for determining angular alignment between the rotor and stator of the rotary motor 2004. The encoder 2040 also provides a position feedback signal necessary to control the screw 2060 position of the linear actuator 2000 and to provide for "instant-on" motor commutation and redundant position feedback monitoring.

The inductively-coupled encoding elements of the encoder 2040 enable the system to determine the absolute rotor-stator alignment (with, for example, 10 bits of resolution per revolution) simultaneously with high-precision incremental rotor position feedback. By cross-checking these redundant feedback elements it is possible to minimize the possibility that an encoder malfunction can cause ankle control instability. The incremental encoder achieves less than 300 μrad of run-out so as to eliminate the sensed velocity fluctuations when the ball-screw transmission assembly 2024 (see below) is operating at constant-speed. As a result, less torque variation is applied by the actuator 2000.

The rotary motor 2004 also includes an integral motor heat-sink 2048. In one embodiment, the heat-sink 2048 draws heat out of the windings of the motor 2004, enabling a wearer to walk at peak levels of non-conservative work without exceeding motor coil temperature limits (typically 160° C.). Motor heating arises due to resistive losses ($i^2R$ losses) in the motor 2004 as the linear actuator 2000 delivers thrust force. As the coil temperature rises, the coil resistance rises at the rate of 0.39%/° C., thereby further increasing the coil temperature. In addition, the motor $K_t$ (a measure of torque as it scales with motor current) typically drops by nearly 20% as the coil temperature increases to its limit. This requires additional current consumption to perform the same amount of work, further driving up the coil temperature. The heat-sink in the linear actuator 2000 reduces coil temperature rise by over 40%. Because the wear out phenomenon that drives premature failure of motor winding insulation and motor bearing reduces in effect by a factor of 2× for every coil temperature reduction of 10° C., the motor life increases significantly if lower motor coil operating temperatures are maintained. And, using this intrinsic coil temperature sensing method, the motor can be protected from exceeding the absolute maximum rating of 160° C. by simply reducing powered plantar-flexion power (currents) as the maximum rating is approached, and ultimately, shutting off battery power when a predefined limit of, for example, 150° C. is reached.

Robotic prostheses typically employ compact light-weight motor drives to deliver power in bursts to the affected limb. In some scenarios, the power bursts may be applied repetitively and at high rate over extended periods of time. The motor copper and eddy current losses will cause an excessive accumulated heating effect that causes the motor winding temperature to rise. Since the copper winding resistance increases with temperature (0.39%/° C.), the copper losses will increase thereby amplifying the heating effect. A critical winding temperature limit can sometimes be reached in which further temperature rise will cause permanent damage to the motor. Sensing when this temperature limit is reached is preferably accomplished by the control system.

Two conventional methods may be used to prevent or detect when the copper winding temperature limit is or will be reached. In the first, the copper and eddy current losses are computed while the control system operates. These are used to drive a thermal model of the windings so that the winding temperature can be estimated. Sometimes the ambient temperature is measured in order to yield a better winding temperature measurement. An advantage of this method is that it is cheap to implement. The disadvantage is that the coil temperature model is hard to obtain and to calibrate. Also, it is often difficult to make a good measurement of the ambient temperature around the motor, causing the winding temperature measurement to be in error.

In the second method, sometimes combined with the first, the case temperature of the motor is measured with a thermistor applied to the outside of the case, or inside the motor. The advantage of this is that it provides a direct measurement. The disadvantage is that it only measures at one point and the application of the sensor is expensive and often unreliable.

A more preferred approach is to both detect the temperature and to mitigate the potential overheating condition. In this, we measure the motor winding resistance on every step at a point during the walking cycle when we can briefly hold the ankle at a fixed position (this to eliminate back-emf effects on the resistance calculation) to make the measurement. In one embodiment, coil temperature is determined by applying a fixed current (alternatively fixed voltage) to the motor winding and measuring the corresponding voltage (alternatively current) in the winding. To increase the accuracy, we apply the voltage (or current) in both the forward and reverse direction and measure the difference in current (or voltage).

Since the motor drive electronics employs PWM current control methods, all the infrastructure to make this measurement exist. By noting the percentage difference between this winding resistance and that when the ankle is at rest (a calibration constant) we can estimate the winding resistance in-situ without cost. In a typical servo system this measurement cannot be made because the actuator must be continually in closed-loop control. But in the ankle prosthesis, there are times (swing phase) when the ankle position does not need to sustain the precision control over the 5 milliseconds typically required to make the measurement. Once the winding temperature is calculated in this way, the control system can detect when the windings are approaching the critical temperature. During these times, the drive power available for walking is reduced or eliminated altogether until the temperature is reduced to a safe level.

In some embodiments, the output of the temperature sensor 2052 is provided to a controller (e.g., the controller 1762 of FIG. 17A) to control torque output by the linear actuator 2000 based on the temperature of the motor 2004.

A belt 2012 couples the pulley 2032 to the threaded shaft 2060 of a ball-screw transmission assembly 2024 such that rotational motion of the motor shaft output 2008 is translated to a linear motion of the ball-nut assembly 2036 portion of the ball-screw transmission assembly 2024. In some embodiments, two or more belts are applied in parallel, each with an ability to drive the linear actuator 2000 ball-screw transmission assembly 2024 by itself, so as to enable the linear actuator 2000 to survive a single belt breakage failure. In such an event, belt break sensor 2056 senses the condition and validates belt integrity during operation (e.g., during each gait cycle of a wearer using a prosthesis).

In one embodiment, an optical sensor (e.g., a thru-beam sensor) is used as the belt break sensor and an output signal of the optical sensor changes in a known manner when a belt breaks. In another embodiment of the invention, a capacitive sensor is used as the belt break sensor and an output of the capacitive sensor changes in a known manner when a belt breaks.

In one embodiment, the pulley 2032 and belt(s) are not used as the apparatus for converting rotary motion to a linear motion. Rather, a set of traction wheels are used as the transmission apparatus. In this embodiment, the threat of belt failure is thereby eliminated.

In one embodiment, in the event of a belt break, a controller of the apparatus in which the linear actuator 2000 is used (e.g., controller 1762 of apparatus 1700 of FIG. 17A), changes the position of the foot member relative to the lower leg member to a safe position that enables the apparatus to operate as a passive ankle prosthesis until the linear actuator 2000 is repaired. In one embodiment, the controller shorts three electrical leads of the rotary motor 2004 in response to the belt breakage sensor detecting a failure of one or more of the plurality of belts. Shorting the three-phase electrical input leads to the motor 2004 introduce a viscous drag on the motor shaft output 2008. While walking, the viscous drag holds roughly fixed the rotor shaft output so that the apparatus operates as a passive prosthesis. However, the apparatus can be moved slowly in a way that enables it to move to a non-fixed equilibrium position when standing or sitting. Each input lead is shorted to ground by its own individual switch.

In one embodiment, the switches are operated by a rechargeable battery (a separate battery from the primary battery used to operate the apparatus). By using a separate battery, the switches would short the input leads (and place the apparatus into a safe mode) even if a failure occurred (or the primary battery was depleted).

In one embodiment, the threaded shaft 2060 includes a hollowed out portion that contains a noise damping material to reduce the noise generated by the actuator 2000 and the apparatus within which the actuator 2000 is used. In one embodiment, the threaded shaft 2060 is 14 mm diameter stainless steel shaft 8.7 mm diameter bore that extends 64 mm of the length of the shaft, filled with ISODAMP® C-1002 acoustic damping material manufactured by 3M (with offices in St. Paul, Minn.).

The actuator 2000 also includes a radial and thrust bearing 2028 that support the belt 2024 tension due to the rotary motor 2004 and the thrust force of the screw 2036. Loads due to the belt tension and thrust force are present both statically and during the gait cycle.

The ball-nut assembly 2036 includes one or more recirculating ball-tracks 2042 that retain a plurality of ball bearings; the combination of which support the linear motion of the ball-nut assembly 2036. In one embodiment, five ball-tracks are used. The actuator 2000 includes a coupling element 2020 (e.g., the second end 1748 of the linear actuator 1716 of FIG. 17A) that couples the actuator 2000 to, for example, a passive elastic member of a foot member of a prosthetic apparatus (e.g., passive elastic member 1724 of FIG. 17A).

Figure 21:
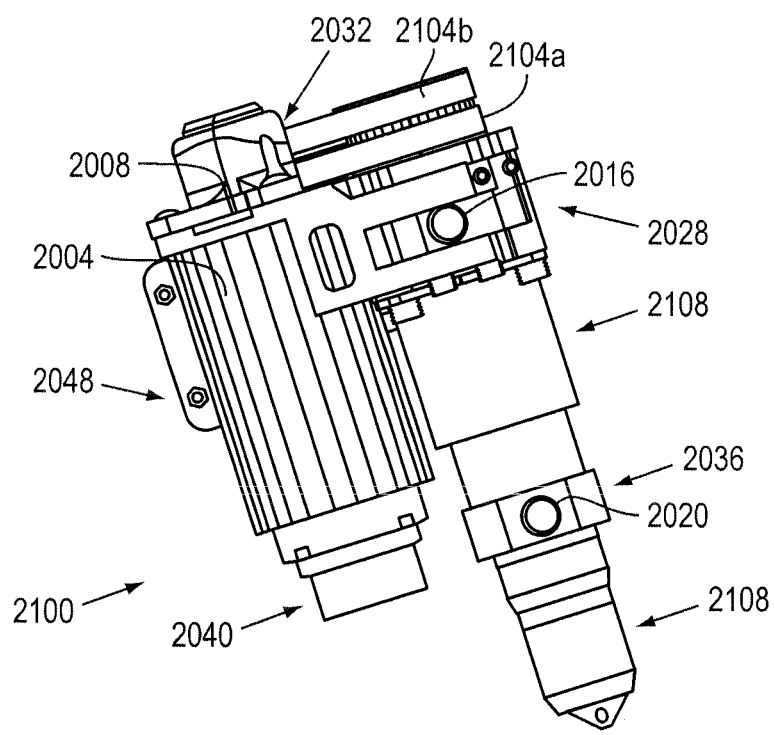
FIG. 21 is an illustration of a perspective view of a linear actuator capable of being used in various lower-extremity prosthetic, orthotic, and exoskeleton apparatus, according to an illustrative embodiment of the invention.

FIG. 21 is an illustration of a perspective view of a linear actuator 2100 for use in various lower-extremity prosthetic, orthotic, and exoskeleton apparatus, according to an illustrative embodiment of the invention. The linear actuator 2100 can be used as, for example, the linear actuator 1016 of apparatus 1000 of FIG. 17A or apparatus 400 of FIG. 4. The linear actuator 2100 is a variation of the actuator 2000 of FIGS. 20A and 20B.

The actuator 2100 includes a rotary motor 2004 that has a motor shaft output 2008. The motor shaft output 2008 has a pulley 2032 welded to the motor shaft output 2008. The motor 2004 includes an inductive incremental-absolute angular encoder 2040 that is integrated into the motor 2004 to for determining angular alignment between the rotary motor 2004 rotor and stator. The rotary motor 2004 also includes an integral motor heat-sink 2048.

Two belts 2104a and 2104b are used in parallel, rather than the single belt 2012 of FIGS. 20A and 20B. Each belt has the ability to drive the linear actuator transmission by itself with 1.5× margin on belt breakage, so as to enable the linear actuator 2100 to survive a single belt breakage failure. In one embodiment, in the event of a belt break, a controller of the apparatus in which the linear actuator 500 is used (e.g., controller 1762 of apparatus 1700 of FIG. 17A) moves the ankle to a safe position in a way that would enable the apparatus to operate as a passive ankle prosthetic until the linear actuator 500 is repaired. In one embodiment, the controller shorts three electrical leads of the rotary motor 504 in response to the belt breakage sensor detecting a failure of one or more of the plurality of belts. In such an event, one or more belt break sensors would sense the condition and move the ankle to a safe position in a way that would enable the system to operate as a passive ankle prosthesis until the linear actuator is repaired.

The two belts 2104a and 2104b couple the pulley 532 to a threaded shaft of a ball-screw transmission assembly (e.g., threaded shaft 2060 of FIG. 20B) such that rotational motion of the motor shaft output 2008 is translated to a linear motion of the ball-nut assembly 2036 portion of the ball-screw transmission assembly. The actuator 2100 also includes a radial and thrust bearing 2028 that support the tension in belts 2104a and 2104b due to the rotary motor 2004 and the thrust force of the threaded screw. Loads due to the belt tension and thrust force are present both statically and during the gait cycle.

The ball-nut assembly 2036 includes recirculating ball-tracks that retain a plurality of ball bearings; the combination of which support the linear motion of the ball-nut assembly 2036. The actuator 2100 includes a coupling element 2020 (e.g., the second end 1748 of the linear actuator 1716 of FIG. 17A) that couples the actuator 2100 to, for example, a passive elastic member of a foot member of a prosthetic apparatus (e.g., passive elastic member 1724 of FIG. 17A).

The actuator 2100 also includes a ball-screw assembly seal 2108. The ball-screw assembly seal 2108 protects the screw from, for example, contaminants (e.g., sand, dirt, corrosive materials, sticky materials). Such contamination would cause the design life of the actuator to become indeterminate.

Exemplary Lower-Extremity Orthotic (Wearable Robotic Knee Brace)

Figure 22C:
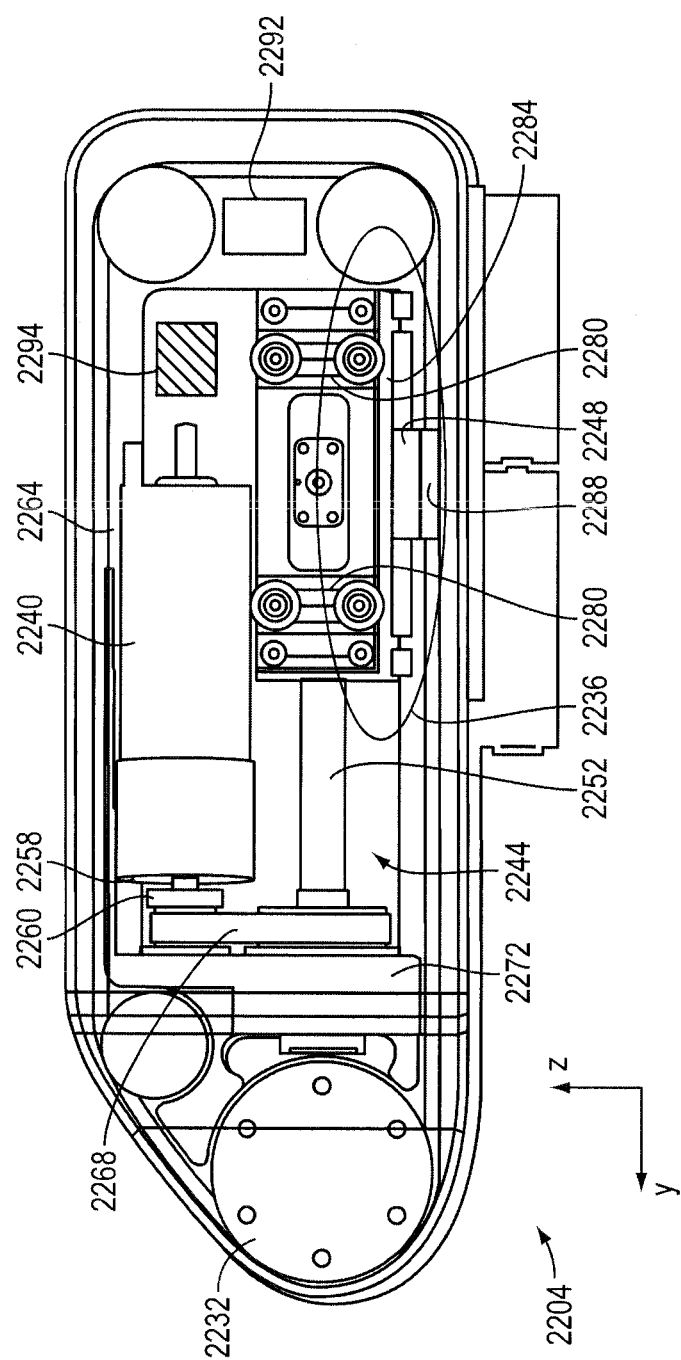
FIG. 22C is a schematic illustration of the interior portion of the knee joint drive assembly of the apparatus of FIGS. 22A and 22B.

FIGS. 22A, 22B and 22C are schematic illustrations of a lower-extremity orthotic or exoskeleton apparatus 2200 (wearable robotic knee brace), according to an illustrative embodiment of the invention. The apparatus 2200 is a knee-brace that augments the wearer's lower-extremity function. FIG. 22A is a top view of the apparatus 2200. FIG. 22B is a side view of the apparatus 2200. FIG. 22C is a view of the interior portion of a knee joint drive assembly 2204 of the apparatus 2200. Typical use cases for the apparatus 2200 include, for example, metabolic augmentation, permanent assistance for wearers with a permanent limb pathology, or rehabilitation for wearers with temporary limb pathology.

An example of a metabolic augmentation use case involves, for example, wearers (e.g., soldiers or other personnel) that need to traverse heavy terrain for extended periods at high speed while carrying heavy loads. In this use case, the knee brace apparatus 2200 augments the wearer's own abilities. An example of a permanent assistance use involves a wearer that suffers from a permanent limb pathology (e.g., knee tendon or meniscus degeneration) with no possibility for rehabilitation. In this use case, the knee brace apparatus 2200 provides permanent assistance to the wearer. An example of a use case involving rehabilitation for wearers with temporary limb pathology involves a wearer recovering from injury or other temporary condition. In this use case, the knee brace apparatus 2200 functions as a programmable telerobotic tool deployed by a physical therapist to accelerate recovery—through progression of kinesthetic rehabilitation and gradually decreasing assistance while the muscle memory and strength recover. In another embodiment, the method includes specifying a physical therapy protocol defining a level of assistance performed by the apparatus on the wearer over a period of time and reducing the level of assistance performed by the apparatus on the wearer to assist in rehabilitation of the limb pathology. In some embodiments, the level of assistance performed by the apparatus is reduced based on impedance and torque contribution of the wearer to the apparatus.

Referring to FIGS. 22A and 22B, the apparatus 2200 includes a lower leg member 2216 (also referred to as a drive arm), a thigh member 2228, a lower leg cuff 2208 and an upper leg cuff 2212. The lower leg cuff 2208 is coupled to the lower leg member 2228. The lower leg cuff 2208 attaches the apparatus 2200 to the lower leg of the wearer. The upper leg cuff 2212 is coupled to the thigh member 2228. The upper leg cuff 2212 attaches the apparatus 2200 to the thigh of the wearer. The apparatus 2200 includes a knee joint 2232 for connecting the thigh member 2228 to the lower leg member 2216. The knee joint 2232 (e.g., a rotary bearing) permits the lower leg member 2216 to rotate about the x-axis relative to the thigh member 2228.

Referring to FIG. 22C, the knee joint drive assembly 2204 includes a linear actuator that drives the knee joint drum 2232 through a belt drive transmission 2236. The linear actuator is a rotary motor 2240 (e.g., brushless motor) and ball-screw transmission assembly 2244 (e.g., the motor 2004 and ball-screw transmission assembly 2024 of FIGS. 20A and 20B). In the apparatus 2200, rotational motion of the motor shaft output 2256 of the motor 2240 is translated to a linear motion of the ball-nut assembly 2248 portion of the ball-screw transmission assembly 2244. The motor shaft output 2256 has a pulley 2260 coupled (e.g., welded) to the motor shaft output 2256. The motor 2240 includes an inductive incremental-absolute angular encoder 2264 that is integrated into the motor 2240 for determining angular alignment between the rotor and stator of the rotary motor 2240. The encoder also provides a position feedback signal necessary to control the screw 2252 position of the ball-screw transmission assembly 2244 and to provide for "instant-on" motor commutation and redundant position feedback monitoring.

A belt 2268 couples the pulley 2260 to the threaded shaft 2252 of the ball-screw transmission assembly 2244 such that rotational motion of the motor shaft output 2256 is translated to a linear motion of the ball-nut assembly 2248 portion of the ball-screw transmission assembly 2244.

In one embodiment, the threaded shaft 2252 includes a hollowed out portion that contains a noise damping material to reduce the noise generated by the knee joint drive assembly 2204. The knee joint drive assembly 2204 also includes a radial and thrust bearing 2272 that support the belt 2268 tension due to the rotary motor 2240 and the thrust force of the screw 2252. Loads due to the belt tension and thrust force are present both statically and during the gait cycle.

The knee joint drive assembly 2204 also includes a spring 2280 for series elasticity, spring cage 2284, drive belt 2236 and a spring cage/belt connection 2288. In some embodiments, a drive band (e.g., thin piece of spring steel) is used in place of the drive belt 2236. In some embodiments, a drive cable (e.g., loop of stranded material) is used instead of the drive belt 2236. Spring 2280 is a series passive elastic element, functioning in the same manner as the series elastic spring element 1728 of FIG. 17A. The spring cage 2284 provides a closed volume in which the spring 2280 is located. The ball-nut transmission assembly 2248 is coupled to the screw 2252. The ball-nut assembly 2248 is also coupled to the drive belt 2236. Linear motion of the screw 2252 causes a linear motion in the ball-nut assembly 2248. The linear motion in the ball-nut assembly 2248 causes a linear motion in the drive belt 2236. The linear motion of the drive belt 2236 drives the knee joint 2232.

The apparatus 2200 includes a controller 2292 (e.g., a printed circuit assembly that incorporates the linear actuator 2204, state and inertial measurement unit 2294 (e.g., inertial measurement unit 1720 of FIG. 17A) control and processing functions) to drive and control the operation of the apparatus 2200. Referring to FIG. 22B, the apparatus 2200 also includes a torque sensor 2220 coupled to the lower leg member 2216 to measure the torque applied to the lower leg member 2216 by the knee joint drive assembly 2204. The sensor 2220 serves as the feedback element in the control loop of the controller 2292 to achieve high fidelity closed loop position, impedance and torque (for reflex) control of the knee joint 2232. In one embodiment, an array of force-sensitive transducers are embedded within the cuff structure to provide force measurements used to achieve rapid, biomimetic response.

In some embodiments, the motor angle sensor (e.g., encoder 2264) measures motor position and the controller controls the rotary motor to modulate position, impedance and torque of the knee joint 2232 based on the motor position.

In some embodiments, the apparatus 2200 includes an angle sensor for determining position of the drum 2232 of the belt drive transmission relative to the output of the motor drive transmission and the controller controls the rotary motor for modulating impedance, position or torque based on the position. In some embodiments, the apparatus 2200 includes a displacement sensor for measuring displacement of a series spring in the motor drive transmission for determining force on the series spring and the controller controls the rotary motor for modulating impedance, position or torque based on the force on the spring. In some embodiments, the inertial measurement unit 2294 is coupled to the thigh member or lower leg member for determining an inertial pose of the lower leg member and the controller controls the rotary motor for modulating impedance, position or torque based on the inertial pose. In some embodiments, the torque sensor 2220 measures the torque applied to the lower leg member by the belt drive transmission and the controller controls the rotary motor for modulating impedance, position or torque based on the torque applied to the lower leg member. In some embodiments, the apparatus 2200 includes an angle sensor for determining an angle between the thigh member and lower leg member and wherein the controller controls the rotary motor for modulating impedance, position or torque based on the angle between the thigh member and lower leg member.

In some embodiments, the apparatus 2200, instead of a motor drive transmission, the apparatus includes a screw transmission assembly coupled to the motor shaft output for converting the rotary motion of the motor shaft output to a linear motion output by the screw transmission assembly. In addition, the drive transmission assembly coupled to the output of the motor drive transmission is a redundant belt, band or cable drive transmission coupled to the screw transmission assembly to convert a linear motion output by the screw transmission assembly to a rotary motion for applying torque to the knee joint to rotate the lower leg member with respect to the thigh member.

Unlike the prosthetic apparatus 2000 of FIG. 20A, the knee brace apparatus 2200 operates in parallel with human actuation. In metabolic augmentation and replacement applications, the knee brace control system will supply all of the impedance and torque needs within the gait cycle. It is desirable for the wearer to be able to walk all day without getting tired and without exertion on the augmented side(s) of the body. In rehabilitation applications, the knee-brace apparatus 2200 supplies only a programmed percentage of the impedance and torque. In such applications, the knee-brace apparatus 2200 serves as a telerobotic extension of the physical therapist supervising the wearer's rehabilitation.

In one embodiment of the knee brace control system, the physical therapist creates a protocol to be executed telerobotically by the knee brace over a period of time between therapist visits. Using a wireless interface, patient performance can be fed back to the physical therapist, thereby achieving telepresence. The protocol specifies the rate at which the assistance diminishes over time. As the knee brace apparatus reduces assistance, the knee brace apparatus would compute via biomechanical models the impedance and torque contribution by the wearer—reducing assistance in accordance with the improved response to maintain the desired net biomimetic response. The biomechanical models would involve solving the inverse dynamics of the knee—incorporating inertial rotation and acceleration of the lower leg member, thigh member and torso. This six degree-of-freedom information would be derived from the inertial measurement unit in the thigh member and knee joint angular displacement. The zero-velocity update for the inertial measurement unit would be accomplished similarly as described herein.

Balance Using Ground Reaction Forces and Zero Moment Pivot

Figure 23A:
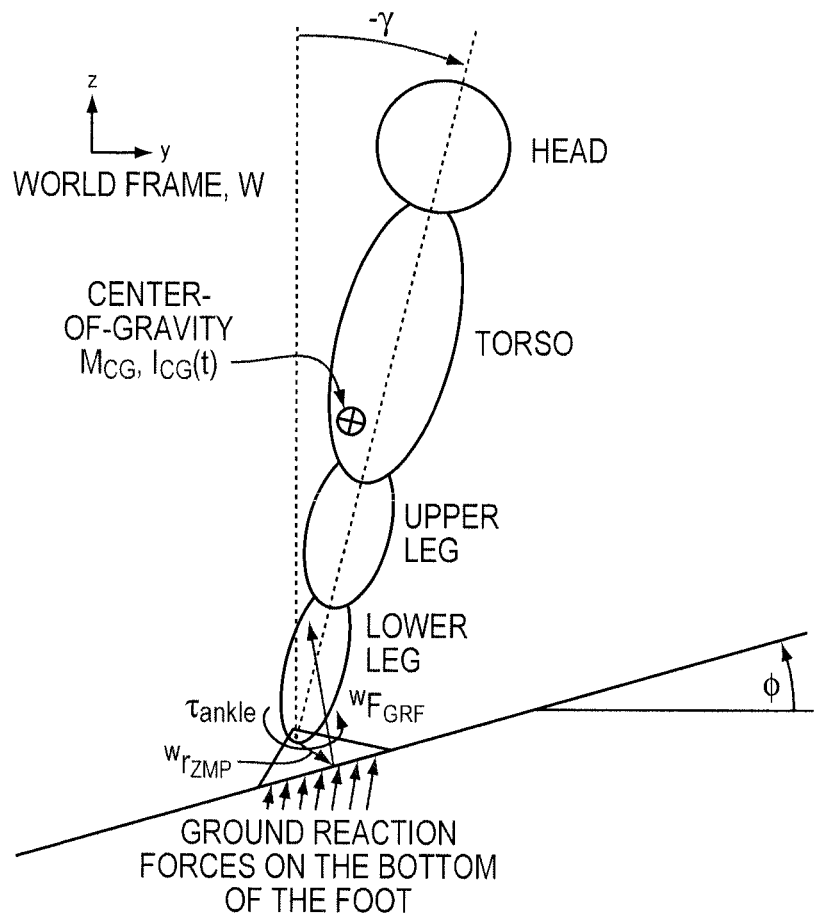
FIG. 23A is a schematic illustration of the human balance problem on an inclined slope.

FIG. 23A illustrates the generic problem of achieving balance on an incline of variable (positive or negative) slope. The problem appears to involve a multi-link, "inverted pendulum" problem, amenable to a non-linear feedback control implementation. In such solutions, knowledge of the link angles and the mass properties of the links (in this case, leg segments, torso, head and arms) are used to explicitly stabilize the multi-link system. But such explicit inputs are not contained within most embodiments of a lower-extremity prosthetic, orthotic or exoskeleton apparatus and would therefore be difficult if not impossible to implement and package reliably on the wearer. Further, in some instances, the wearer will have one intact leg, so part of the stabilization will be achieved outside of the lower-extremity prosthetic, orthotic or exoskeleton apparatus, wherein the lower-extremity prosthetic, orthotic or exoskeleton apparatus augments the function of the intact leg.

Figure 23B:
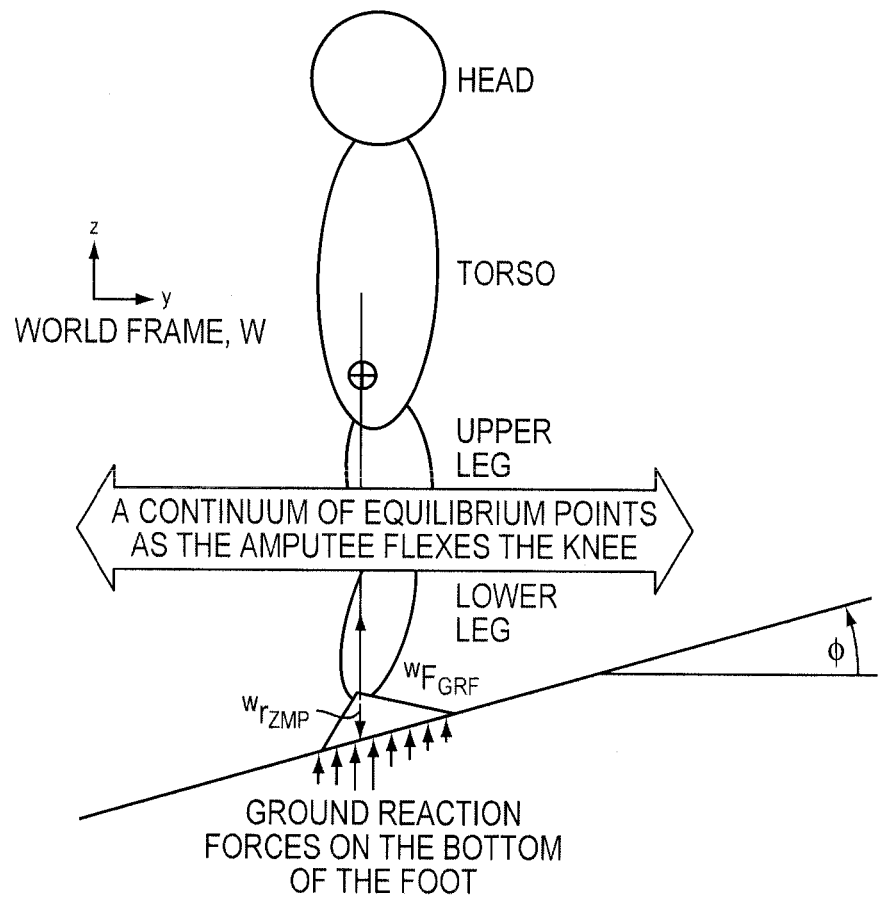
FIG. 23B is a schematic illustration of acceptable solutions to the balance problem based on variable knee flex by a wearer.

In addition, FIG. 23B shows that there is a continuum of acceptable solutions to the balance problem. Specifically, there are an infinite number of bent-knee solutions that are entirely acceptable and even desirable depending on human intent (e.g., picking up heavy luggage or boxes or to achieve balance while playing a game). So we see that the desired solution will employ intrinsic (to the lower-extremity prosthetic, orthotic or exoskeleton apparatus) sensing that complements the intact balance-producing body components to achieve equilibrium in alignment with human intent.

Figure 23C:
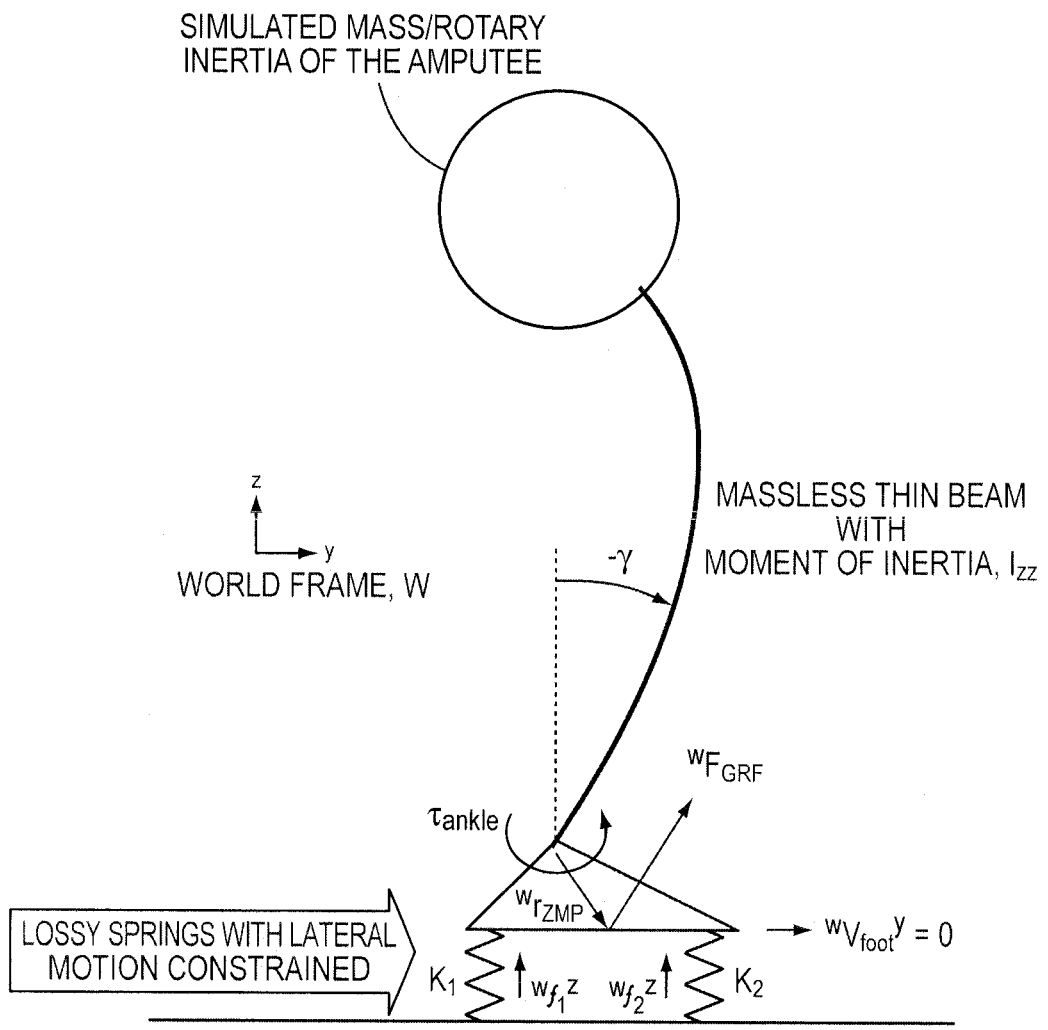
FIG. 23C is a schematic illustration representing the human body and how intrinsic sensing can be used to balance the wearer on level ground.

The solution employed in some embodiments of the lower-extremity prosthetic, orthotic or exoskeleton apparatus uses a simplified representation of the problem as modeled in FIG. 23C. In this representation, intrinsic sensing of lower leg member inertial state, ankle joint angle and inertially-referenced, ground reaction force, are used as the stabilization feedback that drives ankle torque (e.g., torque provided to the ankle joint by a linear actuator of a prosthetic apparatus). The body is modeled as a series of masses (only one shown in the figure) on a massless, thin, buckling beam with time-variable stiffness and moment-of-inertia.

Balance is achieved based on the following details. A desirable equilibrium is achieved when the following conditions are satisfied:

1. $^{W}F_{GRF}$ aligns with World z;
2. The line connecting the zero moment pivot and the ankle joint aligns with the World z unit vector; and
3. All time derivatives of the inertial lower leg member angle, $\gamma$, and ankle joint angle, $\theta$, are zero.

A feedback control law is then derived that drives each of these conditions into equilibrium based on the following:

$$\tau_{ankle} \cong -\hat{I}(t)_{CG} \underline{k}^*(s)[^{\omega}\gamma_{CoP}{}^y {}^{\omega}F_{GRF}{}^y \gamma]^T \qquad \text{EQN. 40}$$

where $$\underline{k}^*(s) = [k_\gamma{}^*(s)\ k_F{}^*(s) k_\gamma{}^*(s)] \qquad \text{EQN. 41}$$

optimizes the quadratic cost index, J, where $$J = \int_0^\infty (\tau_{ankle}^2 + \underline{k}^T[\gamma \dot\gamma \ddot\gamma]^T[\gamma \dot\gamma \ddot\gamma]^T \underline{k}) dt \qquad \text{EQN. 42}$$

and $$\underline{k} = \lfloor k_\gamma \ k_{\dot\gamma} \ k_{\ddot\gamma} \rfloor \qquad \text{EQN. 43}$$

where the components of k are chosen to emphasize link angle dynamic contributions to the cost index. In this embodiment, the control law solution is provided by the linear-quadratic regulator (LQR) methodology. In layman's terms this means that the settings of a (regulating) controller governing either a machine or process are found by using the above mathematical algorithms and minimizing a cost function with weighting factors supplied by a human. The "cost" (function) is often defined as a sum of the deviations of key measurements from their desired values. In effect this algorithm therefore finds those controller settings that minimize the undesired deviations, for example, deviations from desired work performed by a prosthesis for the wearer. Often the magnitude of the control action itself is included in this sum as to keep the energy expended by the control action itself limited. In effect, the LQR algorithm optimizes the controller based on an engineer's specification of the weighting factors. The LQR algorithm is, at its core, just an automated way of finding an appropriate state-feedback controller.

Use of the quadratic cost index is not required; however, in one embodiment, use of the quadratic cost index as an optimization criterion creates an objective framework for analysis and for in-office customization for wearers of the lower-extremity prosthesis to achieve an acceptable feel as the system works to maintain the wearer's equilibrium on different terrain. It is not uncommon to find that control engineers prefer alternative conventional methods like full state feedback (also known as pole placement) to find a controller over the use of the LQR algorithm. With these the engineer has a much clearer linkage between adjusted parameters and the resulting changes in controller behaviour.

Wearer Assist in Getting Up from a Chair

Figure 24A:
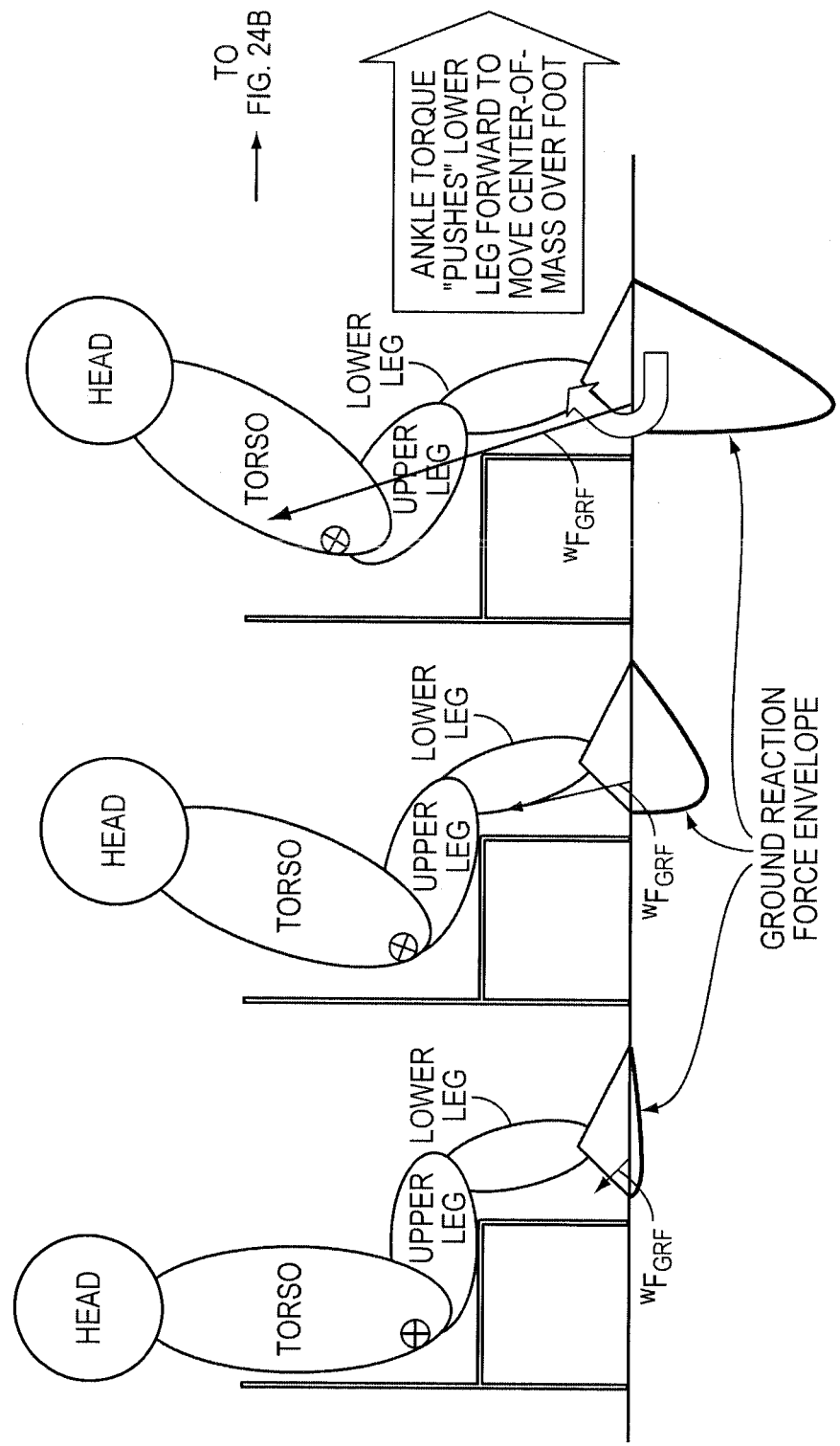
FIGS. 24A-24C are schematic illustrations for a method for balancing a wearer as the wearer stands up from a chair, according to an illustrative embodiment of the invention.
Figure 24B:
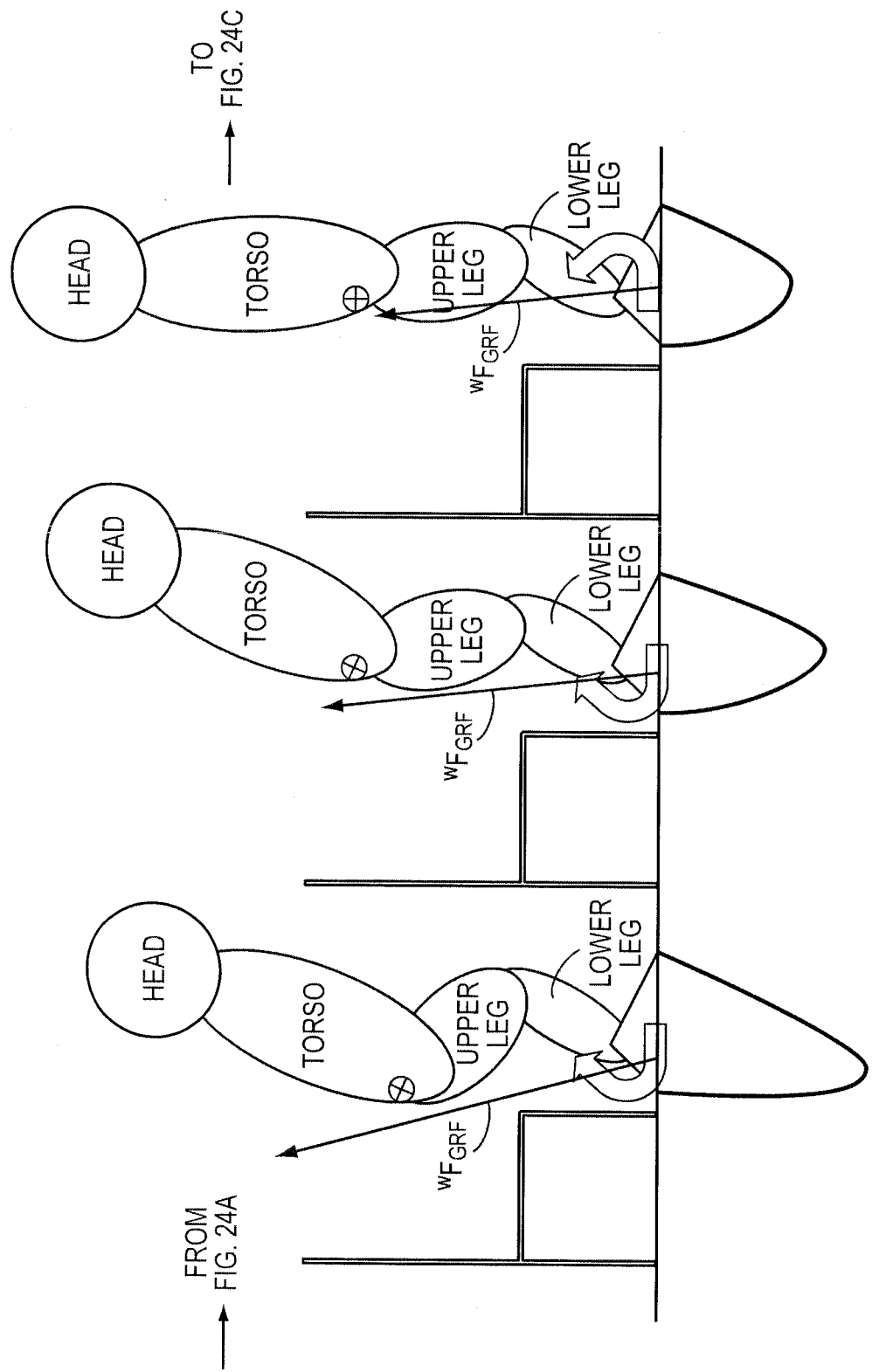
Figure 24C:
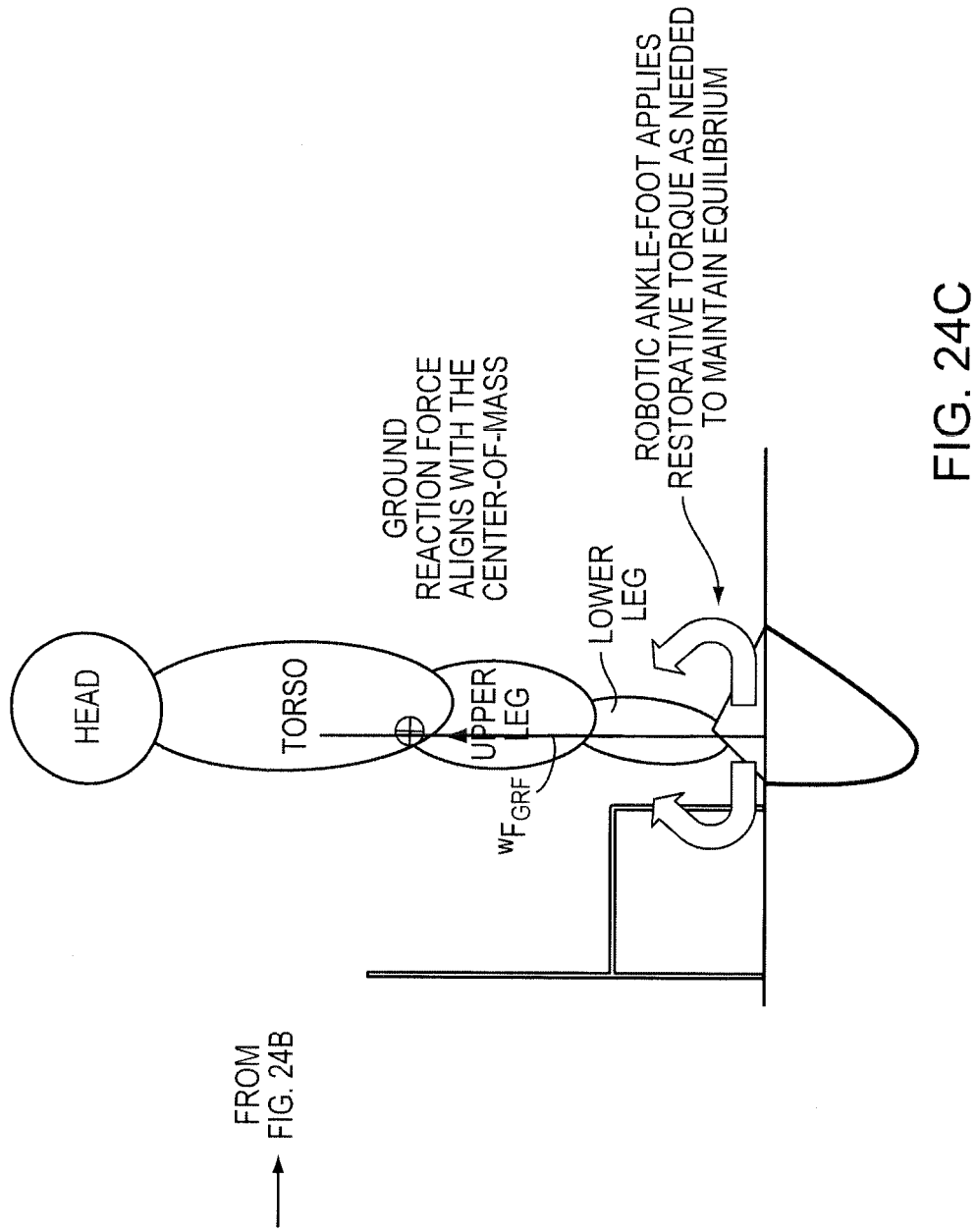

FIGS. 24A, 24B and 24C illustrate a method for applying a balancing control law to assist a wearer of a lower-extremity prosthetic apparatus in getting up from a chair, according an illustrative embodiment of the invention. The Timed Get Up and Go (TUG) is often used as an experimental means to evaluate dynamic and functional balance. Wearers are given a verbal instruction to stand up from a chair, walk 3 meters, cross a line marked on the floor, turn around, walk back, and sit down. To achieve good "TUG" performance, leg prostheses often have a "stand up" and "sit down" button to create the behavioral context for the prosthesis' control system. In the lower-extremity prosthetic apparatus incorporating principles of the present invention, in one embodiment there is no explicit requirement to set behavioral context by, for example, pushing a button. Sitting, standing up and sitting down behavioral context is identified by the intrinsic sensors of the prosthetic apparatus. Control behavior during standing and sitting is simply part of maintaining the wearer's equilibrium.

FIGS. 24A, 24B and 24C illustrate how the intrinsic balance control algorithm works to augment the wearer as she stands up from a chair. Referring to FIG. 24A, initiation of the sitting to standing transition involves three states. In the first, the foot is off the ground or only lightly touching it. The prosthetic apparatus (e.g., apparatus 1700 of FIGS. 17A-17E) knows the mass of the wearer; the inertial orientation of the lower leg member and foot member; and the ground reaction force (as determined, for example, with respect to FIG. 11A). The apparatus therefore "knows" or senses that the wearer is sitting. As the wearer begins to stand up, the increase in ground reaction force is noted and the state of the foot (foot flat) is known via the inertial measurement unit measurements and ankle joint angle sensor measurements. The intrinsic balance control law execution begins. During this second state, the disequilibrium sensed by the imbalance in the ground reaction force is used to drive the lower leg member (e.g., driven forward by the controller 1762 commanding the linear actuator 1716 to increase the torque applied to the ankle joint 1740) forward as a means of pulling the torso (center-of-mass) over the ankle joint.

Referring to FIG. 24B, the intrinsic balance control continues to drive the wearer into equilibrium in front of the chair. FIG. 24C shows the wearer in mid-stance equilibrium, ready to begin walking if desired. As shown, wearer intent, and more specifically the sitting/standing behavioral context can be derived by sensing that is intrinsic to the prosthetic apparatus. The implementation cost and complexity of explicit context switching (pressing of buttons) is thereby avoided. The prosthetic apparatus complements and augments the body function in a natural way.

The ankle torque induced by the ground reaction force (GRF) is a preferred way to achieve exponential hardening during mid-stance. Unlike use of the torque on the lower leg (e.g., torque measured using the structural element 1732 of FIG. 17A), the GRF-computed ankle torque measures the torque applied by the ground on the ankle joint. The GRF is often measured by force plates in gait research settings and is thereby used as a measure of how an intact ankle interacts with the ground while walking. The GRF establishes what is the biomimetic ankle behavior in different terrain contexts. A benefit of using the GRF as the means by which to achieve exponential hardening is the ease by which performance can be measured relative to biomimetic references. Further, use of this measure ensures that invariance to terrain orientation since it derives from intrinsic inertial sensing (e.g., using the inertial measurement unit 1720 of FIG. 17A).

Optimization Methods

Figure 25A:
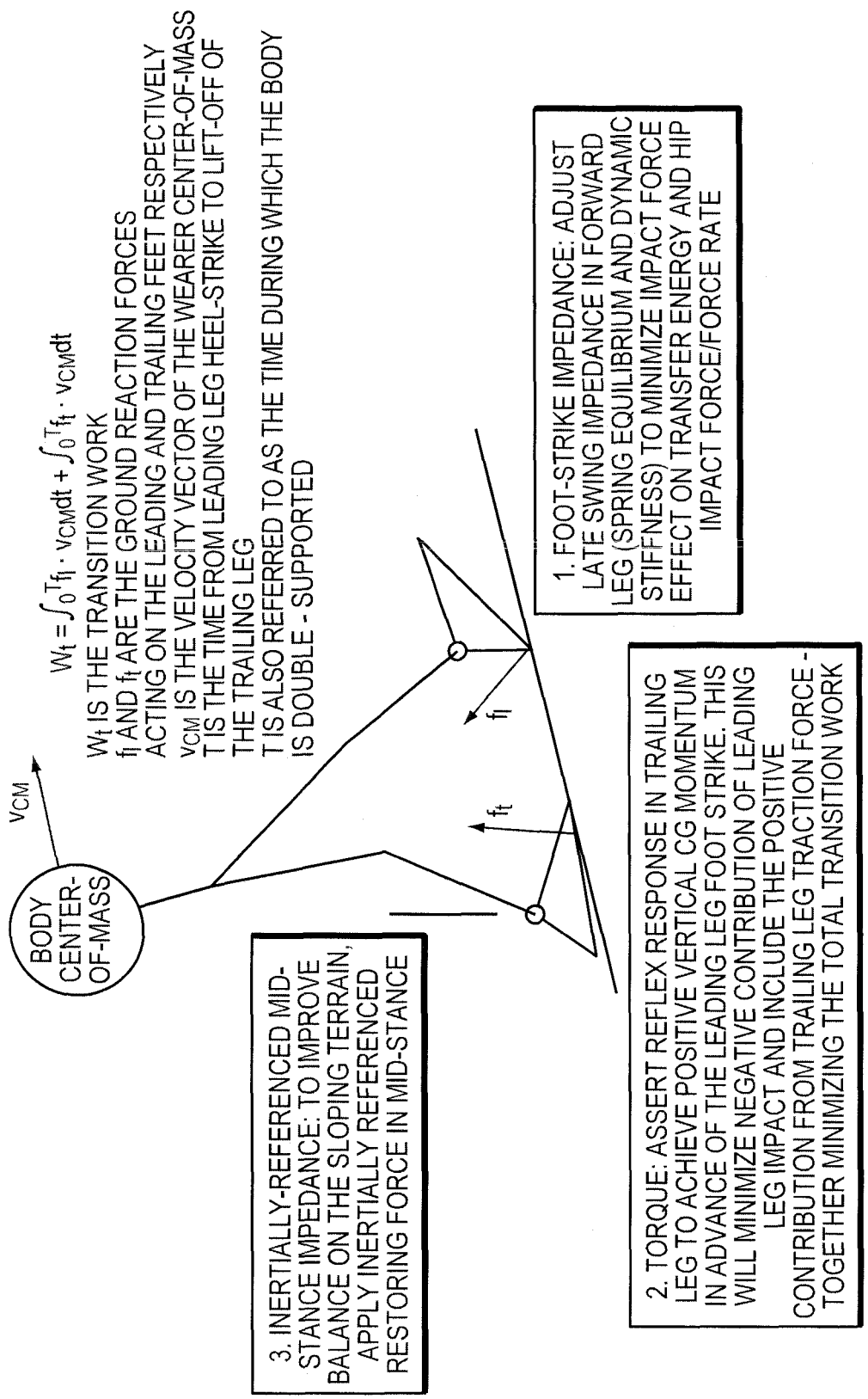
FIG. 25A illustrates a definition of transfer work.

FIGS. 25A and 25B are schematic illustrations for controlling a lower-extremity apparatus based on a stochastic optimization of 1) the transition work, $W_t$, performed to transfer weight from the trailing leg to the leading leg during the double-support phase of the gait cycle 2) minimizing hip impact force and force rate or 3) minimizing a combination of both cost (objective) functions FIG. 25A illustrates the simplified model used to calculate transition work. FIG. 25B illustrates the simplified model used to calculate hip impact force and force rate.

The term stochastic denotes that the optimization minimizes the expected value of the objective function subject to hip impact force and force rate constraints, assuming probability (likelihood) functions for human intent; biomechanical feedback (including walking speed); terrain context, and terrain property. The optimization is achieved through modification of impedance, torque and position control parameters within the control algorithms. Practically speaking, the transfer energy is minimized, and the hip impact force constraints satisfied, by minimizing the negative impact of foot strike forces and maximizing the positive impact of reflex-induced ground forces on the hybrid system energy.

The optimization described above can be implemented in real-time by introducing "evolutionary" perturbations in the key components that contribute to the biomimetic behavior and measuring the transfer energy that arises from those evolutionary perturbations. The transfer energy can be estimated using biomechanical models to augment the inertial measurement unit feedback, or, in special cases, temporary inertial measurement unit subsystems (an IMU mounted on the body in the form of a belt around the torso and/or upper leg) could be used to facilitate estimate of torso pose and body center-of-mass velocity. Using the Fletcher-Powell method (or other suitable optimization method known to those skilled in the art), an intelligent evolution of parameters can be introduced and an optimum can be calculated. This optimum could, due to the rehabilitative effects of the augmentation, change over time. By applying these evolutionary perturbations continually and slowly over time, the optimum can be achieved on a continual basis. Or, as would be the case at the initial fitting or medical checkup of the prosthesis or orthosis, this evolutionary optimization could occur over a much shorter interval, say, in five to ten minutes.

The following is a description of the different phases of a subject's gait cycle and, in one embodiment, the steps performed by a ankle joint prosthesis according to principles of the invention are for sensing the operation of and for controlling the ankle joint prosthesis.

Controlled Plantarflexion

At impact, check that the ground reaction force and the zero moment pivot correspond with the part of the foot that we expect (from the terrain discrimination model) to hit the ground first. Confirm that there is a corresponding change in the ankle angle (or ankle torque) and that the appropriate end of the foot is stationary. After impact look for a condition where the local terrain slope corresponding to the inertial foot-flat angle is significantly less than expected. Saturate ankle spring restoring force and increase damping when this is detected. For terrain discrimination, based upon the biomechanical model feedback confirm that the terrain hypothesis (slope vs. stair) is correct and that the wearer hasn't tripped. For example, a tripping event on a stair might be detected as a large negative force in the y-direction instead of a large z-force centered on the forward part of the foot. For terrain texture, either the heel or the forward part of the foot will impact first. The non-elastic component of the depression associated with this impact will be computed. On hard ground, this depression should be negligible—only an elastic deformation (foot module, linear actuator) will be observed. In mud or soft ground, terrain plasticity will be observed by looking at the trajectory of the impacting foot segment. The terrain plasticity will be used as an attenuator on the net work that is performed on this walking cycle. Slipping can also be detected by noting the forward velocity of the impacting foot segment after impact. An escalator or people mover can be detected by noting that the shank angle is not rotating in accordance with the forward velocity of the foot, signaling that the wearer is well balanced and is stepping onto a moving surface. For impedance control of the ankle joint apply optimal impedance using estimated terrain-referenced velocity attack angle (y) lower-limb momentum, estimated terrain slope and terrain property. For reflex control, in the event that slipping is detected, a balance-restoring reflex will be generated to move the knee over the ankle. For balance control, optimal balance will normally be achieved by inertially referencing the spring equilibrium after the local terrain slope estimate is updated at foot-flat. In the event that the terrain is slippery, the algorithms that maintain balance will introduce a positive torque "reflex" to "pull" the shank forward in order to assist the wearer as she works to position the knee over the ankle—thereby getting the body center-of-mass aligned with the estimated ground reaction force.

Controlled Dorsiflexion

Once foot flat is detected, the controller inertially references the spring equilibrium angle for this local terrain slope so that when the wearer is standing in alignment with gravity on this slope, no restoring torque is applied by the ankle under static conditions. At this point, the local terrain context is now known precisely. Foot reference coordinates at this "foot flat" position are also defined for use in assessing the impact of terrain texture. For terrain texture, the algorithms use integrated measures of slip and deformation relative to the "foot flat" reference to update the terrain property model—specifically to measure plasticity of the surface and it's slipperiness by measuring how the impacted foot segment moves between foot-strike and foot flat. These measures can be used to attenuate ankle impedance and net work (reflex torque in late plantar flexion. Also, if "slipping" is detected between foot-strike and foot-flat, an algorithm implemented in the controller, also looks at shank angular velocity (how the knee is moving in relation to the ankle joint) to discriminate between a slippery surface and an escalator/people-mover. In either event, the zero-velocity update would not be scheduled since no reliable "ankle joint at zero velocity" will be available on this step. In the event that the terrain is slippery, special measures will need to be invoked by the balance function. In the case where the foot lands on a moving escalator or people mover, nominal impedance can be used on the new inertial frame. For impedance control, the control system can apply optimal impedance that maintains an inertially-referenced equilibrium angle; creates a walking speed-dependent stiffness (lower stiffness for faster walking speed) to enable a higher level of net work; and reduces the stiffness in slippery or highly-plastic surfaces. For reflex control, in the event that slipping is detected, a balance-restoring reflex will be generated to move the knee over the ankle. For balance control, optimal balance will normally be achieved by inertially referencing the spring equilibrium after the local terrain slope estimate is updated at foot-flat. In the event that the terrain is slippery, the algorithms that maintain balance will introduce a positive torque "reflex" to "pull" the shank forward in order to assist the wearer as she works to position the knee over the ankle—thereby getting the body center-of-mass aligned with the estimated ground reaction force.

Powered Plantarflexion

The model monitors slippage and sinking into the surface and identifies ankle torque limits that can be used to make ambulation efficient in these conditions. For terrain texture, terrain property estimates are refined in this state and are used as an input to the impedance, reflex and balance functions. For impedance control, nominal impedance parameters will be modified to accommodate changes in walking speed, terrain surface characteristics and deformation and foot slippage. A special "force field"—typically a non-linear actuator force that exponentially increases as the ball-nut approaches a predefined end-stop limit—is applied by the motor controller to make sure that the K3 spring energy (in the parallel elastic member) does not exceed the lower bound of its fracture limit. For reflex control, reflex amplitude will be adjusted to account for the net work "setpoint" from the biomechanical models in combination with the degree to which the terrain can support production of this net work. For balance control, optimal balance will normally be achieved by inertially referencing the spring equilibrium after the local terrain slope estimate is updated at foot-flat. In the event that the terrain is slippery, the algorithms that maintain balance will introduce a positive torque "reflex" to "pull" the shank forward in order to assist the wearer as she works to position the knee over the ankle—thereby getting the body center-of-mass aligned with the estimated ground reaction force.

Early Swing

For early swing, shortly after the toe leaves the ground, the model monitors the inertial trajectory of the ankle, heel and toe and determines when the ankle can be dorsiflexed back to its neutral position without being obstructed by the terrain. The model computes an optimal trajectory with suitable impedance gains and feed-forward torque to move the ankle to the neutral position (to avoid tripping hazards) in the quickest, efficient and stable fashion. For terrain discrimination, the model starts to keep track of the swept ("no contact" with foot member) volume through which the foot has moved thereby informing the adaptive ankle positioning function in late swing when a toe-down solution is the only viable solution (e.g., to land on a shallow stair or ledge). For impedance control in early swing, a neutral value of impedance is applied by the controller. A force-field function is applied to make sure that the linear actuator does not impact the hard stop (end of travel)—a condition that could cause the actuator to stick there (at the end of travel). For impedance control in early swing informed by the hybrid biomechanical model, the controller controls the impedance to create a trajectory that exponentially drives the equilibrium position (ankle angle setpoint) to the desired neutral position. A feed-forward torque function is applied to reduce the interaction between impedance characteristics and the ankle angle following error that could otherwise introduce overshoot and ringing, for instance.

Late Swing

For terrain discrimination, the model keeps track of the "clear" volume through which the foot has moved thereby informing the adaptive ankle positioning function in late swing when a toe-down solution is the only viable solution, say, to land on a shallow stair or ledge. More generally, the ankle trajectory is monitored and pattern recognition functions are used to determine the likelihood that the foot will be landing on a stair/ledge as opposed to a sloping surface. One simple way that we have found to discriminate between the two conditions is to measure the angle that the ankle velocity makes in relation to vertical; where in various experiments it was determined that when this angle is less than 10 degrees, the foot will land on a horizontal step. For impedance control, informed by the terrain discrimination model, the ankle trajectory (equilibrium) will be modified by the controller as needed to avoid tripping hazards. For example, if the terrain discrimination function assigns the maximum likelihood to stair ascent, additional dorsiflexion may be commanded to make sure that the toe does not catch on the stair or ledge. As before, the hybrid biomechanical model plans a continuously updatable equilibrium trajectory that can be followed safely and in a stable fashion with tight tolerances. In the late-stance state, the biomechanical model computes the optimum equilibrium angle and ankle impedance that will minimize an objective function that includes some combination of transfer energy and knee-hip impact forces. This optimization function could be implemented via table lookup in the State Machine ROM. Or, in the preferred embodiment, the State Controller function will perform the optimization in real-time, using approximations of the rigid-body dynamics, to compute and optimize the objective functions.

Variations, modifications, and other implementations of what is described herein will occur to those of ordinary skill in the art without departing from the spirit and the scope of the invention as claimed. Accordingly, the invention is to be defined not by the preceding illustrative description but instead by the spirit and scope of the following claims.

The invention claimed is:

1. A method for a lower extremity prosthesis or orthosis, the lower extremity prosthesis or orthosis comprising a foot member, a lower leg member, and an ankle joint for connecting the foot member to the lower leg member, the method comprising:
   receiving, from an accelerometer coupled to the lower leg member, an accelerometer signal;
   receiving, from an inertial measurement unit coupled to the lower leg member, an inertial pose misalignment signal;
   determining at least one velocity error contribution when the ankle joint is substantially stationary during a walking cycle based in part on the accelerometer signal; and
   determining at least one velocity error contribution when the ankle joint is substantially stationary during the walking cycle based in part on the inertial pose misalignment signal and a world frame-referenced ankle joint parameter, the world frame-referenced ankle joint parameter to include an indication of at least one of a velocity of the ankle joint or a position of the ankle joint.

2. The method of claim 1, wherein the inertial pose misalignment signal is a rate gyro signal output by a rate gyro, the method comprising:
   determining the pose of the lower leg member based in part on the accelerometer signal and the rate gyro signal; and
   determining a corrected pose of the lower leg member using the velocity error contributions.

3. The method of claim 2, wherein the prosthesis or orthosis comprises a thigh member, the method comprising:
   receiving, from an accelerometer coupled to the thigh member, a second accelerometer signal;
   receiving, from an inertial measurement unit coupled to the thigh member, a second inertial pose misalignment signal; and
   determining one or more velocity error contributions based on the second accelerometer signal and the second inertial pose misalignment signal when the ankle joint is substantially stationary during the walking cycle.

4. The method of claim 2, wherein the prosthesis or orthosis comprises a thigh member, the method comprising:
   receiving, from an accelerometer coupled to the thigh member, a second accelerometer signal;
   receiving, from an inertial measurement unit coupled to the thigh member, a second inertial pose misalignment signal; and
   determining one or more velocity error contributions based on the second accelerometer signal and the second inertial pose misalignment signal when a computed position on the foot member is substantially stationary.

5. The method of claim 3, comprising determining an angle of the lower leg member relative to the thigh member.

6. The method of claim 1, wherein the velocity error contributions are determined during a portion of a controlled dorsiflexion state of the walking cycle.

7. A controller for a lower extremity prosthesis or orthosis, the lower extremity prosthesis or orthosis comprising a foot member, a lower leg member, and an ankle joint for connecting the foot member to the lower leg member, the controller comprising:
   logic, at least a portion of which is in hardware, the logic to:
      receive, from an accelerometer coupled to the lower leg member, an accelerometer signal;
      receive, from an inertial measurement unit coupled to the lower leg member, an inertial pose misalignment signal;
      determine at least one velocity error contribution when the ankle joint is substantially stationary during a walking cycle based in part on the accelerometer signal; and
      determine at least one velocity error contribution when the ankle joint is substantially stationary during the walking cycle based in part on the inertial pose misalignment signal and a world frame-referenced ankle joint parameter, the world frame-referenced ankle joint parameter to include an indication of at least one of a velocity of the ankle joint or a position of the ankle joint.

8. The controller of claim 7, wherein the inertial pose misalignment signal is a rate gyro signal output by a rate gyro, the logic to:
   determine the pose of the lower leg member based in part on the accelerometer signal and the rate gyro signal; and
   determine a corrected pose of the lower leg member using the velocity error contributions.

9. The controller of claim 7, wherein the velocity error contributions are determined during a portion of a controlled dorsiflexion state of the walking cycle.

10. The controller of claim 7, wherein the prosthesis or orthosis comprises a thigh member, the logic to:
- receive, from an accelerometer coupled to the thigh member, a second accelerometer signal;
- receive, from an inertial measurement unit coupled to the thigh member, a second inertial pose misalignment signal; and
- determine one or more velocity error contributions based on the second accelerometer signal and the second inertial pose misalignment signal when the ankle joint is substantially stationary during the walking cycle.

11. The controller of claim 10, the logic to determine an angle of the lower leg member relative to the thigh member.

12. The controller of claim 10, the logic to:
- receive, from an accelerometer coupled to a wearer's torso, a third accelerometer signal;
- receive, from an inertial measurement unit coupled to the wearer's torso, a third inertial pose misalignment signal; and
- determine one or more velocity error contributions based on the third accelerometer signal and the third inertial pose misalignment signal when the ankle joint is substantially stationary during the walking cycle.

13. The controller of claim 12, the logic to determine an angle of the thigh member relative to the wearer's torso.

14. The controller of claim 7, wherein the prosthesis or orthosis comprises a thigh member, the logic to:
- receive, from an accelerometer coupled to the thigh member, a second accelerometer signal;
- receive, from an inertial measurement unit coupled to the thigh member, a second inertial pose misalignment signal; and
- determine one or more velocity error contributions based on the second accelerometer signal and the second inertial pose misalignment signal when a computed position on the foot member is substantially stationary.

15. An article comprising a non-transient computer readable medium containing a plurality of instructions that when executed by a processing cause a processor to:
- receive, from an accelerometer coupled to a lower leg member of a lower extremity prosthesis or orthosis, an accelerometer signal;
- receive, from an inertial measurement unit coupled to the lower leg member, an inertial pose misalignment signal;
- determine at least one velocity error contribution when the ankle joint is substantially stationary during a walking cycle based in part on the accelerometer signal; and
- determine at least one velocity error contribution when the ankle joint is substantially stationary during the walking cycle based in part on the inertial pose misalignment signal and a world frame-referenced ankle joint parameter, the world frame-referenced ankle joint parameter to include an indication of at least one of a velocity of an ankle joint coupled to the lower leg member or a position of the ankle joint.

16. The article of claim 15, wherein the inertial pose misalignment signal is a rate gyro signal output by a rate gyro, the plurality of instructions to further cause the processor to:
- determine the pose of the lower leg member based in part on the accelerometer signal and the rate gyro signal; and
- determine a corrected pose of the lower leg member using the velocity error contributions.

17. The article of claim 15, wherein the velocity error contributions are determined during a portion of a controlled dorsiflexion state of the walking cycle.

18. The article of claim 15, wherein the prosthesis or orthosis comprises a thigh member, the plurality of instructions to further cause the processor to:
- receive, from an accelerometer coupled to the thigh member, a second accelerometer signal;
- receive, from an inertial measurement unit coupled to the thigh member, a second inertial pose misalignment signal; and
- determine one or more velocity error contributions based on the second accelerometer signal and the second inertial pose misalignment signal when the ankle joint is substantially stationary during the walking cycle.

19. The article of claim 15, wherein the prosthesis or orthosis comprises a thigh member, the plurality of instructions to further cause the processor to:
- receive, from an accelerometer coupled to the thigh member, a second accelerometer signal;
- receive, from an inertial measurement unit coupled to the thigh member, a second inertial pose misalignment signal; and
- determine one or more velocity error contributions based on the second accelerometer signal and the second inertial pose misalignment signal when a computed position on the foot member is substantially stationary.

20. The article of claim 19, the plurality of instructions to further cause the processor to:
- receive, from an accelerometer coupled to a wearer's torso, a third accelerometer signal;
- receive, from an inertial measurement unit coupled to the wearer's torso, a third inertial pose misalignment signal; and
- determine one or more velocity error contributions based on the third accelerometer signal and the third inertial pose misalignment signal when the ankle joint is substantially stationary during the walking cycle.

* * * * *